US012180239B2

(12) United States Patent
Allred et al.

(10) Patent No.: US 12,180,239 B2
(45) Date of Patent: Dec. 31, 2024

(54) ORGANOSILANES FOR THE TREATMENT OF INFECTIONS

(71) Applicant: Topikos Scientific, Inc., Fort Wayne, IN (US)

(72) Inventors: Gary Allred, Wake Forest, NC (US); Lanny Liebeskind, Atlanta, GA (US); William R. Cast, Fort Wayne, IN (US); Carl Hilliard, Henderson, NV (US)

(73) Assignee: Topikos Scientific, Inc., Fort Wayne, IN (US)

( * ) Notice: Subject to any disclaimer, the term of this patent is extended or adjusted under 35 U.S.C. 154(b) by 787 days.

(21) Appl. No.: 17/232,012

(22) Filed: Apr. 15, 2021

(65) Prior Publication Data

US 2021/0253607 A1 Aug. 19, 2021

Related U.S. Application Data

(63) Continuation of application No. PCT/US2019/057069, filed on Oct. 18, 2019.

(60) Provisional application No. 62/747,588, filed on Oct. 18, 2018.

(51) Int. Cl.
| | |
|---|---|
| *A61K 9/00* | (2006.01) |
| *A61K 9/06* | (2006.01) |
| *A61K 9/19* | (2006.01) |
| *C07F 7/08* | (2006.01) |

(52) U.S. Cl.
CPC .......... *C07F 7/0816* (2013.01); *A61K 9/0014* (2013.01); *A61K 9/06* (2013.01); *A61K 9/19* (2013.01)

(58) Field of Classification Search
None
See application file for complete search history.

(56) References Cited

U.S. PATENT DOCUMENTS

| | | | |
|---|---|---|---|
| 3,551,554 A | 12/1970 | Herschler | |
| 3,560,385 A | 2/1971 | Roth | |
| 3,730,701 A | 5/1973 | Isquith et al. | |
| 3,743,727 A | 7/1973 | Herschler | |
| 3,786,615 A | 1/1974 | Bauer | |
| 3,794,736 A | 2/1974 | Abbott et al. | |
| 3,860,709 A | 1/1975 | Abbott et al. | |
| 4,005,028 A | 1/1977 | Heckert et al. | |
| 4,005,030 A | 1/1977 | Heckert et al. | |
| 4,024,871 A | 5/1977 | Stephenson | |
| 4,282,366 A | 8/1981 | Eudy | |
| 4,394,378 A | 7/1983 | Klein | |
| 4,408,996 A | 10/1983 | Baldwin | |
| 4,414,268 A | 11/1983 | Baldwin | |
| 4,504,541 A | 3/1985 | Yasuda et al. | |
| 4,615,937 A | 10/1986 | Bouchette | |
| 4,631,273 A | 12/1986 | Blehm et al. | |
| 4,692,374 A | 9/1987 | Bouchette | |
| 4,772,593 A * | 9/1988 | Whalen | C07F 7/1804 514/63 |
| 4,842,766 A | 6/1989 | Blehm et al. | |
| 4,856,504 A | 8/1989 | Yamamoto et al. | |
| 4,865,844 A | 9/1989 | Blank et al. | |
| 4,908,355 A | 3/1990 | Gettings et al. | |
| 4,921,691 A | 5/1990 | Stockel et al. | |
| 4,927,687 A | 5/1990 | Nuwayser | |
| 5,064,613 A | 11/1991 | Higgs et al. | |
| 5,358,688 A | 10/1994 | Robertson | |
| 5,359,104 A | 10/1994 | Higgs et al. | |
| 5,883,026 A | 3/1999 | Reader et al. | |
| 5,954,869 A | 9/1999 | Elfersey et al. | |
| 5,959,014 A | 9/1999 | Liebeskind et al. | |
| 6,033,676 A | 3/2000 | Cortright | |
| 6,120,587 A | 9/2000 | Elfersey et al. | |
| 6,146,688 A | 11/2000 | Morgan et al. | |
| 6,160,196 A | 12/2000 | Knieler et al. | |
| 6,221,944 B1 | 4/2001 | Liebeskind et al. | |
| 6,376,696 B1 | 4/2002 | Raab et al. | |
| 6,451,755 B1 | 9/2002 | Norman | |
| 6,613,755 B2 | 9/2003 | Peterson et al. | |
| 6,613,756 B2 | 9/2003 | Duncan et al. | |
| 6,632,805 B1 | 10/2003 | Liebeskind et al. | |
| 6,801,477 B2 | 10/2004 | Braunberger | |
| 7,241,456 B2 | 7/2007 | Vromen | |
| 7,553,983 B2 | 6/2009 | Ranka et al. | |
| 7,589,054 B2 | 9/2009 | Ohlhausen et al. | |
| 8,598,053 B2 | 12/2013 | Whitten et al. | |
| 8,663,705 B2 | 3/2014 | Norton et al. | |

(Continued)

FOREIGN PATENT DOCUMENTS

| | | |
|---|---|---|
| CN | 104403161 A | 3/2015 |
| CN | 105646563 | 6/2016 |

(Continued)

OTHER PUBLICATIONS

AEGIS Environments, "AEM 5700 Antimicrobial"; A Silane Quaternary Ammonium Salt EPA Reg. No. 64881-1 EPA Est. 34292-MI-01; product label, directions for use; [undated]; 1 page, 2006.
The National Institute for Occupational Safety and Health: Emergency Response Safety and Health Database: Methanol: Systemic Agent: CAS#67-56-1: RTECS#PC14000000; UN# 1230(Guide131), available at https://www.cdc.gov/niosh/ershdb/emergencyresponsecard_29750029.html, retrieved Aug. 2, 2017.
Dror, Naama, et al.; "Advances in Microbial biofilm prevention on indwelling medical devices with emphasis on usage of acoustic energy"; Sensors; Apr. 14, 2009; vol. 9, pp. 2539-2554; p. 2542, para. 3.

(Continued)

*Primary Examiner* — Jeffrey H Murray
*Assistant Examiner* — Madeline E Braun
(74) *Attorney, Agent, or Firm* — Knowles Intellectual Property Strategies, LLC

(57) ABSTRACT

Organosilicon quaternary ammonium compounds, their formulations, including lyophilized solid formulations, and methods of use to treat infections in humans and animals.

20 Claims, No Drawings

(56) References Cited

U.S. PATENT DOCUMENTS

| | | |
|---|---|---|
| 8,691,874 B2 | 4/2014 | Karageozian et al. |
| 8,865,605 B2 | 10/2014 | Bender et al. |
| 8,906,115 B2 | 12/2014 | Bender |
| 9,314,407 B2 | 4/2016 | Blizzard et al. |
| 9,364,572 B2 | 6/2016 | Peterson, II et al. |
| 9,764,264 B2 | 9/2017 | Peterson, II et al. |
| 2002/0037260 A1 | 3/2002 | Budny et al. |
| 2003/0175232 A1 | 9/2003 | Elliott et al. |
| 2003/0215417 A1 | 11/2003 | Uchiyama et al. |
| 2003/0225003 A1 | 12/2003 | Ninkov |
| 2004/0101506 A1 | 5/2004 | Fust |
| 2005/0004098 A1 | 1/2005 | Britten et al. |
| 2005/0063997 A1 | 3/2005 | Peyman |
| 2006/0051385 A1 | 3/2006 | Scholz |
| 2006/0110348 A1 | 5/2006 | Ohlhausen et al. |
| 2006/0222675 A1 | 10/2006 | Sabnis et al. |
| 2007/0042198 A1 | 2/2007 | Schonemyr et al. |
| 2007/0184130 A1 | 8/2007 | Carrigan |
| 2007/0196329 A1 | 8/2007 | Xia et al. |
| 2007/0212343 A1 | 9/2007 | Owen |
| 2008/0009643 A1 | 1/2008 | Mehta et al. |
| 2008/0009644 A1 | 1/2008 | Ranka et al. |
| 2008/0026156 A1 | 1/2008 | Mehta et al. |
| 2008/0092909 A1 | 4/2008 | Hahne |
| 2008/0161219 A1 | 7/2008 | Ohlhausen et al. |
| 2009/0005339 A1 | 1/2009 | Scholz et al. |
| 2009/0223411 A1 | 9/2009 | Higgins et al. |
| 2009/0252647 A1 | 10/2009 | Orofino |
| 2010/0093666 A1 | 4/2010 | Moses et al. |
| 2010/0211034 A1 | 8/2010 | Toreki et al. |
| 2010/0211035 A1 | 8/2010 | Toreki et al. |
| 2011/0293681 A1 | 12/2011 | Berlin et al. |
| 2012/0052106 A1 | 3/2012 | Eddy |
| 2012/0196953 A1 | 8/2012 | Ziolkowski et al. |
| 2013/0017242 A1 | 1/2013 | Richardson et al. |
| 2013/0231599 A1 | 9/2013 | Eddy |
| 2014/0011766 A1 | 1/2014 | Krafft |
| 2014/0100504 A1 | 4/2014 | Eddy |
| 2014/0302146 A1 | 10/2014 | Kurose et al. |
| 2015/0024019 A1 | 1/2015 | Ali et al. |
| 2015/0296790 A1 | 10/2015 | Nagai et al. |
| 2015/0328241 A1 | 11/2015 | Hilliard et al. |
| 2016/0039949 A1 | 2/2016 | Zhao et al. |
| 2016/0287717 A1 | 10/2016 | Brinker et al. |
| 2016/0346193 A1 | 12/2016 | Neigel |
| 2016/0354307 A1 | 12/2016 | Hilliard et al. |
| 2017/0042916 A1 | 2/2017 | Hilliard et al. |
| 2017/0094974 A1 | 4/2017 | Smyth et al. |
| 2018/0027804 A1 | 2/2018 | Moudgil et al. |
| 2018/0071326 A1 | 3/2018 | Hilliard et al. |
| 2018/0280201 A1 | 10/2018 | Grossman et al. |
| 2018/0360861 A1 | 12/2018 | Hilliard et al. |

FOREIGN PATENT DOCUMENTS

| | | |
|---|---|---|
| CN | 106478711 | 3/2017 |
| CN | 107130461 | 9/2017 |
| CN | 107199745 | 9/2017 |
| EP | 0108853 B1 | 5/1984 |
| EP | 0408017 A2 | 7/1990 |
| EP | 0408017 | 1/1991 |
| EP | 1787650 A2 | 5/2006 |
| EP | 1787650 | 5/2007 |
| EP | 2119363 A3 | 11/2011 |
| MX | 2012002853 A | 9/2013 |
| WO | WO 1992/14810 A1 | 9/1992 |
| WO | WO 1997/32957 A1 | 9/1997 |
| WO | WO 1998/26807 A1 | 6/1998 |
| WO | WO 2000/54587 A1 | 9/2000 |
| WO | WO 2002030455 A2 | 4/2002 |
| WO | WO 2004/004793 A1 | 1/2004 |
| WO | WO 2004/105687 A2 | 12/2004 |
| WO | WO 2006/049478 A1 | 5/2006 |
| WO | WO 2006/086271 A1 | 8/2006 |
| WO | WO 2006/086271 A2 | 8/2006 |
| WO | WO 2007/092452 A2 | 8/2007 |
| WO | WO 2008/071680 A2 | 8/2007 |
| WO | WO 2008/071680 A1 | 6/2008 |
| WO | WO 2008/071681 A1 | 6/2008 |
| WO | WO 2009/003199 A1 | 12/2008 |
| WO | WO 2009/129470 A2 | 10/2009 |
| WO | WO 2010/013250 A2 | 2/2010 |
| WO | WO 2011/088347 A1 | 7/2011 |
| WO | WO 2011/107781 A1 | 9/2011 |
| WO | WO 2011/123623 A2 | 10/2011 |
| WO | WO 2012/088377 A2 | 6/2012 |
| WO | WO 2012/108850 A1 | 8/2012 |
| WO | WO 2013/106216 A1 | 7/2013 |
| WO | WO 2013/121222 A1 | 8/2013 |
| WO | WO 2015/042268 A1 | 3/2015 |
| WO | WO 2015/124945 A1 | 8/2015 |
| WO | WO 2016/073634 A1 | 5/2016 |
| WO | WO 2016/187391 A1 | 11/2016 |
| WO | WO 2018/183388 A1 | 10/2018 |
| WO | WO 2018/237077 A1 | 12/2018 |
| WO | WO 2020/082026 A1 | 4/2020 |
| WO | WO 2021/077119 | 4/2021 |
| WO | WO 2023/215521 | 11/2023 |

OTHER PUBLICATIONS

Gupta et al., "Microbial Keratinases and Their Prospective Applications: An Overview," Appl Microbial Biotechnology, Jan. 4, 2006, 70: 21-33.

International Search Report and Written Opinion, Oct. 17, 2016, PCT Application No. PCT/US16/33208, filed on May 19, 2016.

Unknown author; "Coeus Technology Material Safety Data Sheet; MonoFoil Antimicrobial (Typical Application Strength)"; Jul. 29, 2009, Revision No. 2; 6 pages.

International search report and written opinion for PCT/US2019/057069 mailed Feb. 6, 2020.

Hamel, Michelle; "NMT-LMT Certified Aroma Therapist Neuromuscular Pain Relief Center Orlando Massage Therapy", Infection-Biofilm Treatment Essential Oils Orlando; 2016.

Jenkins, Ben H.; "Treatment of Otitis Externa and Swimmer's Ear" The JAMA Network; Feb. 4, 1961;175(5):402-404; 2 pages.

Monticello, Robert A.; "The use of reactive silane chemistries to provide durable, non-leaching antimicrobial surfaces"; EGIS Environments; 2017; 77 pages.

MonoFoilUSA Redefining Clean; MonoFoil MSDS 2017; one page.

Saif, et al. "An eco-friendly, permanent, and non-leaching antimicrobial coating on cotton fabrics" 2014 pp. 1-6.

Sander, Robert; "Otitis Externa: A practical guide to treatment and prevention; Practical Therapeutics", Medical College of Wisconsin, Milwaukee, Wisconsin; American Family Physician; vol. 63, No. 5; Mar. 1, 2001; p. 927-936.

Song, Jooyoung, et al. "Bacterial adhesion inhibition of the quaternary ammonium functionalized silica nanoparticles," Colliods and Surfaces B: Biointerfaces 82 (2011) 651-656.

Internet Archive Wayback Machine, CFA Coatings for America, Bioshield '75 Bigstatic Surface Protectant Presentation 2013; 27 pages.

Wang, et al. "Specificity and Enzyme Kinetics of the Quorum-Quenching N-Acyl Homoserine Lactone Lactonase (AHL-lactonase)", The Journal of Biological Chemistry; 2004; vol. 279, No. 14. Issue of April 2, pp. 13645-13651.

U.S. Appl. No. 17/723,168, Allred et al., filed Apr. 18, 2022.

US, 2023/0079298, A1, U.S. Appl. No. 17/723,168, Allred et al., filed Mar. 16, 2023.

US, 2023/0143708, A1, U.S. Appl. No. 18/087,587, Allred et al., filed May 11, 2023.

US, 2023/0295195, A1, U.S. Appl. No. 18/087,555, Allred et al., filed Sep. 21, 2023.

Email to CAS customer center, Re U.S. Pat. No. 4,005,028 (2023).

CAS Abstract and indexed compounds D. Heckert et al. U.S. Pat. No. 4,005,028 (1977).

CAS Abstract and indexed compounds J. Brinker et al. US20160287717 (2016).

International Search Report and Written Opinion for PCT/2023/31069 dated Jan. 9, 2024, 12 pages.

(56) References Cited

OTHER PUBLICATIONS (National Center for Biotechnology Information) "N,N-Dimelhyl-N-(3-(trihydroxysily1)propyl)ocladecan-1-aminium: Pubchem CID 21365909" Pubchem entry (online), pp. 1-14, Dec. 5, 2007; Retrieved on Aug. 7, 2023 from the Internet: [URL:https://pubchem.ncbi.nlm.nlh.gov/compound/21365909].

(National Center for Biotechnology Information) "N-Tris(hydroxymelhyl)methyl-2-aminoethanesulfonlc acid: Pubchem CID 81831" Pubchem entry (online), pp. 1-12, Jun. 24, 2005; Retrieved on Aug. 9, 2023 from the Internet: [URL: https://pubchem.ncbi.nlm.nih.gov/compound/81831].

(National Center for Biotechnology Information) "N-Tris(hydroxymelhyl)methyl-2-aminoethanesulfonlc acid: Pubchem CID 81831" Pubchem entry (online), pp. 1-12, Jun. 24, 2005; Retrieved on Jan. 23, 2024 from the Internet: [URL:https://pubchem.ncbi.nlm.nih.gov/compound/81831].

(National Center for Biotechnology Information) "Tromelhamlne: Pubchem CID 6503" Pubchem entry (online), pp. 1-10, Mar. 26, 2005; Retrieved on Aug. 9, 2023 from the Internet: [URL: https://pubchem.ncbi.nlm.nih.govlcompound/6503].

(National Center for Biotechnology Information) "Tromelhamlne: Pubchem CID 6503" Pubchem entry (online), pp. 1-10, Mar. 26, 2005; Retrieved on Jan. 23, 2024 from the Internet: [URL: https://pubchem.ncbi.nlm.nih.govlcompound/6503].

(National Center for Biotechnology Information) "4-Hydroxy-3,3-bis(hydroxymethyl)butan-1-sulfonic acid: Pubchem CID 296494" Pubchem entry (online), pp. 1-13, Mar. 26, 2005; Retrieved on Aug. 9, 2023 from the Internet: [URL:https://pubchem.ncbi.nlm.nih.gov/compound/296494].

(National Center for Biotechnology Information) "2-[Bis(hydroxymelhyl)amino) ethanesulfonic acid: Pubchem CID 57925512" Pubchem entry (online), pp. 1-11, Aug. 19, 2012; Retrieved on Aug. 9, 2023 from the internet: [URL: https://pubchem.ncbi.nlm.nih.gov/compound/57925512].

(National Center for Biotechnology Information) "Dimethyl-octadecyl-octadecyl-[3-[tris(oxlran-2-ylmethoxy)silyl]propyl)azanium: Pubchem CID 156729836" Pubchem entry (online), pp. 1-9, Nov. 10, 2021; Retrieved on Aug. 9, 2023 from the Internet: [URL:https://pubchem.ncbi.nlm.nih.gov/compound/156729836].

U.S. Pat. No. 12,006,338, B2, U.S. Appl. No. 18/0878,555, Allred et al., filed Jun. 11, 2024.

U.S. Pat. No. 12,024,553, B2, U.S. Appl. No. 18/087,587, Allred et al., filed Jul. 2, 2024.

U.S. Appl. No. 18/642,608, Allred et al., filed Apr. 22, 2024.

International Search Report and Written Opinion for PCT/2020/056392 dated Feb. 26, 2021, 10 pages.

International Search Report and Written Opinion for PCT/2023/21069 dated Jan. 9, 2024, 12 pages.

National Center for Biotechnology Information) "N,N-Dimethyl-N-(3-(trihydroxysilyl)propyl)octadecan-1-aminium: Pubchem CID 21365909" Pubchem entry (online), pp. 1-14, Dec. 5, 2007; Retrieved on Aug. 7, 2023 from the Internet: [URL: https://pubchem.ncbi.nlm.nih.gov/compound/21365909].

(National Center for Biotechnology Information) "N-Tris(hydroxymethyl)methyl-2-aminoethanesulfonic acid: Pubchem CID 81831" Pubchem entry (online), pp. 1-12, Jun. 24, 2005; Retrieved on Aug. 9, 2023 from the Internet: [URL: https://pubchem.ncbi.nlm.nih.gov/compound/81831].

(National Center for Biotechnology Information) "N-Tris(hydroxymethyl)methyl-2-aminoethanesulfonic acid: Pubchem CID 81831" Pubchem entry (online), pp. 1-12, Jun. 24, 2005; Retrieved on Jan. 23, 2024 from the Internet: [URL: https://pubchem.ncbi.nlm.nih.gov/compound/81831].

(National Center for Biotechnology Information) "Tromethamine: Pubchem CID 6503" Pubchem entry (online), pp. 1-10, Mar. 26, 2005; Retrieved on Aug. 9, 2023 from the Internet: [URL: https://pubchem.ncbi.nlm.nih.gov/compound/6503].

(National Center for Biotechnology Information) " Tromethamine: Pubchem CID 6503" Pubchem entry (online), pp. 1-10, Mar. 26, 2005; Retrieved on Jan. 23, 2024 from the Internet: [URL: https://pubchem.ncbi.nlm.nih.gov/compound/6503].

(National Center for Biotechnology Information) "Dimethyl-octadecyl-[3- [tris(oxiran-2-ylmethoxy)silyl]propyl]azanium: Pubchem CID 156729836" Pubchem entry (online), pp. 1-9, Nov. 10, 2021; Retrieved on Aug. 9, 2023 from the Internet: [URL: https://pubchem.ncbi.nlm.nih.gov/compound/156729836].

* cited by examiner

ORGANOSILANES FOR THE TREATMENT OF INFECTIONS

CROSS-REFERENCE TO RELATED APPLICATIONS

This application is a continuation of International Application No. PCT/US2019/057069, filed in the U.S. Receiving Office on Oct. 18, 2019, which claims priority to provisional U.S. Application No. 62/747,588, filed Oct. 18, 2018. The entirety of each of these applications is incorporated herein for all purposes.

FIELD OF THE INVENTION

This disclosure provides organosilicon quaternary ammonium compounds and their formulations, including lyophilized solid formulations, and their methods of use to treat infections in humans and animals.

BACKGROUND OF THE INVENTION

There is an urgent global need to provide new antimicrobial, antibiotic and antifungal drugs to treat infections in humans and animals, including difficult to treat infections that are not or are insufficiently responsive to current therapies.

In September 2018, The PEW Charitable Trusts reported on the critical need for new antibiotics. At that time, there were only 42 antibiotics in clinical development, with a predicted rate of not more than 20% approval. Of these, only 15 were likely to treat infections caused by resistant Gram-negative pathogens. Only 11 antibiotics in development have the potential to treat pathogens considered a critical threat by The World Health Organization.

One of the ways microorganisms evade current therapies is by the formation of a biofilm consisting of a group of microorganisms that adhere to each other and, in many cases, surrounding surfaces. These microorganisms may be bacteria, yeasts, algae, fungi, or, commonly, mixtures thereof. The microbial communities are encased in extracellular polymeric substances (EPS) (see Karatan E., Watnick P. "Signals, regulatory networks, and materials that build and break bacterial biofilms" Microbiol. Mol. Biol Rev. 2009, 73:310-347), a mixture of polysaccharides, extracellular DNA (eDNA), and proteins that function as a matrix holding the microbial cells together. The biofilm matrix contributes to the overall architecture and the resistant phenotype of biofilms (See Sutherland I. W. "The biofilm matrix—An immobilized but dynamic microbial environment" Trends Microbiol. 2001, 9:222-227; and Branda S. S., Vik S., Friedman L., Kolter R. "Biofilms: The matrix revisited" Trends Microbiol. 2005, 13:20-26). This matrix also "confers a spatial organization on biofilms, from which they derive steep gradients, high biodiversity, and complex, dynamic and synergistic interactions, including cell-to-cell communication and enhanced horizontal gene transfer." (see Flemming H.-C., Wingender J., Szewzyk U. Steinberg, P., Rice S. A., Kjelleberg, S. "Biofilms: An emergent form of bacterial life" Nature Reviews Microbiology 2016, 14:563-575). This protective mode of growth allows microorganisms to survive in hostile environments and disperse seeding cells to colonize new niches under desirable conditions.

The increasing microbial resistance to present treatment regimens is at least in part due to the escalating effectiveness of the primary intrinsic defense mechanisms of microorganisms, particularly in biofilms. These defenses include decreased drug uptake, efflux, enzymatic inactivation and target alterations by mutations. Microbes can also acquire resistance by sharing genetic material, called horizontal gene transfer (HGT), which can be a more rapid process than genetic selection involved in the development of intrinsic resistance.

Ear infections can be the result of a biofilm, in humans as well as in animals such as humans, dogs, cats, horses, cattle, and other meat producing animals. In both animals and humans, if not treated properly, the infection can cause hearing loss, and lead to other health problems.

Simultaneous or sequential polymicrobial infection can occur with similar organisms of a different species or a mixture of bacteria and fungi. The available antimicrobials used for treatment often do not have significant activity overlap across multiple groups of potential pathogens (Tuft, S. "Polymicrobial infection and the eye" Br J Ophthalmol. 2006, 90(3):257-258).

Corneal vision impairment is a general term for conditions that result from a variety of infections that scar the cornea. The effective treatment of ocular infections with an affordable medication is clearly a global health priority.

Fungi alone cause over a million eye infections every year, many of which result in blindness. The eye is particularly vulnerable to fungal infections when anatomical barriers are breached. The host's immune system is often unable to combat fungal infections and prevent loss of vision (see Klotz, S., Penn, C., Negvesky, G. and Butrus, S. "Fungal and Parasitic Infections of the Eye" Clin Microbiol Rev 2000, 13(4):662-685). The lack of potent fungicidal agents and poor ocular penetration of existing antifungal agents result in significant ocular morbidity. Bacteria are also a major contributor of ocular infections worldwide. If not treated properly, they can damage the structure of the eye, leading to visual impairment or possible blindness. Bacteria, and in particular gram-positive bacteria, are associated with conjunctivitis, keratitis, endophthalmitis, blepharitis, and orbital cellulitis.

With the aging population, dry eye infections are becoming more prevalent. Dry eye can be very irritating and uncomfortable, especially for elderly patients.

There remains a strong need for new safe and effective topical medicines to treat a range of microbial infections, including mixed infections and biofilms, in humans and other host animals.

SUMMARY OF THE INVENTION

New organosilane quaternary ammonium compounds are provided that are useful in pharmaceutical topical formulations to treat a range of infections, including Gram positive, Gram negative and fungal infections, in a host in need thereof. The fungi can occur as a yeast, a mold or a combination of both forms. The new compounds described herein can treat microorganisms in a biofilm, including mixed organisms.

The topical formulations can be used, for example, to treat ocular infections (including bacterial or fungal infections and dry eye caused by Blepharitis), ear infections, and skin infections including nail bed infections, in a host.

Importantly, in one embodiment, selected new organosilane quaternary ammonium compounds can be provided as a stable lyophilized powder that can be formulated before administration using pharmaceutically acceptable topical carriers.

Non-limiting examples of topical infections that can be treated with the provided organosilane quaternary ammonium compounds include *Pseudomonas* (Gram-negative), *Proteus* (genus of Gram-negative Proteobacteria), *Staphylococcus* (Gram-positive), MRSA (methicillin resistant *S. aureus*), *Escherichia coli* (Gram-negative), *Klebsiella* (Gram-negative), *Enterococcus* (Gram-positive) and fungi such as *Fusarium, Aspergillus* and *Candida*, dermatophyte, *Trichophyton, Microsporum* and *Epidermophyton*.

The present invention provides new organosilicon quaternary amine compounds and compositions thereof, having Formula I through Formula XXIX, optionally in a lyophilized or otherwise solid stable storage form. The invention also provides methods of topical administration of an effective amount of one or more new organosilicon quaternary ammonium compounds of Formula I through Formula XXIX; to treat, prevent, inhibit, or eliminate an infectious disease in a host in need thereof.

In certain embodiments, the organosilane quaternary ammonium compound further includes at least one moiety that can also form a pharmaceutically acceptable salt. In certain embodiments, a substituent moiety in the Compound of any of the Formulas provided herein can be present as a negatively charged moiety, such as —O⁻. This anion can be neutralized with a pharmaceutically acceptable cation, such as sodium, potassium, or other cations as further described herein, typically via pH adjustment.

In one embodiment, the anion of the moiety forms an internal zwitterion with the quarternary ammonium group. In certain embodiments, the balancing anion of the quaternary amine of any of the Compound Formulas presented herein is selected from chloride, fluoride, iodide, bromide, chlorite, chlorate, hydroxide, formate, acetate, lactate, benzoate, hydroxide, or salicylate anion. In a typical embodiment, the anion is chloride. In one embodiment the zwitterionic compound is more soluble in aqueous media than its non-zwitterionic form. In yet another embodiment the zwitterionic compound is more stable in an aqueous solution than its non-zwitterionic form.

In a typical embodiment, the positive charge of the quaternary ammonium compound is paired with a negatively charged ion, such as chloride, as appropriate.

In another embodiment, the anion of the moiety is neutralized with a cation, including but not limited to sodium, potassium, magnesium, lithium, calcium, cesium, or barium.

In one embodiment any mixture of quaternary ammonium compounds as described herein is appropriate as long as the desired stability is achieved.

In one embodiment, the lyophilized powder formulations as described herein, contains less than about 5%, about 4%, about 3%, about 2%, about 1%, about 0.5%, or about 0.1% of methanol by weight; or no methanol is present.

In one aspect of the present invention, a compound of Formula I, II, III, IV, V, VI, VII, VIII, or IX is provided,

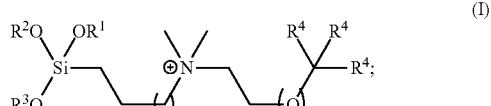
(I)

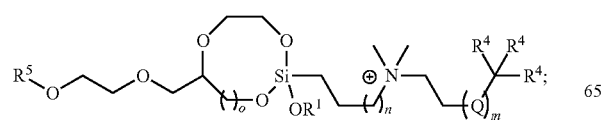
(II)

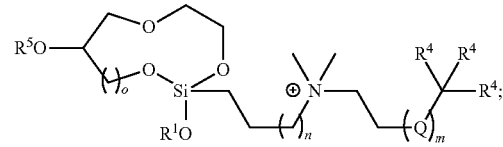
(III)

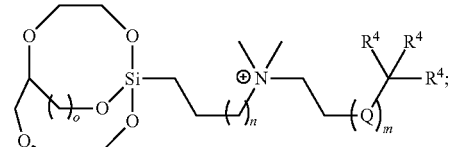
(IV)

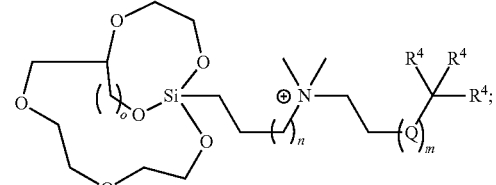
(V)

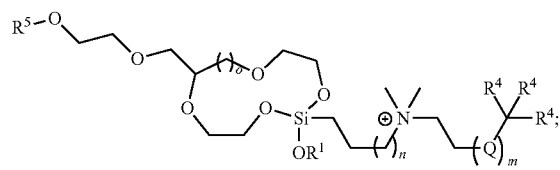
(VI)

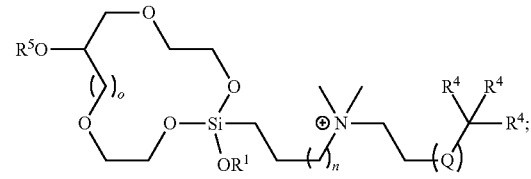
(VII)

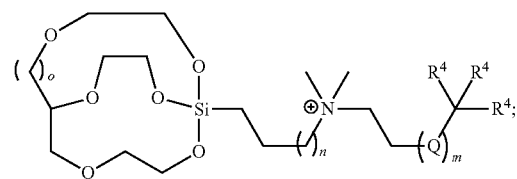
(VIII)

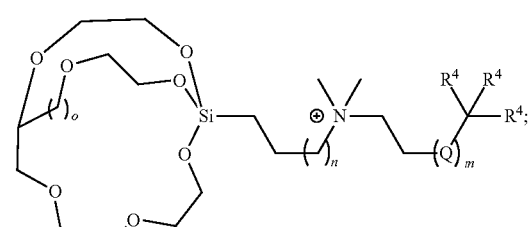
(IX)

wherein:

is 1 or 2;

n is 0, 1, or 2;

m is 0, 1, 2, 3, 4, 5, 6, 7, 8, 9, 10, 11, 12, 13, 14, 15, 16, 17, 18, 19, or 20;

Q is —CR$^4$R$^4$—;

R$^1$ and R$^2$ are both hydrogen; or in an alternative embodiment, $R^1$ and $R^2$ are independently at each occurrence selected from hydrogen and ethyl;

$R^3$ is independently at each occurrence selected from:

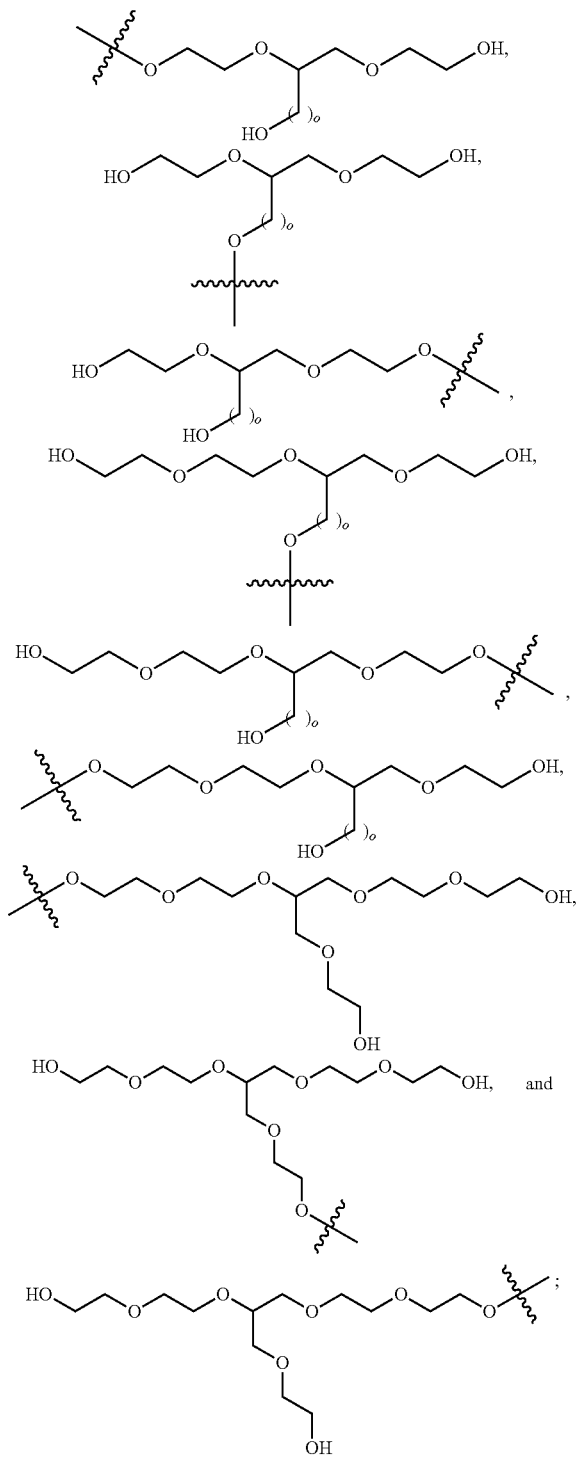

each $R^4$ is independently at each occurrence selected from hydrogen, alkyl, alkenyl, alkynyl, halogen, and haloalkyl; and $R^5$ is hydrogen or —$CH_2CH_2OH$.

In certain embodiments of the quaternary ammonium compounds of Formula I through Formula IX, Formula XI through Formula XXI and Formula XXIII through Formula XXVIII, the variable is m is 6, 7, 8, 9, 10, 11, 12, 13, 14, 15 or 16. In certain embodiments of the quaternary ammonium compounds of Formula I through Formula IX, m is 14. In certain embodiments of the quaternary ammonium compounds of Formula I through Formula IX, m is 12-16.

In one aspect, a lyophilized powder formulation is provided comprising a quaternary ammonium compound of Formula I, II, III, IV, or V, or a combination thereof. In one aspect, a lyophilized powder formulation is provided comprising a quaternary ammonium compound of Formula I, VI, VII, VIII, or IX, or a combination thereof.

In one embodiment, any mixture of quaternary ammonium compounds of Formula I, II, III, IV, V, VI, VII, VIII, and IX is appropriate as long as the desired stability is achieved.

In one embodiment, the quaternary ammonium compound of Formula I, II, III, IV, or V in solution is in equilibrium with other quaternary ammonium compounds of Formula I, II, III, IV, and V. In another embodiment, quaternary ammonium compounds of Formula I, VI, VII, VIII, and IX are in equilibrium. For example, in one embodiment the below compounds may be in equilibrium:

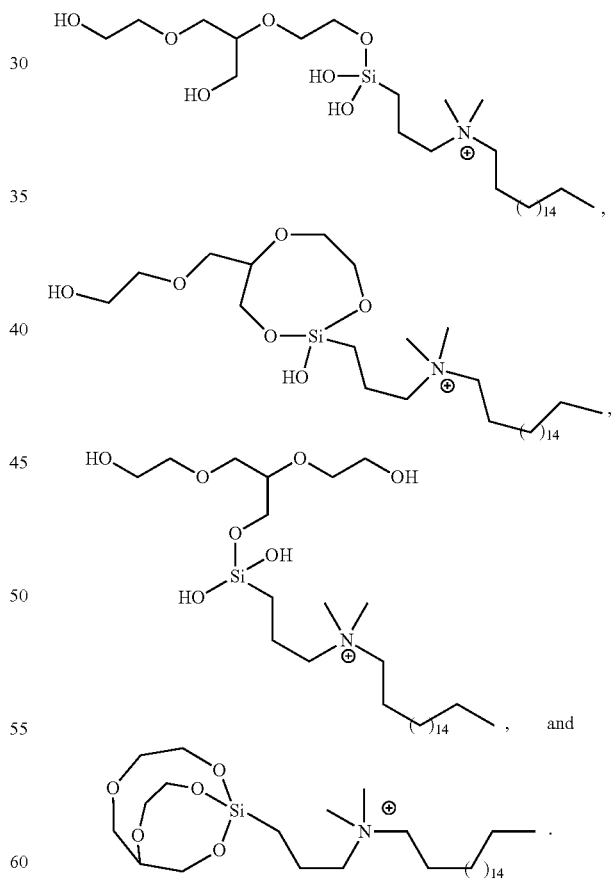

Due to the lability of silicon-oxygen bonds, these structures may interconvert via bond breakage and formation such that a mixture of Formula I, II, III, IV, and V or a mixture of a mixture of Formula I, VI, VII, VIII, or IX may be present.

The present invention, thus contemplates an antimicrobial composition containing one or more quaternary ammonium compounds of Formula I, II, III, IV, or V and an appropriate carrier; or one or more quaternary ammonium compounds of Formula I, VI, VII, VIII, or IX and an appropriate carrier.

The invention also includes a method of treating an infection in a host in need thereof with an effective amount of a quaternary ammonium compound of Formula I, II, III, IV, or V, or a combination thereof.

Alternately, the invention also includes a method of treating an infection in a host in need thereof with an effective amount of one or more quaternary ammonium compounds of Formula I, VI, VII, VIII, or IX, or a combination thereof. In one embodiment, an active quaternary ammonium compound is used in an effective amount to treat an infectious disease in a host in need thereof.

In some embodiments, the quaternary ammonium compound of Formula I, II, III, IV, or V, or a combination thereof, is administered as an aqueous or glycerin solution that has been formed by reconstituting a lyophilized powder formulation comprising the quaternary ammonium compound of Formula I, II, III, IV, or V, or a combination thereof.

In some embodiments, the quaternary ammonium compound of Formula I, VI, VII, VIII, or IX, or a combination thereof, is administered as an aqueous or glycerin solution that has been formed by reconstituting a lyophilized powder formulation comprising quaternary ammonium compound of Formula I, VI, VII, VIII, or IX, or a combination thereof.

In one aspect, a kit is provided comprising a lyophilized powder formulation comprising: a quaternary ammonium compound of Formula I, II, III, IV, or V, or a combination thereof; a sterile aqueous solution; and an application device. In another aspect, a kit is provided comprising a lyophilized powder formulation comprising: a quaternary ammonium compound of Formula I, VI, VII, VIII, or IX, or a combination thereof; a sterile aqueous solution; and an application device.

In another aspect, a kit is provided comprising a sterile aqueous solution comprising a quaternary ammonium compound of Formula I, II, III, IV, or V, or a combination thereof, and an application device. In another aspect, a kit is provided comprising a sterile aqueous solution comprising a quaternary ammonium compound of Formula I, VI, VII, VIII, or IX, or a combination thereof, and an application device. In one embodiment, the application device is a syringe.

In another aspect of the present invention, a compound of Formula X is provided, wherein the compound of Formula X is selected from:

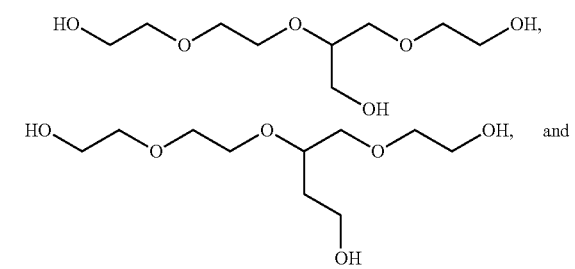

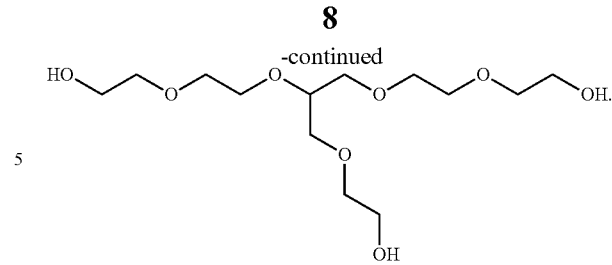

In one embodiment a compound of Formula X is a useful prodrug group. In another embodiment a compound of Formula X is an intermediate in the synthesis of a compound of Formula I, II, III, IV, V, VI, VII, VIII, or IX.

In another aspect of the present invention, a quaternary ammonium compound of Formula XI, XII, XIII, XIV, XV, or XVI is provided:

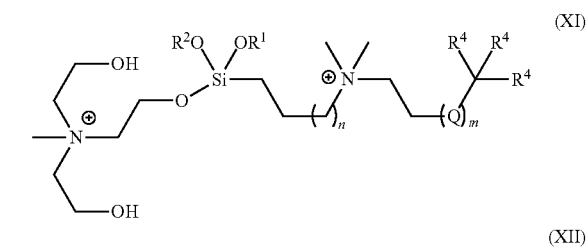

(XI)

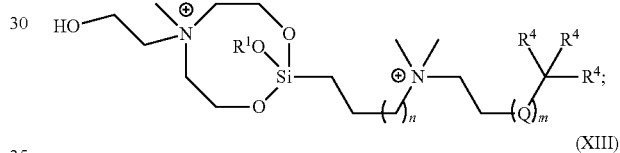

(XII)

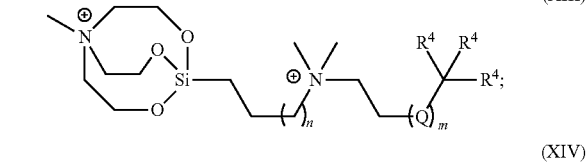

(XIII)

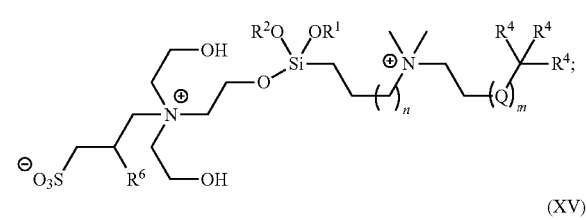

(XIV)

(XV)

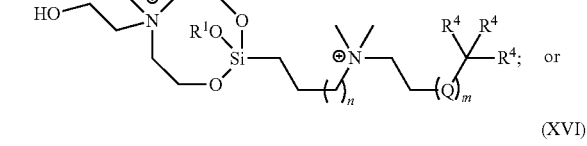

or (XVI)

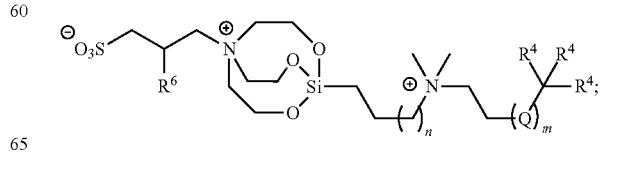

wherein $R^1$, $R^2$, $R^4$, Q, m, and n are as defined herein; and $R^6$ is independently at each occurrence selected from hydrogen, hydroxy, and $C_1$-$C_6$alkoxy.

In one aspect, a lyophilized powder formulation is provided comprising a quaternary ammonium compound of Formula XI, XII, or XIII, or a combination thereof.

In one aspect, a lyophilized powder formulation is provided comprising a quaternary ammonium compound of Formula XIV, XV, or XVI, or a combination thereof.

In one embodiment the quaternary ammonium compound of Formula XI, XII, and XIII in solution is in equilibrium with other quaternary ammonium compounds of Formula XI, XII, and XIII. For example, in one embodiment the below compounds may be in equilibrium:

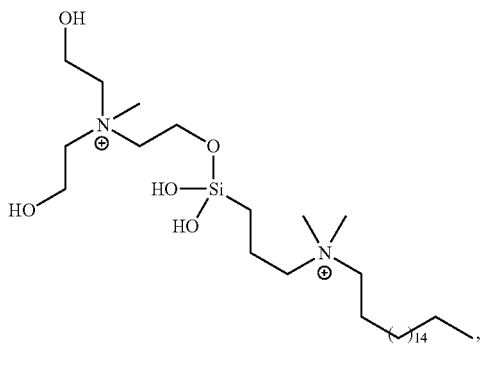

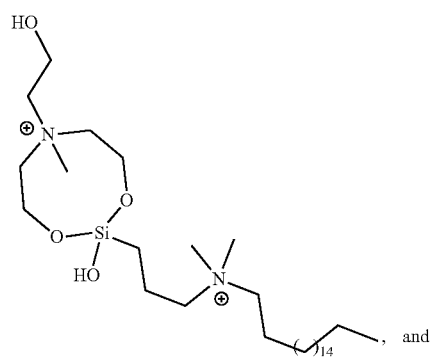

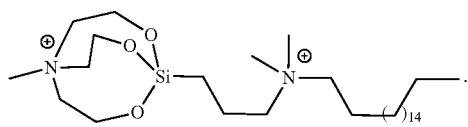

In one embodiment the quaternary ammonium compound of Formula XIV, XV, or XVI is in equilibrium with other quaternary ammonium compounds of Formula XIV, XV, or XVI. In one non-limiting illustrated example, in one embodiment the below compounds may be in equilibrium:

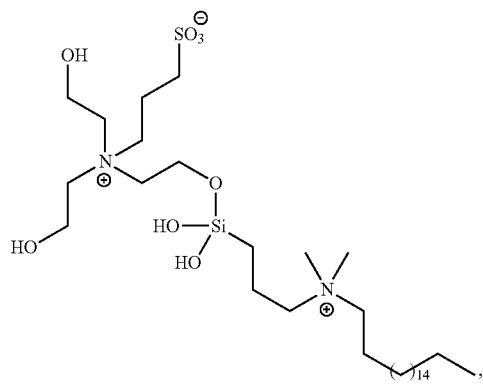

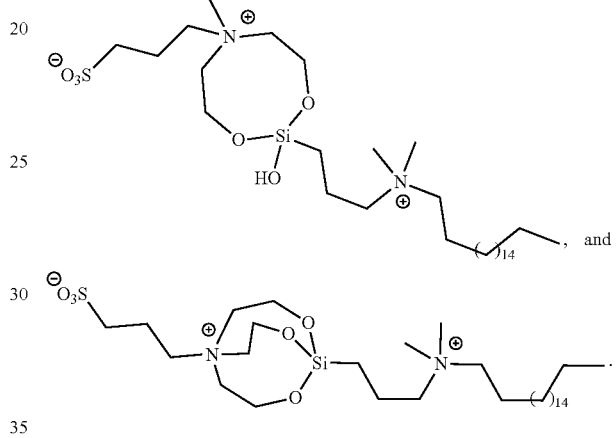

Due to the lability of silicon oxygen bonds, these structures may interconvert via bond breakage and formation such that a mixture of Formula XI, XII, or XIII may be present; or a mixture of Formula XIV, Formula XV, or Formula XVI may be present.

The present invention, among other things, contemplates an antimicrobial composition containing one or more quaternary ammonium compounds of Formula XI, XII, or XIII and an appropriate carrier; or one or more quaternary ammonium compounds of Formula XIV, XV, or XVI and an appropriate carrier.

The invention also includes a method of treating an infection in a host in need thereof with an effective amount of one or more quaternary ammonium compounds of Formula XI, XII, or XIII, or a combination thereof, or a quaternary ammonium compound of Formula XIV, XV, or XVI, or a combination thereof.

In one embodiment, one or more active quaternary ammonium compounds is used in an effective amount to treat an infectious disease in a host in need thereof.

In some embodiments, the quaternary ammonium compound of Formula XI, XII, or XIII, or a combination thereof, is administered as an aqueous or glycerin solution that has been formed by reconstituting a lyophilized powder formulation comprising the quaternary ammonium compound of Formula XI, XII, or XIII, or a combination thereof.

In some embodiments, the quaternary ammonium compound of Formula XIV, XV, or XVI, or a combination thereof, is administered as an aqueous or glycerin solution that has been formed by reconstituting a lyophilized powder formulation comprising the quaternary ammonium compound of Formula XIV, XV, or XVI, or a combination thereof.

In one aspect, a kit is provided comprising a lyophilized powder formulation comprising: a quaternary ammonium compound of Formula XI, XII, or XIII, or a combination thereof, a sterile aqueous solution; and an application device. In one aspect, a kit is provided comprising a sterile aqueous solution comprising a quaternary ammonium compound of Formula XI, XII, or XIII, or a combination thereof, and an application device.

In another aspect, a kit is provided comprising a lyophilized powder formulation comprising: a quaternary ammonium compound of Formula XIV, XV, or XVI, or a combination thereof; a sterile aqueous solution; and an application device.

In one aspect, a kit is provided comprising a sterile aqueous solution comprising a quaternary ammonium compound of Formula XIV, XV, or XVI, or a combination thereof, and an application device. In one embodiment, the application device is a syringe.

In another aspect of the present invention, a quaternary ammonium compound of Formula XVII, XVIII, or XIX is provided:

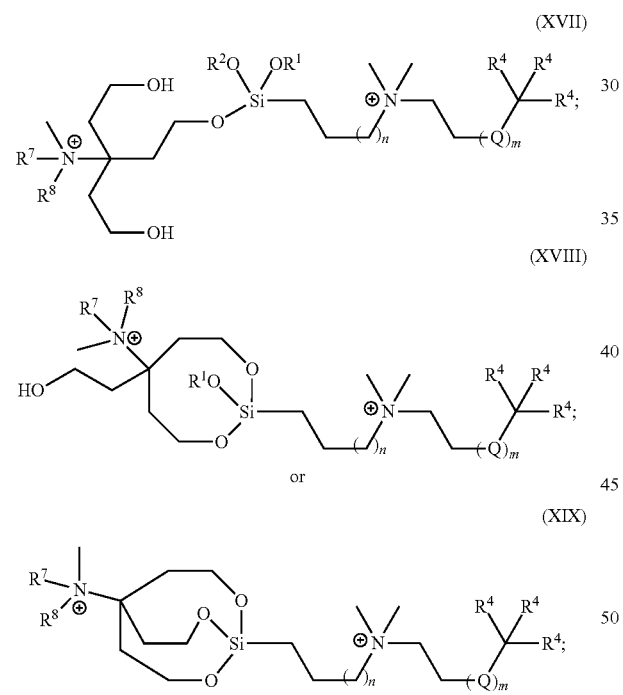

wherein $R^1$, $R^2$, $R^4$, m, n, and Q are as defined herein; and $R^7$ and $R^8$ are independently at each occurrence selected from $C_1$-$C_6$alkyl.

In one aspect, a lyophilized powder formulation is provided comprising a quaternary ammonium compound of Formula XVII, XVIII, or XIX, or a combination thereof. In one embodiment any mixture of quaternary ammonium compounds of Formula XVII, XVIII, or XIX is appropriate as long as the desired stability is achieved.

In one embodiment the compound of Formula XVII, XVIII, or XIX is in equilibrium with other compounds of Formula XVII, XVIII, or XIX. For example, in one embodiment the below compounds may be in equilibrium:

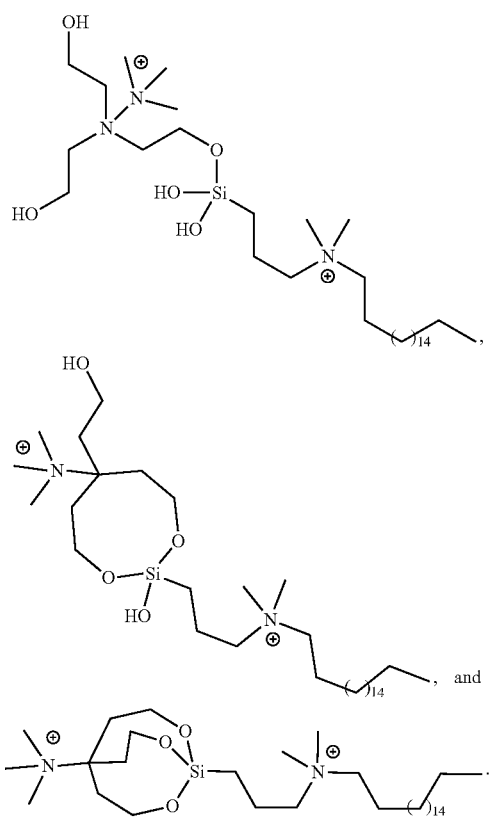

Due to the lability of silicon oxygen bonds, these structures may interconvert via bond breakage and formation such that a mixture of Formula XVI, Formula XVII, or Formula XIX may be present.

The present invention, among other things, contemplates an antimicrobial composition containing one or more compounds of Formula XVII, XVIII, or XIX and an appropriate carrier.

The invention also includes a method of treating an infection, in a host in need thereof, with an effective amount of a quaternary ammonium compound of Formula XVII, XVIII, or XIX, or a combination thereof. In one embodiment, an effective amount of one or more active quaternary ammonium compounds is used in an effective amount to treat an infectious disease in a host in need thereof.

In some embodiments, the quaternary ammonium compound of Formula XVII, XVIII, or XIX, or a combination thereof, is administered as an aqueous or glycerin solution that has been formed by reconstituting a lyophilized powder formulation comprising the quaternary ammonium compound of Formula XVII, XVIII, or XIX, or a combination thereof.

In another aspect, a kit is provided comprising a lyophilized powder formulation comprising: a quaternary ammonium compound of Formula XVII, XVIII, or XIX, or a combination thereof, a sterile aqueous solution; and an application device.

In another aspect, a kit is provided comprising a sterile aqueous solution comprising a quaternary ammonium compound of Formula XVII, XVIII, or XIX, or a combination thereof, and an application device. In one embodiment, the application device is a syringe.

In another aspect of the present invention, a quaternary ammonium compound of Formula XX or XXI is provided:

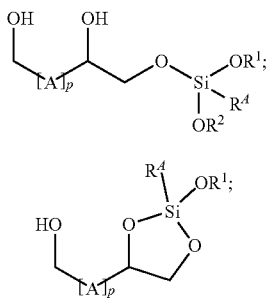
(XX)

(XXI)

wherein $R^A$ is

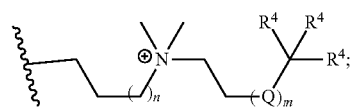

A is independently selected at each occurrence from:

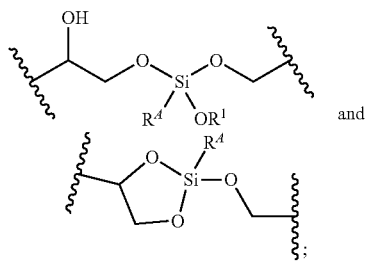

p is 0, 1, 2, 3, 4, 5, 6, 7, 8, 9, or 10; and
$R^1$, $R^2$, $R^4$, m, n, and Q are as defined herein.

In one aspect, a lyophilized powder formulation is provided comprising a quaternary ammonium compound of Formula XX or XXI, or a combination thereof.

In one embodiment the quaternary ammonium compound of Formula XX or XXI is in equilibrium with other quaternary ammonium compounds of Formula XX or XXI.

Due to the lability of silicon oxygen bonds, these structures may interconvert via bond breakage and formation such that a mixture of Formula XX or Formula XXI may be present.

The present invention, among other things, contemplates an antimicrobial composition containing one or more quaternary ammonium compounds of Formula XX or XXI and an appropriate carrier.

The invention also includes a method of treating an infection, in a host in need thereof, with an effective amount of a quaternary ammonium compounds of Formula XX or XXI, or a combination thereof. In one embodiment, an active quaternary ammonium compound is used in an effective amount to treat an infectious disease in a host in need thereof.

In some embodiments, the quaternary ammonium compound of Formula XX or XXI, or a combination thereof, is administered as an aqueous or glycerin solution that has been formed by reconstituting a lyophilized powder formulation comprising the quaternary ammonium compound of Formula XX or XXI, or a combination thereof.

In another aspect, a kit is provided comprising a lyophilized powder formulation comprising: a quaternary ammonium compound of Formula XX or XXI, or a combination thereof; a sterile aqueous solution; and an application device.

In another aspect, a kit is provided comprising a sterile aqueous solution comprising a quaternary ammonium compound of Formula XX or XXI, or a combination thereof, and an application device. In one embodiment, the application device is a syringe.

In another embodiment the invention provides, is a quaternary ammonium compound of Formula XXII:

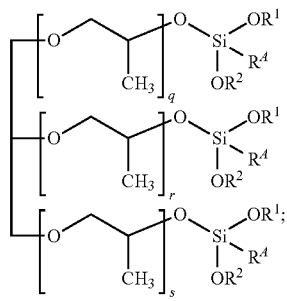
(XXII)

wherein $R^1$, $R^2$, and $R^A$ are as defined herein; and q, r, and s are independently at each occurrence selected from 0, 1, 2, 3, 4, 5, 6, 7, 8, 9, or 10.

In one embodiment, q, r, and s are the same.

In one aspect, a lyophilized powder formulation is provided comprising one or more quaternary ammonium compounds of Formula XXII.

The present invention, among other things, contemplates an antimicrobial composition containing one or more quaternary ammonium compounds of Formula XXII and an appropriate carrier.

The invention also includes a method of treating an infection, in a host in need thereof, with an effective amount of a quaternary ammonium compounds of Formula XXII.

In one embodiment, one or more of an active quaternary ammonium compound is used in an effective amount to treat an infectious disease in a host in need thereof.

In some embodiments, one or more quaternary ammonium compounds of Formula XXII are administered as an aqueous or glycerin solution that has been formed by reconstituting a lyophilized powder formulation comprising one or more compounds of Formula XXII.

In another aspect, a kit is provided comprising a lyophilized powder formulation comprising: one or more quaternary ammonium compounds of Formula XXII; a sterile aqueous solution; and an application device.

In another aspect, a kit is provided comprising a sterile aqueous solution comprising one or more quaternary ammonium compounds of Formula XXII, and an application device. In one embodiment, the application device is a syringe.

In another aspect of the present invention, a quaternary ammonium compound of Formula XXIII, XXIV, or XXV is provided:

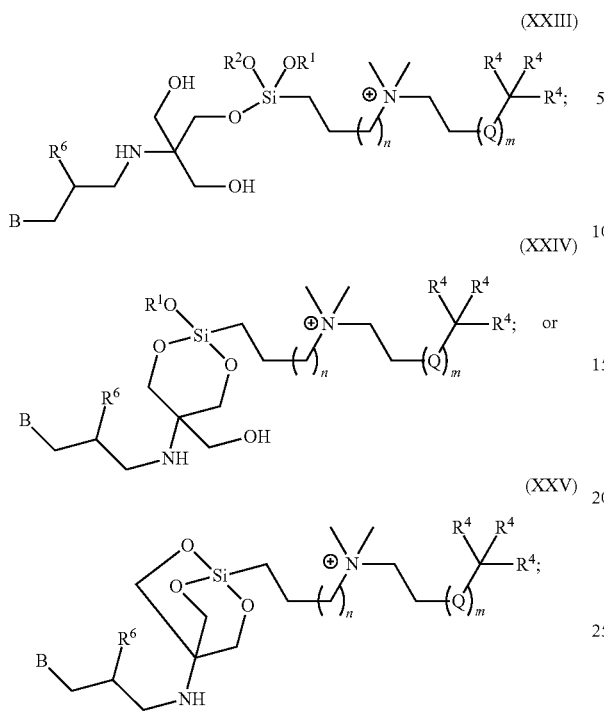

(XXIII)

(XXIV)

(XXV)

wherein $R^1$, $R^2$, $R^4$, $R^6$, m, n, and Q are as defined herein; B is selected from

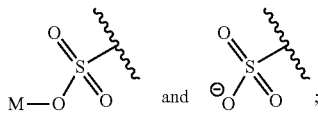

and

M is selected from hydrogen, sodium, potassium, cesium or lithium.

In one aspect, a lyophilized powder formulation is provided comprising a quaternary ammonium compound of Formula XXIII, XXIV, or XXV, or a combination thereof.

In one embodiment the compound of Formula XXIII, XXIV, or XXV is in equilibrium with other compounds of Formula XXIII, XXIV, or XXV. For example, in one embodiment the below compounds may be in equilibrium:

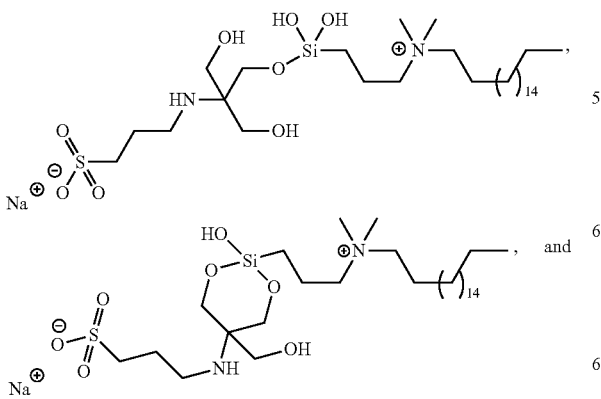

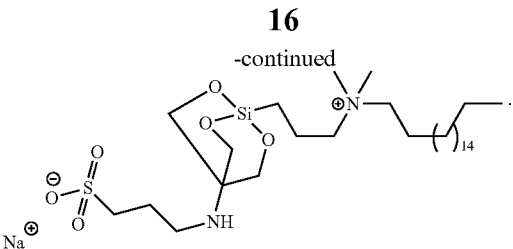

Due to the lability of silicon oxygen bonds, these structures may interconvert via bond breakage and formation such that a mixture of Formula XXIII, XXIV, or XXV may be present.

The present invention, among other things, contemplates an antimicrobial composition containing one or more compounds of Formula XXIII, XXIV, or XXV and an appropriate carrier.

The invention also includes a method of treating an infection, in a host in need thereof, with an effective amount of a quaternary ammonium compound of Formula XXIII, XXIV, or XXV, or a combination thereof. In one embodiment, an active quaternary ammonium compound, or composition thereof is used in an effective amount to treat an infectious disease in a host in need thereof.

In some embodiments, the quaternary ammonium compound of Formula XXIII, XXIV, or XXV, or a combination thereof, is administered as an aqueous or glycerin solution that has been formed by reconstituting a lyophilized powder formulation comprising the quaternary ammonium compound of Formula XXIII, XXIV, or XXV, or a combination thereof.

In another aspect, a kit is provided comprising a lyophilized powder formulation comprising: a quaternary ammonium compound of Formula XXIII, XXIV, or XXV, or a combination thereof, a sterile aqueous solution; and an application device.

In another aspect, a kit is provided comprising a sterile aqueous solution comprising a quaternary ammonium compound of Formula XXIII, XXIV, or XXV, or a combination thereof, and an application device. In one embodiment, the application device is a syringe.

In another aspect of the present invention, a quaternary ammonium compound of Formula XXVI, XXVII, or XXVIII is provided:

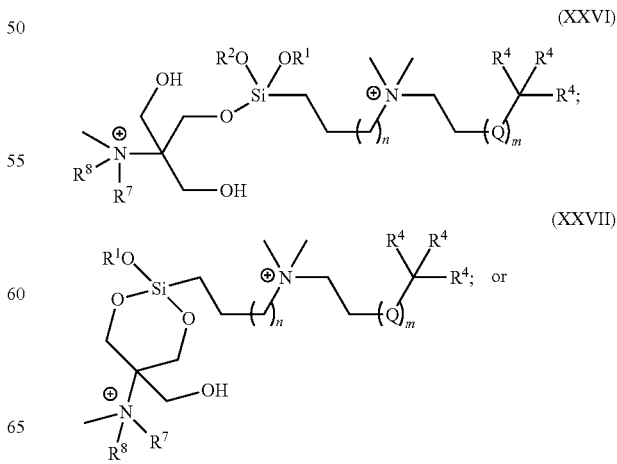

(XXVI)

(XXVII)

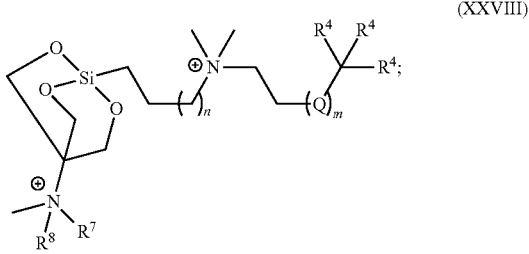

(XXVIII)

wherein R¹, R², R⁴, R⁷, R⁸ m, n, and Q are as defined herein.

In one aspect, a lyophilized powder formulation is provided comprising a quaternary ammonium compound of Formula XXVI, XXVII, or XXVIII, or a combination thereof.

In one embodiment the quaternary ammonium compound of Formula XXVI, XXVII, or XXVIII is in equilibrium with other quaternary ammonium compounds of Formula XXVI, XXVII, or XXVIII. For example, in one embodiment the below compounds may be in equilibrium:

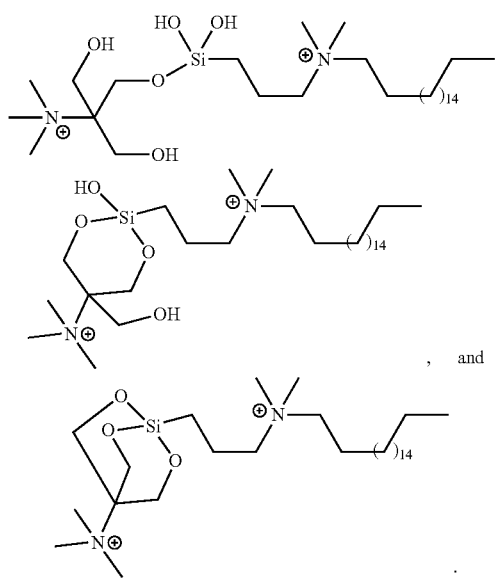

, and

Due to the lability of silicon oxygen bonds, these structures may interconvert via bond breakage and formation such that a mixture of Formula XXVI, XXVII, or XXVIII may be present.

The present invention, among other things, contemplates an antimicrobial composition containing one or more compounds of Formula XXVI, XXVII, or XXVIII and an appropriate carrier.

The invention also includes a method of treating an infection, in a host in need thereof, with an effective amount of a quaternary ammonium compound of Formula XXVI, XXVII, or XXVIII, or a combination thereof. In one embodiment, one or more of an active quaternary ammonium compound is used in an effective amount to treat an infectious disease in a host in need thereof.

In some embodiments, the quaternary ammonium compound of Formula XXVI, XXVII, or XXVIII, or a combination thereof, is administered as an aqueous or glycerin solution that has been formed by reconstituting a lyophilized powder formulation comprising the quaternary ammonium compound of Formula XXVI, XXVII, or XXVIII, or a combination thereof.

In another aspect, a kit is provided comprising a lyophilized powder formulation comprising: a quaternary ammonium compound of Formula XXVI, XXVII, or XXVIII, or a combination thereof; a sterile aqueous solution; and an application device.

In another aspect, a kit is provided comprising a sterile aqueous solution comprising a quaternary ammonium compound of Formula XXVI, XXVII, or XXVIII, or a combination thereof, and an application device. In one embodiment, the application device is a syringe.

In another alternative aspect an oligomeric or polymeric quaternary ammonium compound of Formula XXIX is provided:

(XXIX)

wherein: $R^A$ is as defined above t is 1, 2, 3, 4, 5, 6, 7, 8, 9, or 10;

Z is independently at each occurrence selected from:

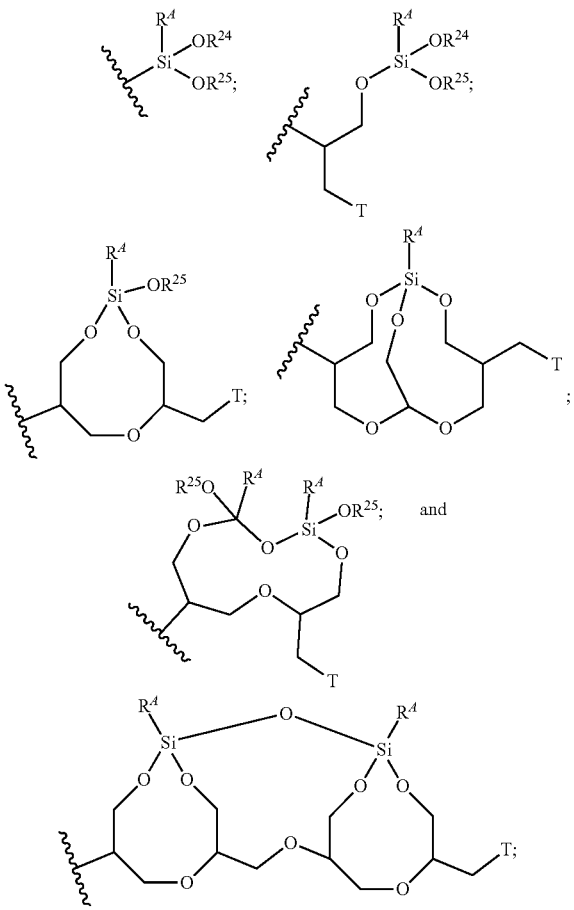

L is independently at each occurrence selected from:

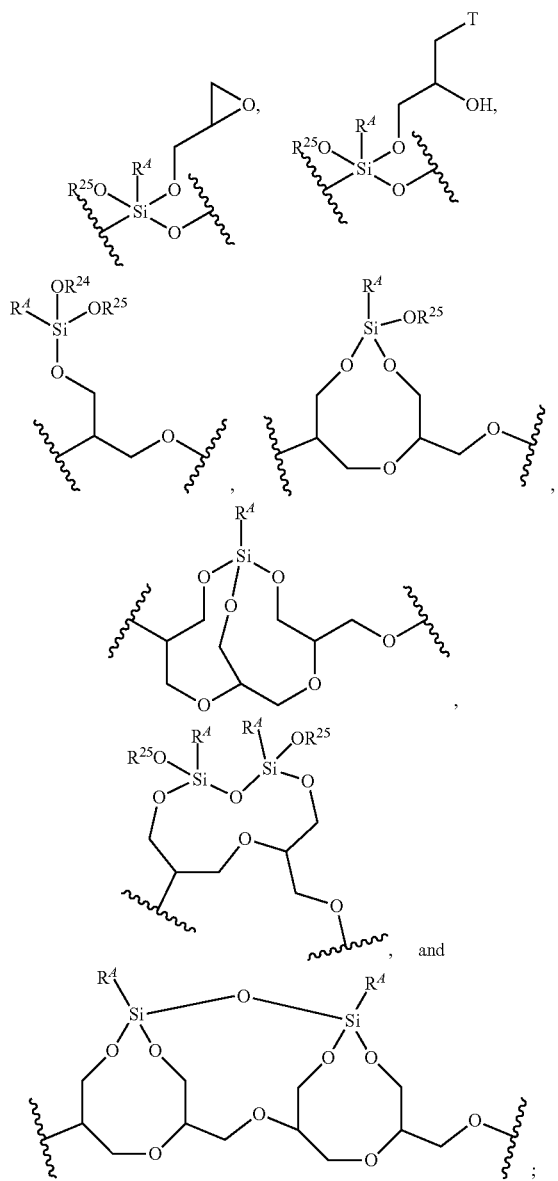

, and

;

$R^{24}$ and $R^{25}$ are independently selected at each occurrence from hydrogen, ethyl,

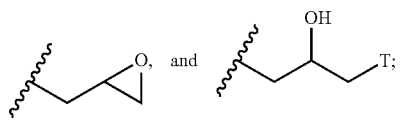

, and

;

T is a monovalent capping group, that may optionally be derived from a curing agent.

All other variables are as defined herein.

The curing agent in Formula XXIX may be any compound that is pharmaceutically acceptable.

In certain embodiments, the curing agent of an oligomer or polymer as described herein comprises a diethylenetriamine (DTA), triethylenetetramine (TTA), tetraethylenepentamine (TEPA), dipropenediamine (DPDA), diethylaminopropylamine (DEAPA), Amine 248, N-aminoethylpiperazine (N-AEP), Lamiron C-260, Araldit HY-964, menthane diamine (MDA), isophoronediamine (IPDA), S Cure 211, S Cure 212, Wandamin HM, 1,3 BAC, m-xylenediamine (m-XDA), Sho-amine X, Amine black, Sho-amine black, Sho-amine N, Sho-amine 1001, Sho-amine 1010, metaphenylene diamine (MPDA), diaminodiphenylmethane (DDM), diaminodiphenylsulfone (DDS), piperidine, N,N-dimethylpiperidine, triethylenediamine, 2,4,6-tris(dimethylaminomethyl)phenol (DMP-30), benzyldimethylamine (BMDA), and 2-(dimethylaminomethyl) phenol (DMP-10); an imidazole such as 2-methylimidazole, 2-ethyl-4-methylimidazole, 1-cyanoethyl-2-undecylimidazolium trimellitate, and an epoxy-imidazole adduct; a liquid polymercaptan or a polysulfide resin; or an acid anhydride such as phthalic anhydride, trimellitic anhydride, pyromellitic anhydride, benzophenone tricarboxylic anhydride, ethylene glycol bistrimellitate, glycerol tritrimellitate, maleic anhydride, tetrahydrophthalic anhydride, methyltetrahydrophthalic anhydride, endomethylene tetrahydrophthalic anyhydride, methylendomethylene tetrahydrophthalic anhydride, methylbutenyl tetrahydrophthalic anhydride, dodecenyl succinic anhydride, hexahydrophthalic anhydride, hexahydrophthalic anhydride, hexahydro-4-methylphthalic anhydride, succinic anhydride, methylcyclohexene dicarboxylic anhydride, alkylstyrene-maleic anhydride copolymer, chlorendic anhydride, and polyazelaic polyanhydride.

In one aspect, a lyophilized powder formulation is provided comprising one or more compounds of Formula XXIX.

The present invention, among other things, contemplates an antimicrobial composition containing one or more compounds of Formula XXIX and an appropriate carrier.

The invention also includes a method of treating an infection, in a host in need thereof, with an effective amount of a quaternary ammonium compounds of Formula XXIX. In one embodiment, one or more of an active quaternary ammonium compound is used in an effective amount to treat an infectious disease in a host in need thereof.

In some embodiments, one or more quaternary ammonium compounds of Formula XXIX are administered as an aqueous or glycerin solution that has been formed by reconstituting a lyophilized powder formulation comprising one or more quaternary ammonium compounds of Formula XXIX.

In another aspect, a kit is provided comprising a lyophilized powder formulation comprising: one or more quaternary ammonium compounds of Formula XXIX; a sterile aqueous solution; and an application device.

In another aspect, a kit is provided comprising a sterile aqueous solution comprising one or more quaternary ammonium compounds of Formula XXIX and an application device. In one embodiment, the application device is a syringe.

In another aspect of the present invention, a product is provided that is formed by reacting a quaternary ammonium compound of Formula A:

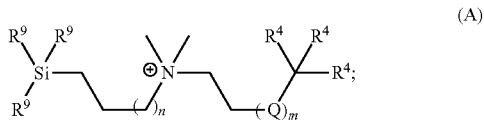

(A)

Wherein R⁴, Q, m, and n are as defined herein; and each $R^9$ is independently at each occurrence selected from halo, hydroxyl, and alkoxy;

with one or more compounds of Formulas B, C, D, E, F, G, H or J;

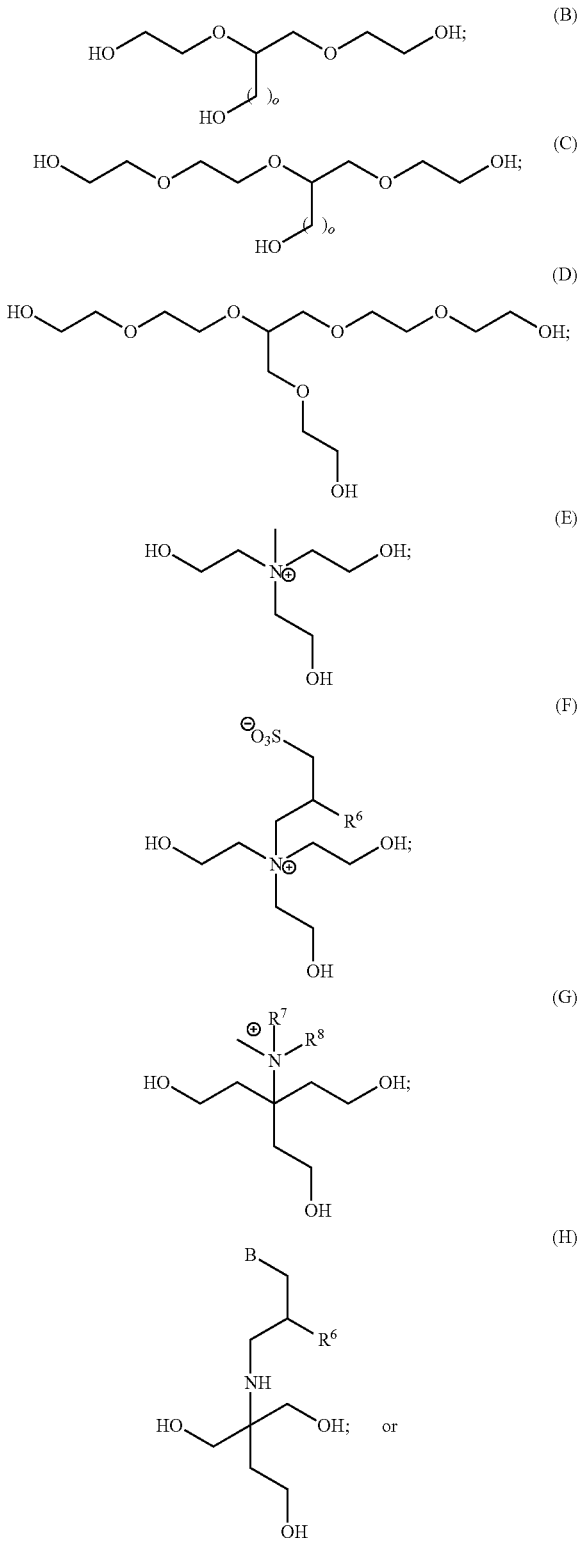

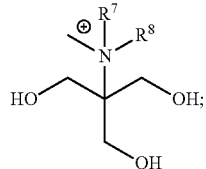

wherein $R^6$, $R^7$, $R^8$, B, and o are as defined herein.

In another aspect of the invention, compound B' is provided wherein compound B' is formed by the reaction of one or more compounds of Formula A with one or more compounds of Formula B. In one embodiment, compound B' is an oligomeric or polymeric compound with one or more Formula B units and one or more Formula A units.

In another aspect of the invention, compound C' is provided wherein compound C' is formed by the reaction of one or more compounds of Formula A with one or more compounds of Formula C. In one embodiment, compound C' is an oligomeric or polymeric compound with one or more Formula C units and one or more Formula A units.

In another aspect of the invention, compound D' is provided wherein compound D' is formed by the reaction of one or more compounds of Formula A with one or more compounds of Formula D. In one embodiment, compound D' is an oligomeric or polymeric compound with one or more Formula D units and one or more Formula A units.

In another aspect of the invention, compound E' is provided wherein compound E' is formed by the reaction of one or more compounds of Formula A with one or more compounds of Formula E. In one embodiment, compound E' is an oligomeric or polymeric compound with one or more Formula E units and one or more Formula A units.

In another aspect of the invention, compound F' is provided wherein compound F' is formed by the reaction of one or more compounds of Formula A with one or more compounds of Formula F. In one embodiment, compound F' is an oligomeric or polymeric compound with one or more Formula F units and one or more Formula A units.

In another aspect of the invention, compound G' is provided wherein compound G' is formed by the reaction of one or more compounds of Formula A with one or more compounds of Formula G. In one embodiment, compound G' is an oligomeric or polymeric compound with one or more Formula G units and one or more Formula A units.

In another aspect of the invention, compound H' is provided wherein compound H' is formed by the reaction of one or more compounds of Formula A with one or more compounds of Formula H. In one embodiment, compound H' is an oligomeric or polymeric compound with one or more Formula H units and one or more Formula A units.

In another aspect of the invention, compound J' is provided wherein compound J' is formed by the reaction of one or more compounds of Formula A with one or more compounds of Formula J. In one embodiment, compound J' is an oligomeric or polymeric compound with one or more Formula J units and one or more Formula A units.

In one aspect, a lyophilized powder formulation is provided comprising a product formed by reacting a compound of Formula A with one or more compounds of Formulas B, C, D, E, F, G, H, or J. In another aspect, a lyophilized powder formulation is provided comprising a compound A', B', C', D'. E', F', G', H', or J'.

The present invention, among other things, contemplates an antimicrobial composition containing the product formed by reacting a compound of Formula A with one or more compounds of Formulas B, C, D, E, F, G, H, or J and an appropriate carrier. In another aspect, an antimicrobial composition is provided containing compound A', B', C', D'. E', F', G', H', or J' and an appropriate carrier.

The invention also include a method of treating an infection, in a host in need thereof, with an effective amount of one or more products formed by reacting a compound of Formula A with one or more compounds of Formulas B, C, D, E, F, G, H, or J. In one embodiment, a product formed by reacting a compound of Formula A with one or more compounds of Formulas B, C, D, E, F, G, H, or J, is used in an effective amount to treat an infectious disease in a host in need thereof.

The invention also includes a method of treating an infection in a host in need thereof with an effective amount of one or more compounds of Formula A', B', C', D'. E', F', G', H', or J'. In one embodiment, compound A', B', C', D'. E', F', G', H', or J' is used in an effective amount to treat an infectious disease in a host in need thereof.

In some embodiments, the product described herein, for treating an infection, is administered as an aqueous or glycerin solution that has been formed by reconstituting a lyophilized powder formulation of the product.

In another aspect, a kit is provided comprising a lyophilized powder formulation comprising: compound A', B', C', D'. E', F', G', H', or J'; a sterile aqueous solution; and an application device. In another aspect, a kit is provided comprising a sterile aqueous or glycerin solution of compound A', B', C', D'. E', F', G', H', or J', and an application device.

In another aspect, a kit is provided comprising a lyophilized powder formulation comprising: a product formed by reacting a compound of Formula A with one or more compounds of Formulas B, C, D, E, F, G, H, or J; a sterile aqueous solution; and an application device. In another aspect, a kit is provided comprising a sterile aqueous or glycerin solution of a product formed by reacting a compound of Formula A with one or more compounds of Formulas B, C, D, E, F, G, H, or J, and an application device.

In one embodiment, the application device is a syringe.

In another aspect, a product is provided that is formed by reacting a compound of Formula A with glycerol. In one aspect, a lyophilized powder formulation is provided comprising a product formed by reacting a compound of Formula A with glycerol.

The present invention, among other things, contemplates an antimicrobial composition containing the product formed by reacting a compound of Formula A with glycerol, and an appropriate carrier.

The invention also includes a method of treating an infection, in a host in need thereof, with an effective amount of one or more products formed by reacting a compound of Formula A with glycerol. In one embodiment, a product formed by reacting a compound of Formula A with glycerol is used in an effective amount to treat an infectious disease in a host in need thereof. In some embodiments, the product described herein is administered as an aqueous or glycerin solution that has been formed by reconstituting a lyophilized powder formulation of the product.

In another aspect, a kit is provided comprising a lyophilized powder formulation comprising: a product formed by reacting a compound of Formula A with glycerol; a sterile aqueous solution; and an application device.

In another aspect, a kit is provided comprising a sterile aqueous or glycerin solution a product formed by reacting a compound of Formula A with glycerol, and an application device. In one embodiment, the application device is a syringe.

In another aspect, a product is provided that is formed by reacting a compound of Formula A with a glycerol-propylene oxide copolymer. In one aspect, a lyophilized powder formulation is provided comprising a product formed by reacting a compound of Formula A with a glycerol-propylene oxide copolymer.

The present invention, among other things, contemplates an antimicrobial composition containing the product formed by reacting a compound of Formula A with a glycerol-propylene oxide copolymer, and an appropriate carrier.

The invention also includes a method of treating an infection, in a host in need thereof, with an effective amount of a product formed by reacting a compound of Formula A with a glycerol-propylene oxide copolymer. In one embodiment, a product formed by reacting a compound of Formula A with a glycerol-propylene oxide copolymer is used in an effective amount to treat an infectious disease in a host in need thereof. In some embodiments, the product described herein is administered as an aqueous or glycerin solution that has been formed by reconstituting a lyophilized powder formulation of the product.

In another aspect, a kit is provided comprising a lyophilized powder formulation comprising: a product formed by reacting a compound of Formula A with a glycerol-propylene oxide copolymer; a sterile aqueous solution; and an application device. In another aspect, a kit is provided comprising a sterile aqueous or glycerin solution a product formed by reacting a compound of Formula A with a glycerol-propylene oxide copolymer, and an application device. In one embodiment, the application device is a syringe.

In another aspect, a product is provided that is formed by reacting a compound of Formula A with solketal, [also named (2,2-Dimethyl-1,3-dioxolan-4-yl)methanol], glycidol [also named oxiranylmethanol], or epichlorohydrin [also named 2-(chloromethyl)oxirane], or a mixture thereof. In one aspect, a lyophilized powder formulation is provided comprising a product formed by reacting a compound of Formula A with solketal, glycidol, or epichlorohydrin, or a mixture thereof.

The present invention, among other things, contemplates an antimicrobial composition containing the product formed by reacting a compound of Formula A with solketal, glycidol, or epichlorohydrin, or a mixture thereof, and an appropriate carrier.

The invention also includes a method of treating an infection in a host in need thereof with an effective amount of a product formed by reacting a compound of Formula A with solketal, glycidol, or epichlorohydrin, or a mixture thereof. In one embodiment, a product formed by reacting a compound of Formula A with solketal, glycidol, or epichlorohydrin, or a mixture thereof is used in an effective amount to treat an infectious disease in a host in need thereof. In some embodiments, the product described herein is administered as an aqueous or glycerin solution that has been formed by reconstituting a lyophilized powder formulation of the product.

In another aspect, a kit is provided comprising a lyophilized powder formulation comprising: a product formed by reacting a compound of Formula A with solketal, glycidol, or epichlorohydrin, or a mixture thereof, a sterile aqueous solution; and an application device.

In another aspect, a kit is provided comprising a sterile aqueous or glycerin solution a product formed by reacting a compound of Formula A with solketal, glycidol, or epichlorohydrin, or a mixture thereof, and an application device. In one embodiment, the application device is a syringe.

In another alternative aspect, an oligomer or polymer product Y1 is provided that is formed by reacting a compound of Formula XXIX with one or more compounds selected from glycidol, glycerol, glycerol-propylene oxide copolymer, ethylene glycol, propylene glycol, polyethylene glycol, polypropylene glycol, and polyvinyl alcohol.

In one aspect, a lyophilized powder formulation is provided comprising an oligomer or polymer product Y1 as described herein.

The present invention, among other things, contemplates an antimicrobial composition containing an oligomer or polymer product Y1 as described herein and an appropriate carrier.

The invention also includes a method of treating an infection, in a host in need thereof, with an effective amount of one or more oligomer or polymer products of Y1 as described herein.

In one embodiment, an active compound, or composition thereof is used in an effective amount to treat an infectious disease in a host in need thereof.

In some embodiments, an oligomer or polymer product Y1 as described herein is administered as an aqueous or glycerin solution that has been formed by reconstituting a lyophilized powder formulation comprising the oligomer or polymer product Y1.

In another aspect, a kit is provided comprising a lyophilized powder formulation comprising: an oligomer or polymer product Y1 as described herein; a sterile aqueous solution; and an application device. In another aspect, a kit is provided comprising a sterile aqueous solution comprising an oligomer or polymer product Y1 as described herein and an application device. In one embodiment, the application device is a syringe.

In another alternative aspect, an oligomer or polymer product Y2 is provided that is formed by reacting a compound of Formula XXIX with one or more compounds selected from glycidol, glycerol, glycerol-propylene oxide copolymer, ethylene glycol, propylene glycol, polyethylene glycol, polypropylene glycol, and polyvinyl alcohol to form a first oligomer or polymer product Y1; and then further reacting this first oligomer or polymer with boric acid.

In one aspect, a lyophilized powder formulation is provided comprising an oligomer or polymer product Y2 as described herein.

The present invention, among other things, contemplates an antimicrobial composition containing an oligomer or polymer product Y2 as described herein and an appropriate carrier.

The invention also includes a method of treating an infection, in a host in need thereof, with an effective amount of one or more oligomer or polymer products of Y2 as described herein.

In one embodiment, an active compound, or composition thereof is used in an effective amount to treat an infectious disease in a host in need thereof.

In some embodiments, an oligomer or polymer product Y2 as described herein is administered as an aqueous or glycerin solution that has been formed by reconstituting a lyophilized powder formulation comprising the oligomer or polymer product Y2.

In another aspect, a kit is provided comprising a lyophilized powder formulation comprising: an oligomer or polymer product Y2 as described herein; a sterile aqueous solution; and an application device. In another aspect, a kit is provided comprising a sterile aqueous solution comprising an oligomer or polymer product Y2 as described herein and an application device. In one embodiment, the application device is a syringe.

In another aspect, an oligomer or polymer product Y3 is provided that is formed by reacting a compound of Formula XXIX with one or more curing agents as described herein.

In one aspect, a lyophilized powder formulation is provided comprising an oligomer or polymer product Y3 as described herein.

The present invention, among other things, contemplates an antimicrobial composition containing an oligomer or polymer product Y3 as described herein and an appropriate carrier.

The invention also includes a method of treating an infection, in a host in need thereof, with an effective amount of one or more oligomer or polymer products of Y3 as described herein.

In one embodiment, an active compound, or composition thereof is used in an effective amount to treat an infectious disease in a host in need thereof.

In some embodiments, an oligomer or polymer product Y3 as described herein is administered as an aqueous or glycerin solution that has been formed by reconstituting a lyophilized powder formulation comprising the oligomer or polymer product Y3.

In another aspect, a kit is provided comprising a lyophilized powder formulation comprising: an oligomer or polymer product Y3 as described herein; a sterile aqueous solution; and an application device. In another aspect, a kit is provided comprising a sterile aqueous solution comprising an oligomer or polymer product Y3 as described herein and an application device. In one embodiment, the application device is a syringe.

In another aspect, a method is provided for the treatment of an ear infection in a host in need thereof comprising administering an effective amount of one or more quaternary ammonium compounds described herein, which may include an additional pharmaceutically acceptable salt or a composition thereof. In one embodiment, one or more compounds of Formula I, II, III, IV, or V, are used in an effective amount to treat an ear infection in a host in need thereof.

In another embodiment, one or more quaternary ammonium salts of Formula I, VI, VII, VIII, or IX, which may include an additional pharmaceutically acceptable salt, or a composition thereof, are used in an effective amount to treat an ear infection in a host in need thereof.

In another embodiment, one or more quaternary ammonium salts of Formula XI, XII, or XIII, or VIII, which may include an additional pharmaceutically acceptable salt, or a composition thereof, are used in an effective amount to treat an ear infection in a host in need thereof.

In another embodiment, one or more quaternary ammonium salts of Formula XIV, XV, or XVI, which may include an additional pharmaceutically acceptable salt, or a composition thereof, are used in an effective amount to treat an ear infection in a host in need thereof.

In another embodiment, one or more quaternary ammonium salts of Formula XVII, XVIII, or XIX, which may include an additional pharmaceutically acceptable salt, or a composition thereof, are used in an effective amount to treat an ear infection in a host in need thereof.

In another embodiment, one or more quaternary ammonium salts of Formula XX, XXI, or XXII, which may include an additional pharmaceutically acceptable salt, or a composition thereof, are used in an effective amount to treat an ear infection in a host in need thereof.

In another embodiment, one or more quaternary ammonium salts of Formula XXIII, XXIV, or XXV, which may include an additional pharmaceutically acceptable salt, or a composition thereof, are used in an effective amount to treat an ear infection in a host in need thereof.

In another embodiment, one or more quaternary ammonium salts of Formula XXVI, XXVII, or XXVIII, which may include an additional pharmaceutically acceptable salt, or a composition thereof, are used in an effective amount to treat an ear infection in a host in need thereof.

In another embodiment, one or more quaternary ammonium salts of Formula XXIX, which may include an additional pharmaceutically acceptable salt, or a composition thereof, are used in an effective amount to treat an ear infection in a host in need thereof.

In another embodiment, a product formed by reacting a quaternary ammonium salts of Formula A with one or more compounds of Formula B, C, D, E, F, G, H or J; which may include an additional pharmaceutically acceptable salt, or a composition thereof; is used in an effective amount to treat an ear infection in a host in need thereof.

In one embodiment, a product formed by reacting a quaternary ammonium salts of Formula A with glycerol is used in an effective amount to treat an ear infection in a host in need thereof.

In one embodiment, a product formed by reacting a compound of Formula A with a glycerol-polypropylene oxide copolymer is used in an effective amount to treat an ear infection in a host in need thereof.

In one embodiment, a product formed by reacting a compound of Formula A with solketal, glycidol, or epichlorohydrin is used in an effective amount to treat an ear infection in a host in need thereof.

In some embodiments the compounds of the present invention exist as a mixture of related structures. As one non-limiting example, a composition that is primarily composed of molecule

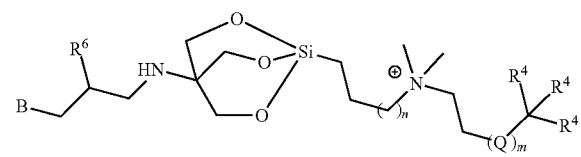

may also have some molecules of

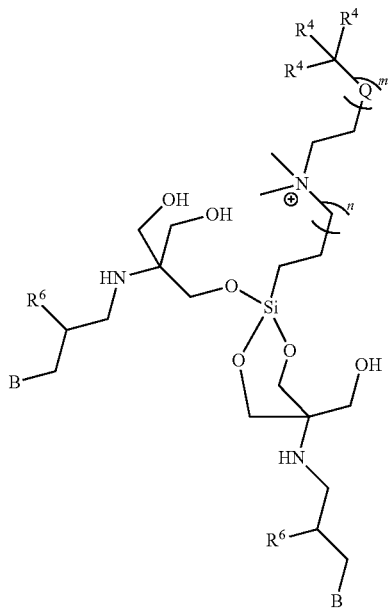

and/or

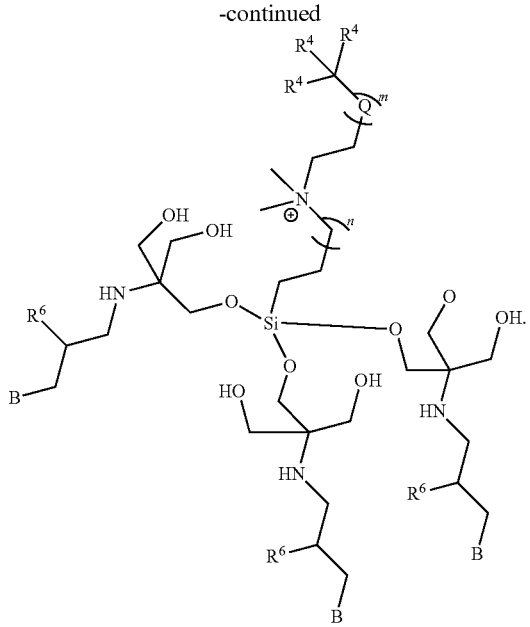

These related structures may interconvert in solution.

In certain embodiments the composition of any of the aspects of the present invention is independently a mixture of related molecules, but the drawn structure comprises at least 50%, 51%, at least 60%, at least 70%, at least 80%, at least 90%, or at least 95% of the mixture by mole, or alternatively, by weight.

The skilled artisan will also recognize that the compounds of the present invention may exist in various forms in solution while still accomplishing their intended goal. Thus, in certain embodiments the invention is a solution of the drawn compound, wherein that solution can include various related structures but the total ratio of silicon sidechain groups to silicone is the same as what is drawn. For example, in one embodiment the invention is a solution of

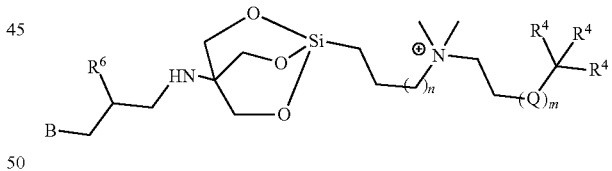

wherein that solution comprises various related molecules but the total number of

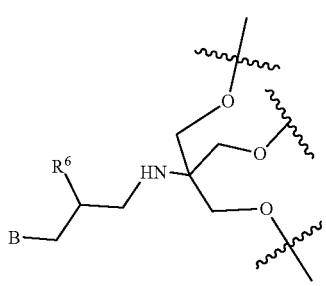

moieties to

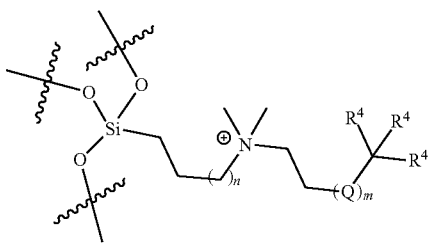

moieties is approximately 1 to 1 by ratio (i.e., by mole). In certain embodiments approximately 1 to 1 includes any ratio between 0.6:1 and 1.4:1. In other embodiments approximately 1 to 1 includes any ratio between 0.8:1 and 1.2:1.

In an alternative embodiment, an oligomer or polymer product Y1 or a composition thereof is used in an effective amount to treat an ear infection in a host in need thereof.

In an alternative embodiment, an oligomer or polymer product Y2 or a composition thereof is used in an effective amount to treat an ear infection in a host in need thereof.

In an alternative embodiment, an oligomer or polymer product Y3 or a composition thereof is used in an effective amount to treat an ear infection in a host in need thereof.

In one embodiment, the ear infection is an outer ear infection (otitis externa). In another embodiment, the ear infection is a middle ear infection (otitis media).

In one embodiment, the ear infection is caused by a bacterium. In another embodiment, the ear infection is caused by a fungus. In another embodiment, the ear infection is caused by both a bacterium and a fungus. In another embodiment, the infection is caused by a biofilm which may contain a combination of bacterial and fungal cells.

In some embodiments, one or more compounds described herein are administered as an aqueous or glycerin solution that has been formed by reconstituting a lyophilized powder formulation of one or more compounds.

In another aspect, a method is provided for the treatment of an ocular infection in a host in need thereof comprising administering an effective amount of one or more compounds described herein, or compositions thereof.

In one embodiment, one or more compounds of Formula I, II, III, IV, or V, or compositions thereof, are used in an effective amount to treat an ocular infection in a host in need thereof.

In another embodiment, one or more compounds of Formula I, VI, VII, VIII, or IV, or compositions thereof, are used in an effective amount to treat an ocular infection in a host in need thereof.

In another embodiment, one or more compounds of Formula XI, XII, or XIII, or compositions thereof, are used in an effective amount to treat an ocular infection in a host in need thereof.

In another embodiment, one or more compounds of Formula XIV, XV, or XVI, or compositions thereof, are used in an effective amount to treat an ocular infection in a host in need thereof.

In another embodiment, one or more compounds of Formula XVII, XVIII, or XIX, or compositions thereof, are used in an effective amount to treat an ocular infection in a host in need thereof.

In another embodiment, one or more compounds of Formula XX or XXI, or compositions thereof, are used in an effective amount to treat an ocular infection in a host in need thereof.

In one embodiment, a compound of Formula XXII, or its salt of composition, is used in an effective amount to treat an ocular infection in a host in need thereof.

In another embodiment, one or more compounds of Formula XXIII, XXIV, or XXV, or compositions thereof, are used in an effective amount to treat an ocular infection in a host in need thereof.

In an alternative embodiment, one or more compounds of Formula XXVI, XXVII, or XXVIII, or compositions thereof, are used in an effective amount to treat an ocular infection in a host in need thereof.

In an alternative embodiment, one or more compounds of Formula XXIX, or compositions thereof, are used in an effective amount to treat an ocular infection in a host in need thereof.

In another embodiment, a product formed by reacting a compound of Formula A with one or more compounds of Formula B, C, D, E, F, G, H or J is used in an effective amount to treat an ocular infection in a host in need thereof.

In one embodiment, a product formed by reacting a compound of Formula A with glycerol is used in an effective amount to treat an ocular infection in a host in need thereof.

In one embodiment, a product formed by reacting a compound of Formula A with a glycerol-polypropylene oxide copolymer is used in an effective amount to treat an ocular infection in a host in need thereof.

In one embodiment, a product formed by reacting a quaternary ammonium compound of Formula A with solketal, glycidol, or epichlorohydrin, or a mixture thereof, is used in an effective amount to treat an ocular infection in a host in need thereof.

In an alternative embodiment, an oligomer or polymer product Y1 or compositions thereof is used in an effective amount to treat an ocular infection in a host in need thereof.

In an alternative embodiment, an oligomer or polymer product Y2 or compositions thereof is used in an effective amount to treat an ocular infection in a host in need thereof.

In an alternative embodiment, an oligomer or polymer product Y3 or compositions thereof is used in an effective amount to treat an ocular infection in a host in need thereof.

In one embodiment, the ocular infection is corneal keratitis. In another embodiment, the ocular infection is bacterial keratitis, for example bacterial keratitis caused by *Staphylococcus aureus* or *Pseudomonas aeruginosa*.

In another embodiment, the ocular infection is fungal keratitis, for example keratitis caused by *Fusarium, Aspergillus, Candida albicans*, or *Curvularia* spp. In one embodiment, the ocular infection is *Acanthamoebic keratitis*.

In another embodiment, the ocular infection is viral keratitis, for example Herpes simplex virus (HSV) keratitis.

In another embodiment, the ocular infection is bacterial conjunctivitis, for example conjunctivitis caused by *Staphylococcus aureus, Haemophilus influenzae, Streptococcus pneumoniae* or *Pseudomonas aeruginosa*.

In another embodiment, the ocular infection is viral conjunctivitis, for example conjunctivitis caused by adenovirus or enterovirus.

In another embodiment, the ocular infection is polymicrobial, which is more difficult to diagnose and treat.

In another embodiment, the ocular infection is sequential with one or more opportunistic organisms that can also cause infection. For example, a herpetic corneal ulcer can provide a niche for establishment of bacterial or fungal pathogens.

In another aspect, an ocular formulation is provided comprising one or more quaternary ammonium compounds described herein, in a carrier that is suitable for the eye. The ocular formulation does not contain any byproducts or additives that would be deemed toxic or irritating for the eye, for example an alcohol.

In one embodiment, the ocular formulation is substantially free of methanol.

In some embodiments, one or more quaternary ammonium compounds described herein are administered as an aqueous or glycerin solution that has been formed by reconstituting a lyophilized powder formulation of one or more quaternary ammonium compounds.

In another aspect, a method is provided for the treatment of onychomycosis, i.e. a nail fungal infection, in a host in need thereof comprising administering an effective amount of one or more quaternary ammonium compounds described herein, or compositions thereof.

In one embodiment, one or more quaternary ammonium compounds of Formula I, II, III, IV, or V, or compositions thereof, are used in an effective amount to treat onychomycosis in a host in need thereof.

In another embodiment, one or more quaternary ammonium compounds of Formula I, VI, VII, VIII, or IV, or compositions thereof, are used in an effective amount to treat onychomycosis in a host in need thereof.

In another embodiment, one or more quaternary ammonium compounds of Formula XI, XII, or XIII, or compositions thereof, are used in an effective amount to treat onychomycosis in a host in need thereof.

In another embodiment, one or more quaternary ammonium compounds of Formula XIV, XV, or XVI, or compositions thereof, are used in an effective amount to treat onychomycosis in a host in need thereof.

In another embodiment, one or more quaternary ammonium compounds of Formula XVII, XVIII, or XIX, or compositions thereof, are used in an effective amount to treat onychomycosis in a host in need thereof.

In another embodiment, one or more quaternary ammonium compounds of Formula XX or XXI, or compositions thereof, are used in an effective amount to treat onychomycosis in a host in need thereof.

In one embodiment, a quaternary ammonium compound of Formula XXII, or composition thereof, is used in an effective amount to treat onychomycosis in a host in need thereof.

In another embodiment, one or more quaternary ammonium compounds of Formula XXIII, XXIV, or XXV, or compositions thereof, are used in an effective amount to treat onychomycosis in a host in need thereof.

In an alternative embodiment, one or more quaternary ammonium compounds of Formula XXVI, XXVII, or XXVIII, or compositions thereof, are used in an effective amount to treat onychomycosis in a host in need thereof.

In an alternative embodiment, one or more quaternary ammonium compounds of Formula XXIX, or compositions thereof, are used in an effective amount to treat onychomycosis in a host in need thereof.

In another embodiment, a product formed by reacting a quaternary ammonium compound of Formula A with one or more quaternary ammonium compounds of Formula B, C, D, E, F, G, H or J is used in an effective amount to treat onychomycosis in a host in need thereof.

In one embodiment, a product formed by reacting a quaternary ammonium compound of Formula A with glycerol is used in an effective amount to treat onychomycosis in a host in need thereof.

In one embodiment, a product formed by reacting a quaternary ammonium compound of Formula A with a glycerol-polypropylene oxide copolymer is used in an effective amount to treat onychomycosis in a host in need thereof.

In one embodiment, a product formed by reacting a quaternary ammonium compound of Formula A with solketal, glycidol, or epichlorohydrin, or a mixture thereof, is used in an effective amount to treat onychomycosis in a host in need thereof.

In an alternative embodiment, an oligomer or polymer product Y1 or compositions thereof is used in an effective amount to treat onychomycosis in a host in need thereof.

In an alternative embodiment, an oligomer or polymer product Y2 or compositions thereof is used in an effective amount to treat onychomycosis in a host in need thereof.

In an alternative embodiment, an oligomer or polymer product Y3 or compositions thereof is used in an effective amount to treat onychomycosis in a host in need thereof.

In another aspect, a formulation for the treatment of onychomycosis in a host in need thereof is provided comprising one or more quaternary ammonium compounds described herein, in a carrier suitable for delivery to the nail bed.

In one embodiment, the carrier is dimethylsulfoxide.

In some embodiments, one or more quaternary ammonium compounds described herein are administered as an aqueous, glycerin, or dimethyl sulfoxide (DMSO solution) that has been formed by reconstituting a lyophilized powder formulation of one or more quaternary ammonium compounds.

In another embodiment, a method is provided for the treatment or prevention of an infection in a chronic wound, in a host in need thereof, comprising administering an effective amount of one or more quaternary ammonium compounds described herein, or compositions thereof.

In one embodiment, one or more quaternary ammonium compounds of Formula I, II, III, IV, or V, or compositions thereof, are used in an effective amount to treat or prevent infection in a chronic wound in a host in need thereof.

In another embodiment, one or more quaternary ammonium compounds of Formula I, VI, VII, VIII, or IV, or compositions thereof, are used in an effective amount to treat or prevent infection in a chronic wound in a host in need thereof.

In another embodiment, one or more quaternary ammonium compounds of Formula XI, XII, or XIII, or compositions thereof, are used in an effective amount to treat or prevent infection in a chronic wound in a host in need thereof.

In another embodiment, one or more quaternary ammonium compounds of Formula XIV, XV, or XVI, or compositions thereof, are used in an effective amount to treat or prevent infection in a chronic wound in a host in need thereof.

In another embodiment, one or more quaternary ammonium compounds of Formula XVII, XVIII, or XIX, or compositions thereof, are used in an effective amount to treat or prevent infection in a chronic wound in a host in need thereof.

In another embodiment, one or more quaternary ammonium compounds of Formula XX or XXI, or compositions thereof, are used in an effective amount to treat or prevent infection in a chronic wound in a host in need thereof.

In one embodiment, a quaternary ammonium compound of Formula XXII, of composition, is used in an effective amount to treat or prevent infection in a chronic wound in a host in need thereof.

In another embodiment, one or more quaternary ammonium compounds of Formula XXIII, XXIV, or XXV, or compositions thereof, are used in an effective amount to treat or prevent infection in a chronic wound in a host in need thereof.

In an alternative embodiment, one or more quaternary ammonium compounds of Formula XXVI, XXVII, or XXVIII, or compositions thereof, are used in an effective amount to treat or prevent infection in a chronic wound in a host in need thereof.

In an alternative embodiment, one or more quaternary ammonium compounds of Formula XXIX, or compositions thereof, are used in an effective amount to treat or prevent infection in a chronic wound in a host in need thereof.

In another embodiment, a product formed by reacting a quaternary ammonium compound of Formula A with one or more quaternary ammonium compounds of Formula B, C, D, E, F, G, H or J is used in an effective amount to treat or prevent infection in a chronic wound in a host in need thereof.

In one embodiment, a product formed by reacting a quaternary ammonium compound of Formula A with glycerol is used in an effective amount to treat or prevent infection in a chronic wound in a host in need thereof.

In one embodiment, a product formed by reacting a quaternary ammonium compound of Formula A with a glycerol-polypropylene oxide copolymer is used in an effective amount to treat or prevent infection in a chronic wound in a host in need thereof.

In one embodiment, a product formed by reacting a quaternary ammonium compound of Formula A with solketal, glycidol, or epichlorohydrin, or a mixture thereof, is used in an effective amount to treat or prevent infection in a chronic wound in a host in need thereof.

In an alternative embodiment, an oligomer or polymer product Y1 or compositions thereof is used in an effective amount to treat or prevent infection in a chronic wound in a host in need thereof.

In an alternative embodiment, an oligomer or polymer product Y2 or compositions thereof is used in an effective amount to treat or prevent infection in a chronic wound in a host in need thereof.

In an alternative embodiment, an oligomer or polymer product Y3 or compositions thereof is used in an effective amount to treat or prevent infection in a chronic wound in a host in need thereof.

In one embodiment, the chronic wound is a diabetic ulcer. In another embodiment, the chronic wound is a decubitus ulcer. In another embodiment, the infection is caused by a biofilm.

In some embodiments, one or more quaternary ammonium compounds described herein are administered as an aqueous or glycerin solution that has been reconstituted from a lyophilized powder formulation of one or more quaternary ammonium compounds.

In one embodiment, a quaternary ammonium compound is provided of Formula I, II, III, IV, V, VI, VII, VIII, IX, XI, XII, XIII, XIV, XV, XVI, XVII, XVIII, XIX, XX, XXI, XXII, XXIII, XXIV, XXV, XXVI, XXVII, XXVIII, or XXIX, and which optionally includes an additional pharmaceutically acceptable salt thereof, is provided, wherein:
  (i) the balancing anion of the quaternary amine of any of the Compound Formulas presented herein is selected from chloride, fluoride, iodide, bromide, chlorite, chlorate, hydroxide, formate, acetate, lactate, benzoate, hydroxide, or salicylate anion, and in a typical embodiment, the anion is chloride; and
  (ii) in certain embodiments, a substituent moiety in the Compound of any of the Formulas provided herein can be present as a negatively charged moiety, such as —O⁻, and wherein the anion can be neutralized with a pharmaceutically acceptable cation, such as sodium, potassium, or other cations as further described herein, typically via pH adjustment.

In one embodiment, at least one hydrogen of any of the Compound Formulas provided herein has been replaced by deuterium.

Thus, the present invention includes at least the following features:
  (a) a quaternary ammonium compound of Formula I, II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, or XXIX;
  (b) a quaternary ammonium compound of Formula I, II, III, IV, V, VI, VII, VIII, IX, XI, XII, XIII, XIV, XV, XVI, XVII, XVIII, XIX, XX, XXI, XXII, XXIII, XXIV, XXV, XXVI, XXVII, or XXVIII, which may include an additional pharmaceutically acceptable salt, or a composition thereof; for use in the treatment of a bacterial, fungal and/or a viral infection;
  (c) use of one or more quaternary ammonium compounds of Formula I, II, III, IV, V, VI, VII, VIII, IX, XI, XII, XIII, XIV, XV, XVI, XVII, XVIII, XIX, XX, XXI, XXII, XXIII, XXIV, XXV, XXVI, XXVII, XXVIII, or XXIX, which may include an additional pharmaceutically acceptable salt, or a composition thereof; in the manufacture of a medicament for the treatment of a bacterial, fungal and/or a viral infection;
  (d) a method for manufacturing a medicament intended for the therapeutic use of treating a bacterial, fungal and/or a viral infection, characterized in that one or more quaternary ammonium compounds of Formula I, II, III, IV, V, VI, VII, VIII, IX, XI, XII, XIII, XIV, XV, XVI, XVII, XVIII, XIX, XX, XXI, XXII, XXIII, XXIV, XXV, XXVI, XXVII, XXVIII, or XXIX, and which may include an additional pharmaceutically acceptable salt, or a composition thereof; is used in the manufacture;
  (e) a method for treating a bacterial, fungal, and/or viral infection, comprising administering an effective amount of one or more quaternary ammonium compounds of Formula I, II, III, IV, V, VI, VII, VIII, IX, XI, XII, XIII, XIV, XV, XVI, XVII, XVIII, XIX, XX, XXI, XXII, XXIII, XXIV XXV, XXVI, XXVII, XXVIII, or XXIX, and which may include an additional pharmaceutically acceptable salt, or a composition thereof; to a patient in need thereof; (f) a method for treating a bacterial, fungal and/or viral infection, comprising administering one or more quaternary ammonium compounds of Formula I, II, III, IV, V, VI, VII, VIII, IX, XI, XII, XIII, XIV, XV, XVI, XVII, XVIII, XIX, XX, XXI, XXII, XXIII, XXIV, XXV, XXVI, XXVII, XXVIII, or XXIX, which may include an additional pharmaceutically acceptable salt, or a composition thereof; thereof to a patient in need thereof;
  (g) an antimicrobial composition comprising one or more quaternary ammonium compounds of Formula I, II, III, IV, V, VI, VII, VIII, IX, XI, XII, XIII, XIV, XV, XVI, XVII, XVIII, XIX, XX, XXI, XXII, XXIII, XXIV, XXV, XXVI, XXVII, XXVIII, or XXIX, which may include an additional pharmaceutically acceptable salt, or a composition thereof; and a pharmaceutically acceptable excipient;
  (h) a lyophilized powder formulation comprising one or more quaternary ammonium compounds Formula I, II, III, IV, V, VI, VII, VIII, IX, XI, XII, XIII, XIV, XV, XVI, XVII, XVIII, XIX, XX, XXI, XXII, XXIII, XXIV, XXV, XXVI, XXVII, XXVIII, or XXIX, or which may include an additional pharmaceutically acceptable salt, or a composition thereof;

(i) a kit comprising a lyophilized powder formulation of one or more quaternary ammonium compounds of Formula I, II, III, IV, V, VI, VII, VIII, IX, XI, XII, XIII, XIV, XV, XVI, XVII, XVIII, XIX, XX, XXI, XXII, XXIII, XXIV, XXV, XXVI, XXVII, XXVIII, or XXIX, or which may include an additional pharmaceutically acceptable salt, or a composition thereof; a sterile aqueous solution, and an application device;

(j) a kit comprising a sterile aqueous solution comprising one or more quaternary ammonium compounds of Formula I, II, III, IV, V, VI, VII, VIII, IX, XI, XII, XIII, XIV, XV, XVI, XVII, XVIII, XIX, XX, XXI, XXII, XXIII, XXIV, XXV, XXVI, XXVII, XXVIII, or XXIX, which may include an additional pharmaceutically acceptable salt, or a composition thereof, and an application device;

(k) a process to synthesize a quaternary ammonium compound of Formula I, II, III, IV, V, VI, VII, VIII, IX, XI, XII, XIII, XIV, XV, XVI, XVII, XVIII, XIX, XX, XXI, XXII, XXIII, XXIV, XXV, XXVI, XXVII, XXVIII, or XXIX;

(l) a quaternary ammonium compound of Formula I, II, III, IV, V, VI, VII, VIII, IX, XI, XII, XIII, XIV, XV, XVI, XVII, XVIII, XIX, XX, XXI, XXII, XXIII, XXIV, XXV, XXVI, XXVII, XXVIII, or XXIX as a mixture of enantiomers or diastereomers (as relevant), including as a racemate;

(m) a quaternary ammonium compound of Formula I, II, III, IV, V, VI, VII, VIII, IX, XI, XII, XIII, XIV, XV, XVI, XVII, XVIII, XIX, XX, XXI, XXII, XXIII, XXIV, XXV, XXVI, XXVII, XXVIII, or XXIX, in an enantiomerically or diastereomerically (as relevant) enriched form, including as an isolated enantiomer or disastereomer (i.e., greater than 85, 90, 95, 97 or 99% pure);

(n) a process for the preparation of therapeutic products that contain an effective amount of one or more quaternary ammonium compounds Formula I, II, III, IV, V, VI, VII, VIII, IX, XI, XII, XIII, XIV, XV, XVI, XVII, XVIII, XIX, XX, XXI, XXII, XXIII, XXIV, XXV, XXVI, XXVII, XXVIII, or XXIX;

(o) a product formed by reacting a quaternary ammonium compound of Formula A with one or more quaternary ammonium compounds of Formula B, Formula C, Formula D, Formula E, Formula F, Formula G, Formula H, Formula J, glycerol, a glycerol-propylene oxide copolymer, solketal, glycidol, or epichlorohydrin;

(p) a product formed by reacting a quaternary ammonium compound of Formula A with one or more quaternary ammonium compounds of Formula B, Formula C, Formula D, Formula E, Formula F, Formula G, Formula H, Formula J, glycerol, a glycerol-propylene oxide copolymer, solketal, glycidol, or epichlorohydrin; which may include an additional pharmaceutically acceptable salt, or a composition thereof; for use in the treatment of a bacterial, fungal and/or viral infection;

(q) use of a product formed by reacting a quaternary ammonium compound of Formula A with one or more quaternary ammonium compounds of Formula B, Formula C, Formula D, Formula E, Formula F, Formula G, Formula H, Formula J, glycerol, a glycerol-propylene oxide copolymer, solketal, glycidol, or epichlorohydrin; which may include an additional pharmaceutically acceptable salt, or a composition thereof; in the manufacture of a medicament for the treatment of a bacterial, fungal and/or viral infection;

(r) a method for manufacturing a medicament intended for the therapeutic use of treating a bacterial, fungal and/or viral infection, characterized in that a product formed by reacting a quaternary ammonium compound of Formula A with one or more quaternary ammonium compounds of Formula B, Formula C, Formula D, Formula E, Formula F, Formula G, Formula H, Formula J, glycerol, a glycerol-propylene oxide copolymer, solketal, glycidol, or epichlorohydrin; which may include an additional pharmaceutically acceptable salt, or a composition thereof; is used in the manufacture;

(s) a method for treating a bacterial, fungal and/or viral infection, comprising administering an effective amount of a product formed by reacting a quaternary ammonium compound of Formula A with one or more quaternary ammonium compounds of Formula B, Formula C, Formula D, Formula E, Formula F, Formula G, Formula H, Formula J, glycerol, a glycerol-propylene oxide copolymer, solketal, glycidol, or epichlorohydrin to a patient in need thereof;

(t) a method for treating a bacterial, fungal and/or viral infection, comprising administering a product formed by reacting a quaternary ammonium compound of Formula A with one or more quaternary ammonium compounds of Formula B, Formula C, Formula D, Formula E, Formula F, Formula G, Formula H, Formula J, glycerol, a glycerol-propylene oxide copolymer, solketal, glycidol, or epichlorohydrin to a patient in need thereof;

(u) an antimicrobial composition comprising a product formed by reacting a quaternary ammonium compound of Formula A with one or more quaternary ammonium compounds of Formula B, Formula C, Formula D, Formula E, Formula F, Formula G, Formula H, Formula J, glycerol, a glycerol-propylene oxide copolymer, solketal, glycidol, or epichlorohydrin and a pharmaceutically acceptable excipient;

(v) a lyophilized powder formulation comprising a product formed by reacting a quaternary ammonium compound of Formula A with one or more quaternary ammonium compounds of Formula B, Formula C, Formula D, Formula E, Formula F, Formula G, Formula H, Formula J, glycerol, a glycerol-propylene oxide copolymer, solketal, glycidol, or epichlorohydrin;

(w) a kit comprising a lyophilized powder formulation of a product formed by reacting a quaternary ammonium compound of Formula A with one or more quaternary ammonium compounds of Formula B, Formula C, Formula D, Formula E, Formula F, Formula G, Formula H, Formula J, glycerol, a glycerol-propylene oxide copolymer, solketal, glycidol, or epichlorohydrin, a sterile aqueous solution, and an application device;

(x) a kit comprising a sterile aqueous or glycerin solution comprising a product formed by reacting a quaternary ammonium compound of Formula A with one or more quaternary ammonium compounds of Formula B, Formula C, Formula D, Formula E, Formula F, Formula G, Formula H, Formula J, glycerol, a glycerol-propylene oxide copolymer, solketal, glycidol, or epichlorohydrin; and an application device;

(y) a process for the preparation of therapeutic products that a product formed by reacting a quaternary ammonium compound of Formula A with one or more quaternary ammonium compounds of Formula B, Formula C, Formula D, Formula E, Formula F, Formula G, Formula H, Formula J, glycerol, a glycerol-propylene oxide copolymer, solketal, glycidol, or epichlorohydrin;

(z) an oligomer or polymer product Y1, Y2, or Y3;

(aa) an oligomer or polymer product Y1, Y2, or Y3; which may include an additional pharmaceutically acceptable salt, or a composition thereof, for use in the treatment of a bacterial and/or fungal infection;

(bb) use of an oligomer or polymer product Y1, Y2, or Y3 in the manufacture of a medicament for the treatment of a bacterial and/or fungal infection;

(cc) a method for manufacturing a medicament intended for the therapeutic use of treating a bacterial, fungal and/or viral infection, characterized in that an oligomer or polymer product Y1, Y2, or Y3 is used in the manufacture;

(dd) a method for treating a bacterial, fungal and/or viral infection, comprising administering an effective amount of one or more oligomer or polymer products of Y1, Y2, or Y3 to a patient in need thereof;

(ee) an antimicrobial composition comprising an oligomer or polymer product Y1, Y2, or Y3 and a pharmaceutically acceptable excipient;

(ff) a lyophilized powder formulation comprising an oligomer or polymer product Y1, Y2, or Y3;

(gg) a kit comprising a lyophilized powder formulation of an oligomer or polymer product Y1, Y2, or Y3, a sterile aqueous solution, and an application device;

(hh) a kit comprising a sterile aqueous or glycerin solution comprising an oligomer or polymer product Y1, Y2, or Y3; and an application device; and, (ii) a process for the preparation of therapeutic products that contain an oligomer or polymer product Y1, Y2, or Y3.

(jj) a method for treating an ocular infection, comprising administering an effective amount of one or more quaternary ammonium compounds of Formula I, II, III, IV, V, VI, VII, VIII, IX, XI, XII, XIII, XIV, XV, XVI, XVII, XVIII, XIX, XX, XXI, XXII, XXIII, XXIV, XXV, XXVI, XXVII, XXVIII, or XXIX, or an effective amount of a quaternary ammonium compound of Formula A with one or more quaternary ammonium compounds of Formula B, Formula C, Formula D, Formula E, Formula F, Formula G, Formula H, Formula J, glycerol, a glycerol-propylene oxide copolymer, solketal, glycidol, or epichlorohydrin; which may include an additional pharmaceutically acceptable salt, or a composition thereof;

(kk) a method for treating an ear infection, comprising administering an effective amount of one or more quaternary ammonium compounds of Formula I, II, III, IV, V, VI, VII, VIII, IX, XI, XII, XIII, XIV, XV, XVI, XVII, XVIII, XIX, XX, XXI, XXII, XXIII, XXIV, XXV, XXVI, XXVII, XXVIII, or XXIX, or a quaternary ammonium compound of Formula A with one or more quaternary ammonium compounds of Formula B, Formula C, Formula D, Formula E, Formula F, Formula G, Formula H, Formula J, glycerol, a glycerol-propylene oxide copolymer, solketal, glycidol, or epichlorohydrin; which may include an additional pharmaceutically acceptable salt, or a composition thereof;

(ll) a method for treating an onychomycosis infection, comprising administering an effective amount of one or more quaternary ammonium compounds of Formula I, II, III, IV, V, VI, VII, VIII, IX, XI, XII, XIII, XIV, XV, XVI, XVII, XVIII, XIX, XX, XXI, XXII, XXIII, XXIV, XXV, XXVI, XXVII, XXVIII, or XXIX, which may include an additional pharmaceutically acceptable salt, or a composition thereof;

(mm) a method for treating or preventing infection in a chronic wound, comprising administering an effective amount one or more quaternary ammonium compounds of Formula I, II, III, IV, V, VI, VII, VIII, IX, XI, XII, XIII, XIV, XV, XVI, XVII, XVIII, XIX, XX, XXI, XXII, XXIII, XXIV, XXV, XXVI, XXVII, XXVIII, or XXIX; which may include an additional pharmaceutically acceptable salt, or a composition thereof;

DETAILED DESCRIPTION OF THE INVENTION

The present invention includes the following non-limiting embodiments:

1. A quaternary ammonium compound of Formula:

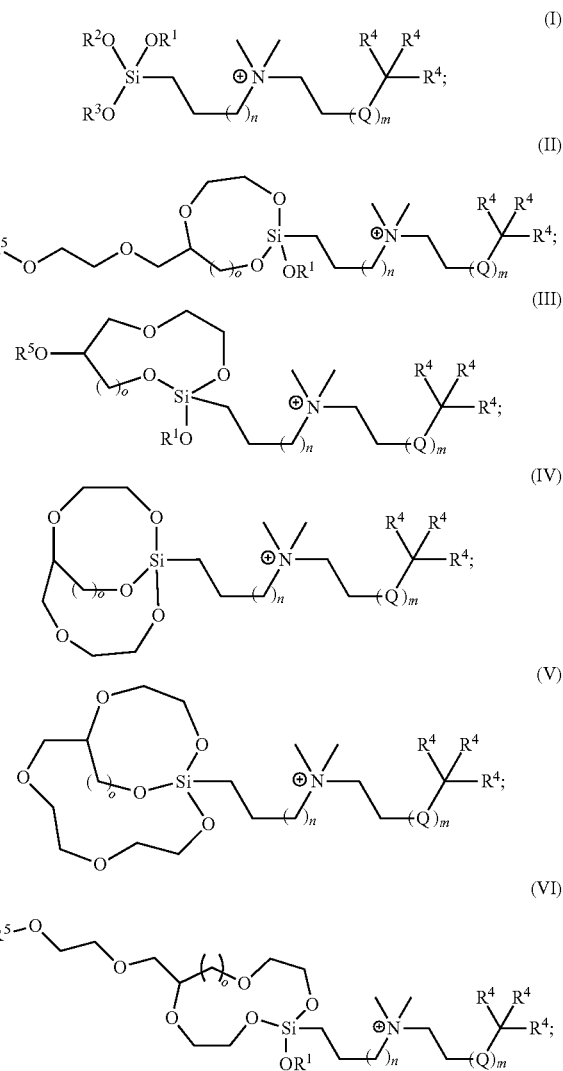

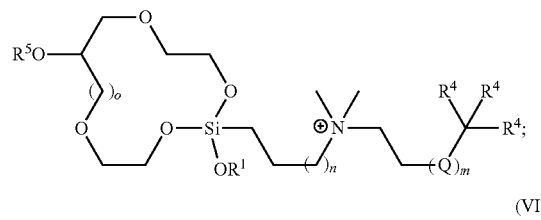
(VII)
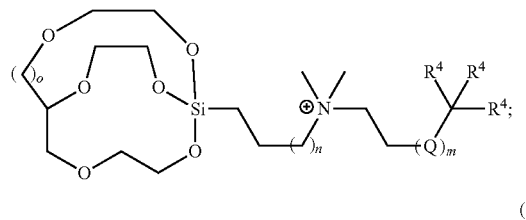
(VIII)
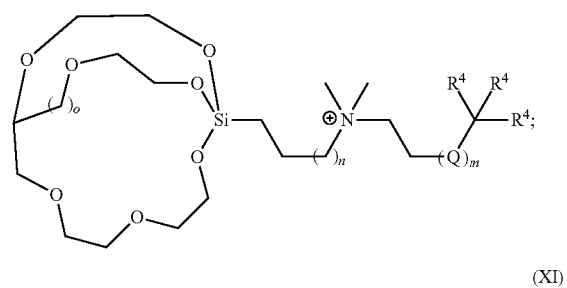
(IX)
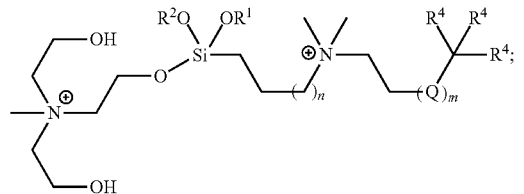
(XI)
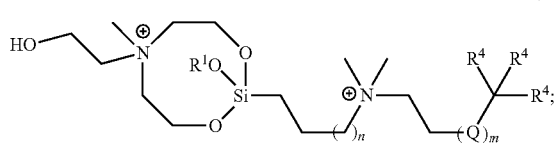
(XII)
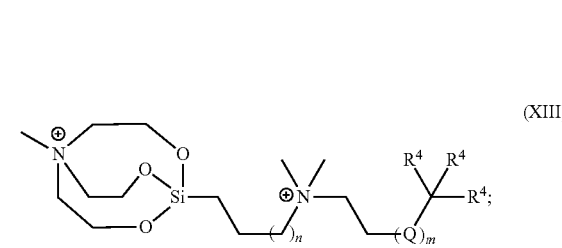
(XIII)
(XIV)
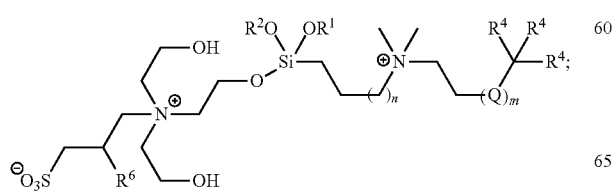
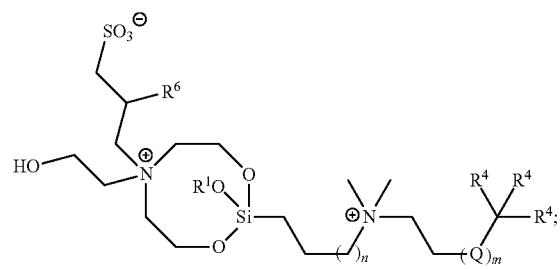
(XV)
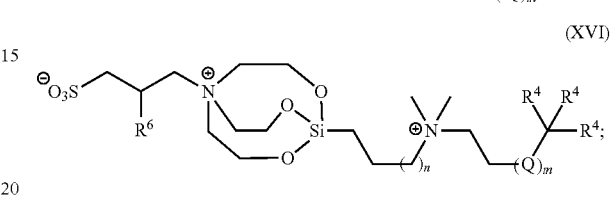
(XVI)
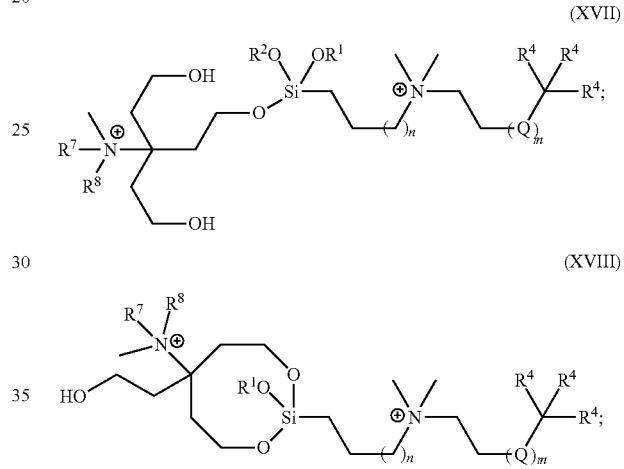
(XVII)
(XVIII)
(XIX)
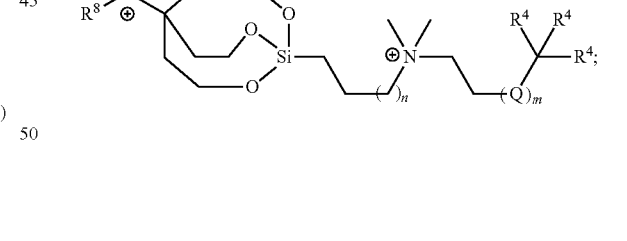
(XX)
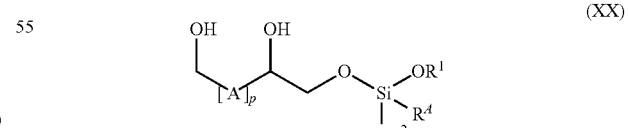
(XXI)

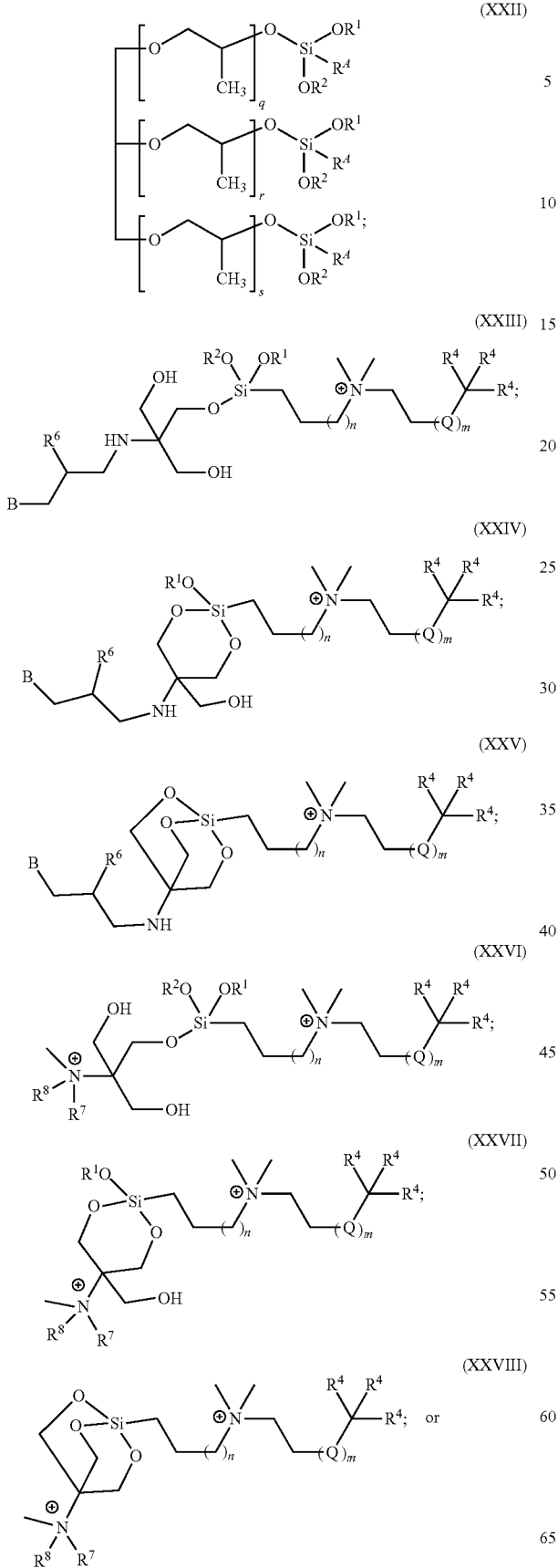
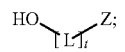

wherein the quaternary amine has a balancing pharmaceutically acceptable anion, or a pharmaceutically acceptable composition thereof, which may include an additional pharmaceutically acceptable salt;

wherein m is 5, 6, 7, 8, 9, 10, 11, 12, 13, 14, 15, 16, 17;

n is 0, 1, or 2;

o is 1 or 2;

p is 0, 1, 2, 3, 4, 5, 6, 7, 8, 9, or 10;

q, r, and s are independently at each occurrence selected from 0, 1, 2, 3, 4, 5, 6, 7, 8, 9, or 10;

Q is $-CR^4R^4-$;

$R^1$ and $R^2$ are independently at each occurrence selected from hydrogen and ethyl;

$R^3$ is independently at each occurrence selected from:

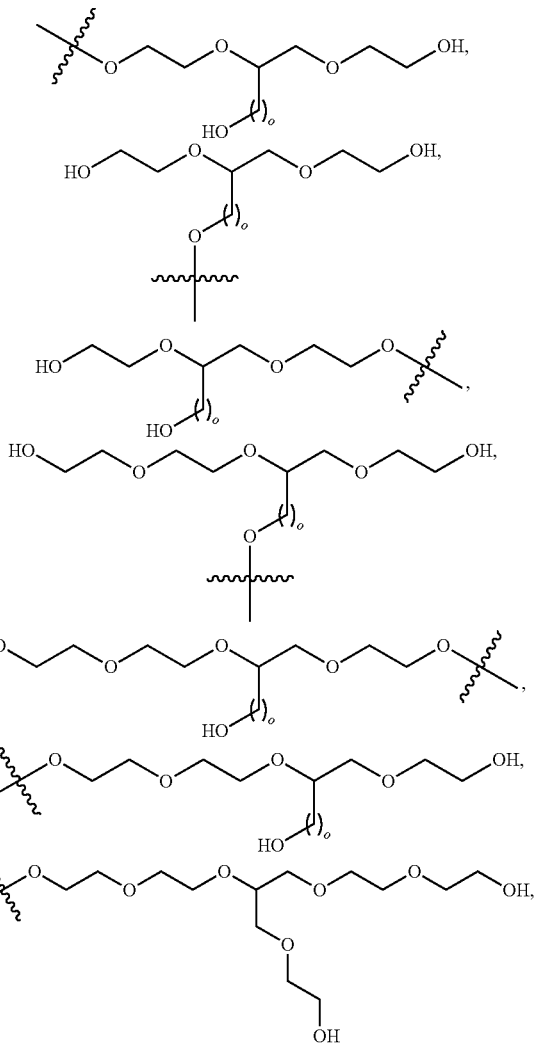

-continued

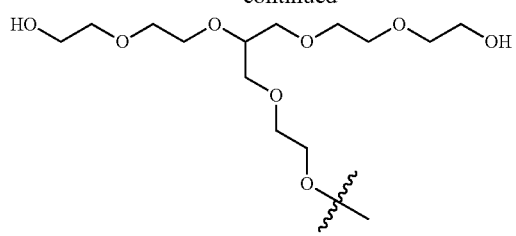
, and

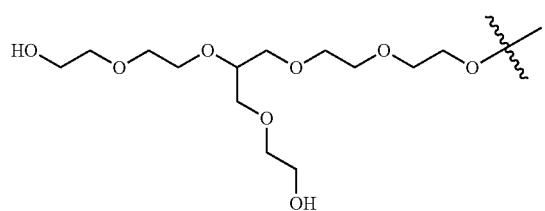
;

R⁴ is independently at each occurrence selected from hydrogen, $C_{1-3}$alkyl, $C_{2-4}$alkenyl, $C_{2-4}$alkynyl, halogen, and halo$C_{1-3}$alkyl;

R⁵ is hydrogen or —CH₂CH₂OH;

R⁶ is independently at each occurrence selected from hydrogen, hydroxy, and $C_1$-$C_6$alkoxy;

R⁷ and R⁸ are independently at each occurrence selected from $C_1$-$C_6$alkyl;

$R^A$ is

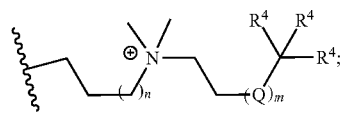

A is independently at each occurrence selected from:

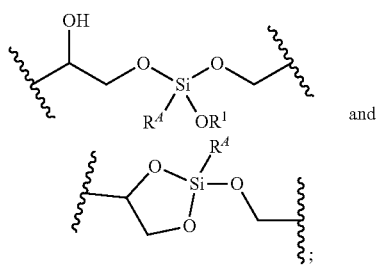

B is independently at each occurrence selected from

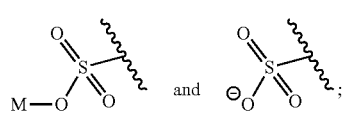

M is hydrogen, sodium, potassium, cesium or lithium;

t is 1, 2, 3, 4, 5, 6, 7, 8, 9, or 10;

Z is independently at each occurrence selected from:

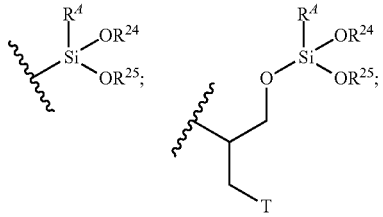

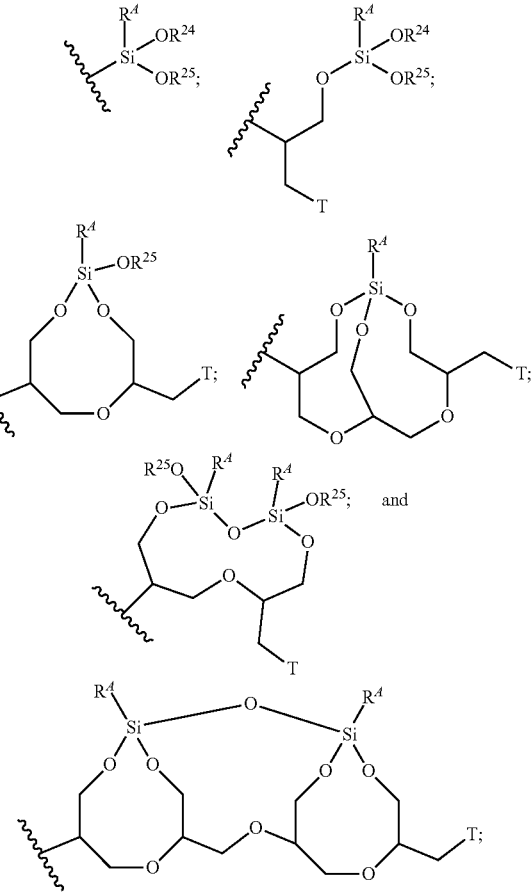

L is independently at each occurrence selected from:

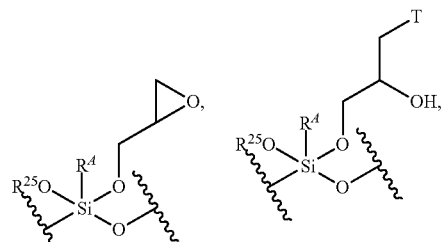

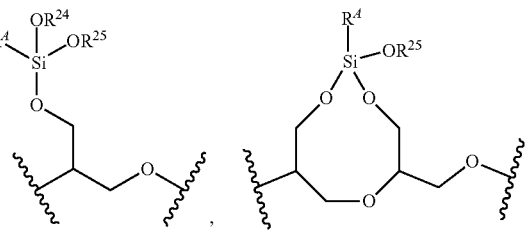

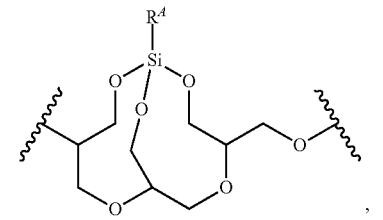

-continued

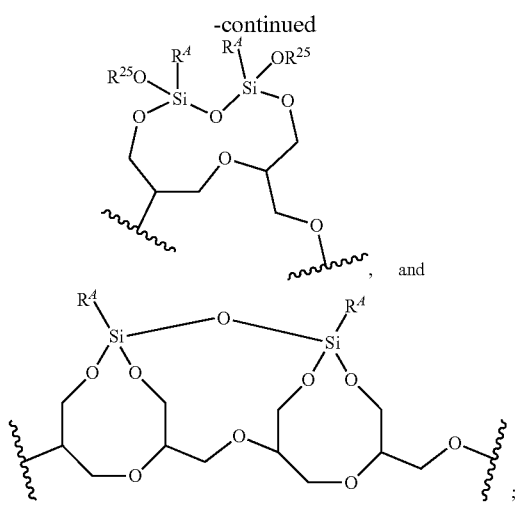
, and ;

$R^{24}$ and $R^{25}$ are independently selected at each occurrence from hydrogen, ethyl,

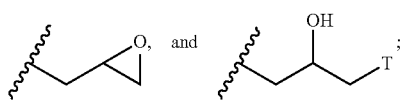
and

T is a monovalent capping group.

2. The quaternary ammonium compound of embodiment 1, wherein at least two $R_4$ s are hydrogen.
3. The quaternary ammonium compound of embodiment 1, wherein the balancing anion is selected from chloride, fluoride, iodide, bromide, hydroxide, chlorite, chlorate, hydroxide, formate, acetate, lactate, benzoate, or salicylate anion.
4. The quaternary ammonium compound of embodiment 1, wherein the balancing anion is chloride.
5. The quaternary ammonium compound of embodiment 1, wherein quaternary ammonium compound includes a substituent that has a negative charge.
6. The quaternary ammonium compound of embodiment 4, wherein the substituent with the negative charge is neutralized with a pharmaceutically acceptable cation.
7. The quaternary ammonium compound of embodiment 5, where the cation is selected from sodium or potassium.
8. The quaternary ammonium compound of embodiment 1 which is in a composition that comprises at least 50% of that quaternary ammonium compound by mole relative to other quaternary ammonium compounds in the composition.
9. The quaternary ammonium compound of embodiment 1 that is a zwitterion.
10. The compound of embodiment 1 selected from:

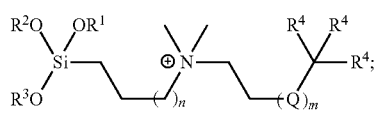
(I)

-continued

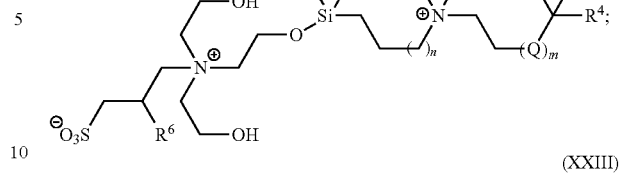
(XIV)

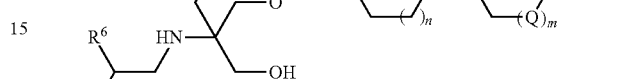
(XXIII)

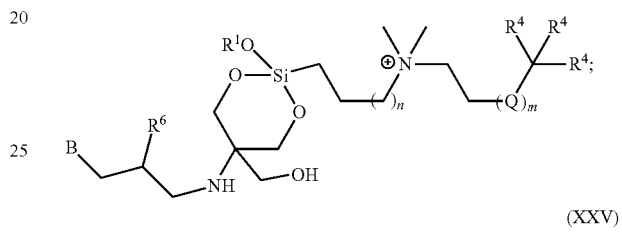
(XXIV)

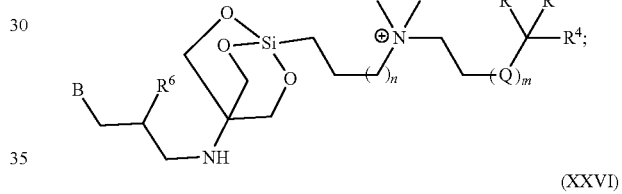
(XXV)

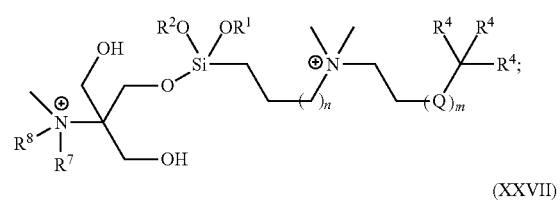
(XXVI)

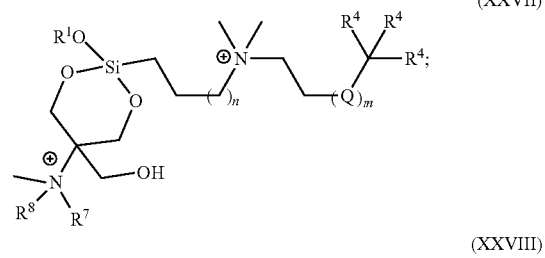
(XXVII)

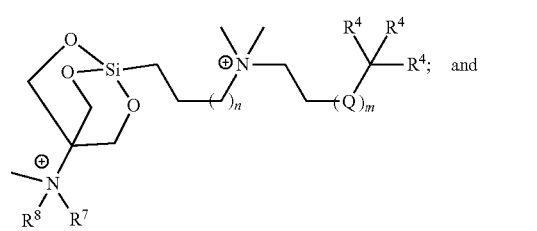
(XXVIII)

HO—[L]$_t$—Z; (XXIX)

or a pharmaceutically acceptable composition thereof.

11. The compound of embodiment 9 selected from:
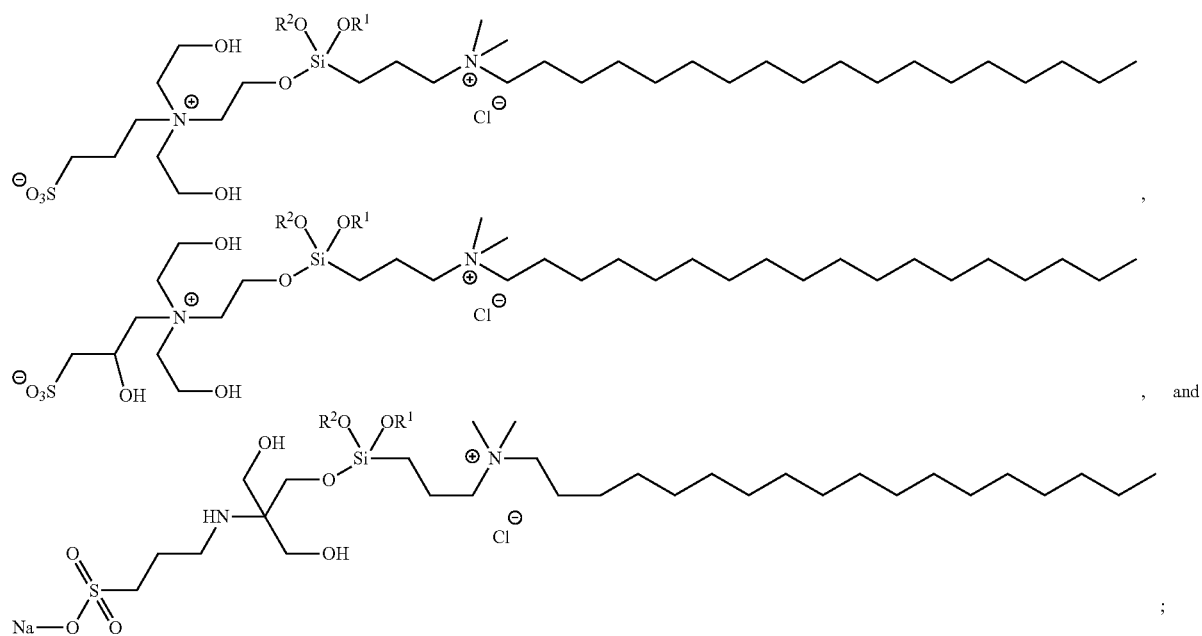
or a pharmaceutically acceptable salt thereof, optionally in a pharmaceutically acceptable composition thereof.
12. The compound of embodiment 1 selected from:
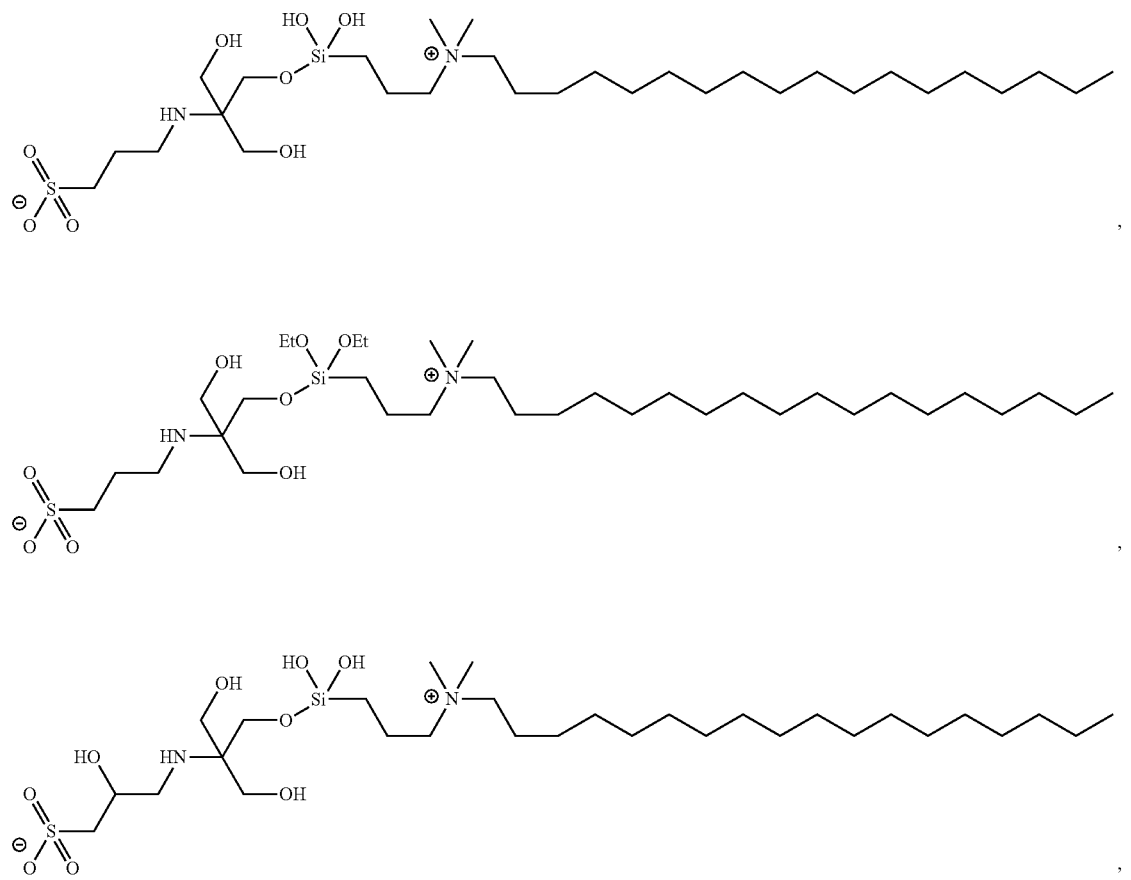
, and -continued

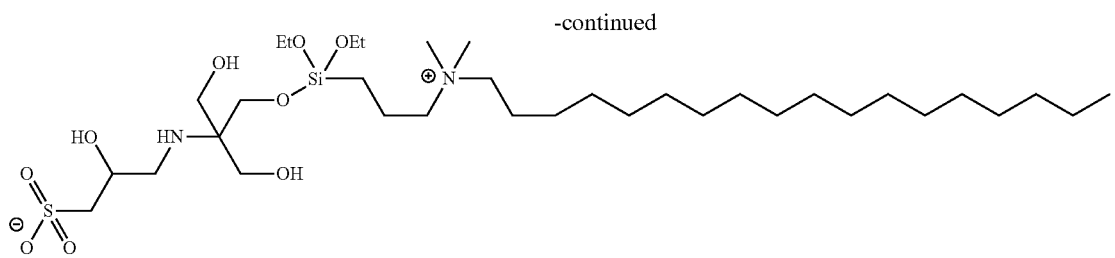

or a pharmaceutically acceptable salt, or a pharmaceutically acceptable composition thereof 13. The compound of embodiment 1 selected from:

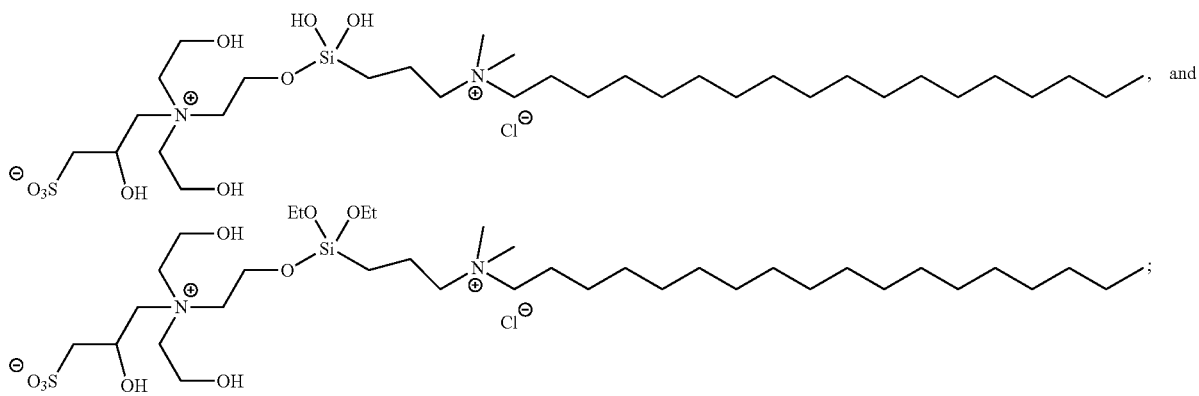

or a pharmaceutically acceptable salt, or a pharmaceutically acceptable composition thereof.

14. A compound formed by reacting a compound of Formula A with a one or more compounds of Formulas B, C, D, E, F, G, H or J:

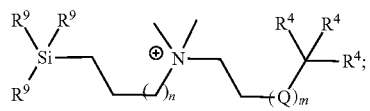 (A)

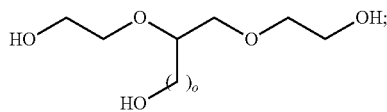 (B)

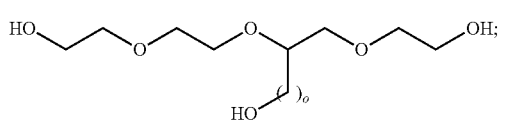 (C)

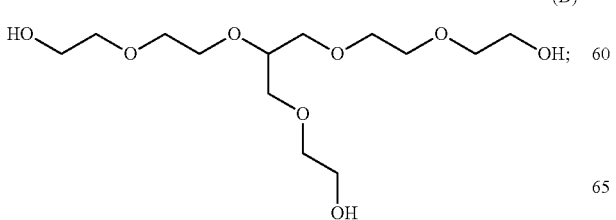 (D)

-continued

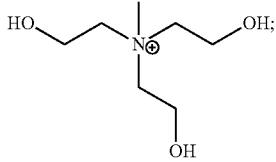 (E)

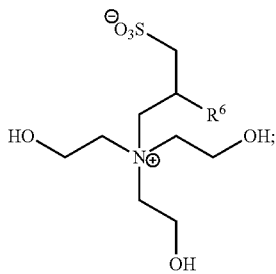 (F)

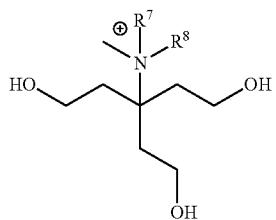 (G)

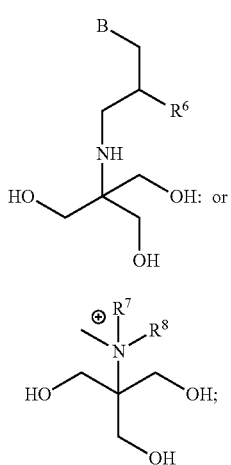

wherein
m is 5, 6, 7, 8, 9, 10, 11, 12, 13, 14, 15, 16 or 17;
n is 0, 1, or 2;
o is 1 or 2;
Q is —$CR^4R^4$—;
B is independently at each occurrence selected from

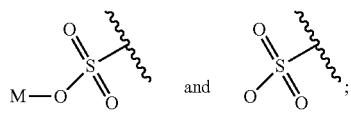

M is hydrogen, sodium, potassium, cesium or lithium;
$R^4$ is independently at each occurrence selected from hydrogen, alkyl, alkenyl, alkynyl, halogen, and haloalkyl;
$R^6$ is independently at each occurrence selected from hydrogen, hydroxy, and $C_1$-$C_6$alkoxy;
$R^7$ and $R^8$ are independently at each occurrence selected from $C_1$-$C_6$alkyl; and $R^9$ is independently at each occurrence selected from halo, hydroxyl, and alkoxy.

15. The quaternary ammonium compound of any one of embodiments 1-14, wherein the compound is a lyophilized powder.

16. A pharmaceutical composition comprising a compound of any one of embodiments 1-15, and optionally a pharmaceutically carrier.

17. The pharmaceutical composition of embodiment 16, wherein the composition is suitable for topical delivery.

18. The pharmaceutical composition of any one of embodiments 16 or 17, wherein the composition is in the form of a liquid, cream, gel, spray, foam, wipe, powder, paste or solid.

19. A compound of any one of embodiments 1-15 or pharmaceutical composition of any one of embodiments 16-18, for use in the treatment of an infection of the eye, ear, skin or nail.

20. A method for the treatment of a topical infection, wherein the treatment comprises administering an effective amount of a compound of any one of embodiments 1-15, to a host in need thereof.

21. A method for manufacturing a medicament intended for the therapeutic use to treat a topical infection, wherein the treatment comprises administering an effective amount of a compound of any one of embodiments 1-15, to a host in need thereof.

22. The method of any one of embodiments 20-21, wherein the host is human.

23. The method of any one of embodiments 20-21, wherein the host is a mammal.

24. The method of embodiment 23, wherein the mammal is selected from a dog, cat, horse or bovine.

25. The method of any one of embodiments 20-24, wherein the infection is bacterial, fungal, amoeba, or viral.

26. The method of any one of embodiment 20-25, wherein the infection is caused by *Staphylococcus aureus, Pseudomonas aeruginosa, Fusarium, Aspergillus, Candida albicans, Curvularia* spp., *Haemophilus influenzae,* or *Acanthamoebic keratitis.*

27. The method of any one of embodiments 20-21, wherein the infection is an ocular infection.

28. The method of any one of embodiments 20-21, wherein the infection is an ear infection; wherein the infection is present in the outer ear (otitis externa), the middle ear (otitis media), or the inner ear (otitis interna).

29. The method of any one of embodiments 20-21, wherein the infection is a nail infection.

30. The method of any one of embodiments 20-21, wherein the infection is a chronic wound.

31. The method of any one of embodiments 20-21, wherein the infection causes periodontal disease.

32. The method of embodiment 20-21, wherein the ocular infection is bacterial or viral conjunctivitis (pink eye), corneal ulcers, corneal keratitis, bacterial, fungal, herpal infectious keratitis, endophthalmitic, or blepharitis.

33. A kit comprising a vial with a compound of any one of embodiments 1-15, a vial with pharmaceutically acceptable solvent and an application device.

34. The kit of embodiment 33, wherein the solvent is selected from water, phosphate buffered saline, solketal, glycidol, epichlorohydrin, glycidol, glycerol, glycerin, glycerol-propylene oxide copolymer, ethylene glycol, propylene glycol, polyethylene glycol, polypropylene glycol, and polyvinyl alcohol.

35. The kit of embodiment 25, wherein the application device is a syringe or a dropper.

36. A compound selected from the group consisting of:

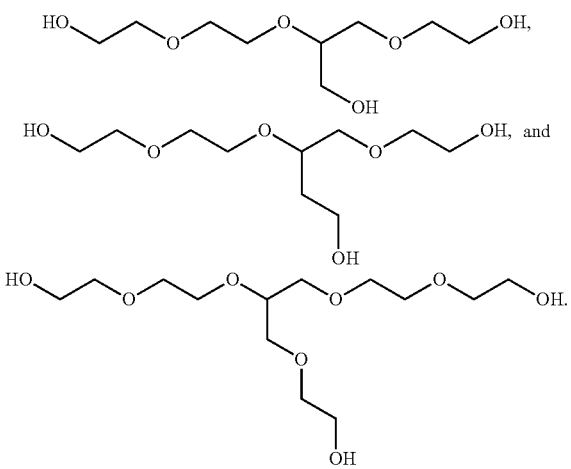

Terminology

Unless defined otherwise, all technical and scientific terms used herein have the same meaning as is commonly understood by one of skill in the art to which this invention belongs.

The quaternary ammonium compounds in any of the Formulas described herein include racemates, enantiomers, mixtures of enantiomers, diastereomers, mixtures of diastereomers, tautomers, isomers; such as rotamers, as if each is specifically described.

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed. Unless defined otherwise, technical and scientific terms used herein have the same meaning as is commonly understood by one of skill in the art to which this invention belongs.

The present invention includes quaternary ammonium compounds of Formula I, II, III, IV, V, VI, VII, VIII, IX, XI, XII, XIII, XIV, XV, XVI, XVII, XVIII, XIX, XX, XXI, XXII, XXIII, XXIV, XXV, XXVI, XXVII, XXVIII, and XXIX, with at least one desired isotopic substitution of an atom, at an amount above the natural abundance of the isotope, i.e., enriched. Isotopes are atoms having the same atomic number but different mass numbers, i.e., the same number of protons but a different number of neutrons.

Examples of isotopes that can be incorporated into quaternary ammonium compounds of the invention include isotopes of hydrogen, carbon, nitrogen, oxygen, fluorine, chlorine and iodine such as $^2$H, $^3$H, $^{11}$C, $^{13}$C, $^{14}$C, $^{15}$N, $^{17}$O, $^{18}$O, $^{18}$F, $^{36}$Cl, and $^{125}$I respectively. In one non-limiting embodiment, isotopically labelled quaternary ammonium compounds can be used in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F labeled compound may be particularly desirable for PET or SPECT studies. Isotopically labeled quaternary ammonium compounds of this invention and prodrugs thereof can generally be prepared by carrying out the procedures disclosed in the schemes or in the examples and preparations described below by substituting a readily available isotopically labeled reagent for a non-isotopically labeled reagent.

By way of general example and without limitation, isotopes of hydrogen, for example, deuterium (2H) and tritium (3H) may be used anywhere in described structures that achieves the desired result. Alternatively or in addition, isotopes of carbon, e.g., $^{13}$C and $^{14}$C, may be used.

Isotopic substitutions, for example deuterium substitutions, can be partial or complete. Partial deuterium substitution means that at least one hydrogen is substituted with deuterium. In certain embodiments, the isotope is at least about 90, 95 or 99% or more enriched in an isotope at any location of interest. In one non-limiting embodiment, deuterium is at least about 90, 95 or 99% enriched at a desired location.

In one non-limiting embodiment, the substitution of one or more hydrogen atoms for a deuterium atoms can be provided in any of Formula I, II, III, IV, V, VI, VII, VIII, IX, XI, XII, XIII, XIV, XV, XVI, XVII, XVIII, XIX, XX, XXI, XXII, XXIII, XXIV, XXV, XXVI, XXVII, XXVIII, and XXIX. In one non-limiting embodiment, the substitution of a hydrogen atom for a deuterium atom occurs within a group selected from any of $R^1$, $R^2$, $R^3$, $R^4$, or $R^5$. For example, when any of the groups are, or contain for example through substitution, methyl, ethyl, or methoxy, the alkyl residue may be deuterated (in non-limiting embodiments, $CDH_2$, $CD_2H$, $CD_3$, $CH_2CD_3$, $CD_2CD_3$, $CHDCH_2D$, $CH_2CD_3$, $CHDCHD_2$, $OCDH_2$, $OCD_2H$, or $OCD_3$ etc.). In certain other embodiments, when two substituents are combined to form a cycle the unsubstituted carbons may be deuterated.

The quaternary ammonium compound of the present invention may form a solvate with solvents (including water). Therefore, in one non-limiting embodiment, the invention includes a solvated form of the quaternary ammonium compound. The term "solvate" refers to a molecular complex of a quaternary ammonium compound of the present invention with one or more solvent molecules. Non-limiting examples of solvents are water, ethanol, dimethyl sulfoxide (DMSO), acetone and other common organic solvents. The term "hydrate" refers to a molecular complex comprising a quaternary ammonium compound of the invention and water. Pharmaceutically acceptable solvates in accordance with the invention include those wherein the solvent may be isotopically substituted, e.g. $D_2O$, $d_6$-acetone, $d_6$-DMSO. A solvate can be in a liquid or solid form.

A dash ("-") that is not between two letters or symbols is used to indicate a point of attachment for a substituent. For example, —(C=O)NH$_2$ is attached through carbon of the keto (C=O) group.

"Alkyl" is a branched or straight chain saturated aliphatic hydrocarbon group. In one non-limiting embodiment, the alkyl group contains from 1 to about 12 carbon atoms, more generally from 1 to about 6 carbon atoms or from 1 to about 4 carbon atoms. In one non-limiting embodiment, the alkyl contains from 1 to about 8 carbon atoms. In certain embodiments, the alkyl is $C_1$-$C_2$, $C_1$-$C_3$, $C_1$-$C_4$, $C_1$-$C_5$, or $C_1$-$C_6$. The specified ranges as used herein indicate an alkyl group having each member of the range described as an independent species. For example, the term $C_1$-$C_6$ alkyl as used herein indicates a straight or branched alkyl group having from 1, 2, 3, 4, 5, or 6 carbon atoms and is intended to mean that each of these is described as an independent species. For example, the term $C_1$-$C_4$ alkyl as used herein indicates a straight or branched alkyl group having from 1, 2, 3, or 4 carbon atoms and is intended to mean that each of these is described as an independent species. Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane, and 2,3-dimethylbutane. In an alternative embodiment, the alkyl group is optionally substituted. The term "Alkyl" also encompasses cycloalkyl or carbocyclic groups. For example, when a term is used that includes "alk" then "cycloalkyl" or "carbocyclic" can be considered part of the definition, unless unambiguously excluded by the context. For example, and without limitation, the terms alkyl, haloalkyl, etc. can all be considered to include the cyclic forms of alkyl, unless unambiguously excluded by context.

"Alkenyl" is a linear or branched aliphatic hydrocarbon groups having one or more carbon-carbon double bonds that may occur at a stable point along the chain. The specified ranges as used herein indicate an alkenyl group having each member of the range described as an independent species, as described above for the alkyl moiety. Examples of alkenyl radicals include, but are not limited to ethenyl, propenyl, allyl, propenyl, butenyl and 4-methylbutenyl. The term "alkenyl" also embodies "cis" and "trans" alkenyl geometry, or alternatively, "E" and "Z" alkenyl geometry. In an alternative embodiment, the alkenyl group is optionally substituted. The term "Alkenyl" also encompasses cycloalkyl or carbocyclic groups possessing at least one point of unsaturation.

"Alkynyl" is a branched or straight chain aliphatic hydrocarbon group having one or more carbon-carbon triple bonds that may occur at any stable point along the chain. The specified ranges as used herein indicate an alkynyl group having each member of the range described as an independent species, as described above for the alkyl moiety. Examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl. In an alternative embodiment, the alkynyl group is optionally substituted. The term "Alkynyl" also encompasses cycloalkyl or carbocyclic groups possessing at least one point of unsaturation.

"Halo" and "Halogen" is fluorine, chlorine, bromine or iodine.

"Haloalkyl" is a branched or straight-chain alkyl groups substituted with 1 or more halogen atoms, up to the maximum allowable number of halogen atoms. Examples of haloalkyl groups include, but are not limited to, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perhaloalkyl" means an alkyl group having all hydrogen atoms replaced with halogen atoms. Examples include but are not limited to, trifluoromethyl and pentafluoroethyl.

The term "carrier" applied to compositions/combinations of the invention refers to a diluent, excipient, or vehicle with which an active quaternary ammonium compound is provided.

A "patient" or "host" or "subject" is a human or non-human animal in need of treatment or prevention of any of an infection as described herein. In some embodiments, the host is a human. A "patient" or "host" or "subject" also refers to for example, an animal such as a mammal, primate (e.g., human), cows, sheep, goat, horse, dog, cat, rabbit, rat, mice, fish, bird and the like.

A "therapeutically effective amount" of a composition/combination of this invention means an amount effective, when administered to a host, to provide a therapeutic benefit such as an amelioration of symptoms or reduction or diminution of the disease itself. In one embodiment, a therapeutically effective amount is an amount sufficient to inhibit progression, cause a regression, cause a cure, or inhibit or prevent an infection in a host in need thereof.

As used herein, "salt" is a derivative of the disclosed quaternary ammonium compound in which the parent quaternary ammonium compound is modified by making inorganic or organic, non-toxic, acid or base addition salts thereof. The salts (i.e, not the quaternary ammonium salt) of the present quaternary ammonium compounds can be synthesized from a parent quaternary ammonium compound that contains a basic or acidic moiety by conventional chemical methods. Generally, such salts can be prepared by reacting free acid forms of these quaternary ammonium compounds with a stoichiometric or excess amount of the appropriate base (such as Na, Ca, Mg, or K hydroxide, carbonate, bicarbonate, or the like), or by reactive free base forms of these quaternary ammonium compounds with a stoichiometric amount of the appropriate acid. Such reactions are typically carried out in water or in an appropriate organic solvent, or in a mixture of the two as desired or necessary based on the compound solubility and stability. Generally, non-aqueous media like ether, ethyl acetate, ethanol, isopropanol, or acetonitrile are typical, where practical.

Examples of salts may further include, but are not limited to, mineral or organic acid salts of basic residues such as amines; alkali or organic salts of acidic residues such as carboxylic acids; and the like. The acceptable salts include the conventional non-toxic salts and the quaternary ammonium salts of the parent quaternary ammonium compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—(CH2)n-COOH where n is 0-4, and the like, or using a different acid that produces the same counterion. Lists of additional suitable salts may be found, e.g., in Remington's Pharmaceutical Sciences, $_{17}$th 20 ed., Mack Publishing Company, Easton, Pa., p. 1418 (1985).

In a typical embodiment, the positive charge of the quaternary ammonium compound is paired with a negatively charged ion, such as chloride or another anion as described herein, as appropriate.

Chemistry

Embodiments of "Alkyl"

In one embodiment "alkyl" is a $C_1$-$C_{10}$alkyl, $C_1$-$C_9$alkyl, $C_1$-$C_8$alkyl, $C_1$-$C_7$alkyl, $C_1$-$C_6$alkyl, $C_1$-$C_5$alkyl, $C_1$-$C_4$alkyl, $C_1$-$C_3$alkyl, or $C_1$-$C_2$alkyl.

In one embodiment "alkyl" has one carbon.
In one embodiment "alkyl" has two carbons.
In one embodiment "alkyl" has three carbons.
In one embodiment "alkyl" has four carbons.
In one embodiment "alkyl" has five carbons.
In one embodiment "alkyl" has six carbons.

Non-limiting examples of "alkyl" include: methyl, ethyl, propyl, butyl, pentyl, and hexyl.

Additional non-limiting examples of "alkyl" include: isopropyl, isobutyl, isopentyl, and isohexyl.

Additional non-limiting examples of "alkyl" include: sec-butyl, sec-pentyl, and sec-hexyl.

Additional non-limiting examples of "alkyl" include: tert-butyl, tert-pentyl, and tert-hexyl.

Additional non-limiting examples of "alkyl" include: neopentyl, 3-pentyl, and active pentyl.

In one embodiment "alkyl" is "substituted alkyl"
In one embodiment "alkenyl" is "substituted alkenyl"
In one embodiment "alkynyl" is "substituted alkynyl"

Embodiments of "Haloalkyl"

In one embodiment "haloalkyl" is a $C_1$-$C_{10}$haloalkyl, $C_1$-$C_9$haloalkyl, $C_1$-$C_8$haloalkyl, $C_1$-$C_7$haloalkyl, $C_1$-$C_6$haloalkyl, $C_1$-$C_5$haloalkyl, $C_1$-$C_4$haloalkyl, $C_1$-$C_3$haloalkyl, and $C_1$-$C_2$haloalkyl.

In one embodiment "haloalkyl" has one carbon.
In one embodiment "haloalkyl" has one carbon and one halogen.
In one embodiment "haloalkyl" has one carbon and two halogens.
In one embodiment "haloalkyl" has one carbon and three halogens.
In one embodiment "haloalkyl" has two carbons.
In one embodiment "haloalkyl" has three carbons.
In one embodiment "haloalkyl" has four carbons.
In one embodiment "haloalkyl" has five carbons.
In one embodiment "haloalkyl" has six carbons.

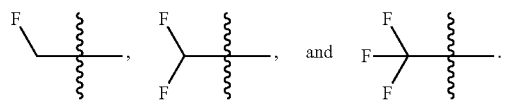

Non-limiting examples of "haloalkyl" include:

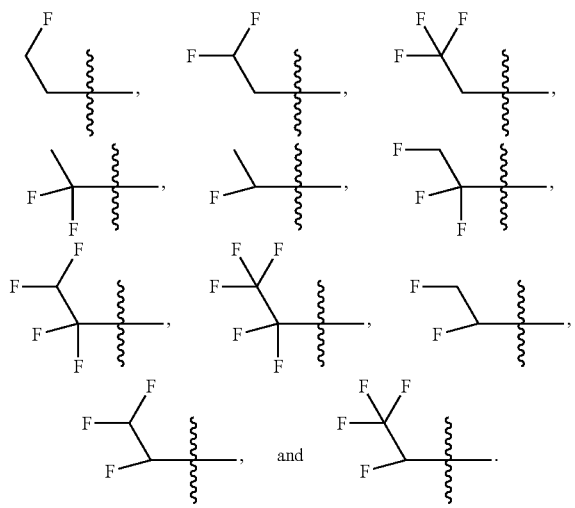

Additional non-limiting examples of "haloalkyl" include:

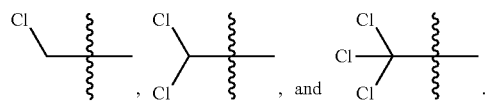

Additional non-limiting examples of "haloalkyl" include:

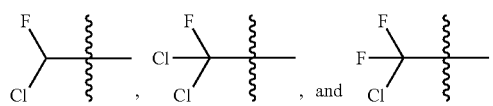

Compounds of the Present Invention

The organosilane quaternary ammonium compounds of the present invention are described below. In one aspect of the present invention, a quaternary ammonium compound of Formula I, II, III, IV, V, VI, VII, VIII, or IX is provided:

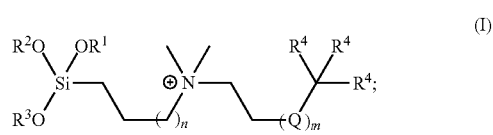
(I)

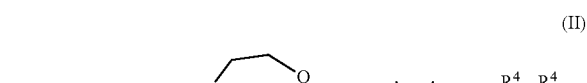
(II)

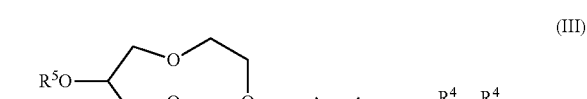
(III)

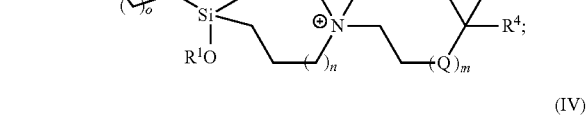
(IV)

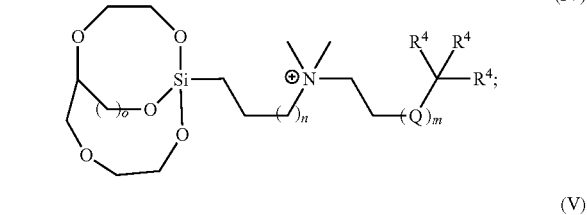
(V)

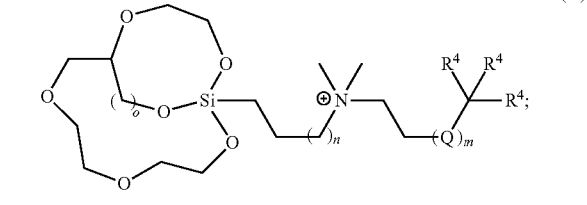
(VI)

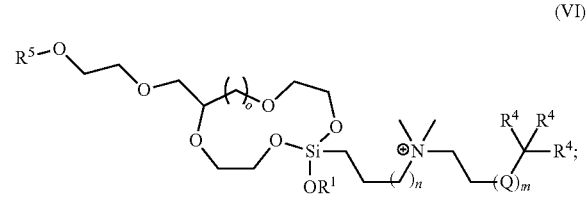
(VII)

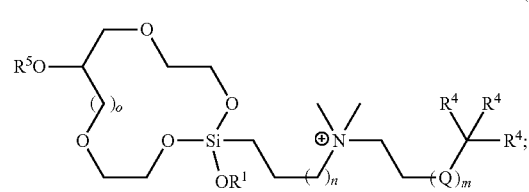
(VIII)

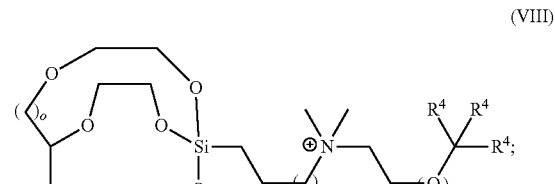

(IX)

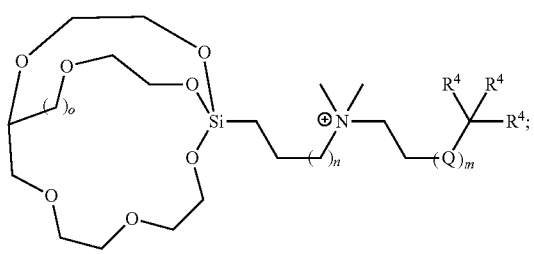

wherein $R^1$, $R^2$, $R^3$, $R^4$, $R^5$, Q, m, n, and o are as defined herein.

In another aspect of the present invention, a quaternary ammonium compound of Formula XI, XII, or XIII is provided:

(XI)

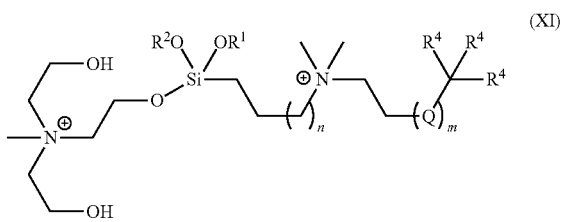

(XII)

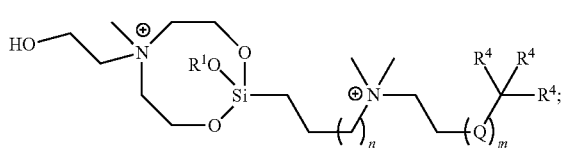

(XIII)

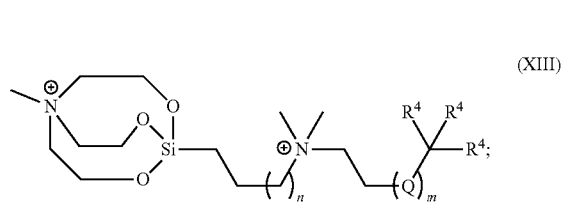

or a pharmaceutically acceptable composition thereof;
wherein $R^1$, $R^2$, $R^4$, Q, m, and n are as defined herein.

In another aspect of the present invention, a quaternary ammonium compound of Formula XIV, XV, or XVI is provided:

(XIV)

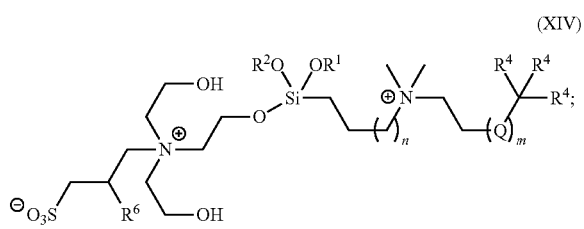

(XV)

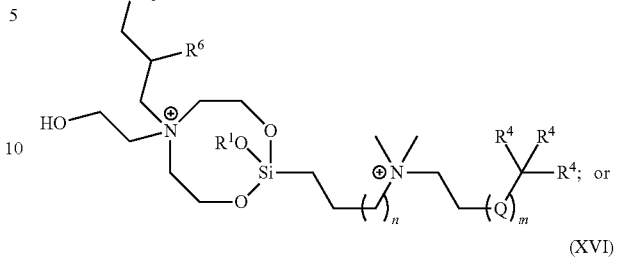

(XVI)

wherein $R^1$, $R^2$, $R^4$, $R^6$, Q, m, and n are as defined herein.

In another aspect of the present invention, a quaternary ammonium compound of Formula XVII, XVIII, or XIX is provided:

(XVII)

(XVIII)

(XIX)

wherein $R^1$, $R^2$, $R^4$, $R^7$, $R^8$, m, n, and Q are as defined herein.

In another aspect of the present invention, a quaternary ammonium compound of Formula XX or XXI is provided:

(XX)

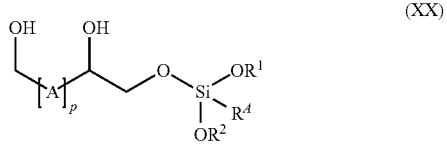

-continued (XXI)

wherein $R^A$, $R^1$, $R^2$, p, A and Q are as defined herein.

In another embodiment of the present invention, a quaternary ammonium compound of Formula XXII is provided:

(XXII)

wherein $R^1$, $R^2$, $R^A$, q, r, and s are as defined herein.

In another aspect of the present invention, a quaternary ammonium compound of Formula XXIII, XXIV, or XXV is provided:

(XXIII)

(XXIV)

(XXV)

wherein $R^1$, $R^2$, $R^4$, $R^6$, m, n, B and Q are as defined herein.

In another aspect of the present invention, a quaternary ammonium compound of Formula XVII, XVIII, or XIX is provided:

(XVI)

(XVII)

(XVIII)

wherein $R^1$, $R^2$, $R^4$, $R^7$, $R^8$, m, n, and Q are as defined herein.

In an alternative aspect of the present invention a quaternary ammonium compound of Formula XXIX is provided:

(XXIX)

wherein L, Z and t are as defined herein.

In one embodiment, o is 1. In one embodiment, o is 2.

In one embodiment, n is 0. In one embodiment, n is 1. In one embodiment, n is 2.

In one embodiment, m is 0. In one embodiment, m is 1. In one embodiment, m is 2. In one embodiment, m is 3. In one embodiment, m is 4. In one embodiment, m is 5. In one embodiment, m is 6. In one embodiment, m is 7. In one embodiment, m is 8. In one embodiment, m is 9. In one embodiment, m is 10. In one embodiment, m is 11. In one embodiment, m is 12. In one embodiment, m is 13. In one embodiment, m is 14. In one embodiment, m is 15. In one embodiment, m is 16. In one embodiment, m is 17. In one embodiment, m is 18. In one embodiment, m is 19. In one embodiment, m is 20.

In one embodiment, n is 0 and m is 0. In one embodiment, n is 0 and m is 1. In one embodiment, n is 0 and m is 2. In one embodiment, n is 0 and m is 3. In one embodiment, n is 0 and m is 4. In one embodiment, n is 0 and m is 5. In one embodiment, n is 0 and m is 6. In one embodiment, n is 0 and m is 7. In one embodiment, n is 0 and m is 8. In one embodiment, n is 0 and m is 9. In one embodiment, n is 0 and m is 10. In one embodiment, n is 0 and m is 11. In one embodiment, n is 0 and m is 12. In one embodiment, n is 0 and m is 13. In one embodiment, n is 0 and m is 14. In one embodiment, n is 0 and m is 15. In one embodiment, n is 0 and m is 16. In one embodiment, n is 0 and m is 17. In one embodiment, n is 0 and m is 18. In one embodiment, n is 0 and m is 19. In one embodiment, n is 0 and m is 20.

In one embodiment, n is 1 and m is 0. In one embodiment, n is 1 and m is 1. In one embodiment, n is 1 and m is 2. In one embodiment, n is 1 and m is 3. In one embodiment, n is 1 and m is 4. In one embodiment, n is 1 and m is 5. In one embodiment, n is 1 and m is 6. In one embodiment, n is 1 and m is 7. In one embodiment, n is 1 and m is 8. In one embodiment, n is 1 and m is 9. In one embodiment, n is 1 and m is 10. In one embodiment, n is 1 and m is 11. In one embodiment, n is 1 and m is 12. In one embodiment, n is 1 and m is 13. In one embodiment, n is 1 and m is 14. In one embodiment, n is 1 and m is 15. In one embodiment, n is 1 and m is 16. In one embodiment, n is 1 and m is 17. In one embodiment, n is 1 and m is 18. In one embodiment, n is 1 and m is 19. In one embodiment, n is 1 and m is 20.

In one embodiment, n is 2 and m is 0. In one embodiment, n is 2 and m is 1. In one embodiment, n is 2 and m is 2. In one embodiment, n is 2 and m is 3. In one embodiment, n is 2 and m is 4. In one embodiment, n is 2 and m is 5. In one embodiment, n is 2 and m is 6. In one embodiment, n is 2 and m is 7. In one embodiment, n is 2 and m is 8. In one embodiment, n is 2 and m is 9. In one embodiment, n is 2 and m is 10. In one embodiment, n is 2 and m is 11. In one embodiment, n is 2 and m is 12. In one embodiment, n is 2 and m is 13. In one embodiment, n is 2 and m is 14. In one embodiment, n is 2 and m is 15. In one embodiment, n is 2 and m is 16. In one embodiment, n is 2 and m is 17. In one embodiment, n is 2 and m is 18. In one embodiment, n is 2 and m is 19. In one embodiment, n is 2 and m is 20.

In one embodiment, p is 0. In one embodiment, p is 1. In one embodiment, p is 2. In one embodiment, p is 3. In one embodiment, p is 4. In one embodiment, p is 5. In one embodiment, p is 6. In one embodiment, p is 7. In one embodiment, p is 8. In one embodiment, p is 9. In one embodiment, p is 10.

In one embodiment, q is 0. In one embodiment, q is 1. In one embodiment, q is 2. In one embodiment, q is 3. In one embodiment, q is 4. In one embodiment, q is 5. In one embodiment, q is 6. In one embodiment, q is 7. In one embodiment, q is 8. In one embodiment, q is 9. In one embodiment, q is 10.

In one embodiment, r is 0. In one embodiment, r is 1. In one embodiment, r is 2. In one embodiment, r is 3. In one embodiment, r is 4. In one embodiment, r is 5. In one embodiment, r is 6. In one embodiment, r is 7. In one embodiment, r is 8. In one embodiment, r is 9. In one embodiment, r is 10.

In one embodiment, s is 0. In one embodiment, s is 1. In one embodiment, s is 2. In one embodiment, s is 3. In one embodiment, s is 4. In one embodiment, s is 5. In one embodiment, s is 6. In one embodiment, s is 7. In one embodiment, s is 8. In one embodiment, s is 9. In one embodiment, s is 10.

In one embodiment, t is 1. In one embodiment, t is 2. In one embodiment, t is 3. In one embodiment, t is 4. In one embodiment, t is 5. In one embodiment, t is 6. In one embodiment, t is 7. In one embodiment, t is 8. In one embodiment, t is 9, In one embodiment, t is 10.

In one embodiment of Formula I, $R^3$ is selected from:

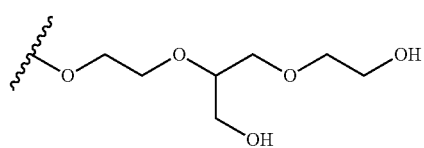

-continued

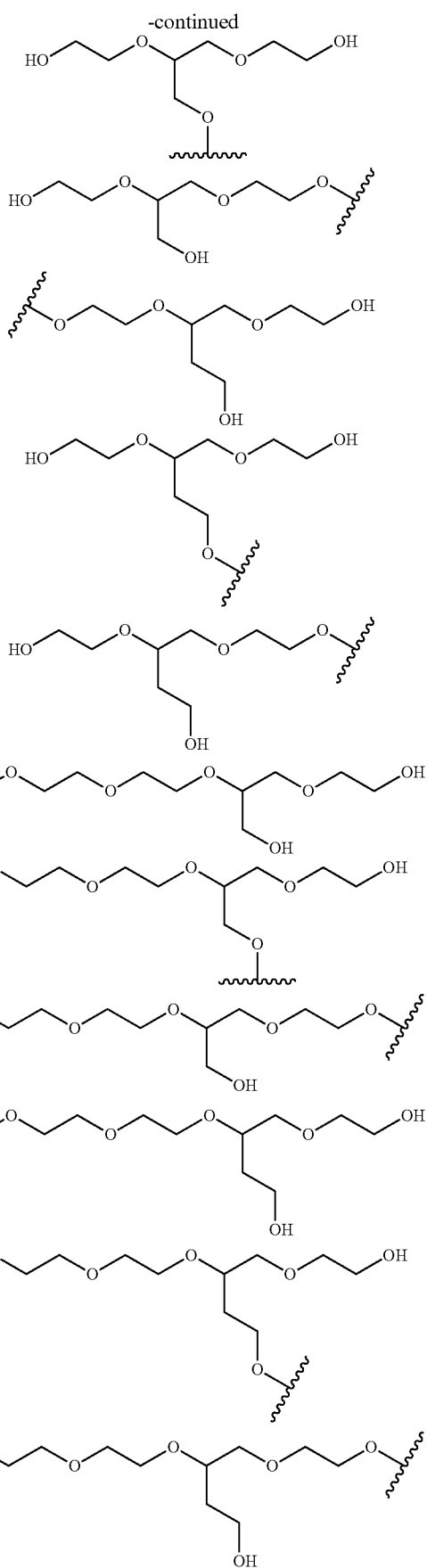

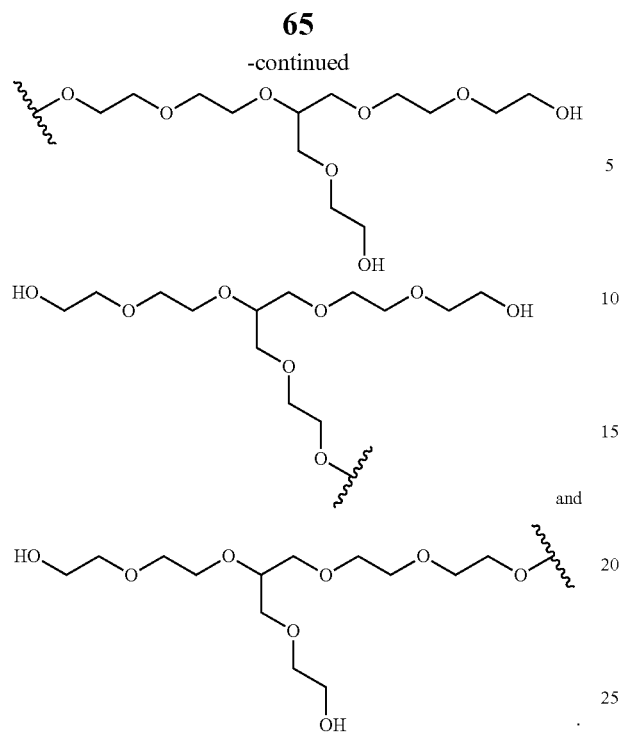
Non-limiting examples of
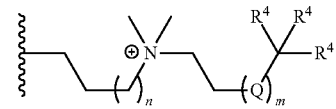
include:
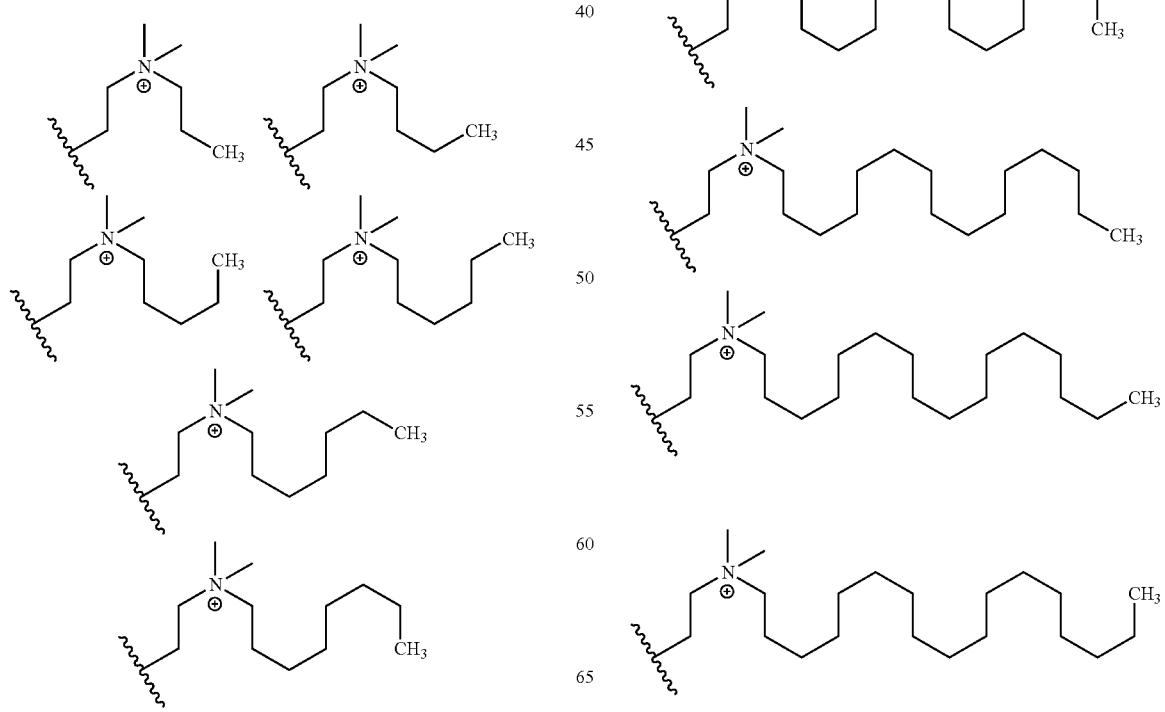

67
-continued
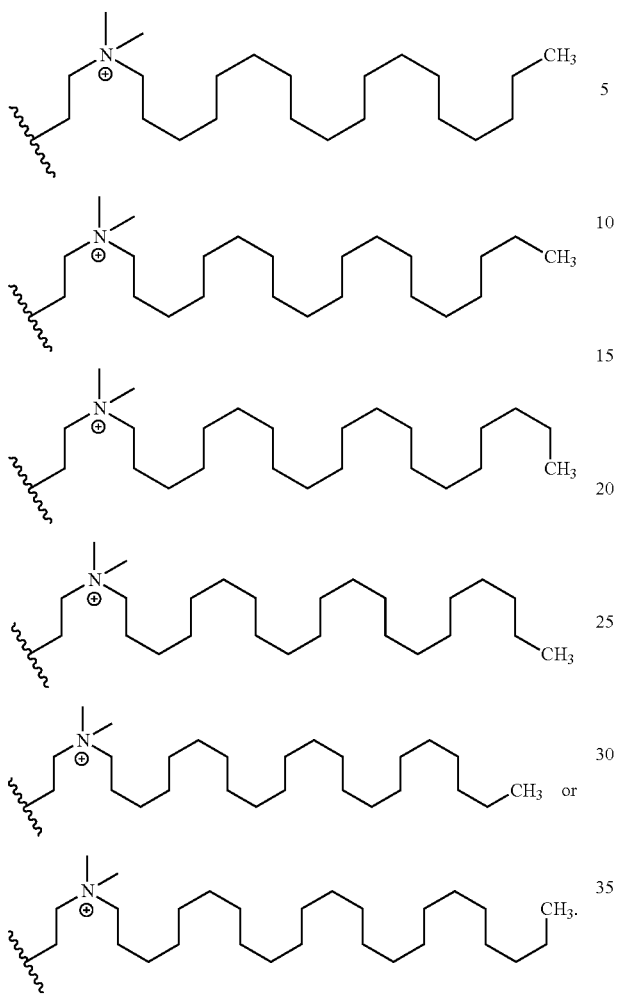
Additional non-limiting examples of
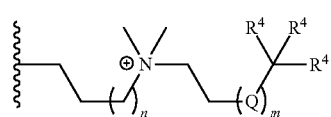
include:
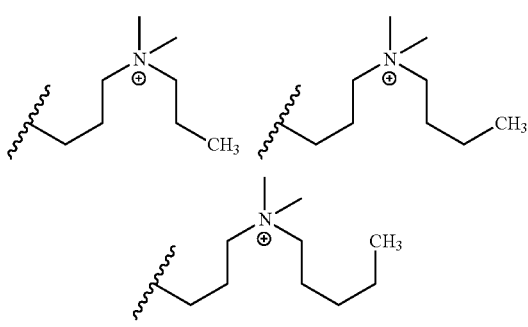
68
-continued
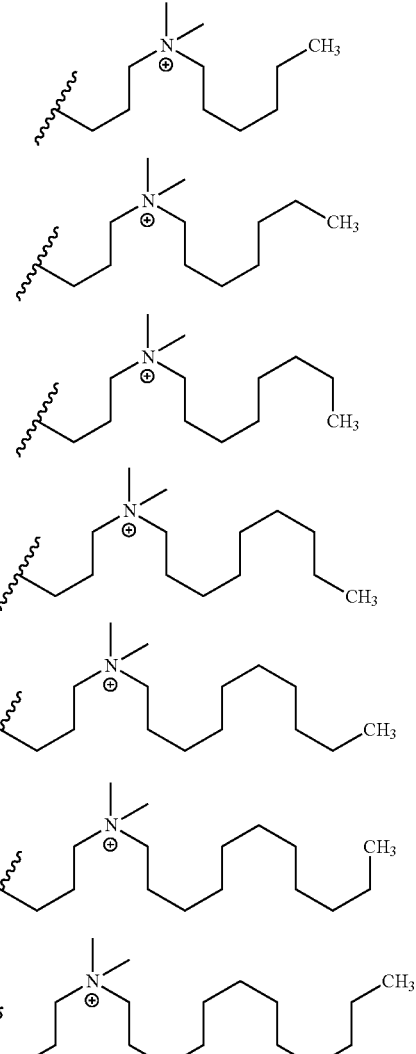

69
-continued
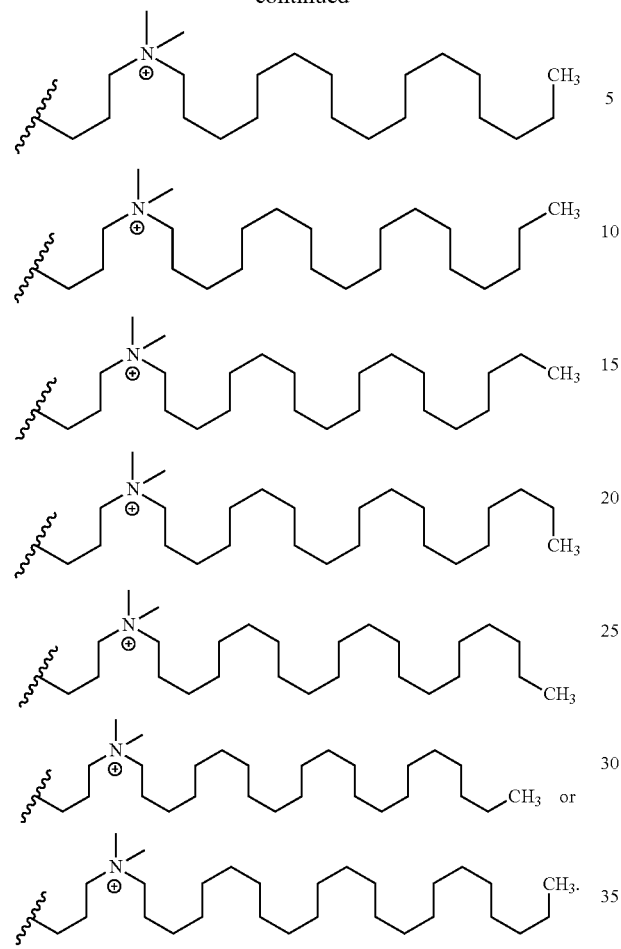
Additional non-limiting examples of
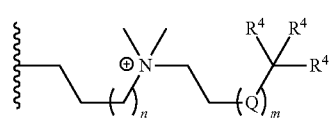
include:
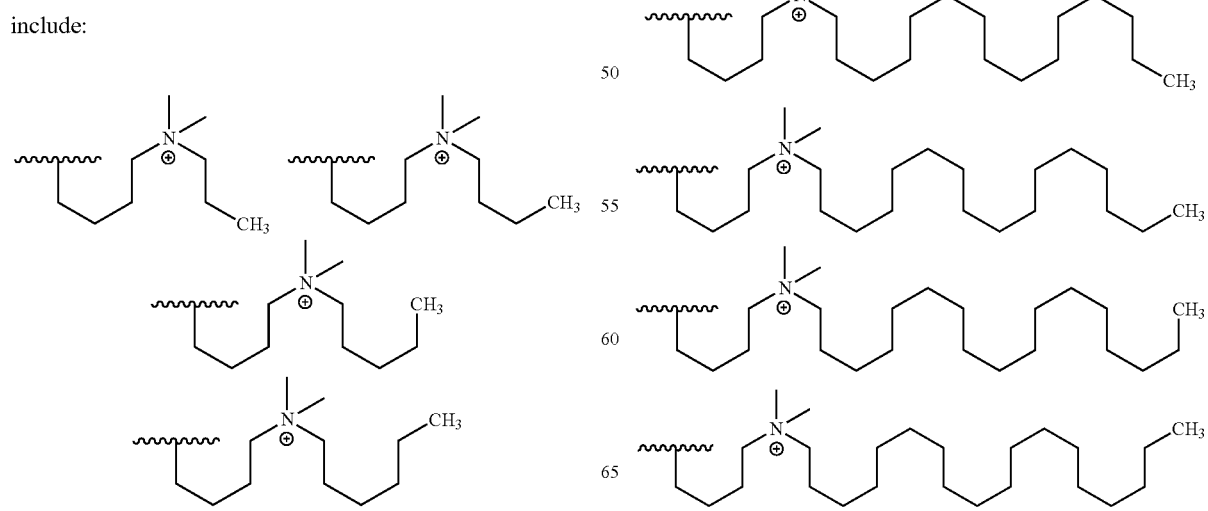
70
-continued
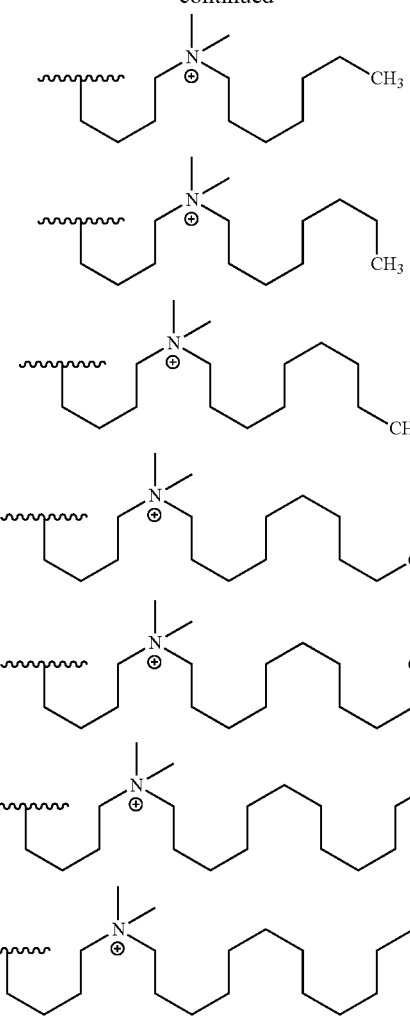
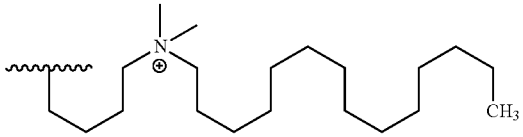
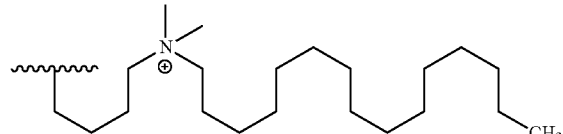

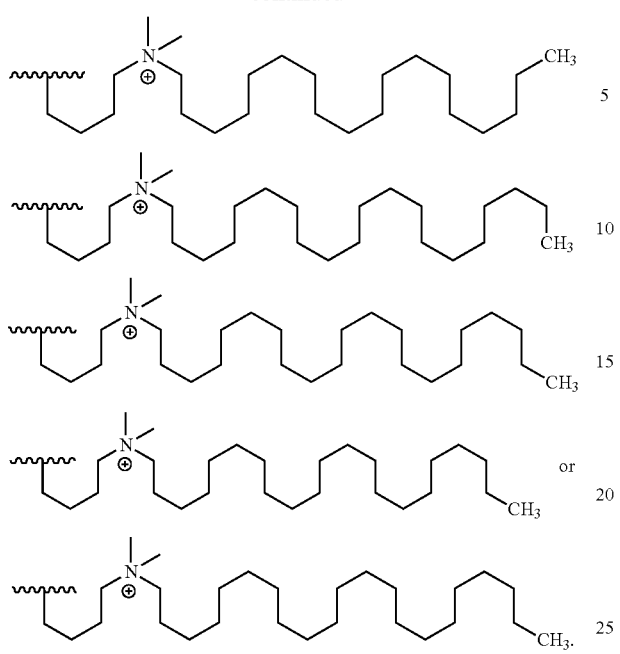
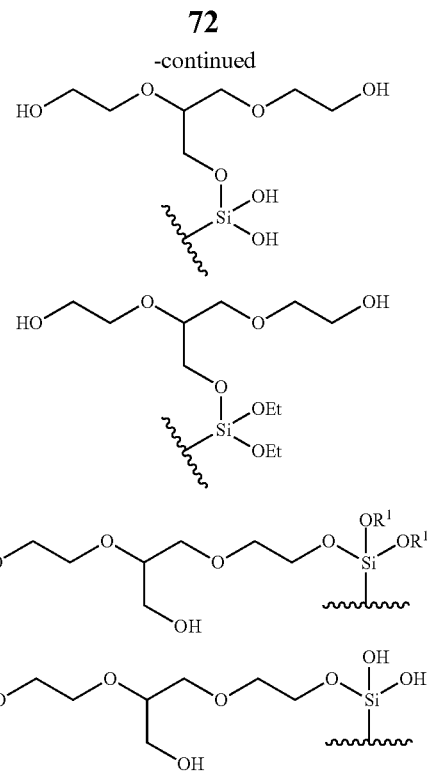
In one embodiment of Formula I,
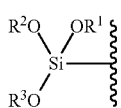
is selected from:
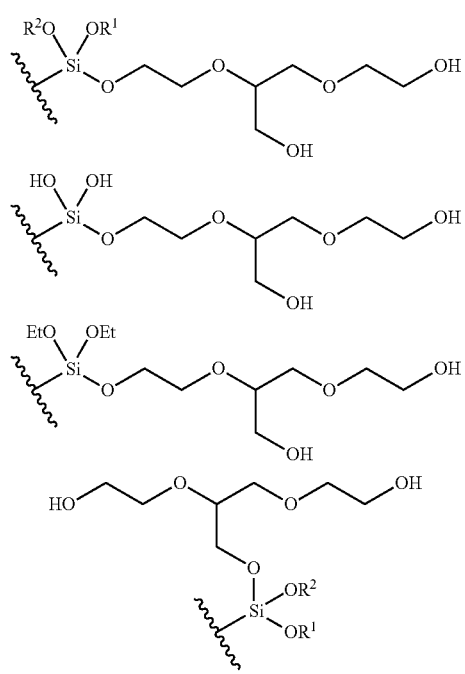

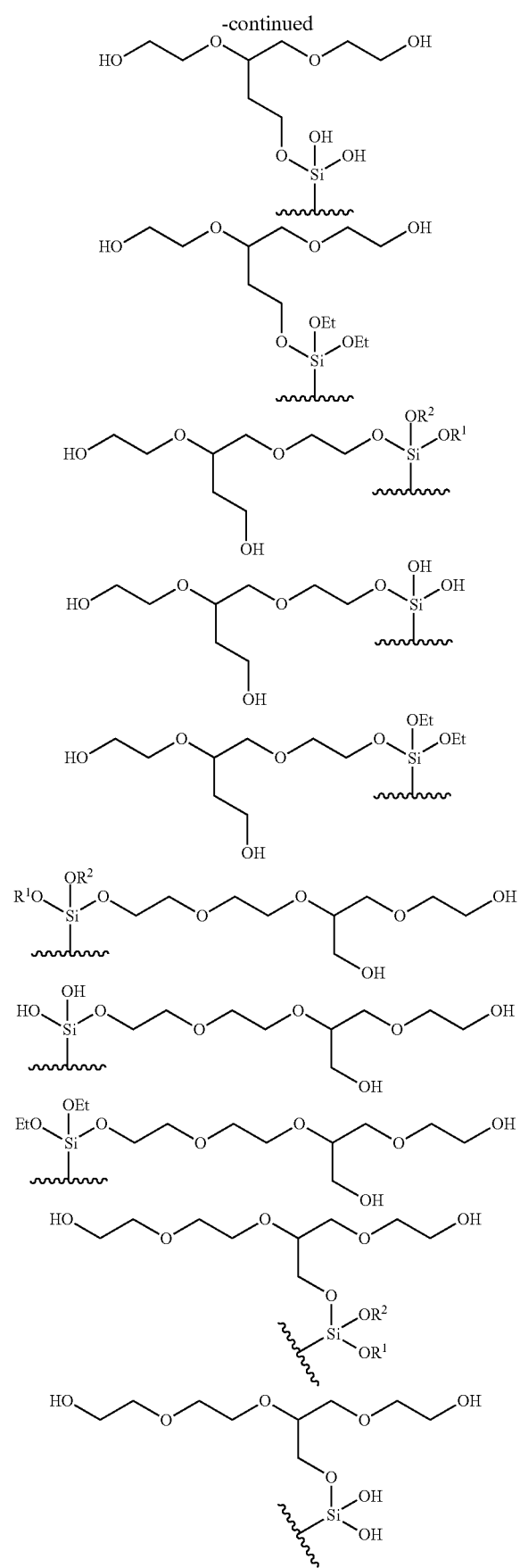
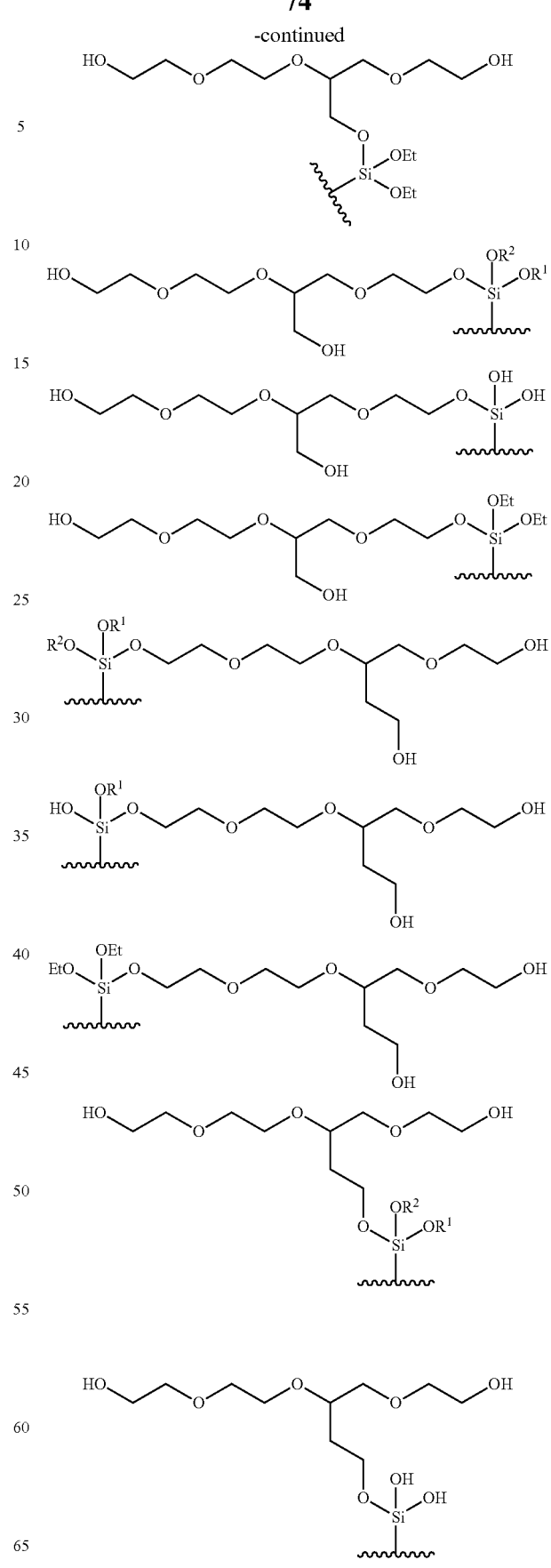

75
-continued
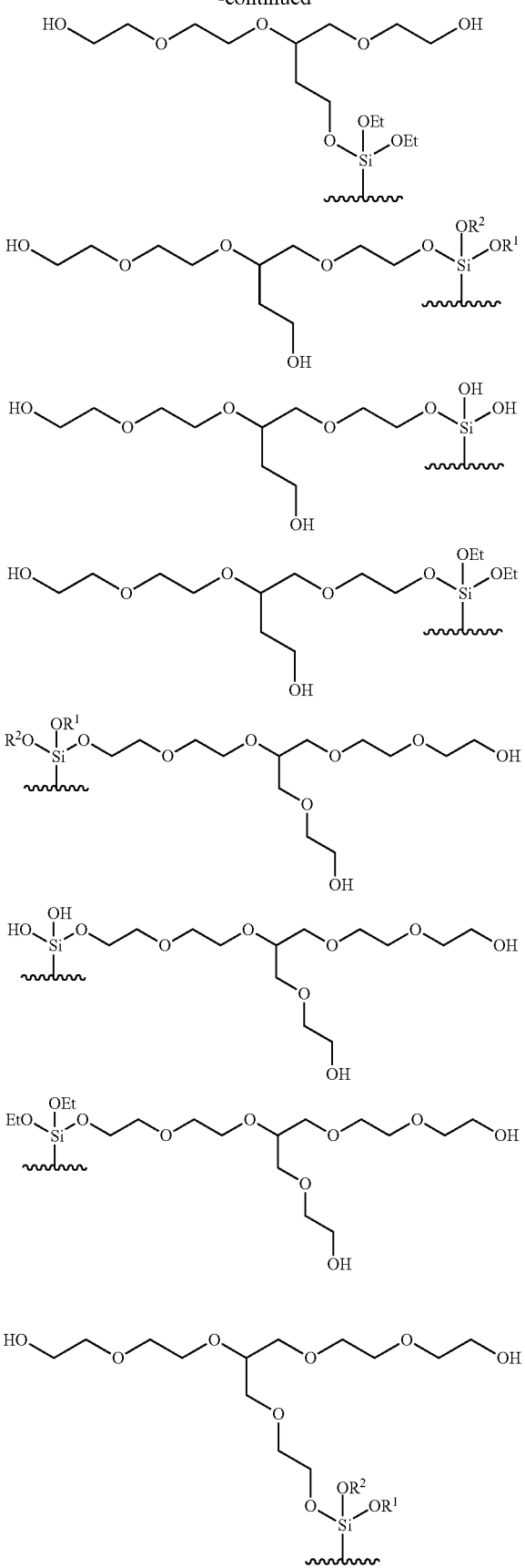
76
-continued
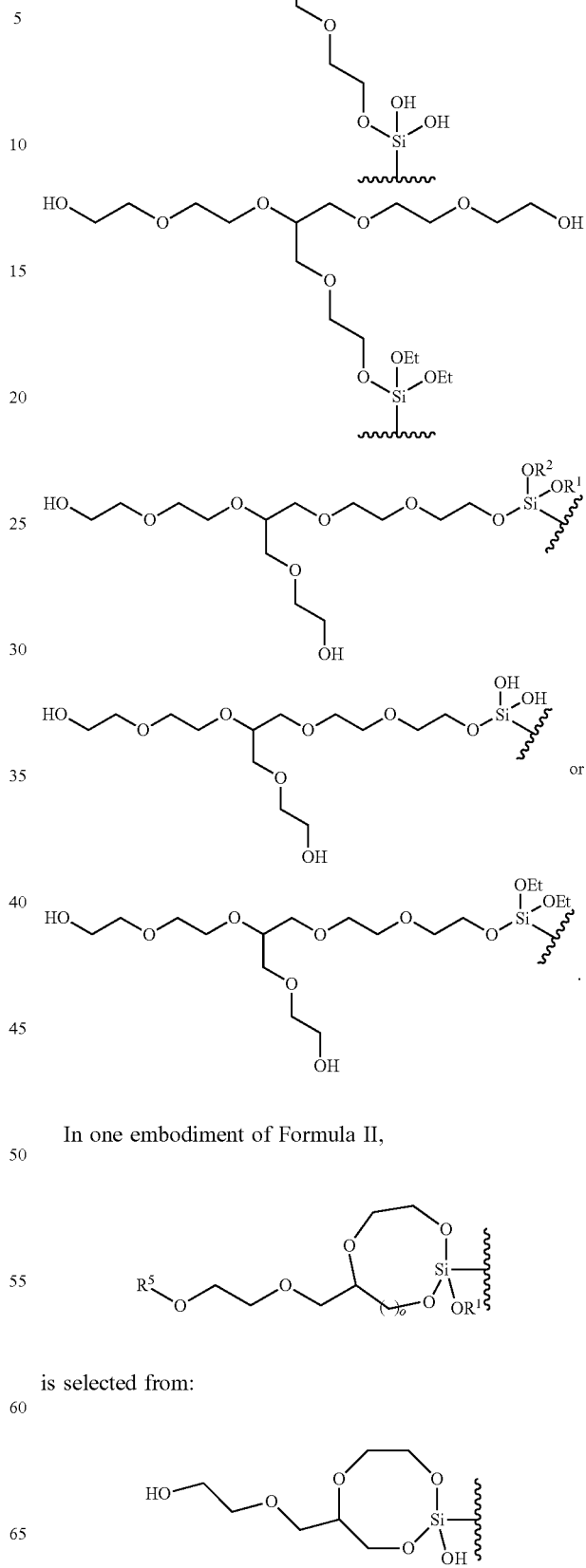
or
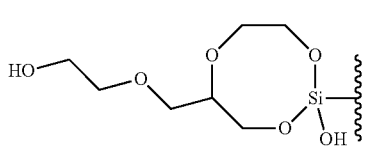
In one embodiment of Formula II,
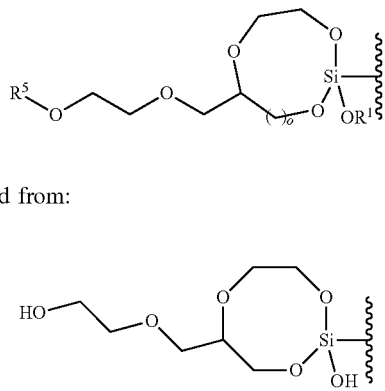
is selected from:

-continued
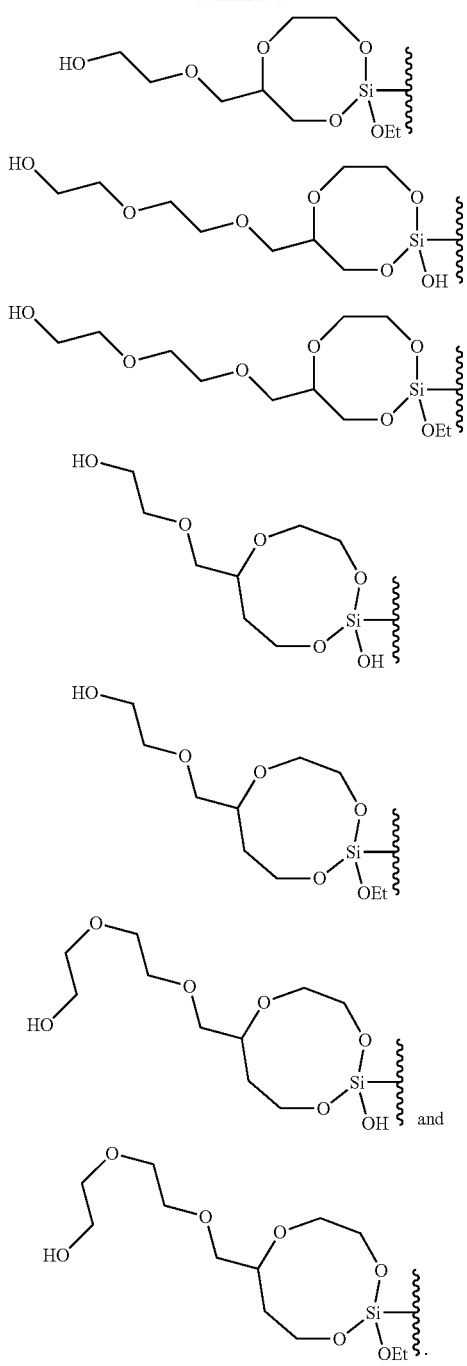
In one embodiment of Formula III,
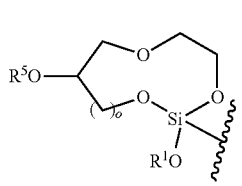
is selected from:
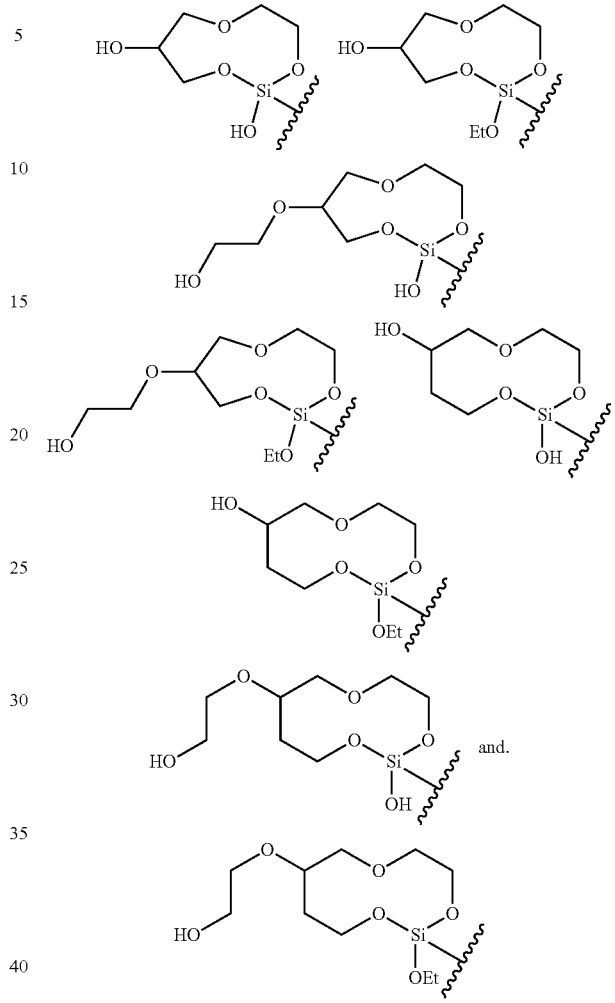
In one embodiment of Formula IV,
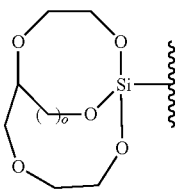
is selected from
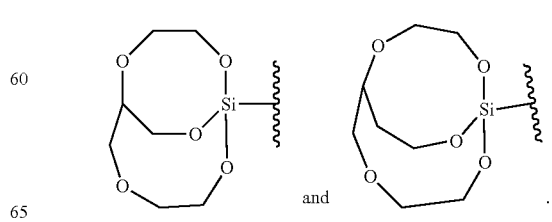

In one embodiment of Formula V,
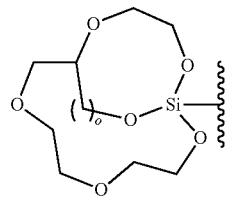
is selected from
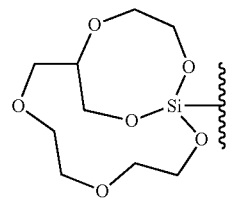 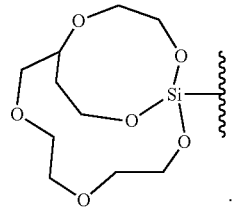
and
In one embodiment of Formula VI,
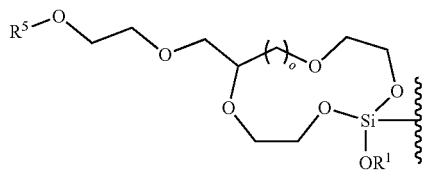
is selected from:
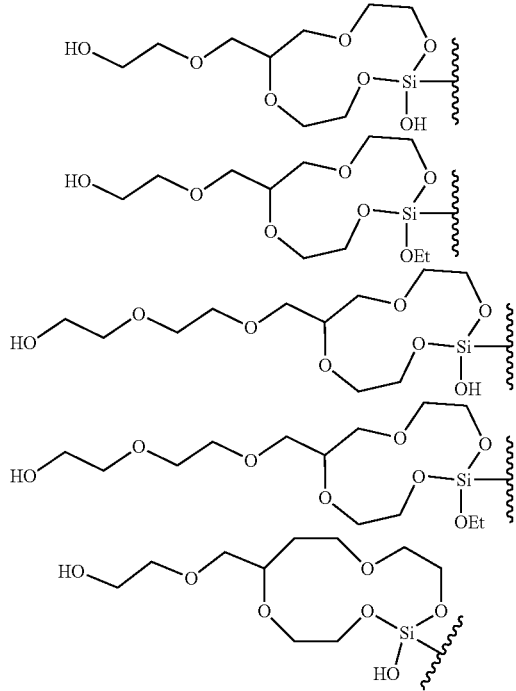
-continued
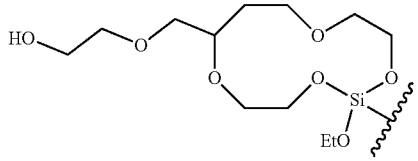
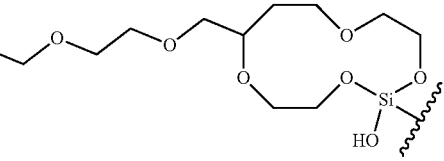
and
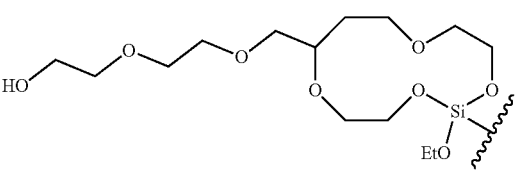
In one embodiment of Formula VII,
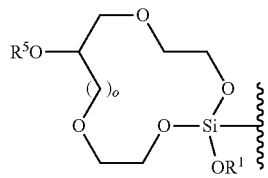
is selected from:
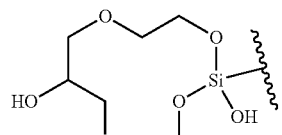
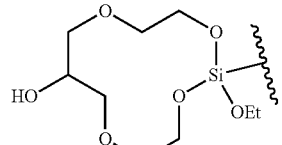
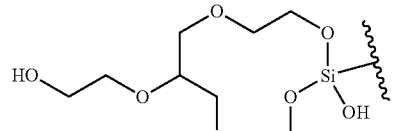
and
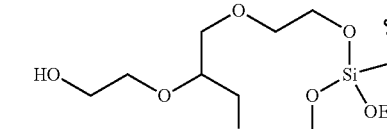

81
In one embodiment of Formula VIII,
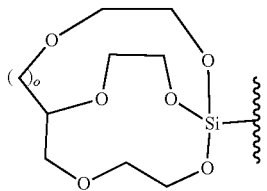
is selected from and
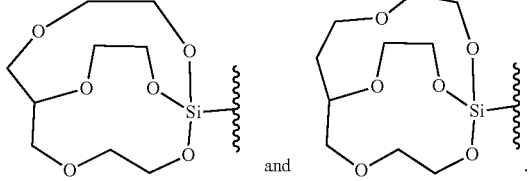
82
In one embodiment of Formula IX,
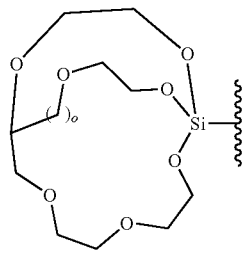
is selected from
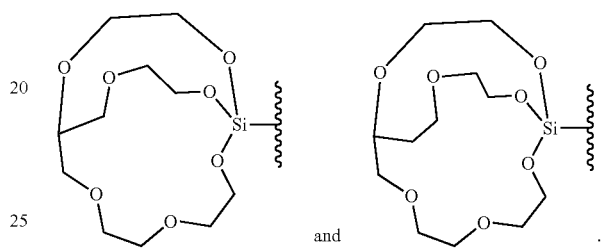
Non-limiting examples of quaternary ammonium compounds of Formula I include:
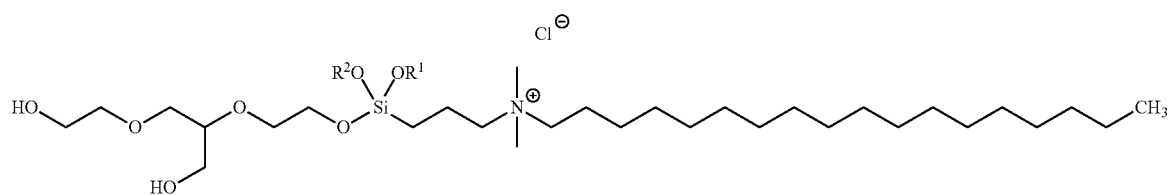
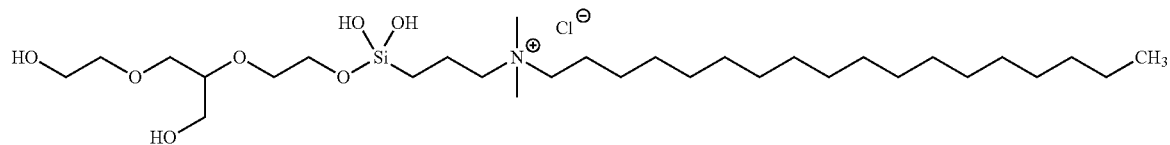
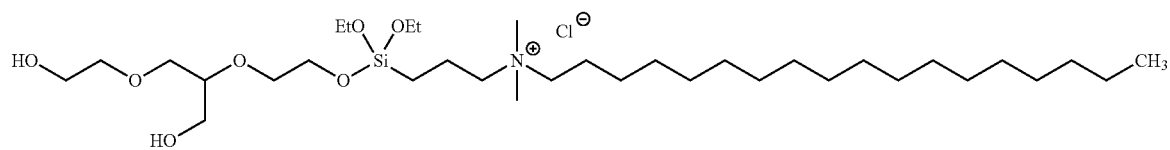
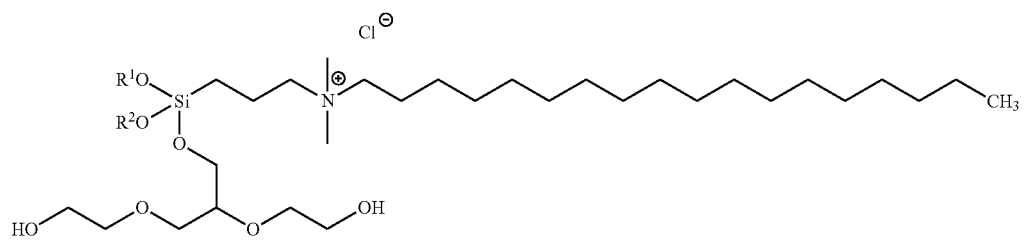

-continued
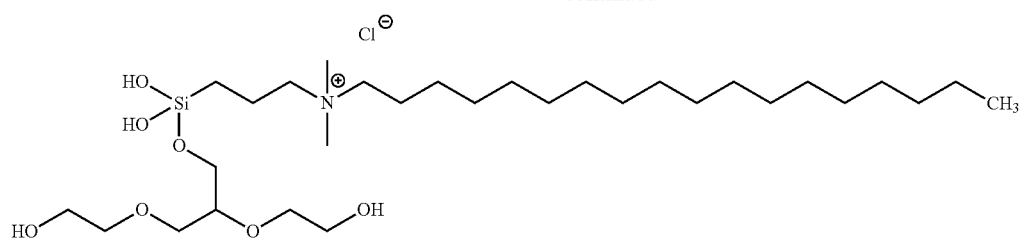
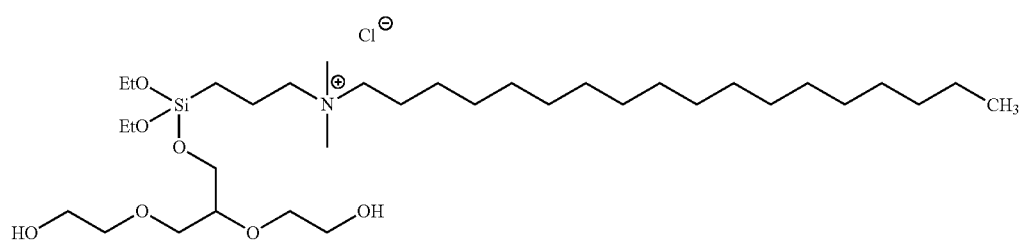
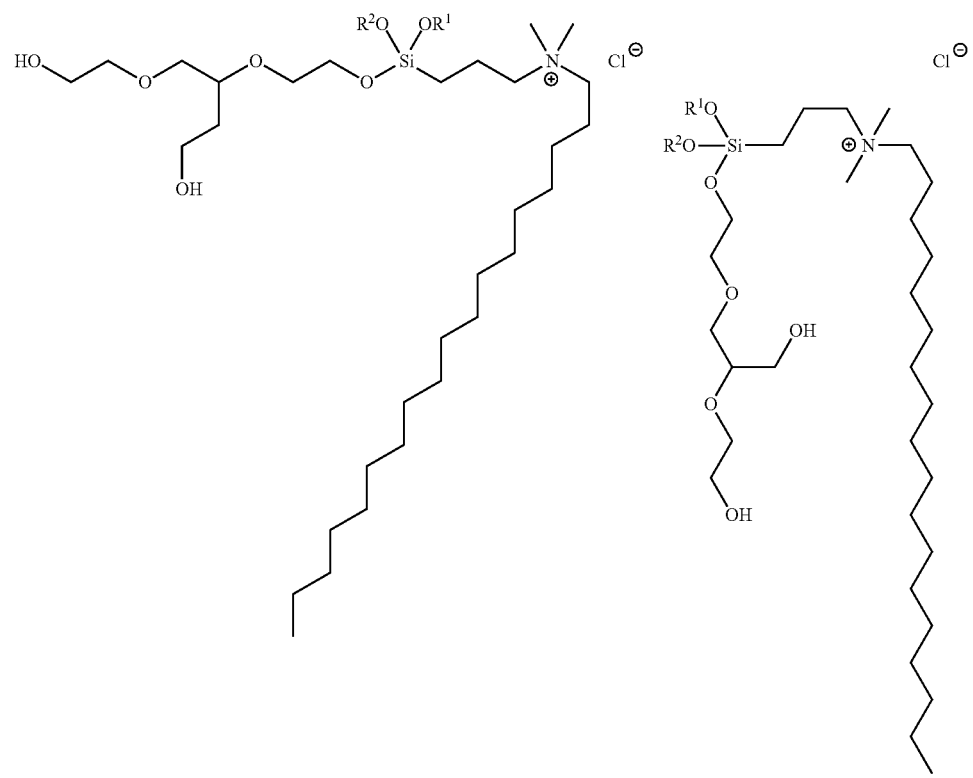

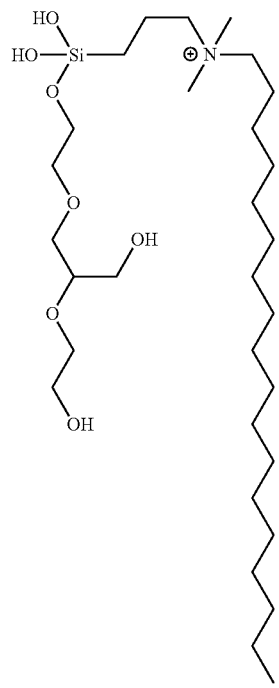
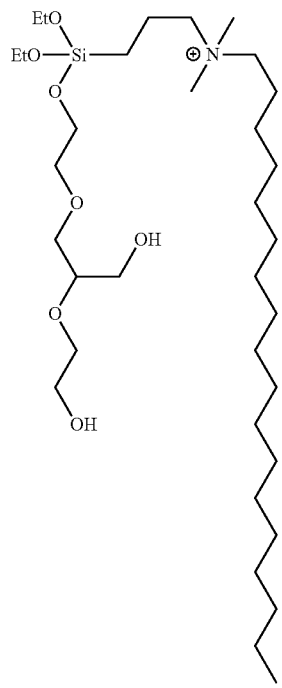
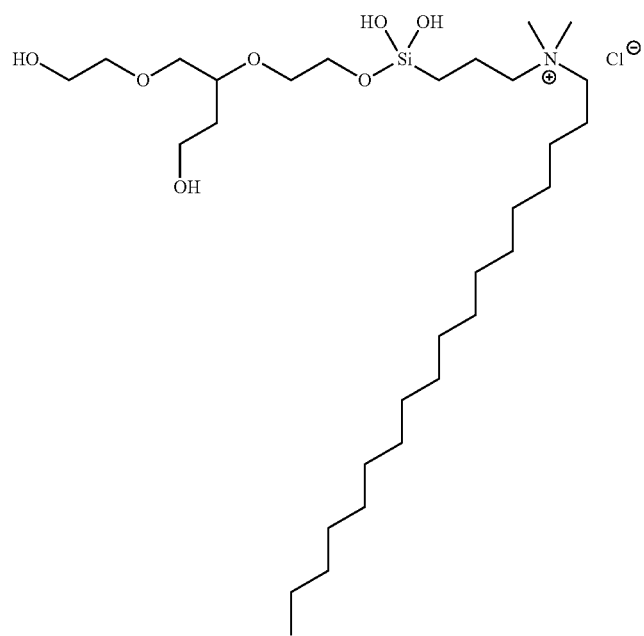

-continued
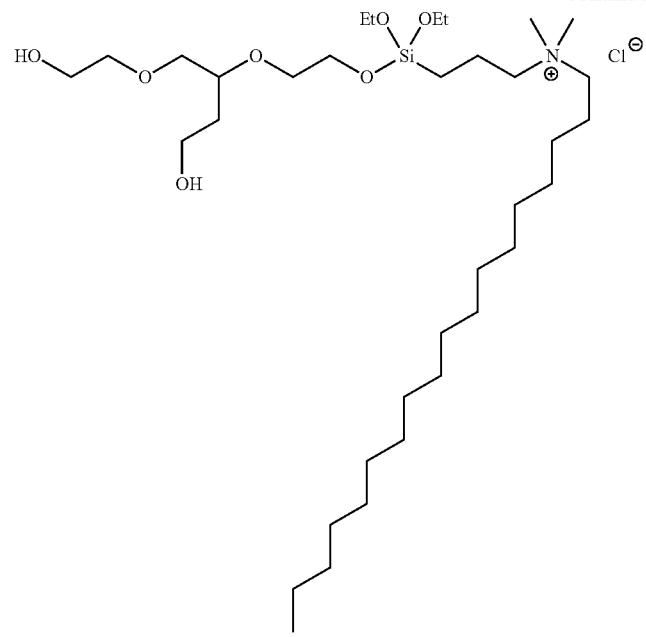
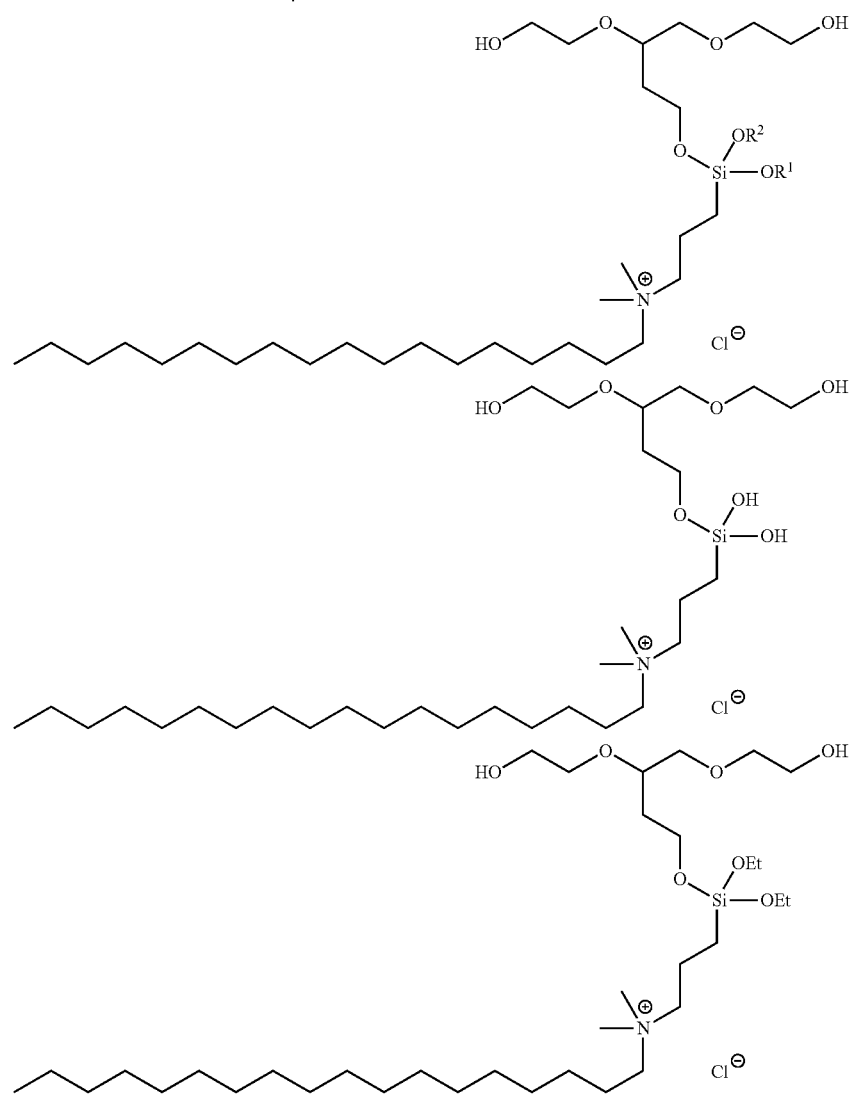

-continued
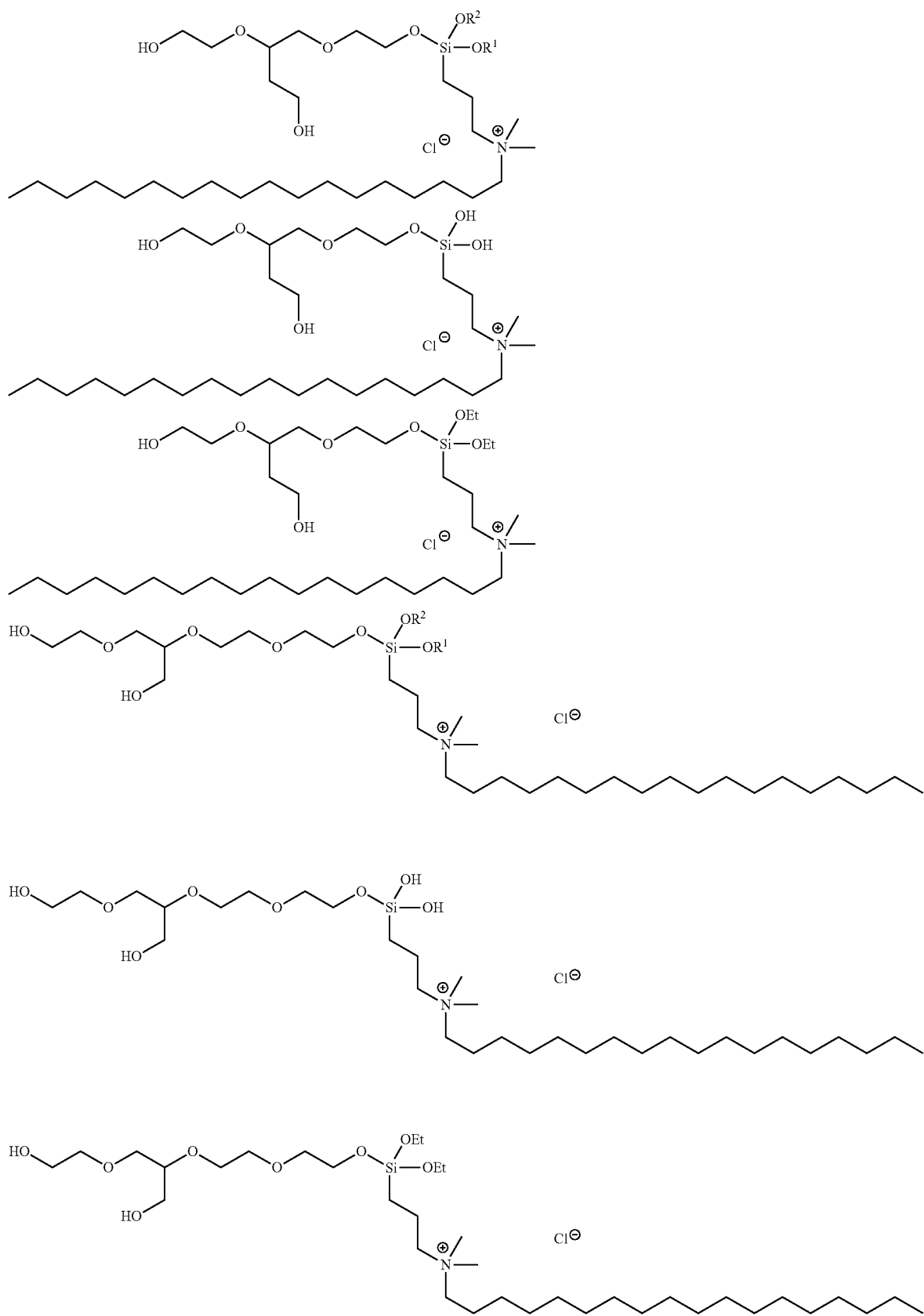

91
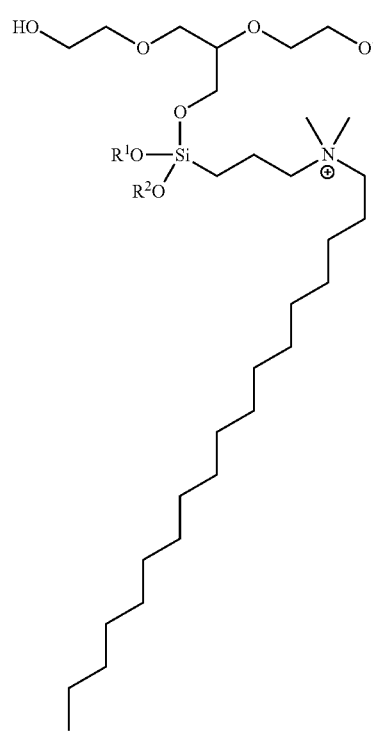
92
-continued
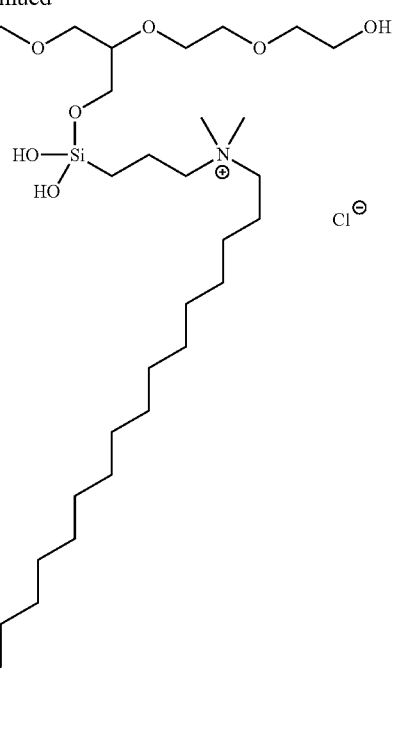
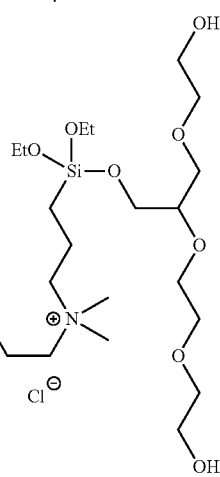
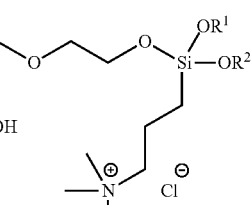
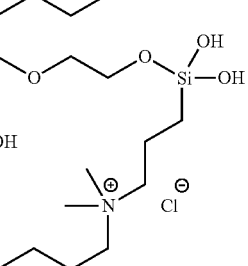

-continued
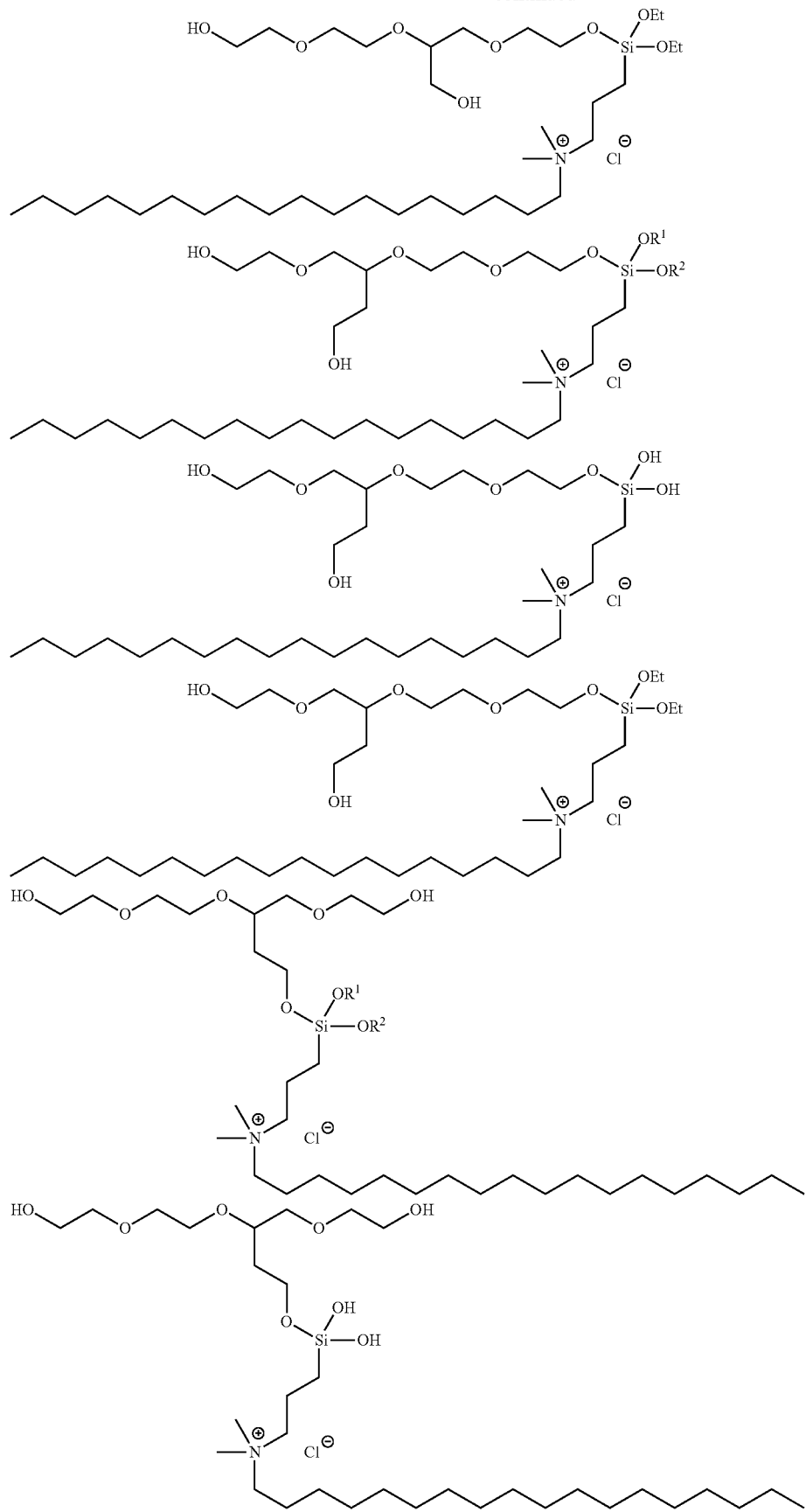

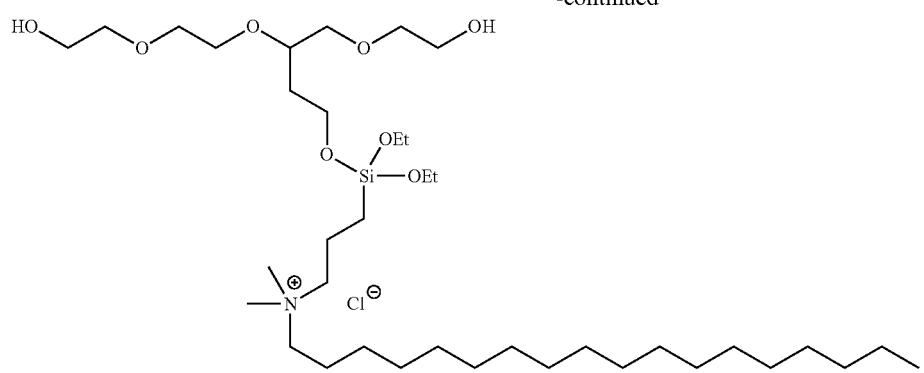
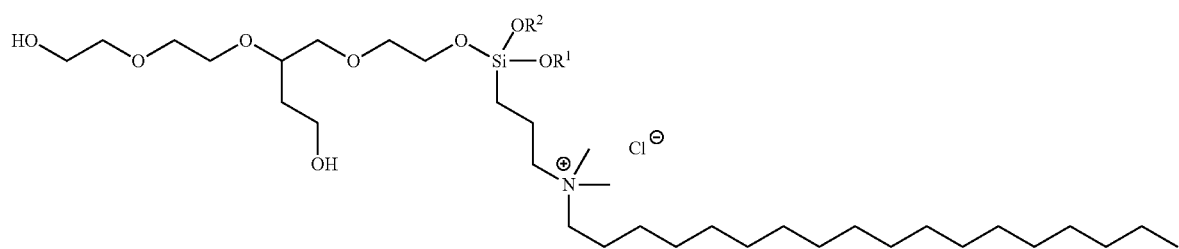
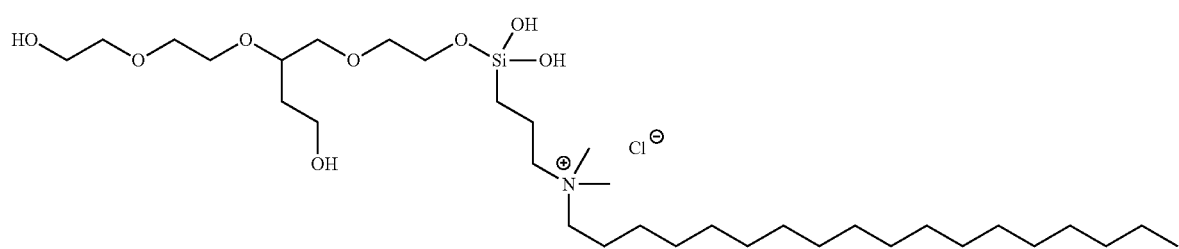
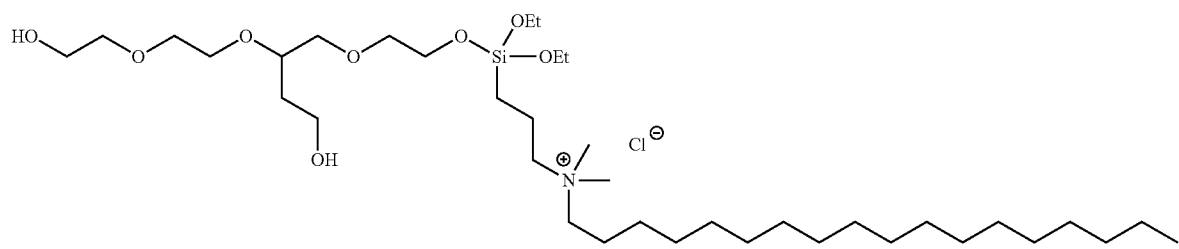

-continued
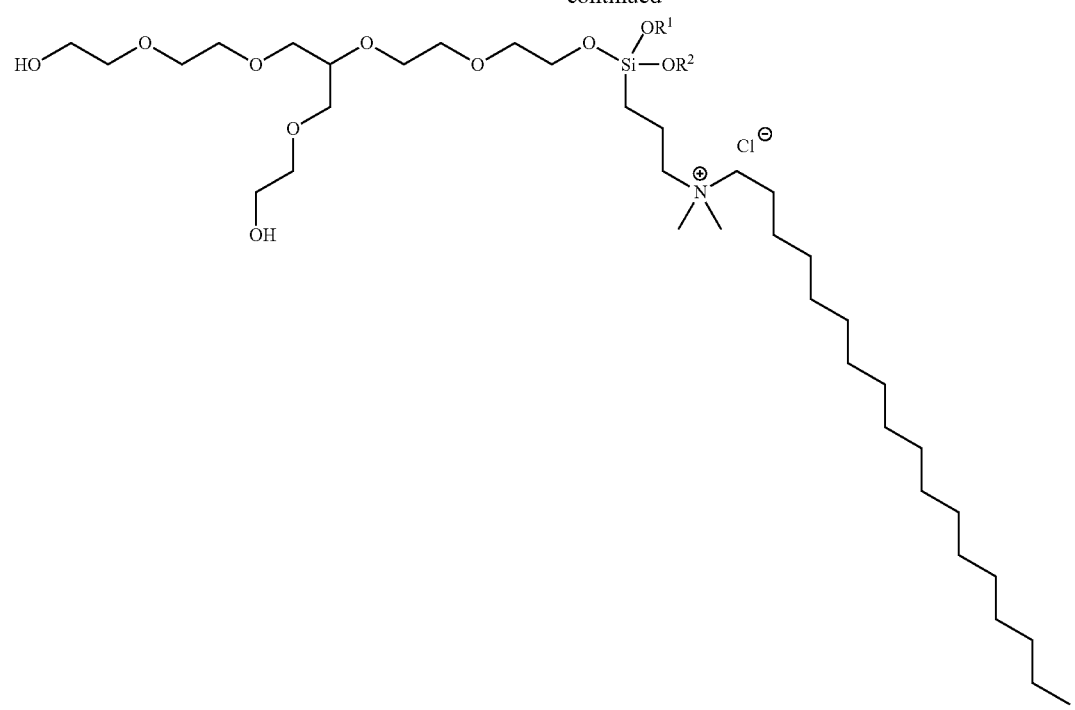
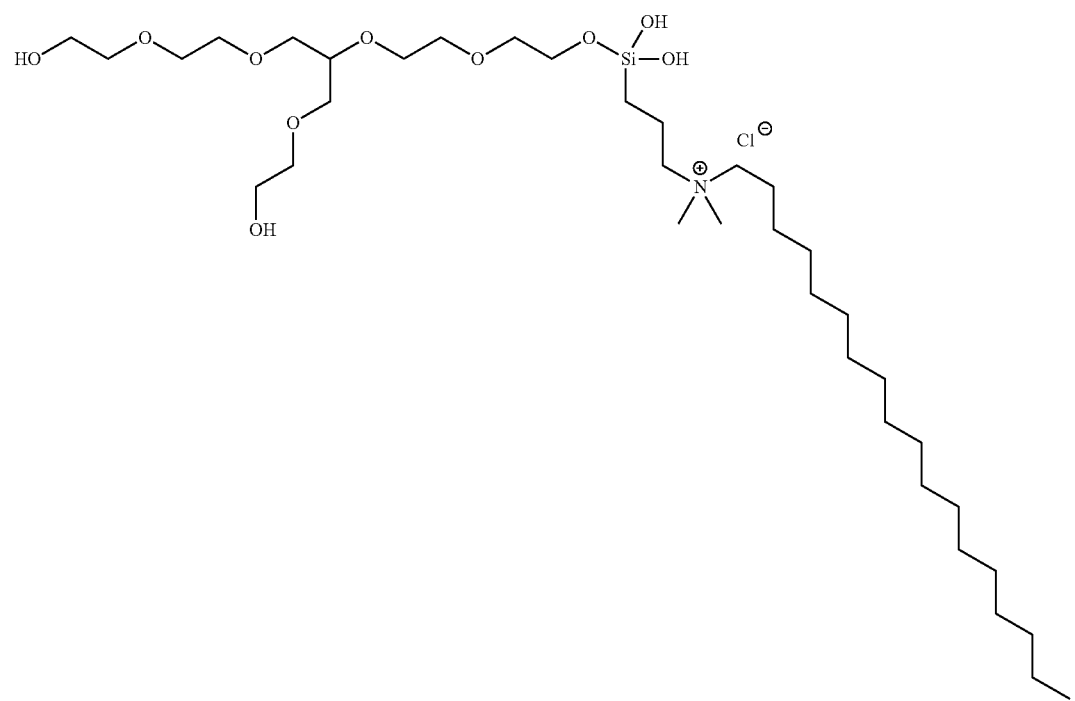

-continued
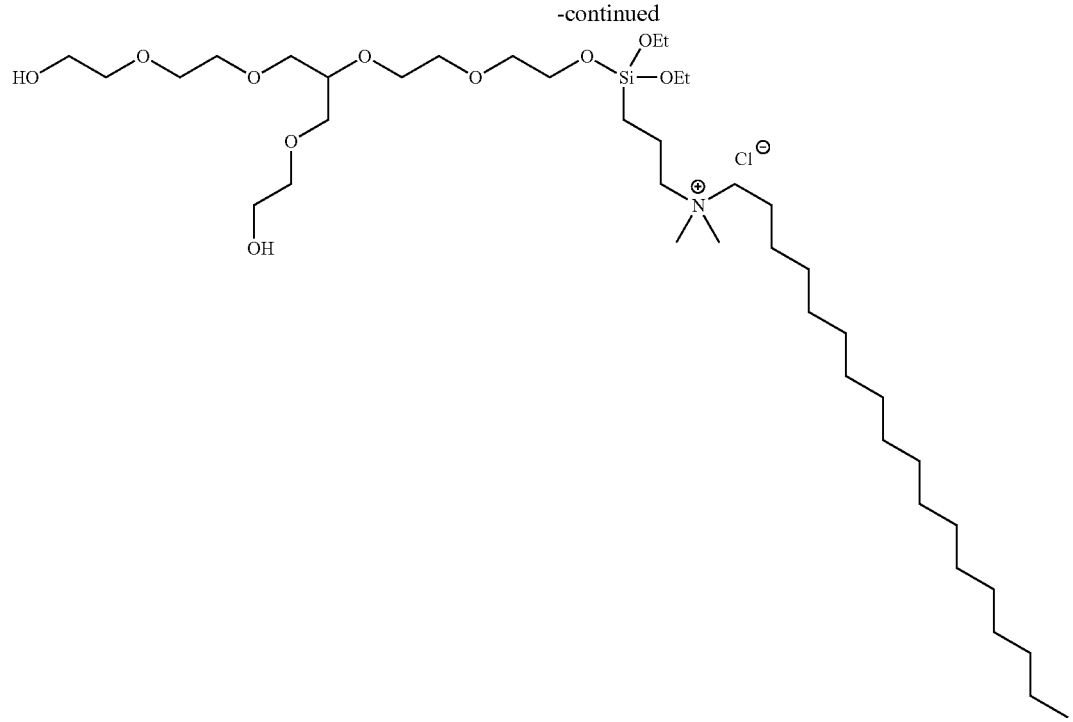
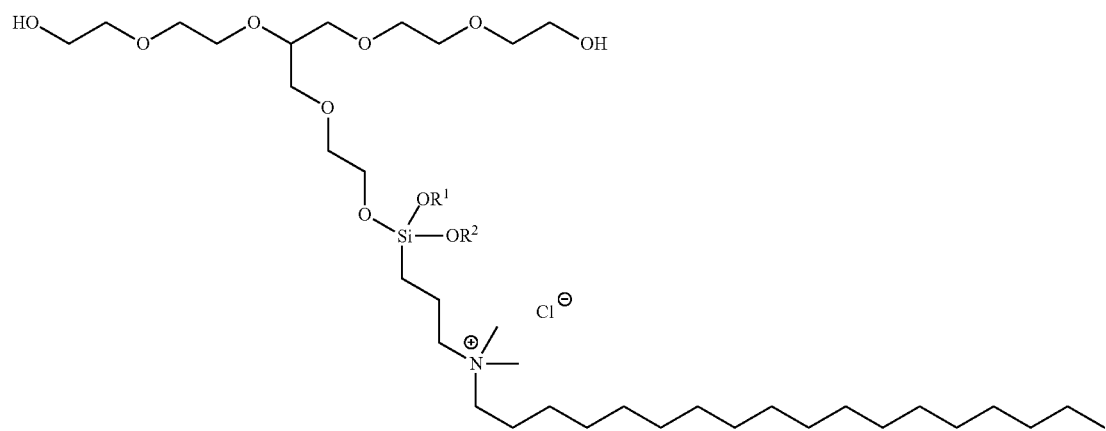
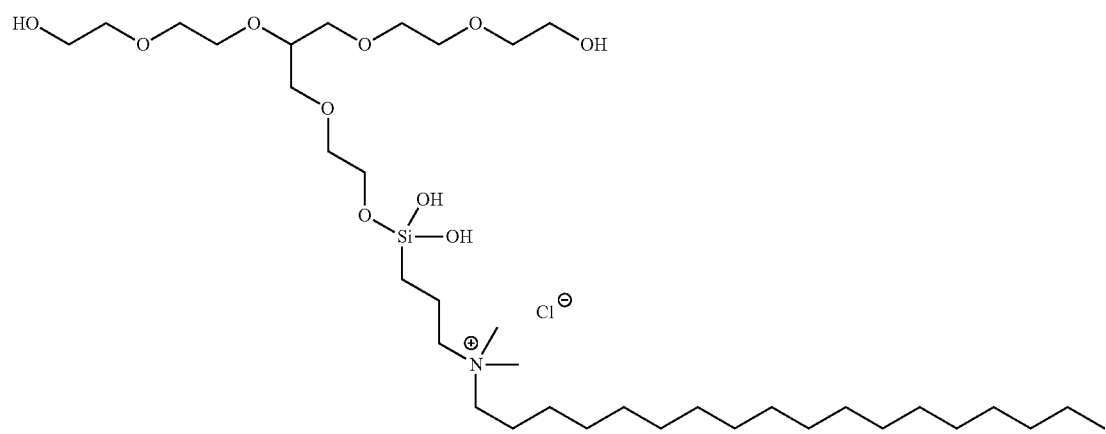

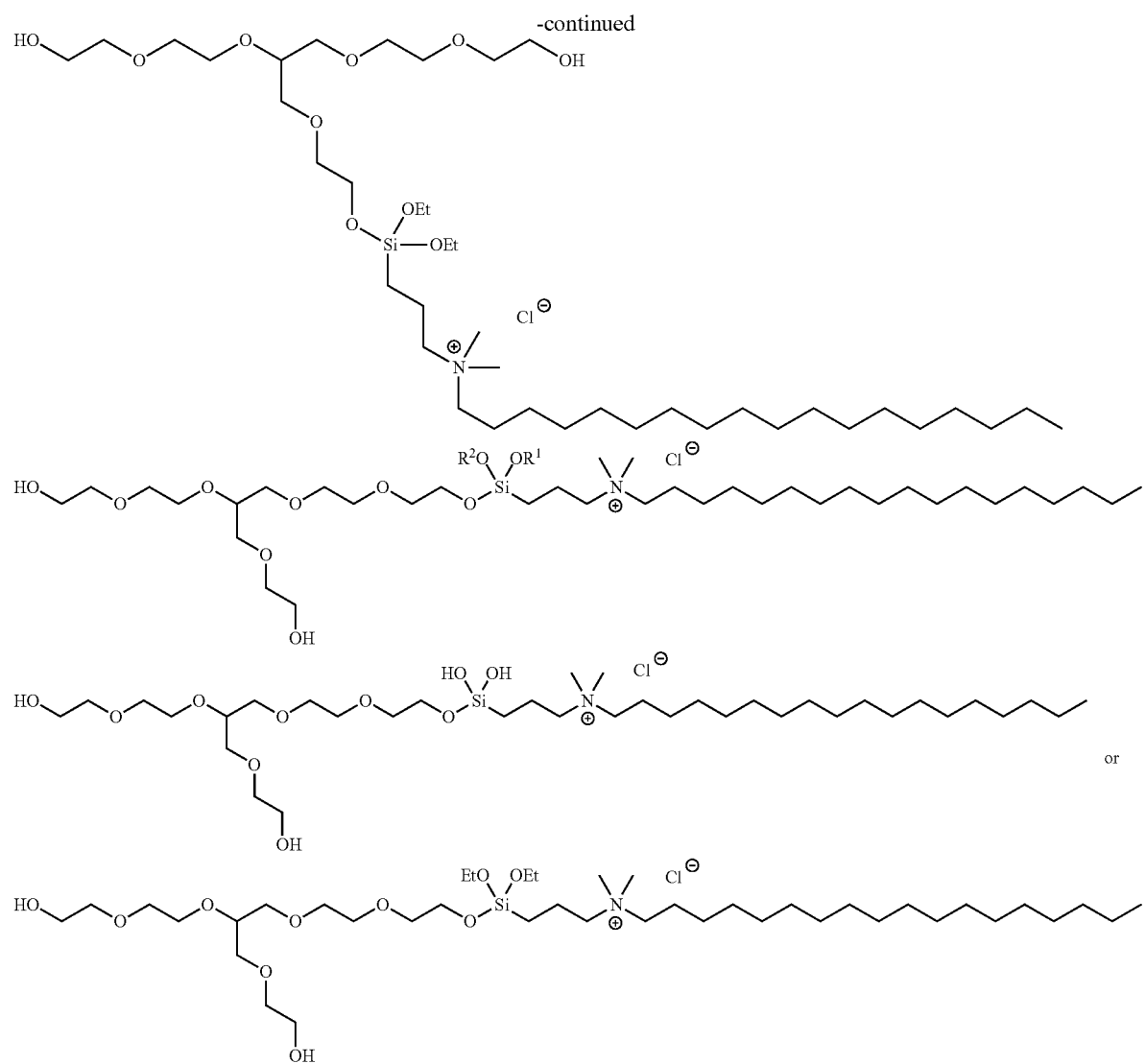
Non-limiting examples of quaternary ammonium compounds of Formula II include:
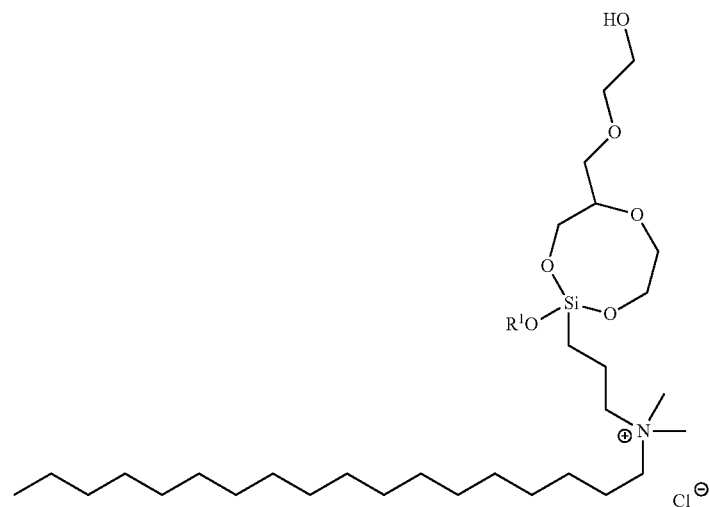

-continued
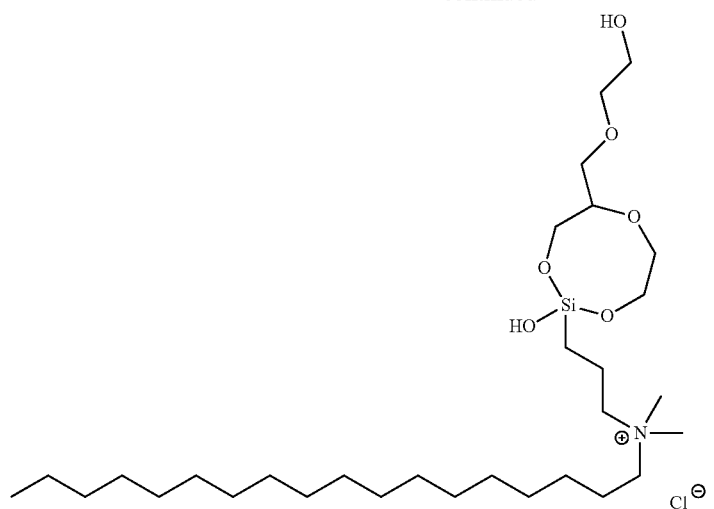
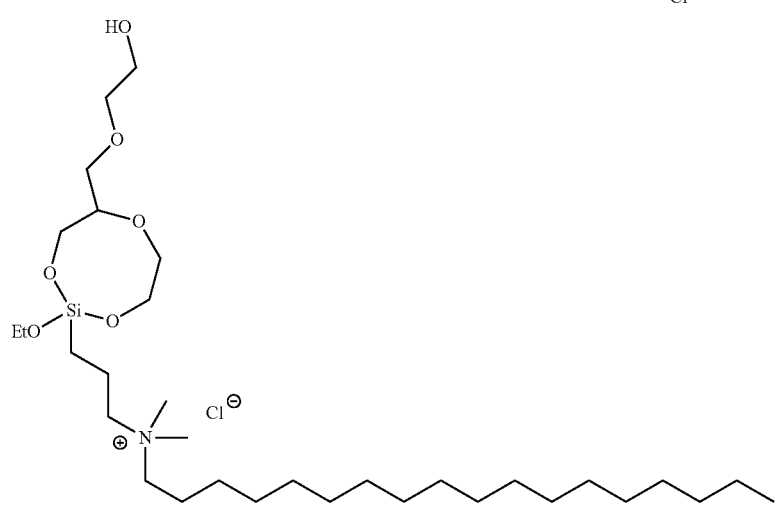
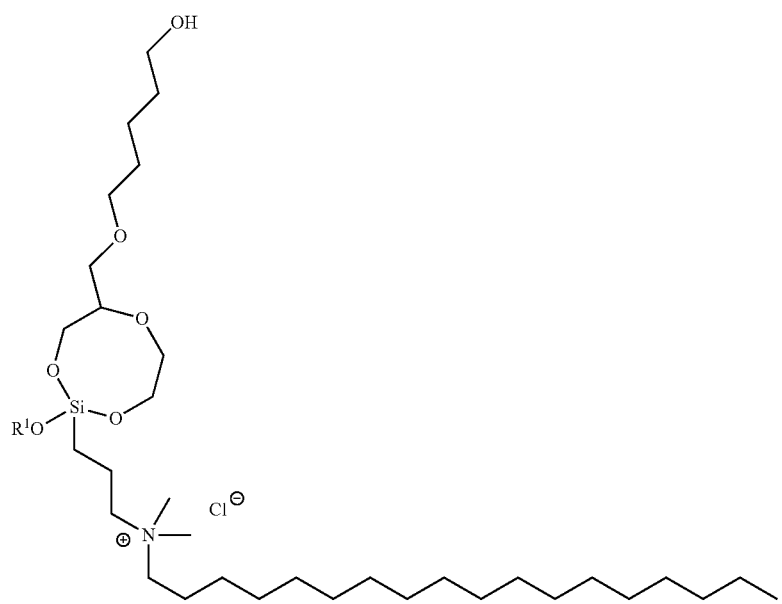

-continued
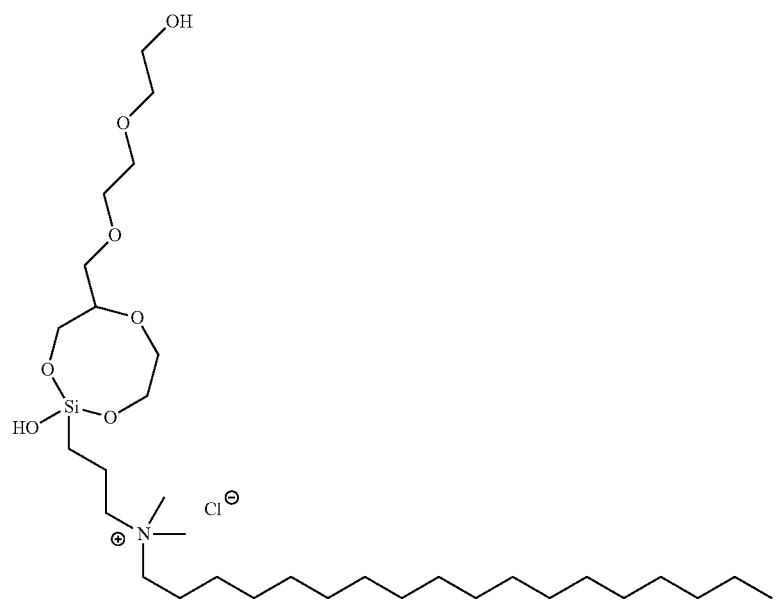
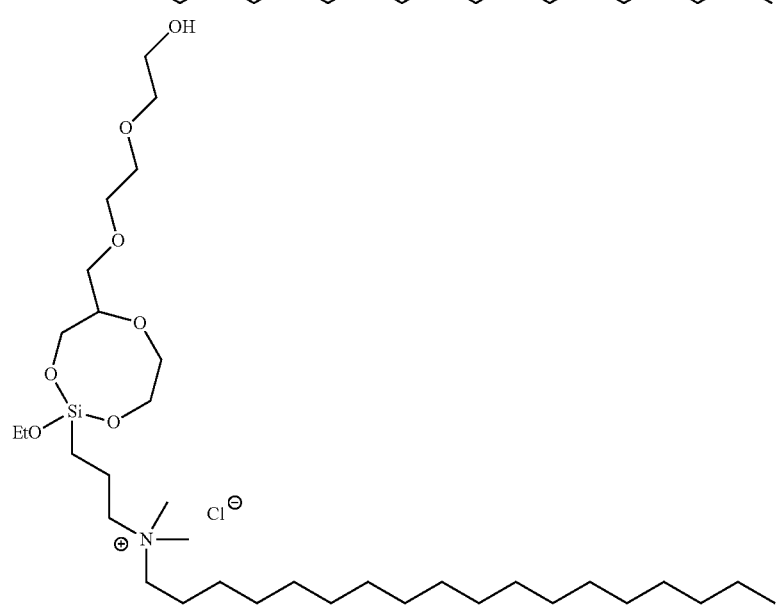
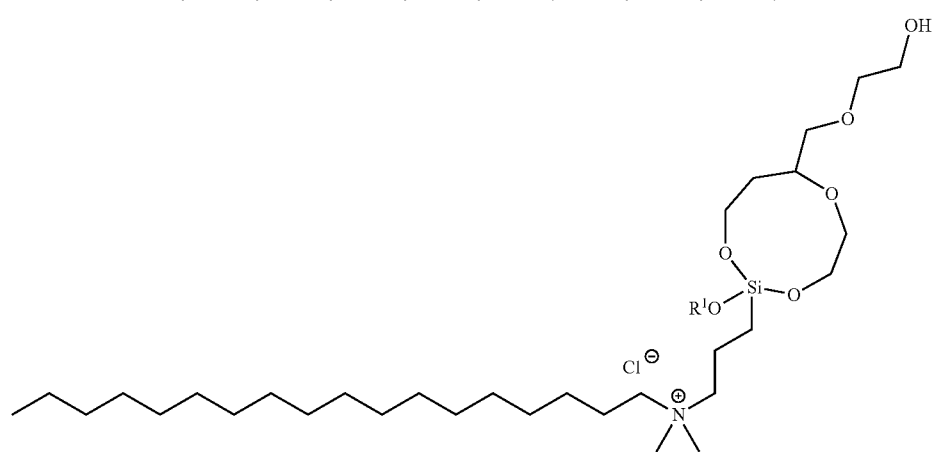

-continued
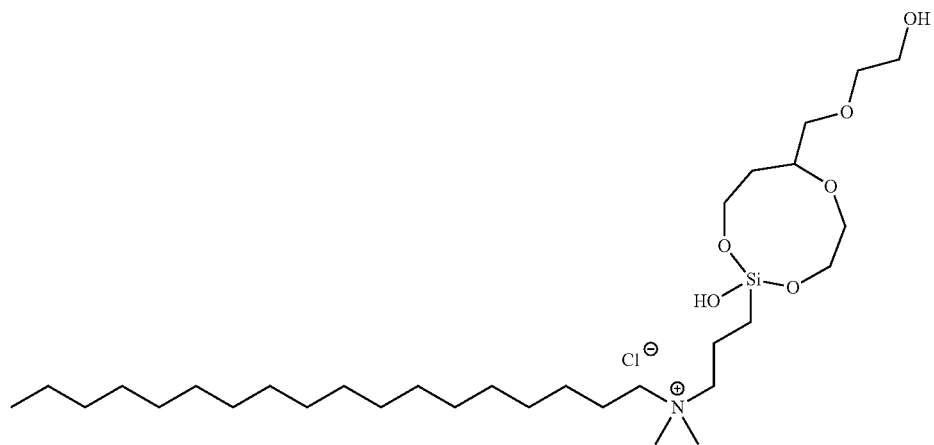
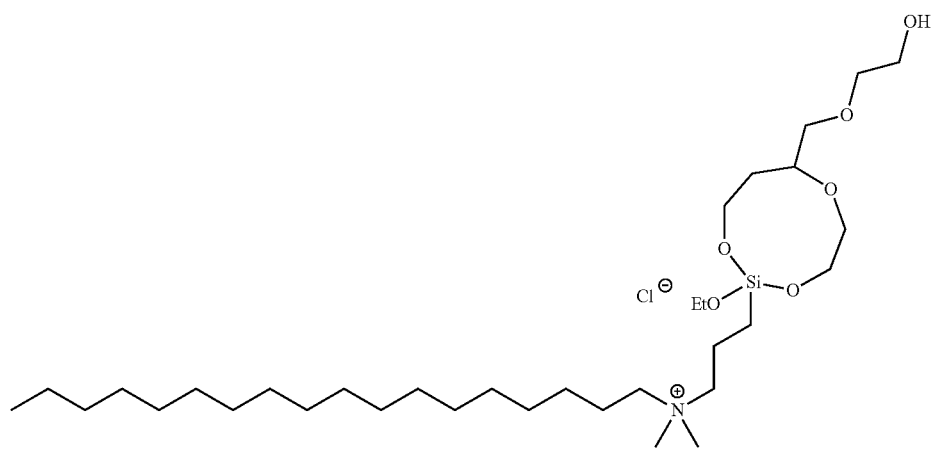
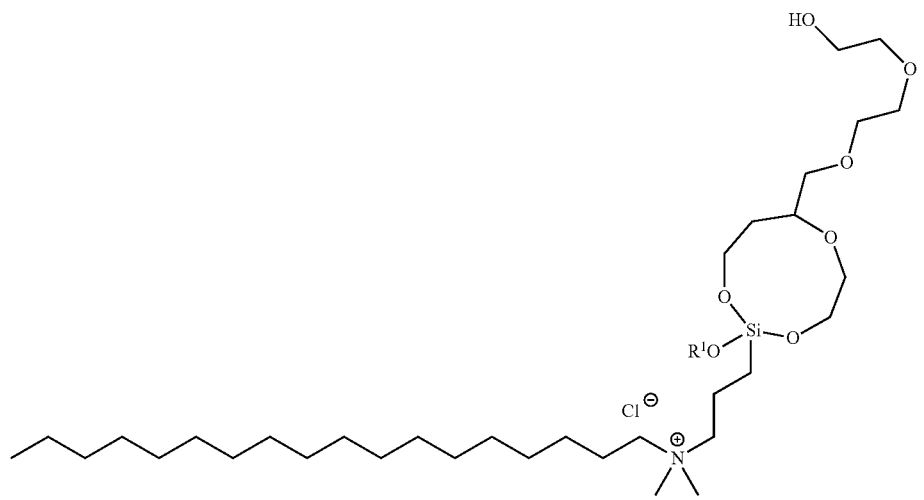 [SMILES: CCCCCCCCCCCCCCCCCC[N+](C)(C)CCC[Si]1(OCC)OCCOC(COCCOCCO)CCO1 ; [Cl-]]

-continued
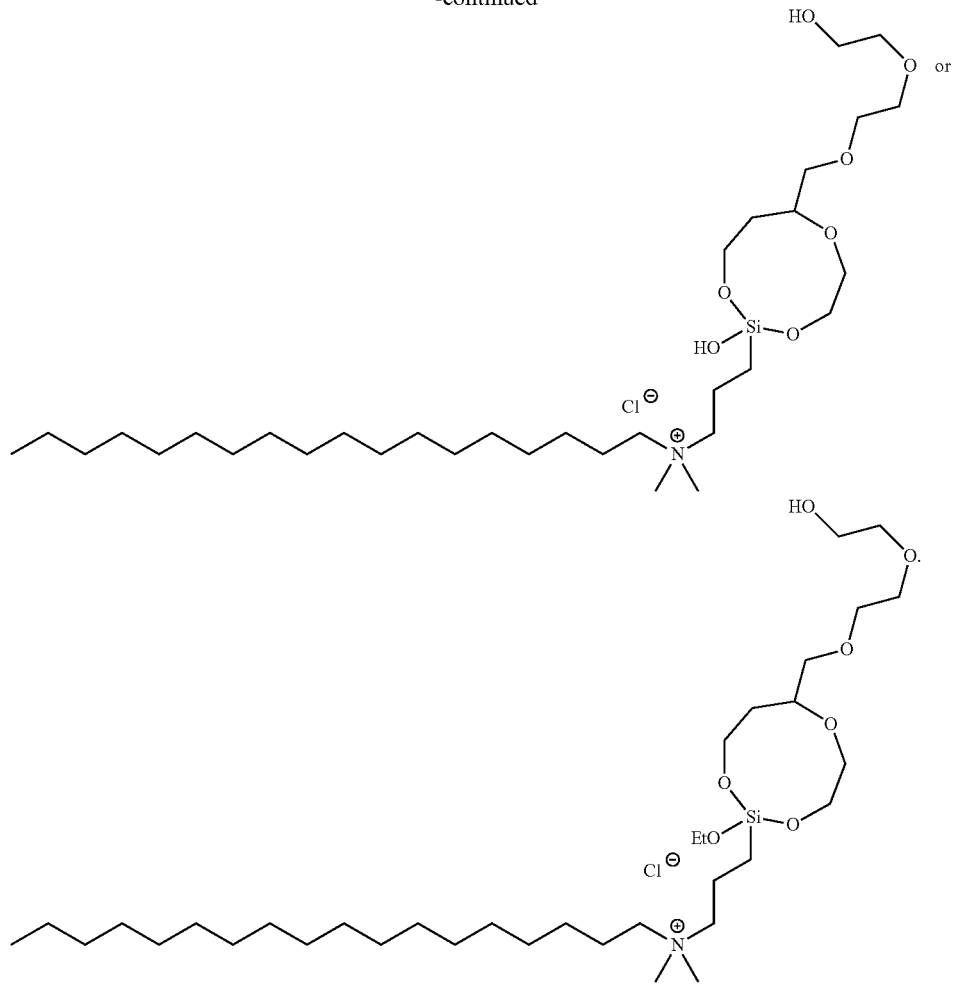
40
Non-limiting examples of quaternary ammonium compounds of Formula III include:
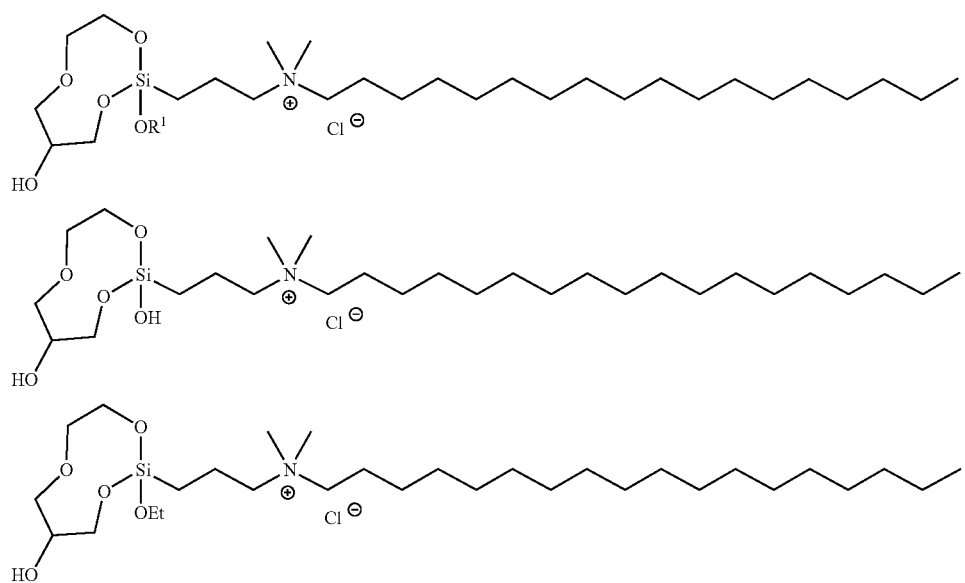

-continued
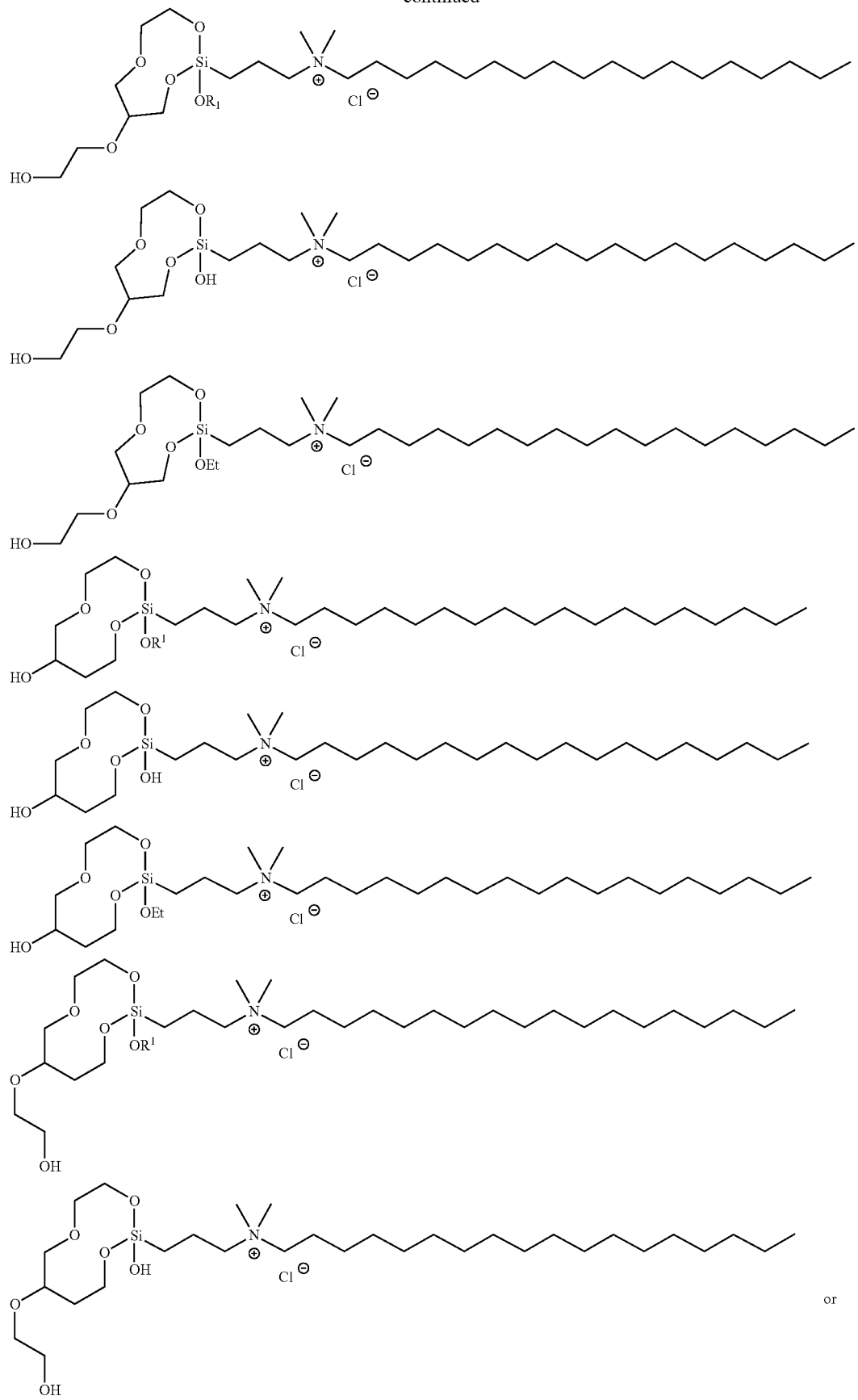

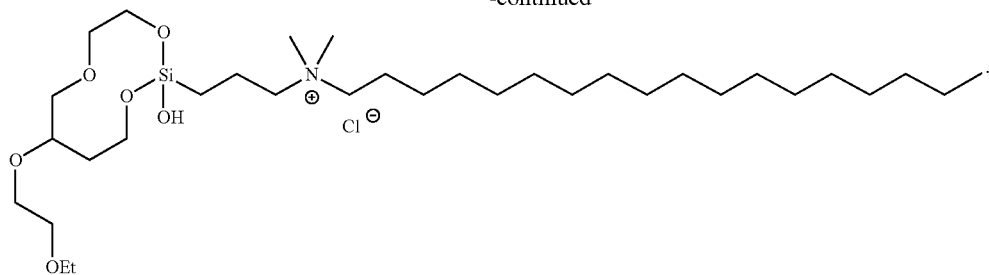
Non-limiting examples of quaternary ammonium compounds of Formula IV include:
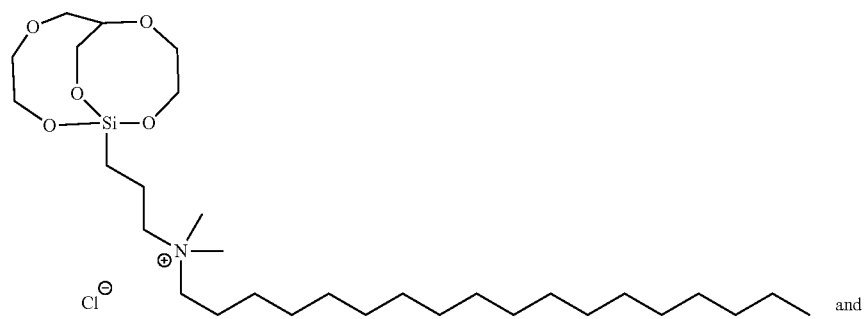
and
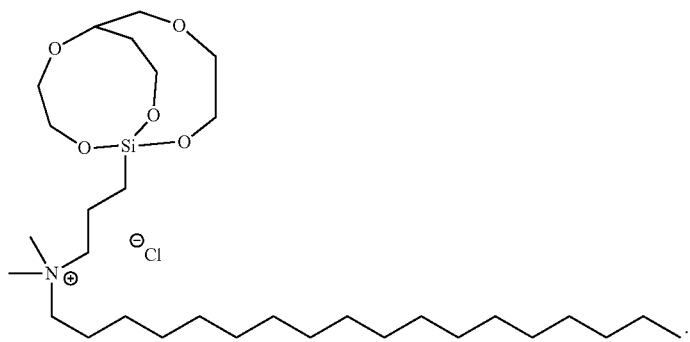
Non-limiting examples of quaternary ammonium compounds of Formula V include:
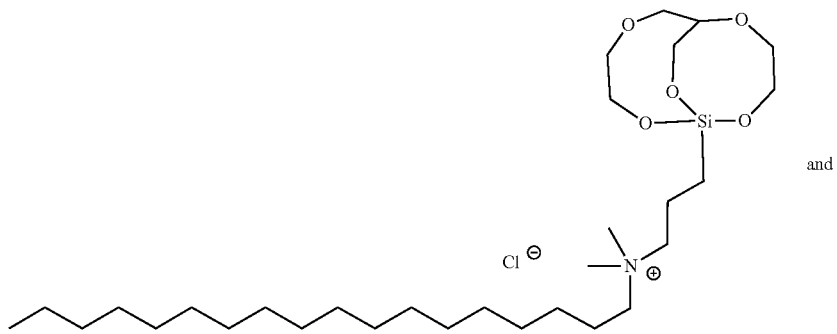
and

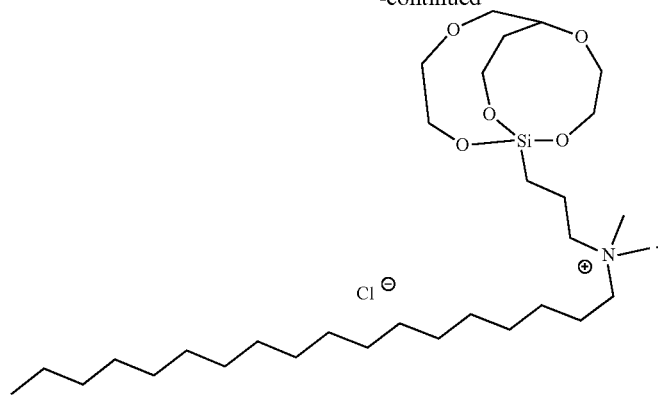
Non-limiting examples of quaternary ammonium compounds of Formula VI include:
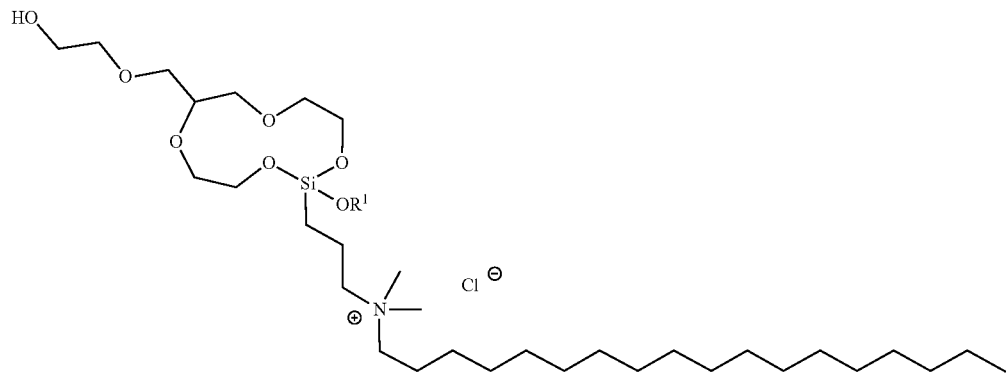
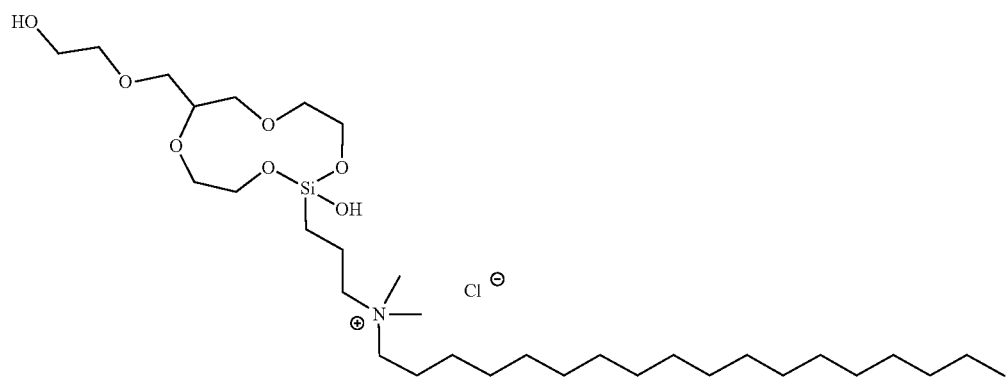
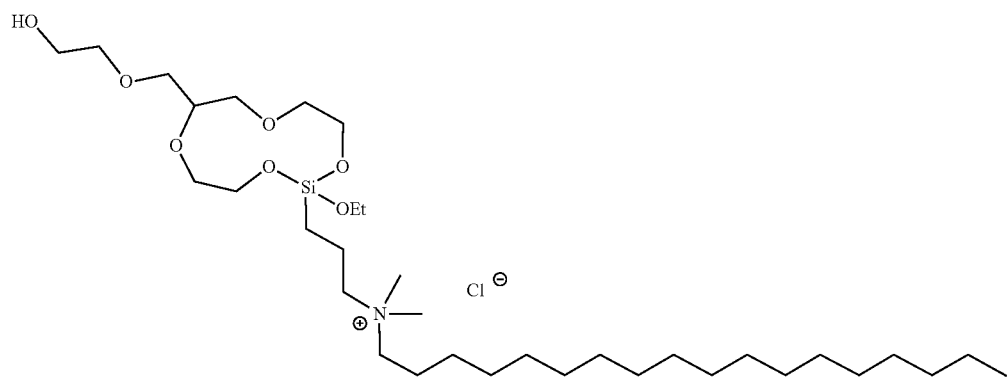

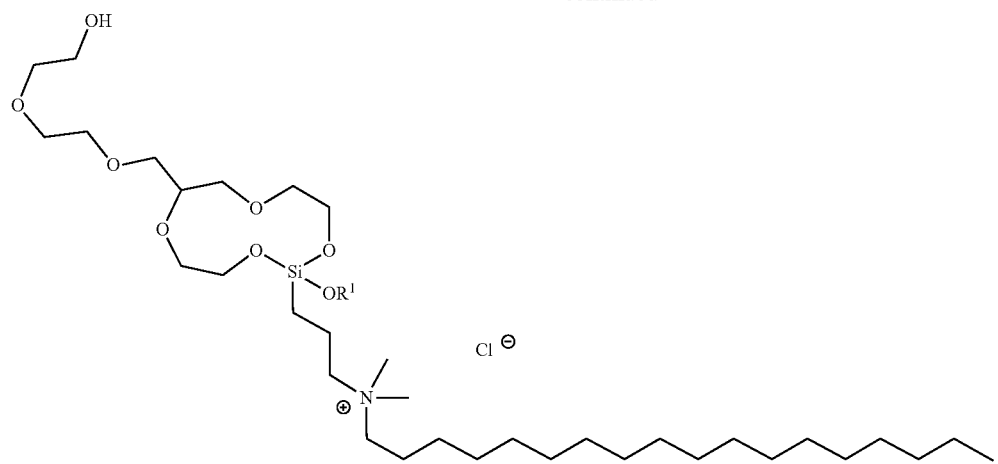
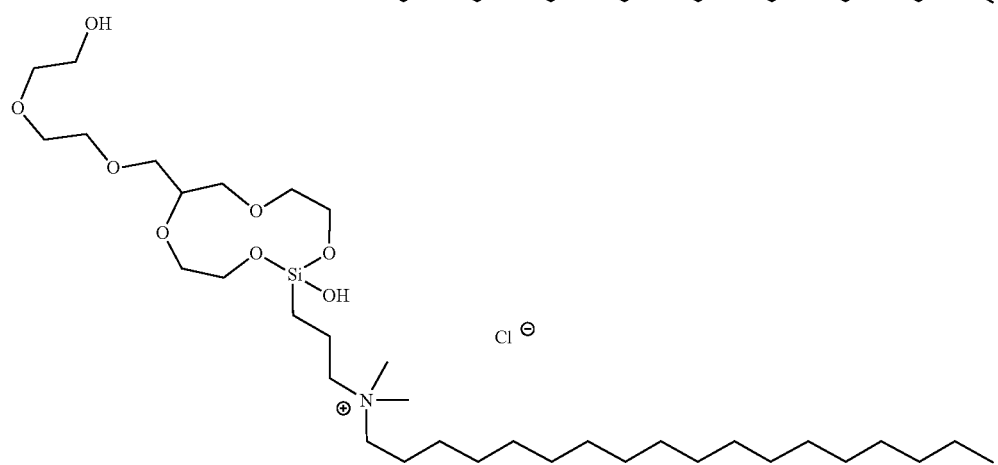
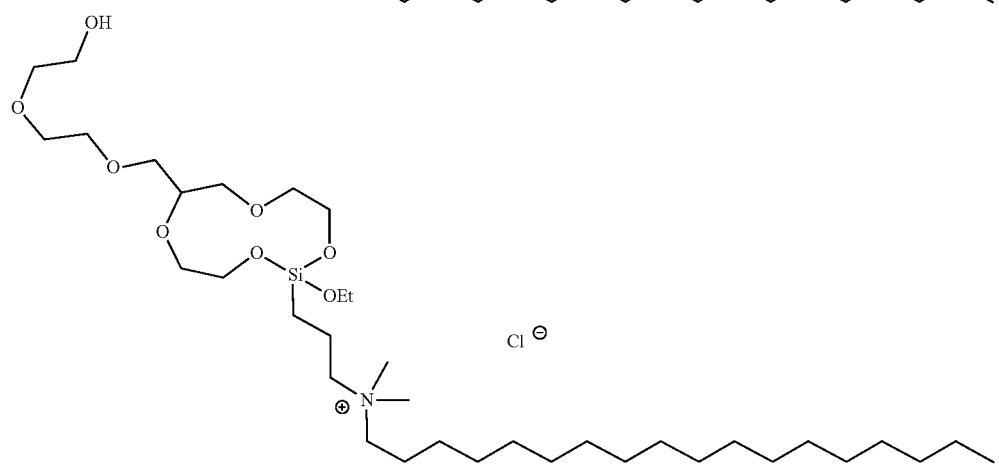
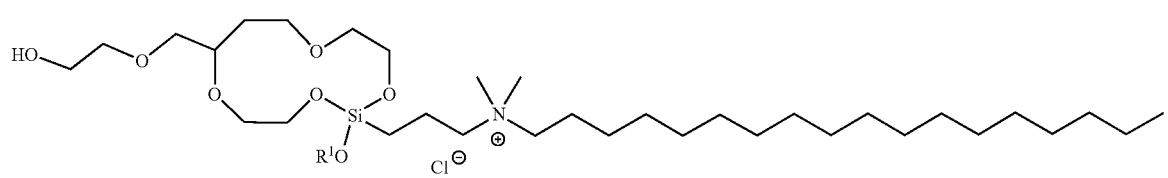
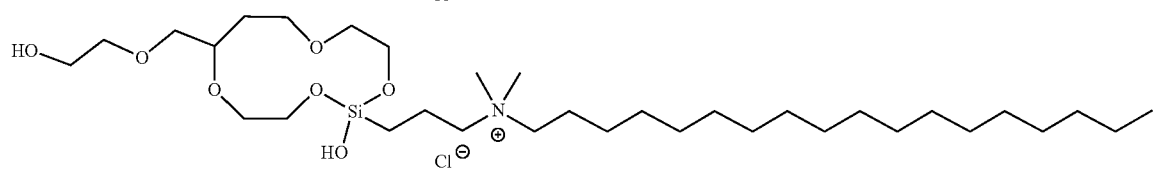

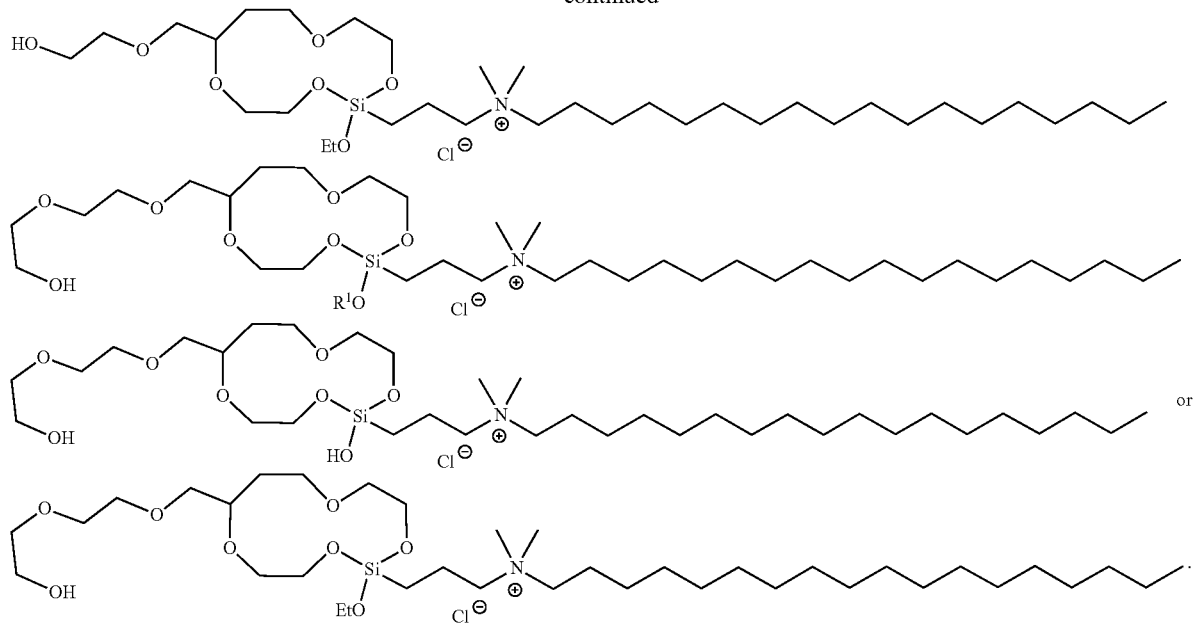
Non-limiting examples of quaternary ammonium compounds of Formula VII include:
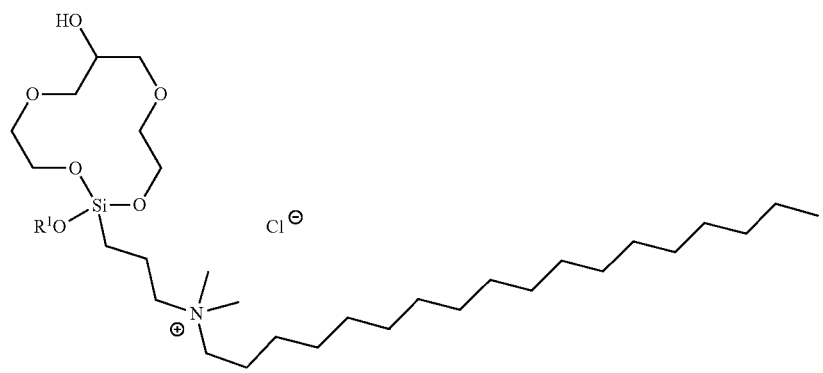
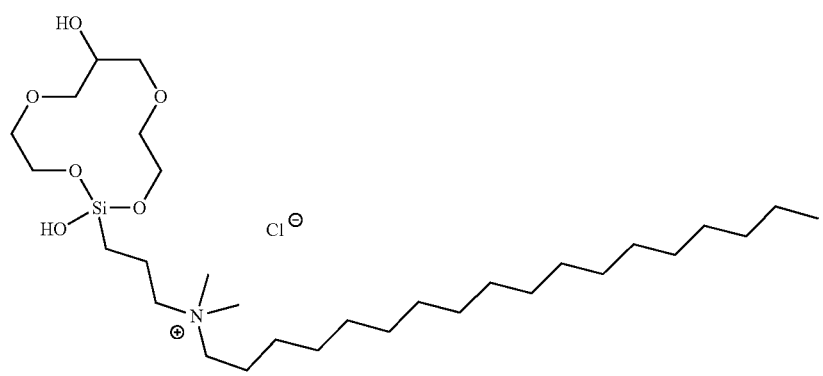

-continued
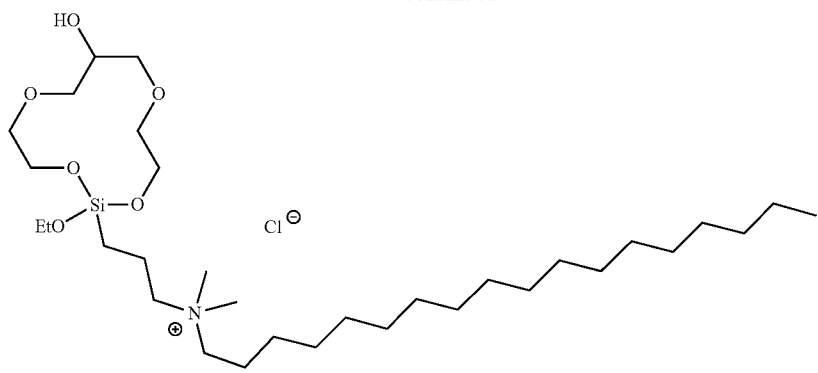
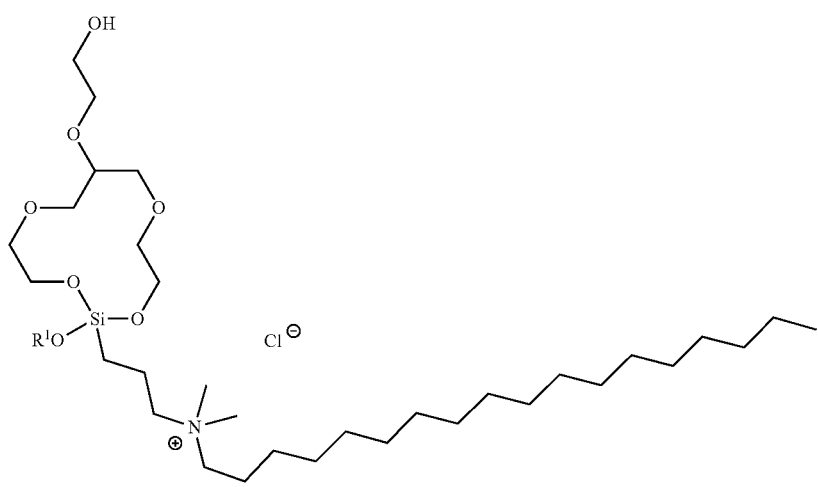
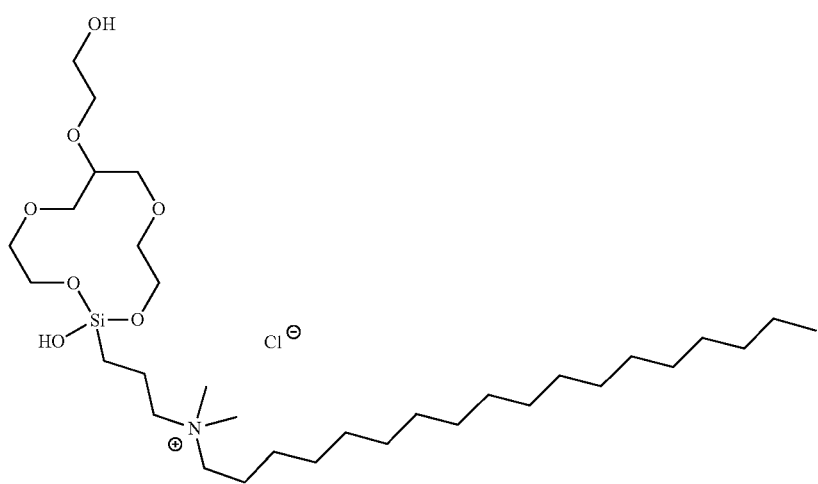
or

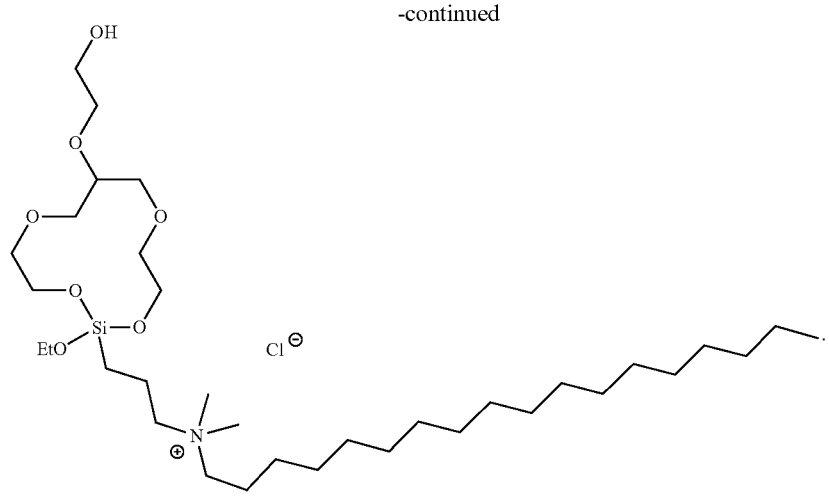
Non-limiting examples of quaternary ammonium compounds of Formula VIII include:
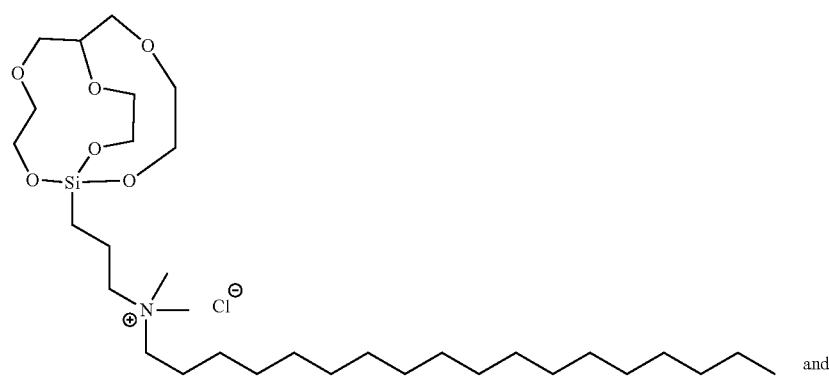
and
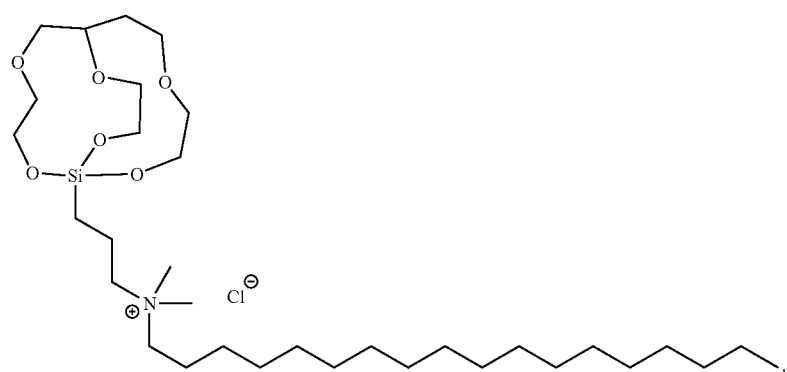

Non-limiting examples of quaternary ammonium compounds of Formula IX include:
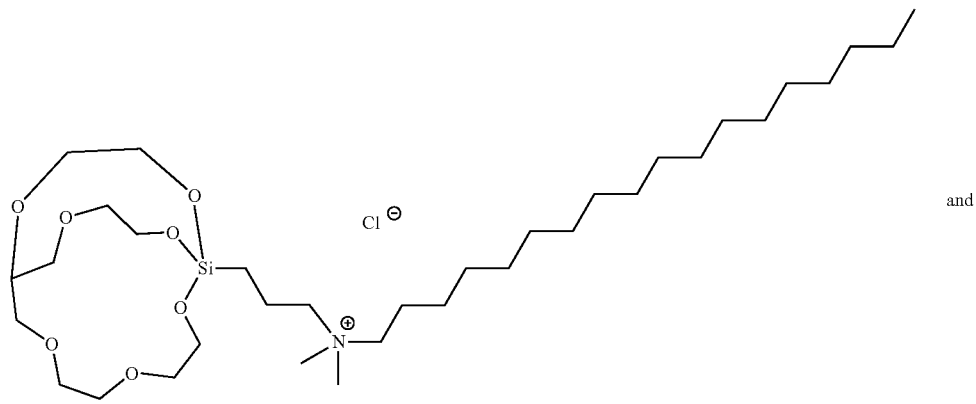
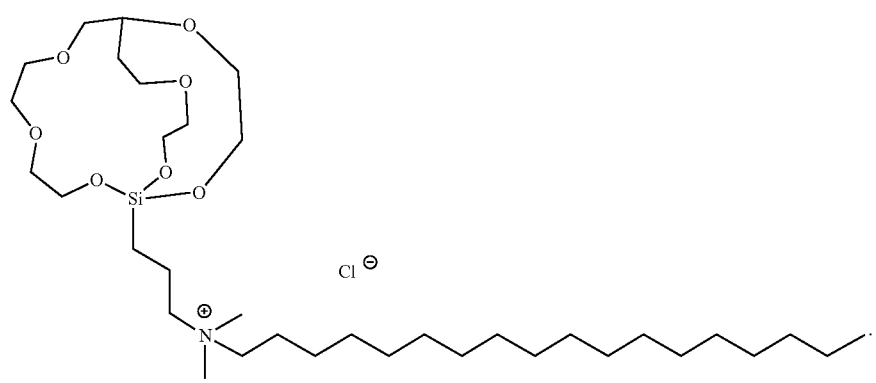
Non-limiting examples of quaternary ammonium compounds of Formula XI include:
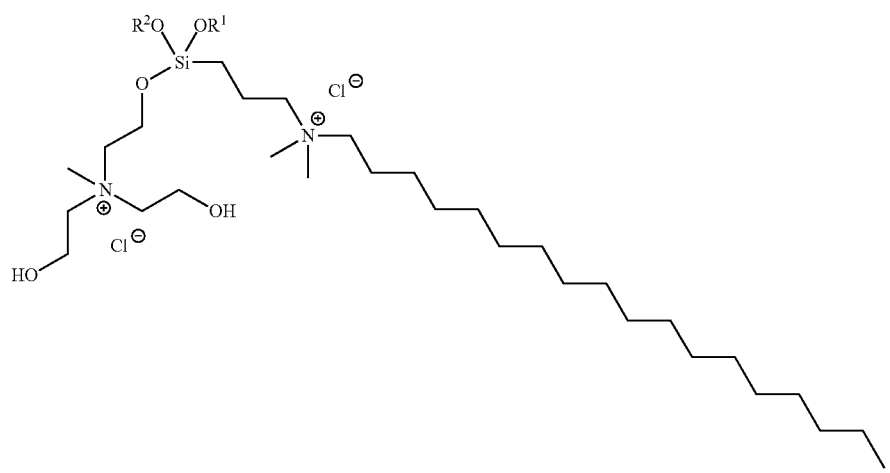

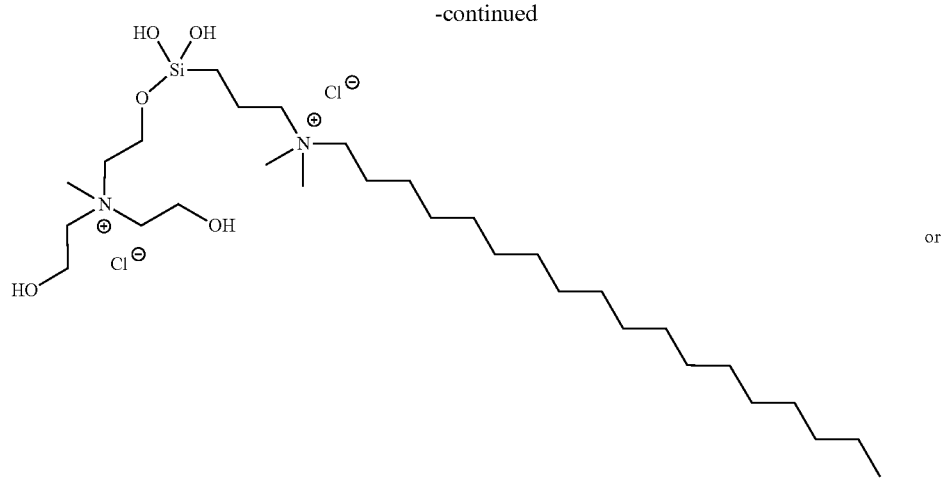
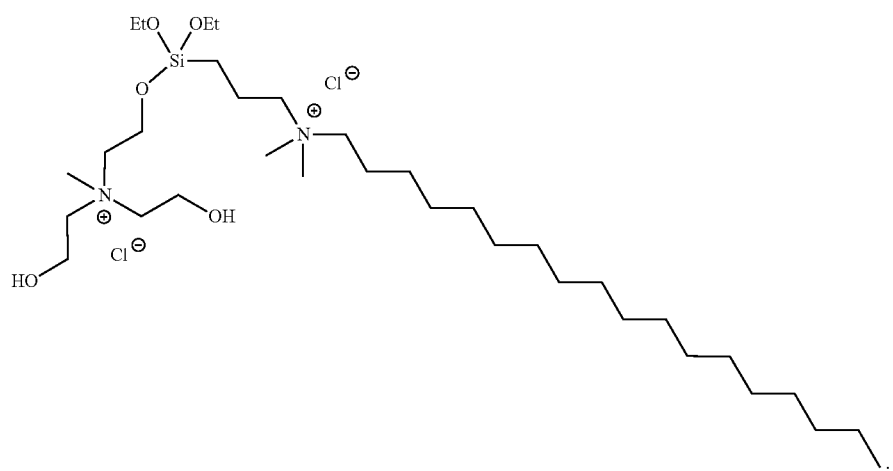
Non-limiting Examples of quaternary ammonium compounds of Formula XII include:
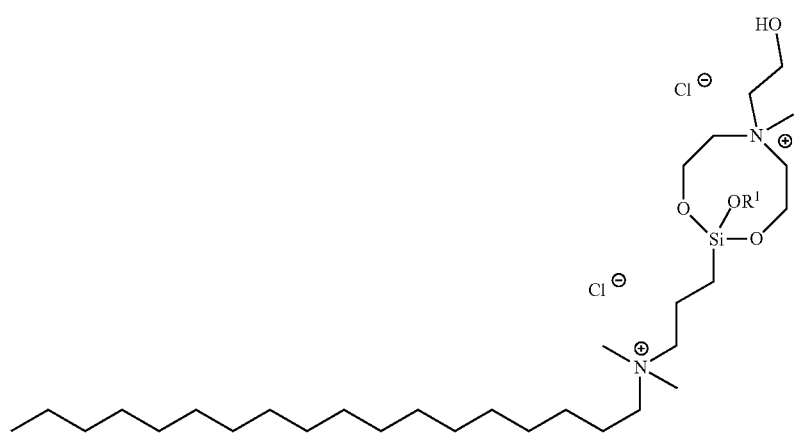

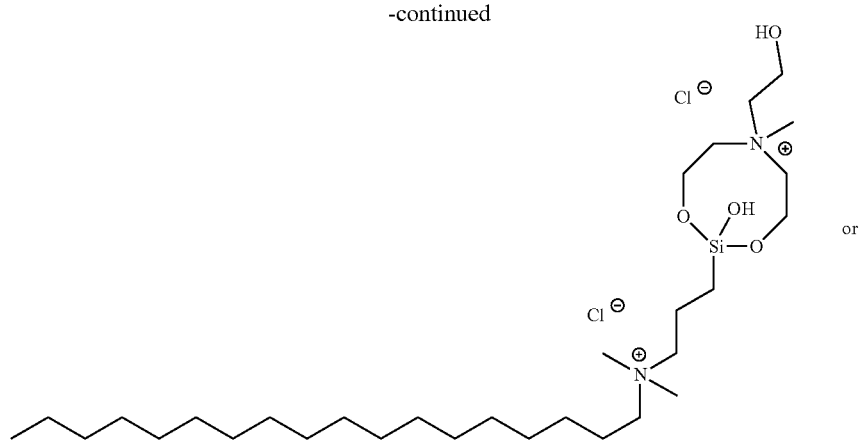
or
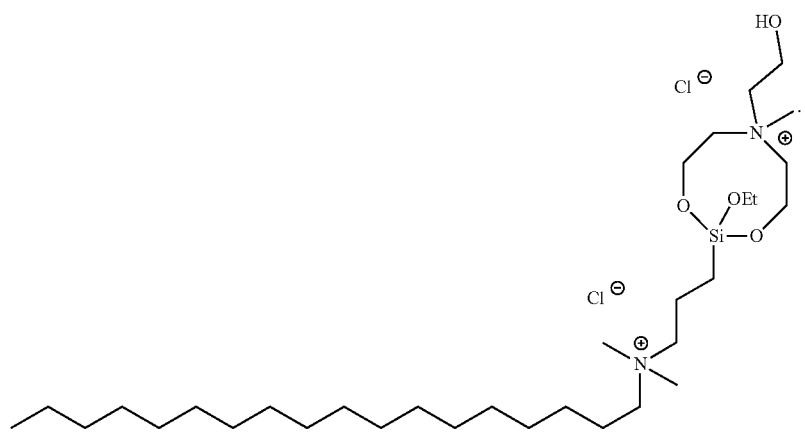
In one embodiment, the quaternary ammonium compound of Formula XIII is of the formula
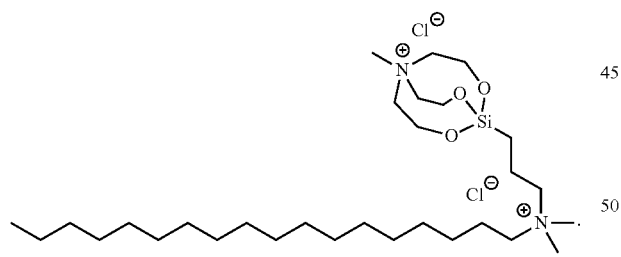
In one embodiment, the quaternary ammonium compound of Formula XIV is of the formula:
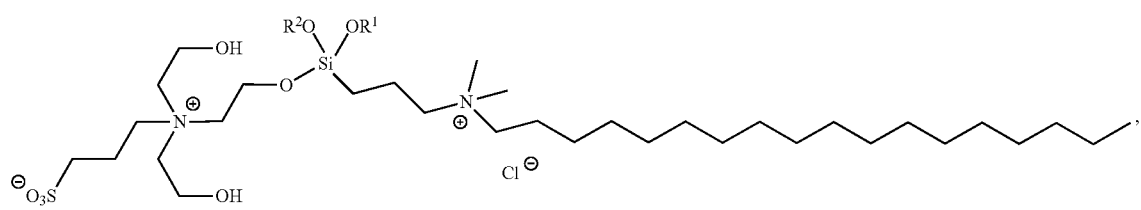

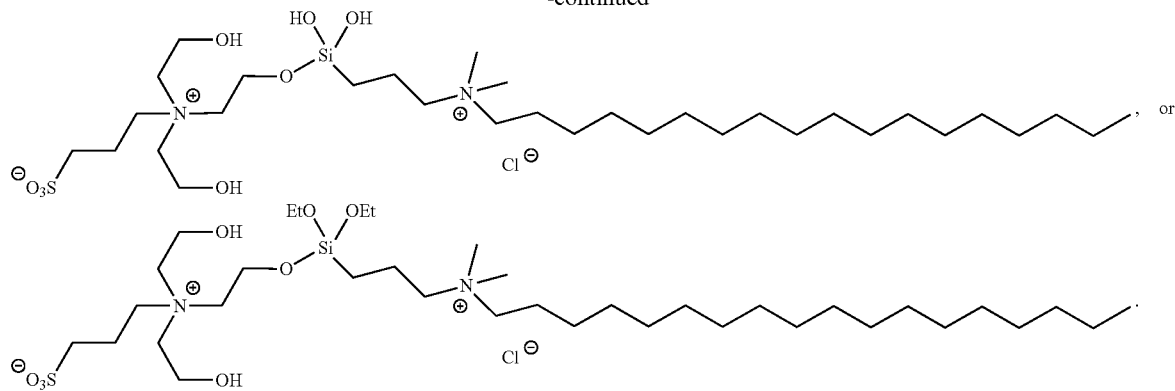
, or
In one embodiment, the quaternary ammonium compound of Formula XIV is of the formula:
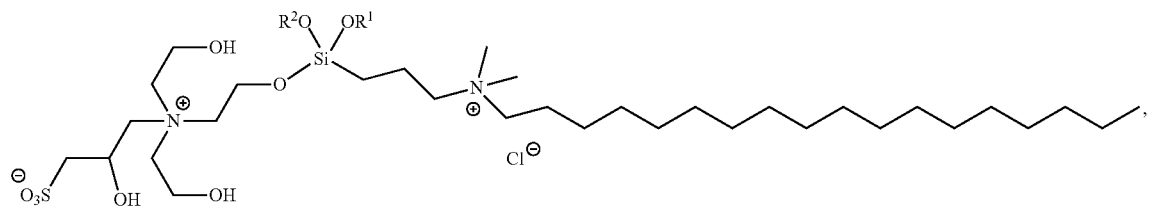
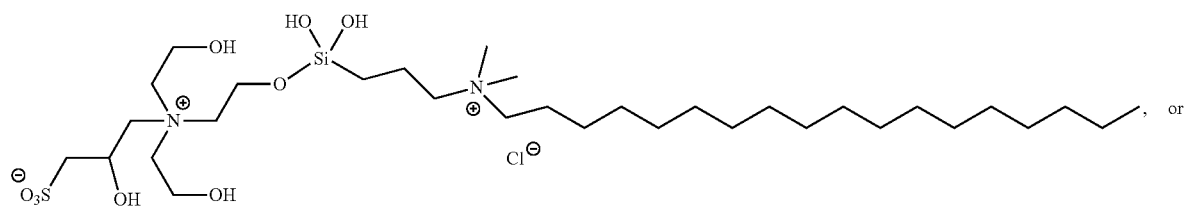
, or
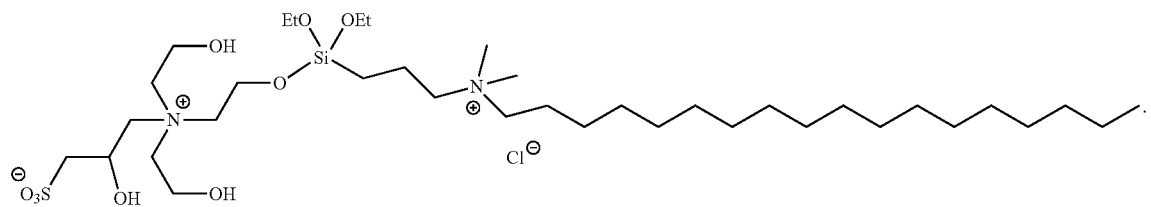
In one embodiment, the quaternary ammonium compound of Formula XV is of the formula:
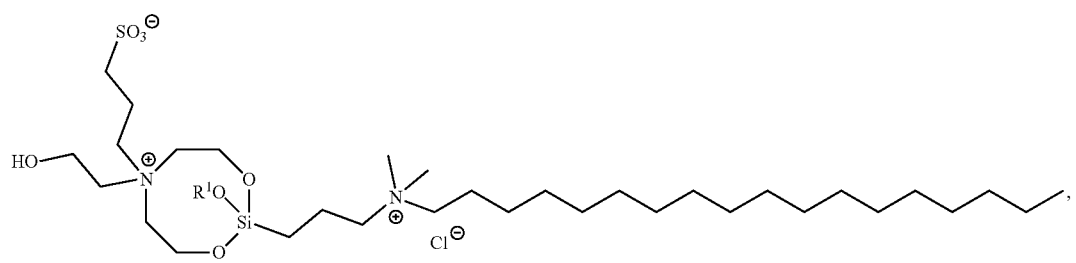

-continued
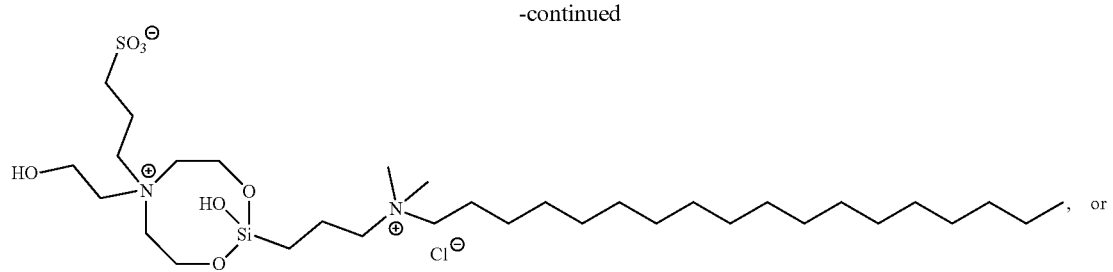, or
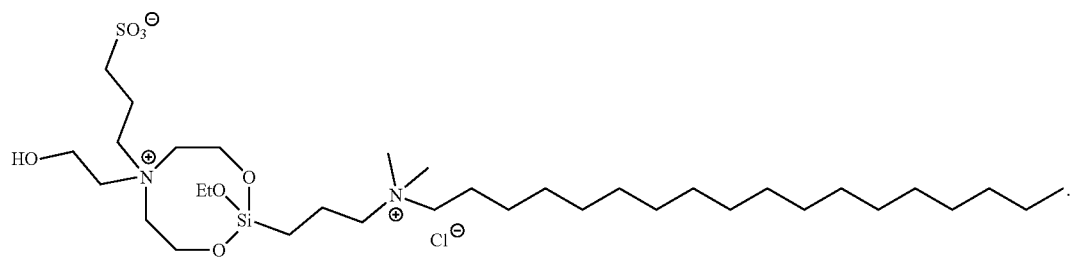.
In one embodiment, the quaternary ammonium compound of Formula XV is of the formula:
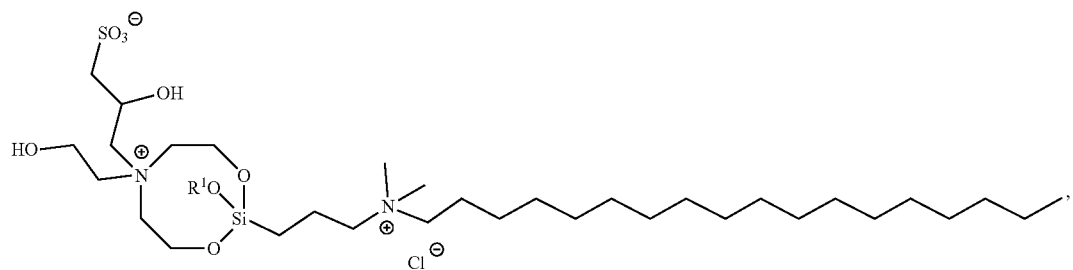,
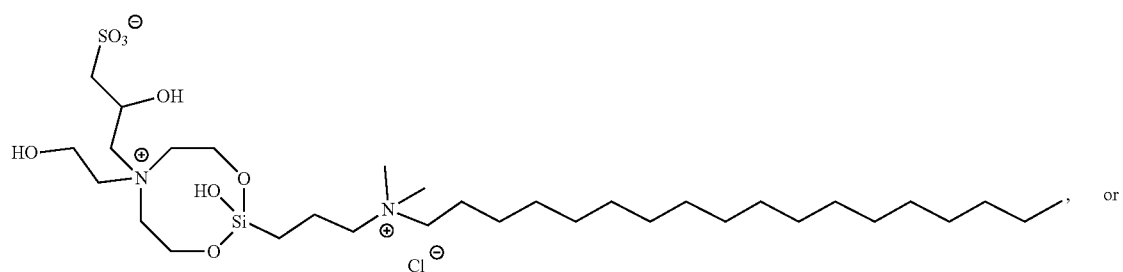, or
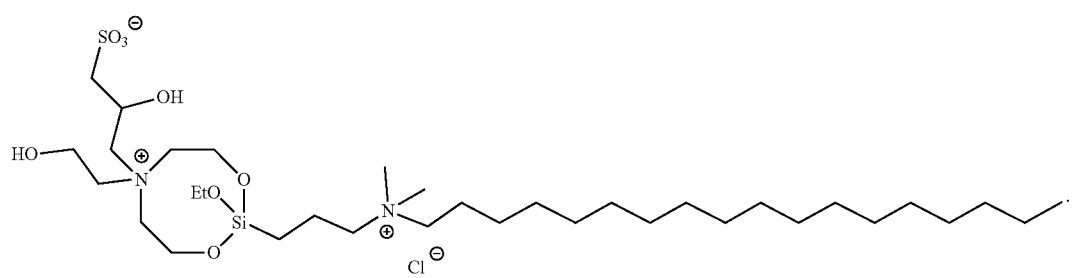.

In one embodiment, the quaternary ammonium compound of Formula XVI is of the formula
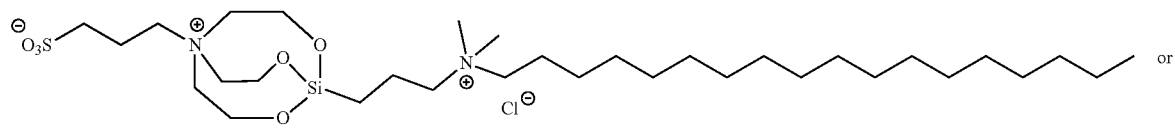
or
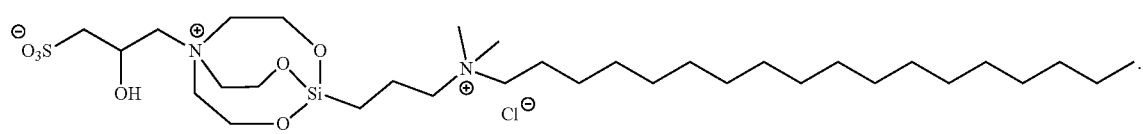
In one embodiment, the quaternary ammonium compound of Formula XVII is of the formula
-continued
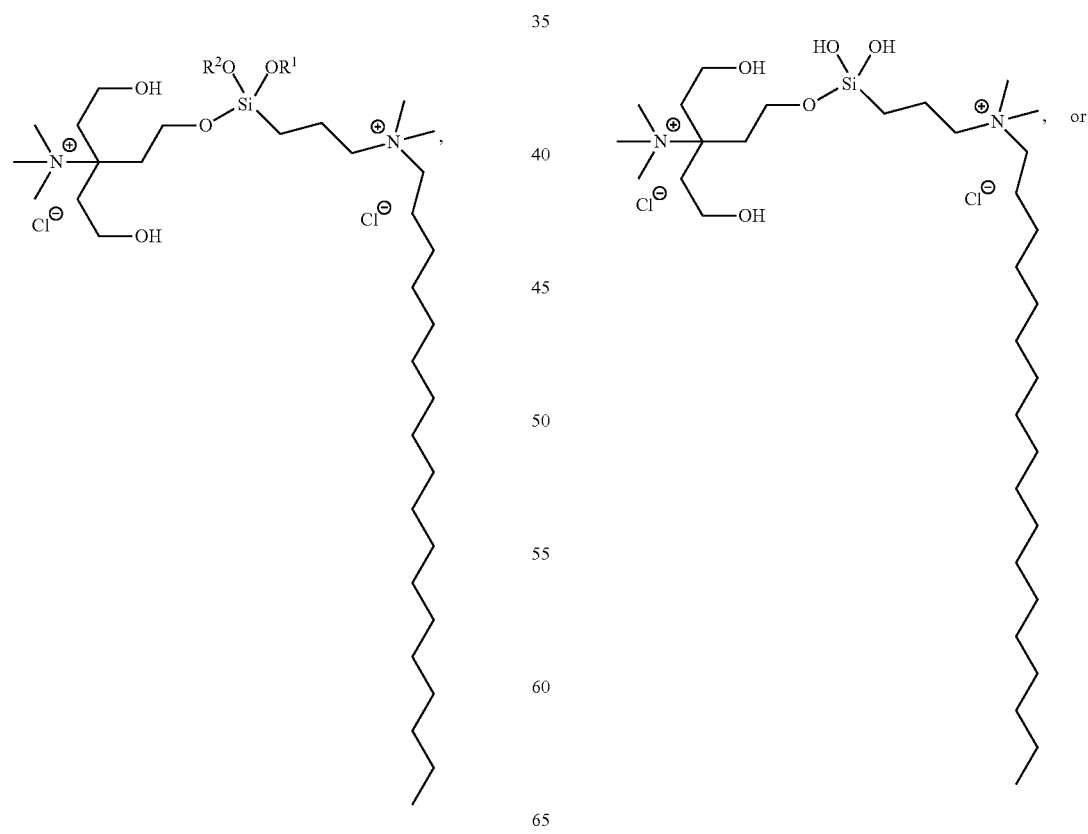

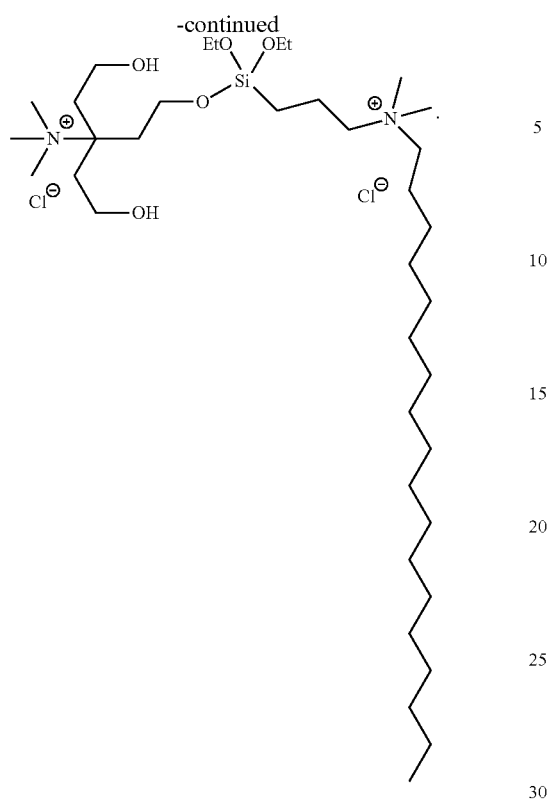
In one embodiment, the quaternary ammonium compound of Formula XVIII is of the formula
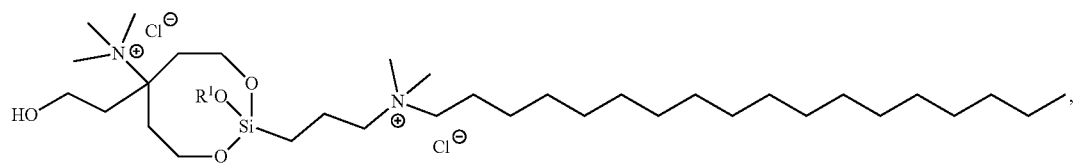
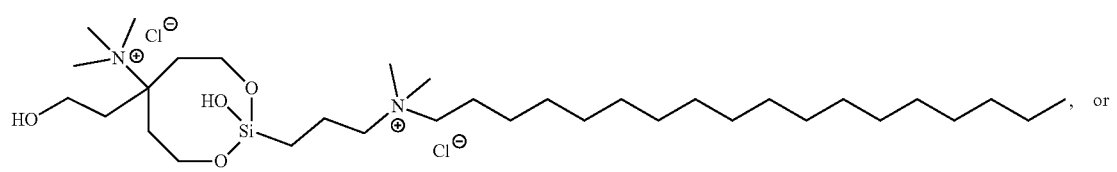, or
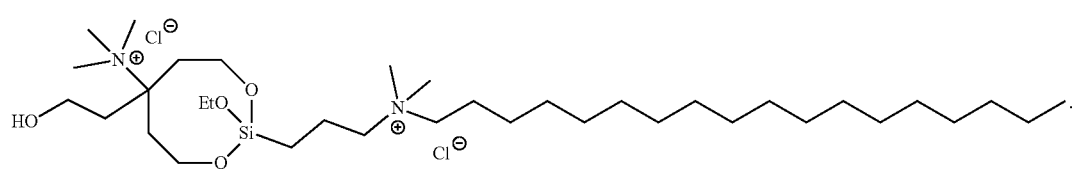

In one embodiment, the quaternary ammonium compound of Formula XIX is of the formula
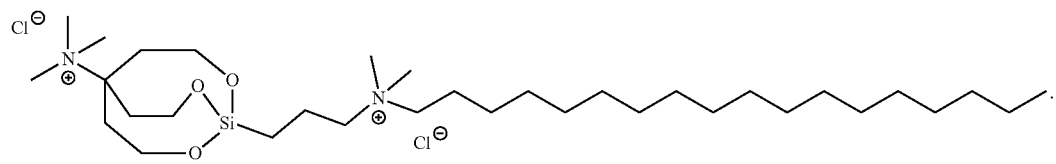 [SMILES: [Cl-] ; CCCCCCCCCCCCCCCCCC[N+](C)(C)CCC[Si]12OCCC([N+](C)(C)C)(CCO1)CCO2 ; [Cl-]]
In one embodiment, the quaternary ammonium compound of Formula XX is of the formula
-continued
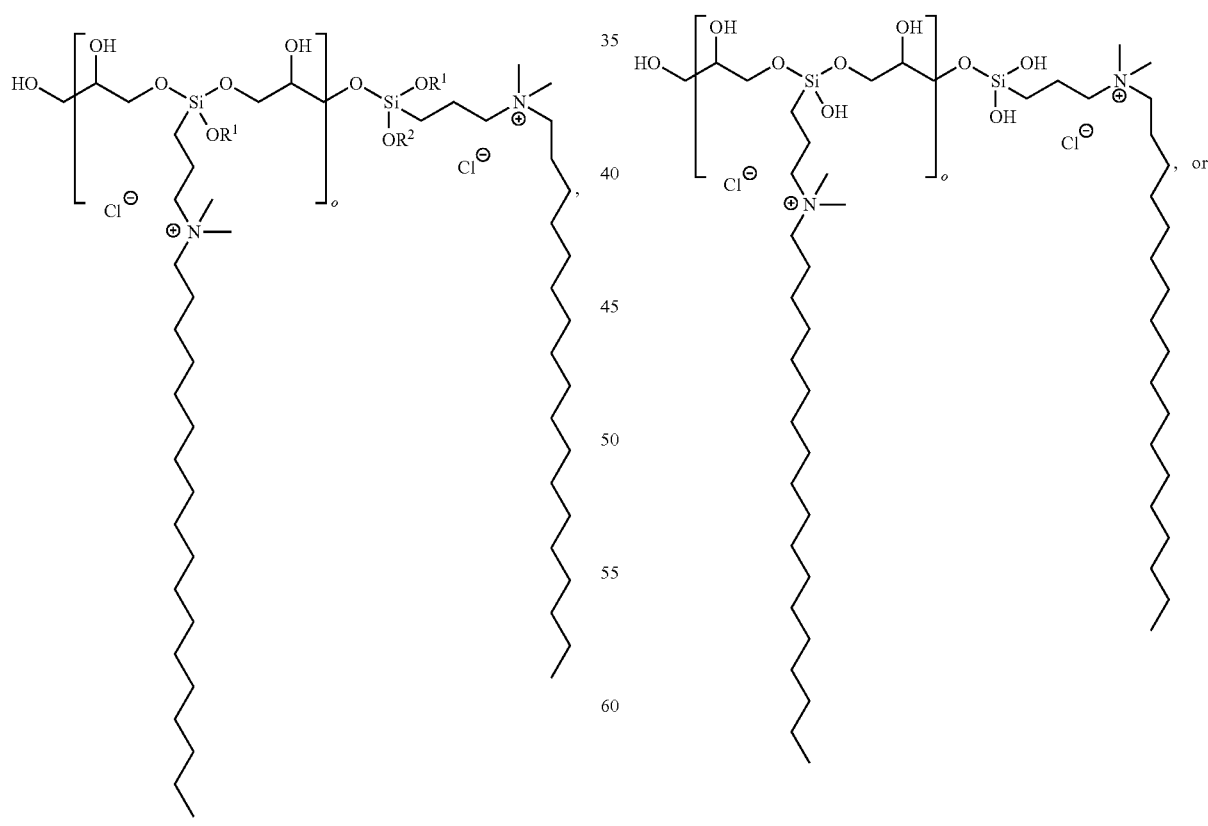

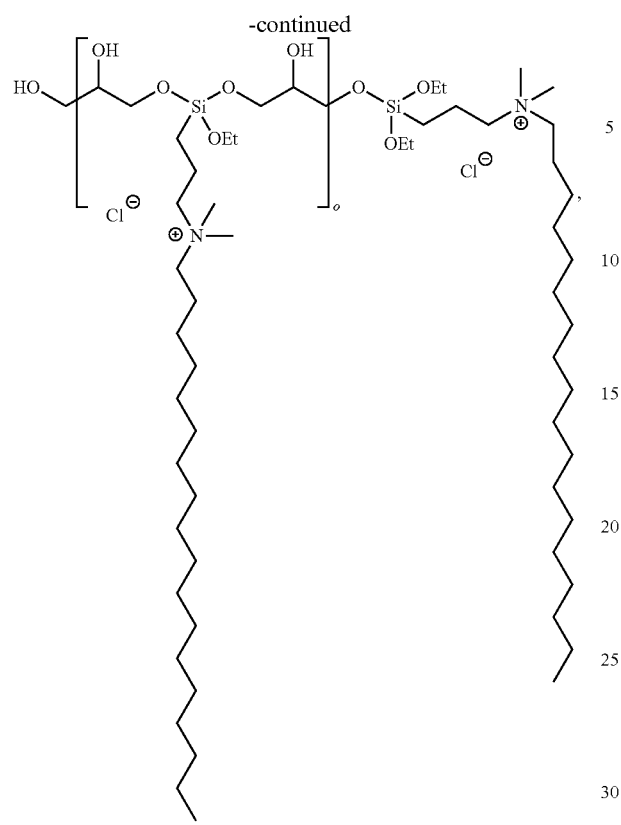
In one embodiment, the quaternary ammonium compound of Formula XXI is of the formula
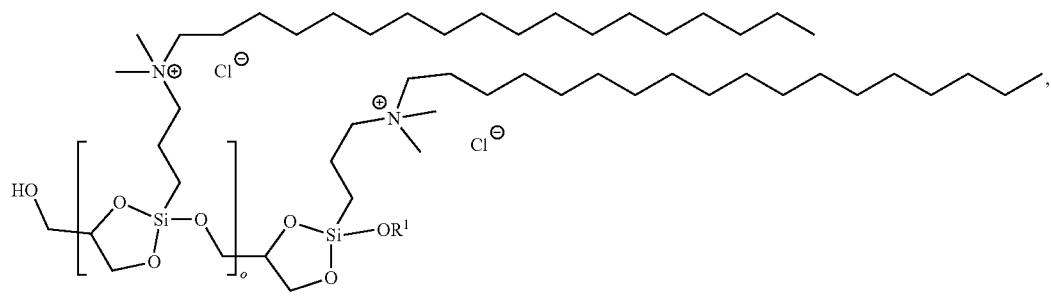
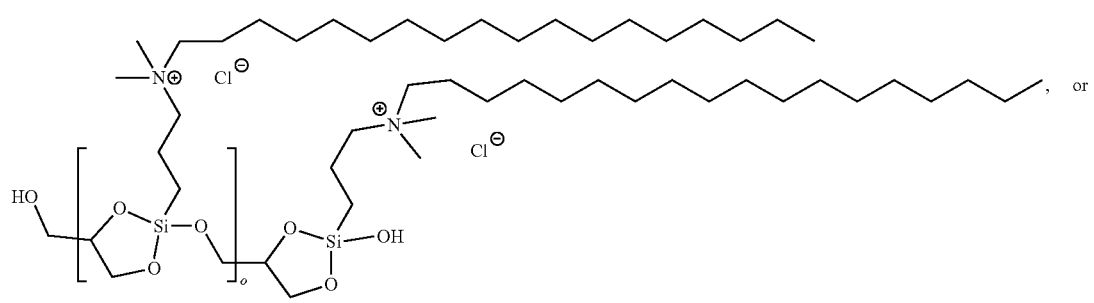
or

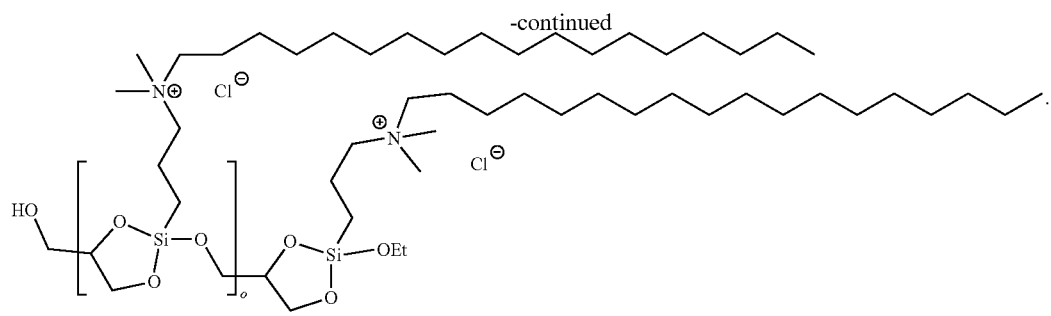
In one embodiment, the quaternary ammonium compound of Formula XXII is of the formula
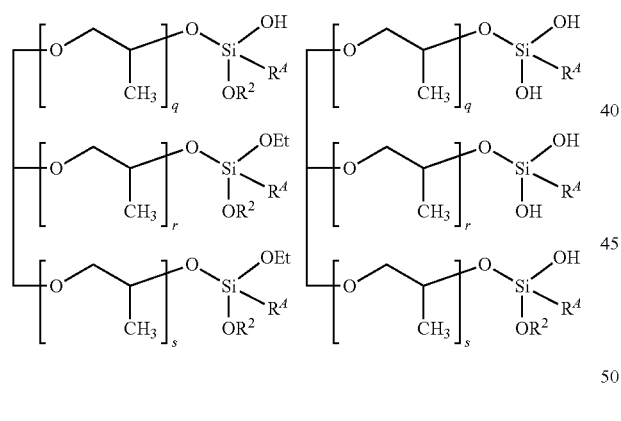
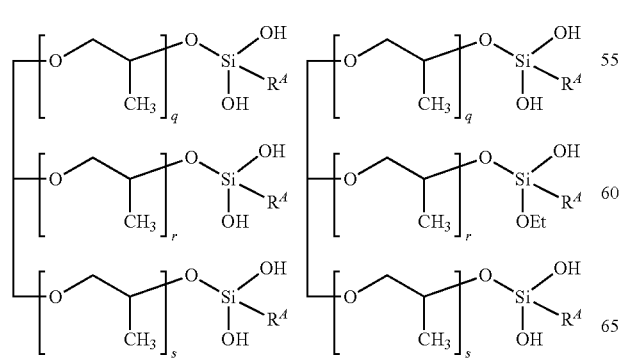
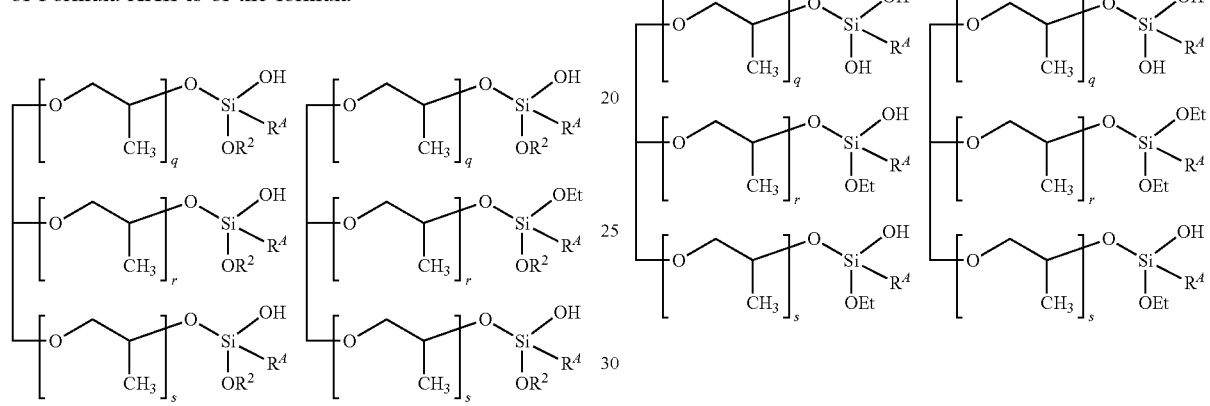
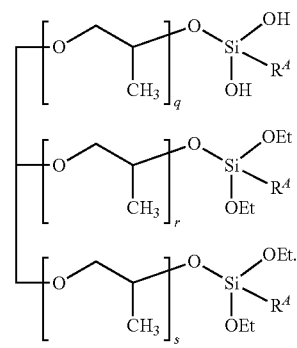
In one embodiment, the quaternary ammonium compound of Formula XXII is of the formula

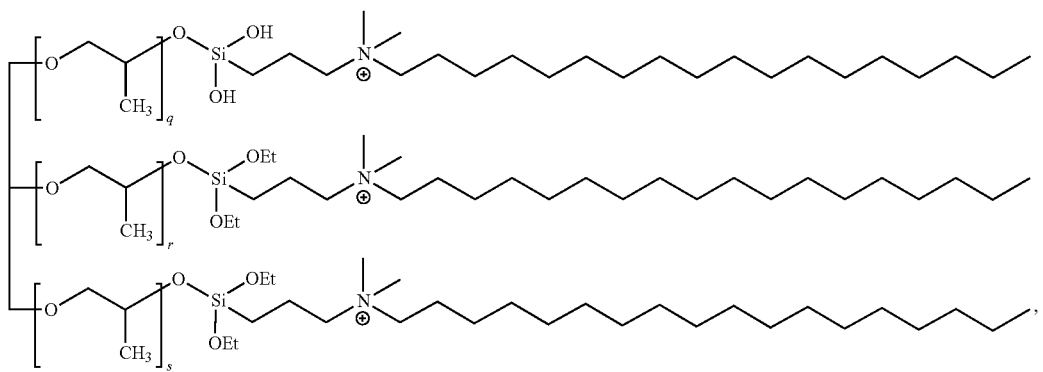
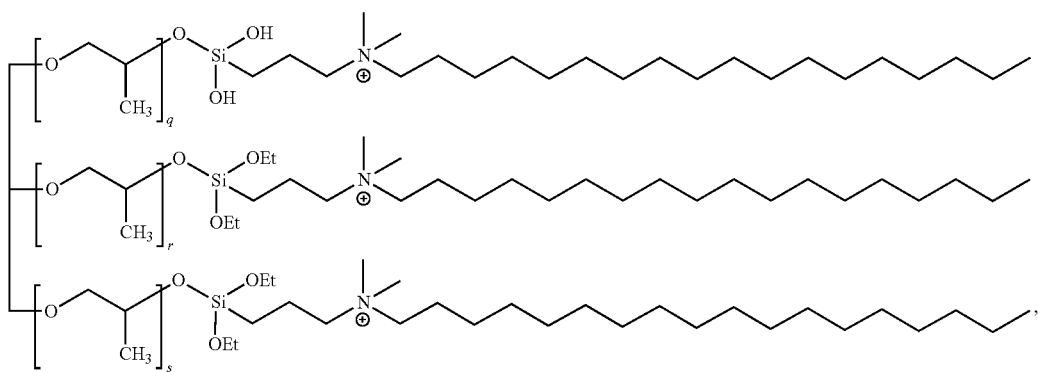
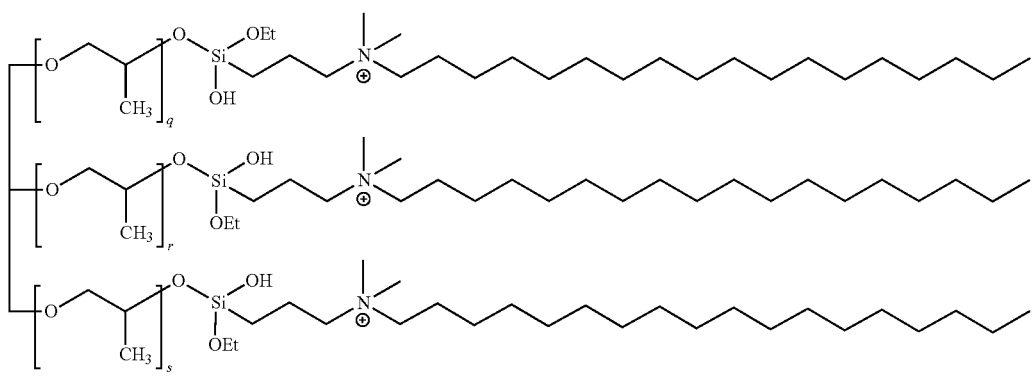
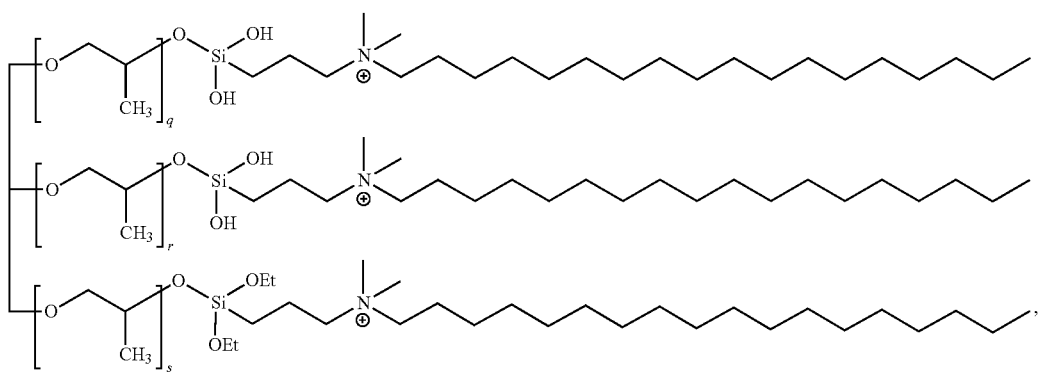

-continued
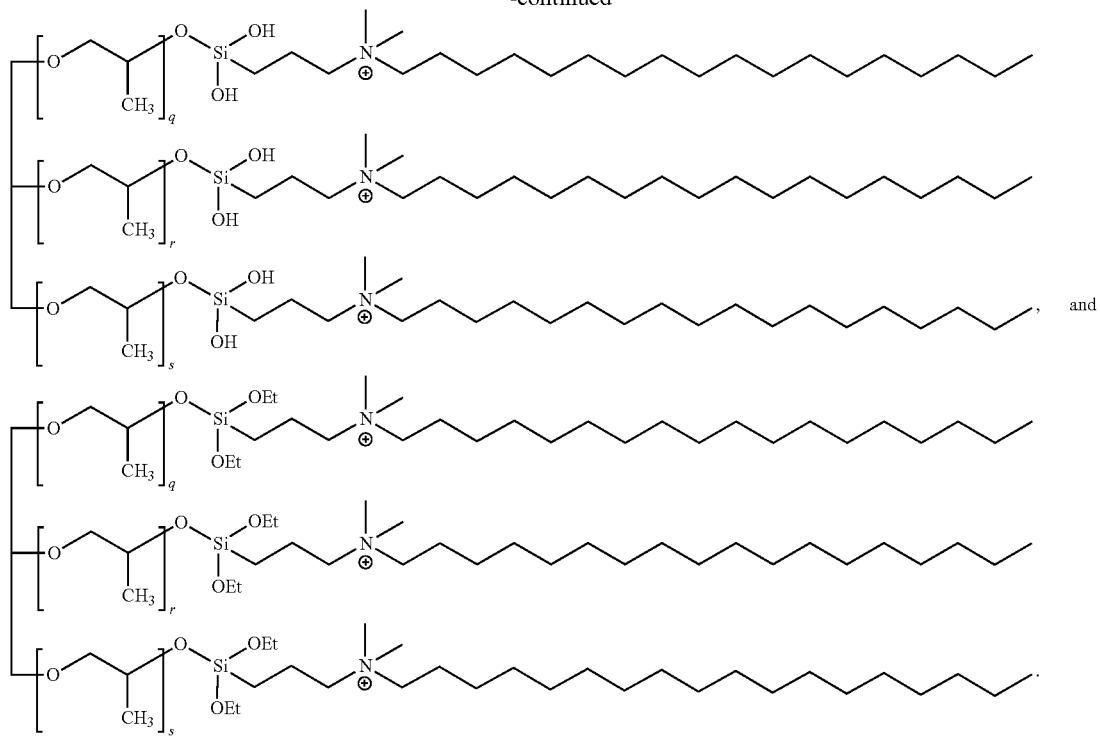
In one embodiment, the quaternary ammonium compound of Formula XXIII is of the formula
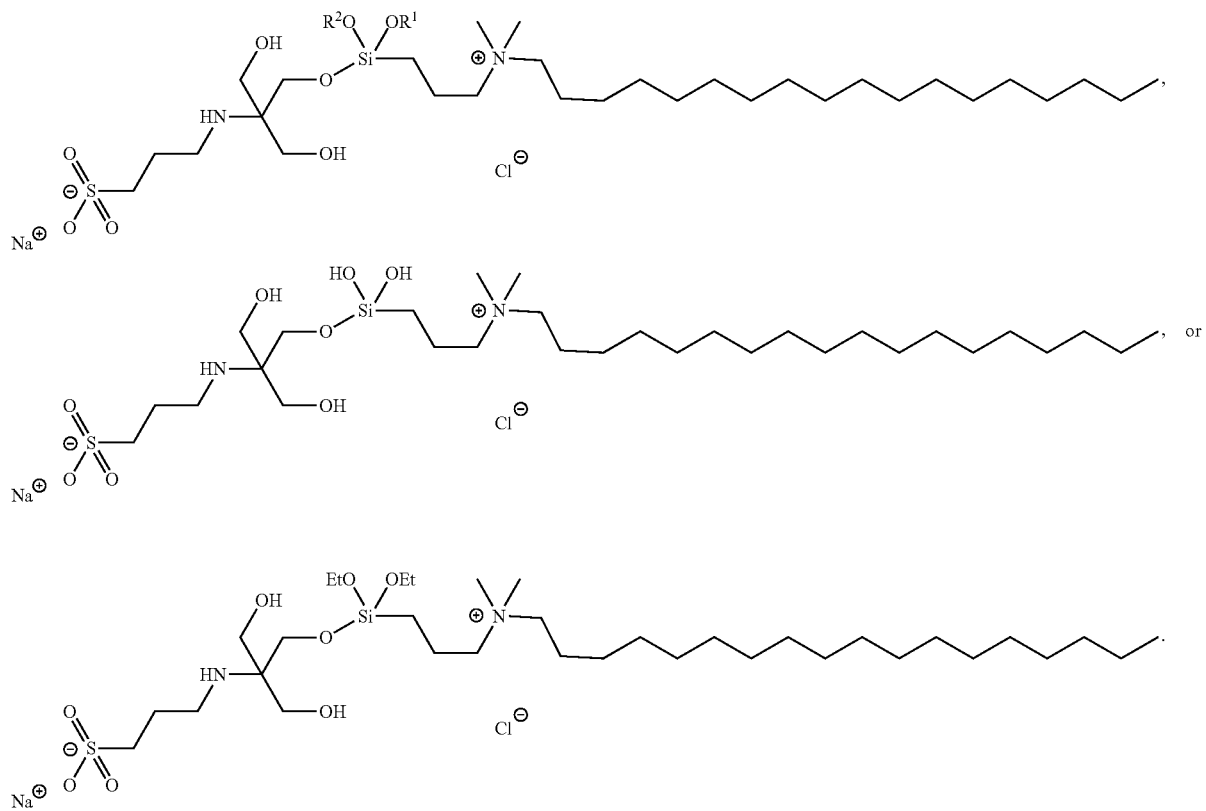

In one embodiment, the quaternary ammonium compound of Formula XXIII is of the formula:
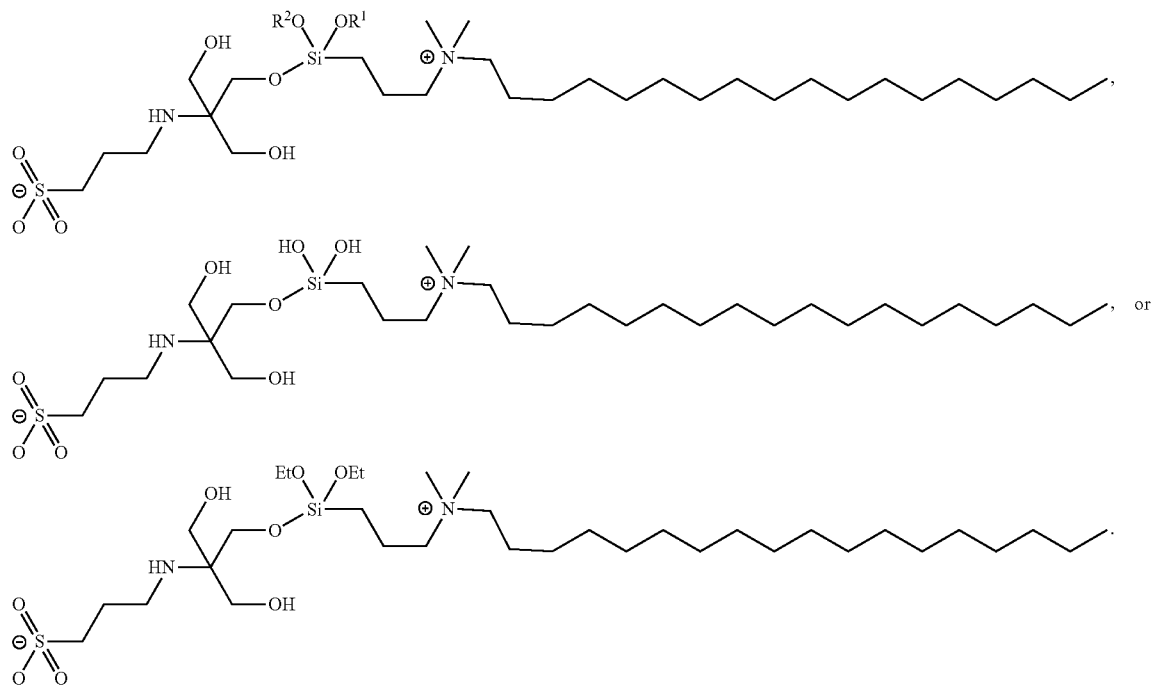
In one embodiment, the quaternary ammonium compound of Formula XXIII is of the formula:
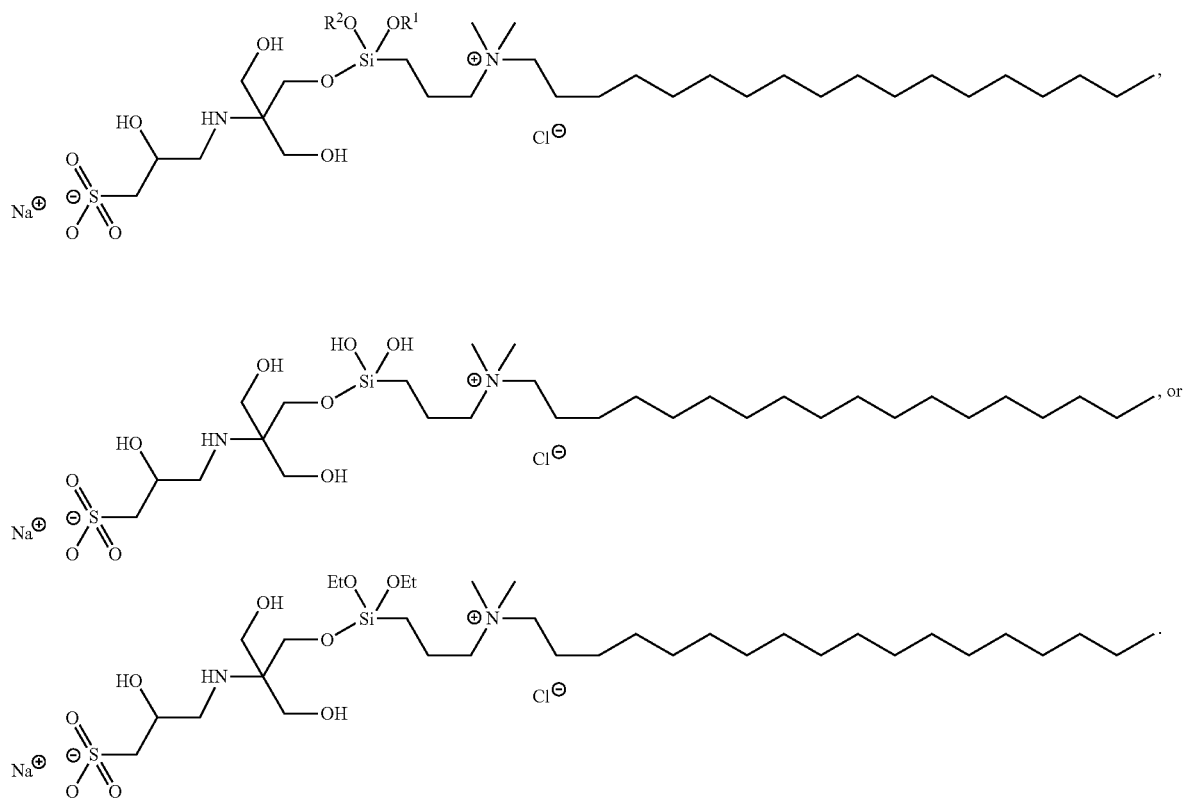

In one embodiment, the quaternary ammonium compound of Formula XXIII is of the formula:
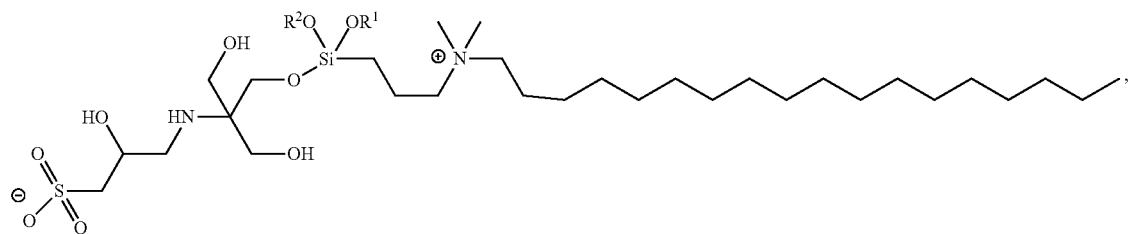
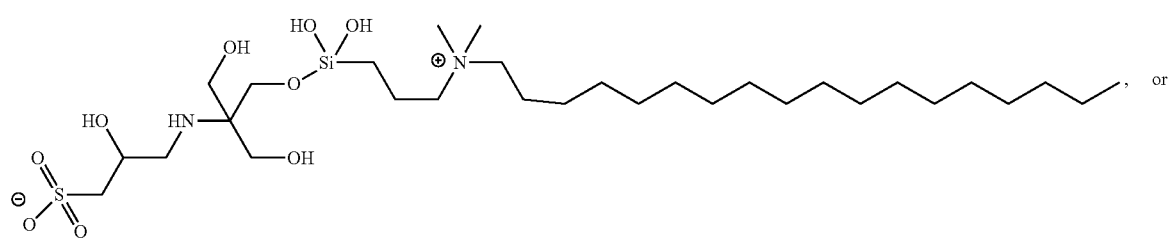
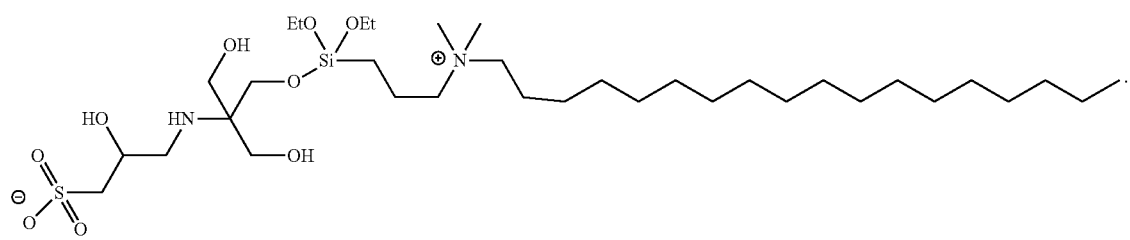
In one embodiment, the quaternary ammonium compound of Formula XXIV is of the formula:
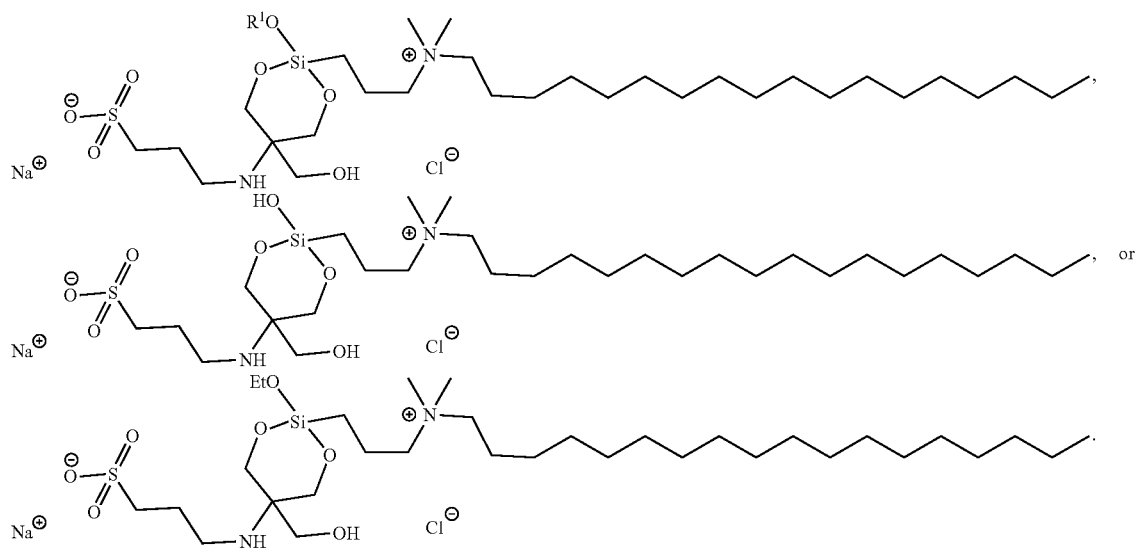

In one embodiment, the quaternary ammonium compound of Formula XXIV is of the formula:
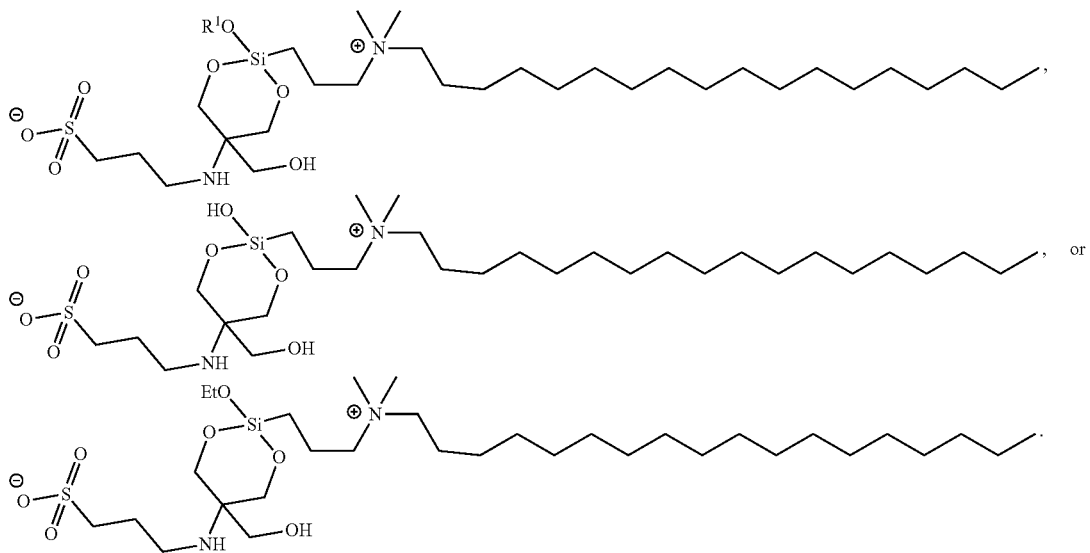
In one embodiment, the quaternary ammonium compound of Formula XXIV is of the formula
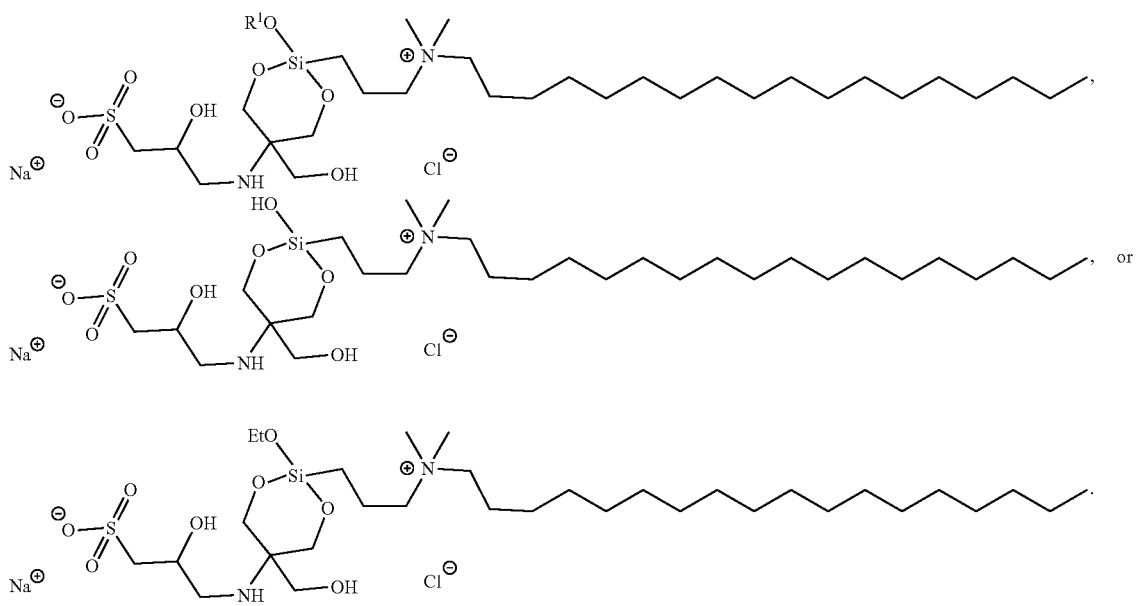
In one embodiment, the quaternary ammonium compound of Formula XXIV is of the formula:
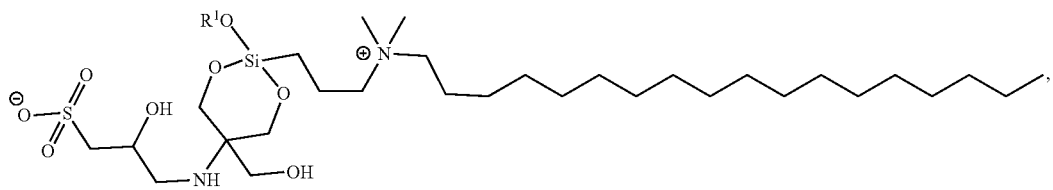

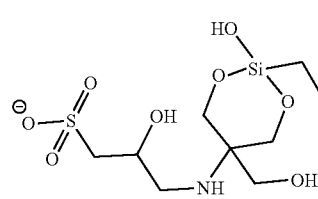
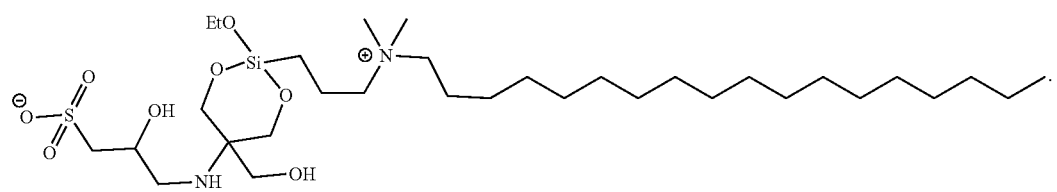
In one embodiment, the quaternary ammonium compound of Formula XXV is of the formula
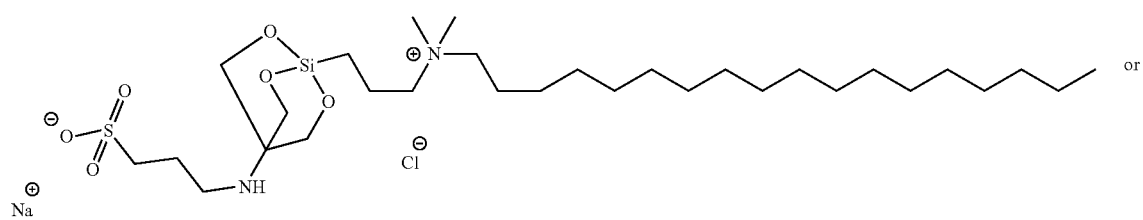
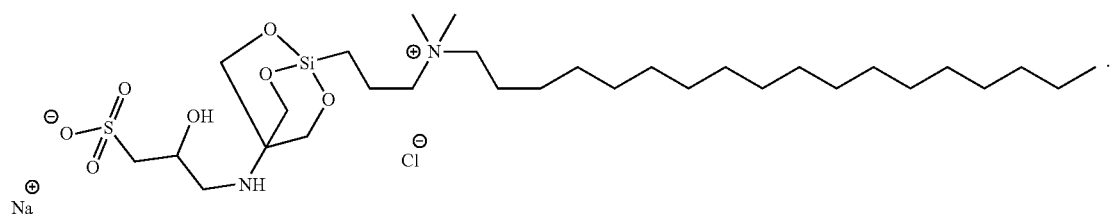
In one embodiment, the quaternary ammonium compound of Formula XXV is of the formula
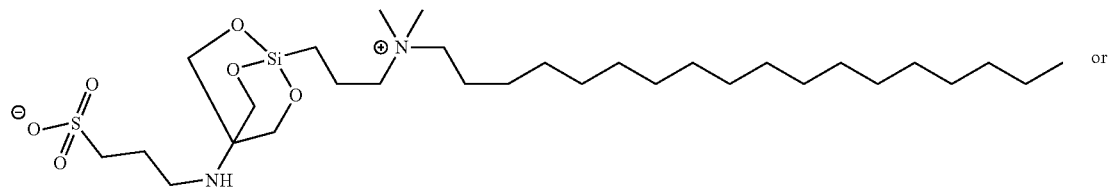
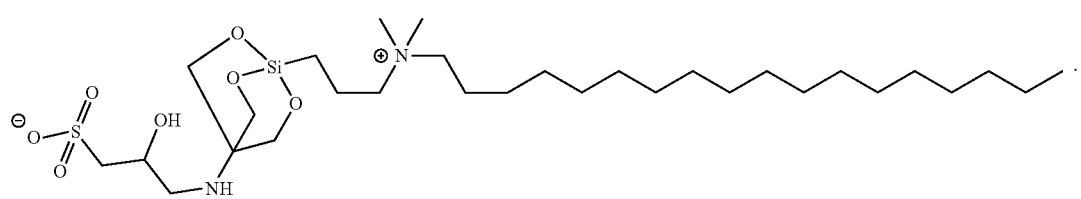

In one embodiment, the quaternary ammonium compound of Formula XXVI is of the formula
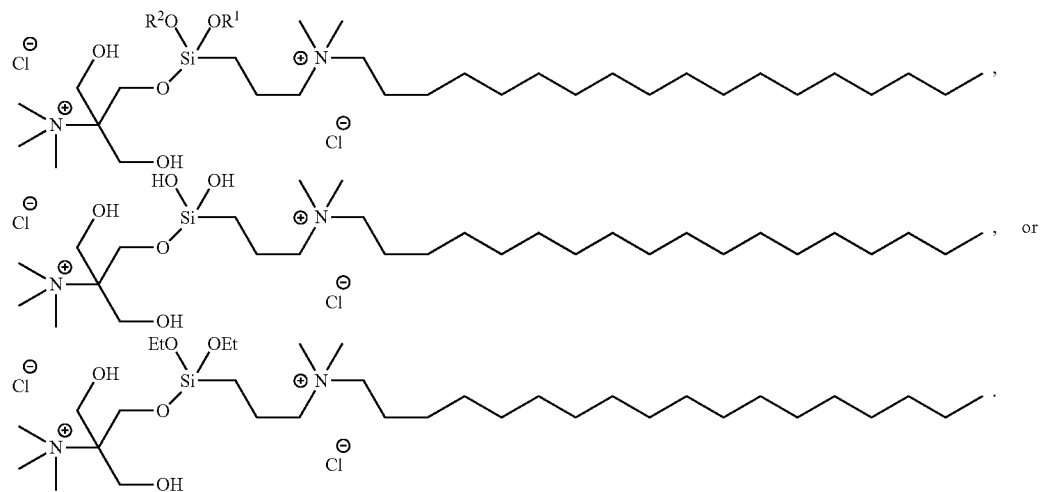
In one embodiment, the quaternary ammonium compound of Formula XXVII is of the formula
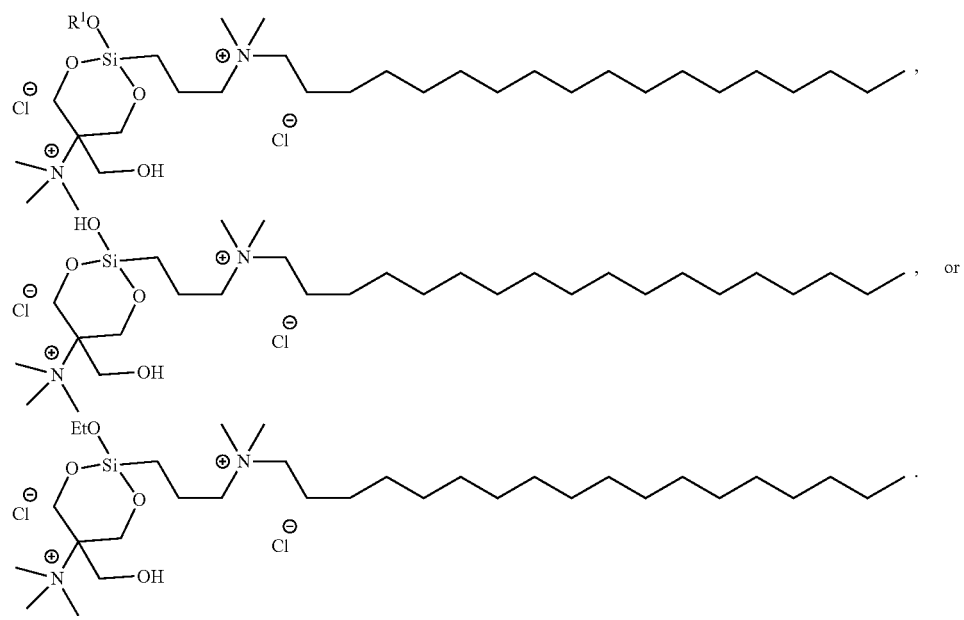
In one embodiment, the quaternary ammonium compound of Formula XXVIII is of the formula
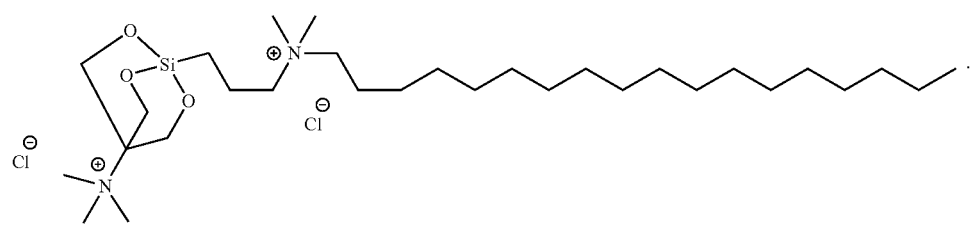 [SMILES: [Cl-] ; CCCCCCCCCCCCCCCCCC[N+](C)(C)CCC[Si]12OCC([N+](C)(C)C)(CO1)CO2 ; [Cl-]]

In one embodiment of Formula XXIX,
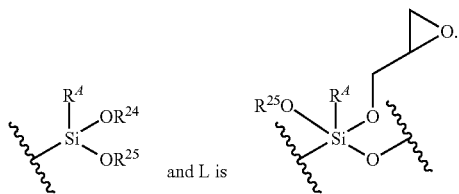
and L is
In one embodiment of Formula XXIX, Z is
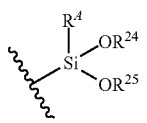
and L is
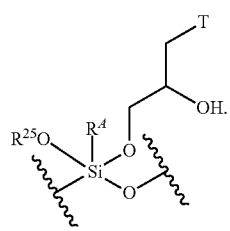
In one embodiment of Formula XXIX, Z is
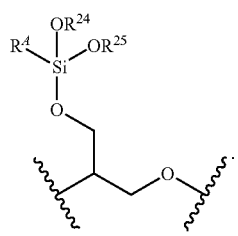
and L is
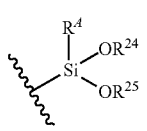
In one embodiment of Formula XXIX, Z is
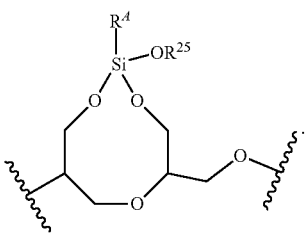
and L is
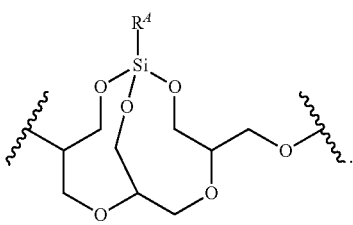
In one embodiment of Formula XXIX, Z is
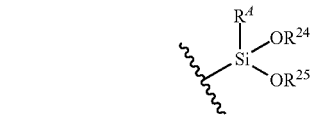
and L is
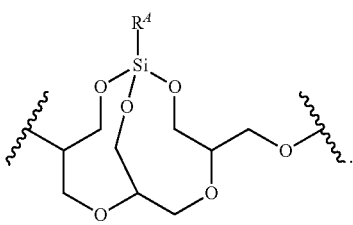
In one embodiment of Formula XXIX, Z is
and L is
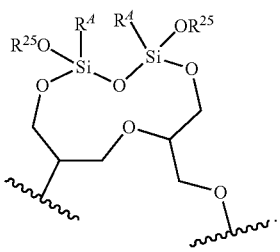

In one embodiment of Formula XXIX, Z is
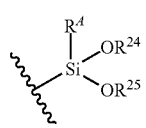
and L is
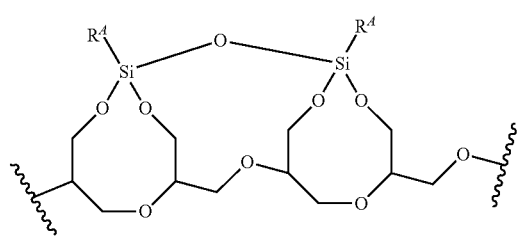
In one embodiment of Formula XXIX, Z is
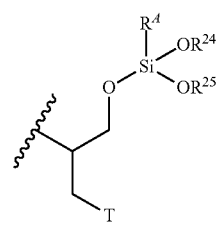
L is
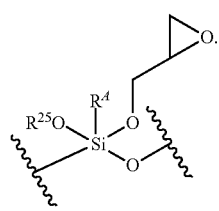
In one embodiment of Formula XXIX, Z is
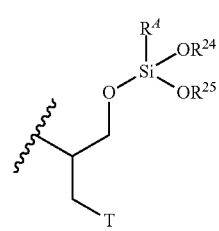
and L is
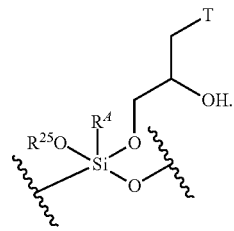
In one embodiment of Formula XXIX, Z is
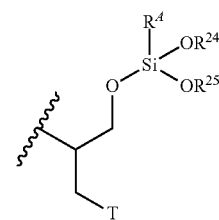
and L is
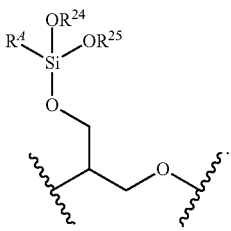
In one embodiment of Formula XXIX, Z is
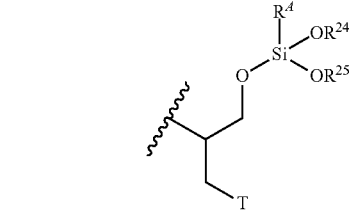
and L is
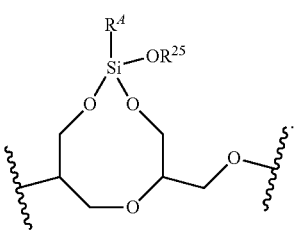

In one embodiment of Formula XXIX, Z is
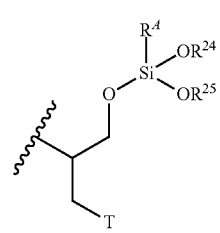
and L is
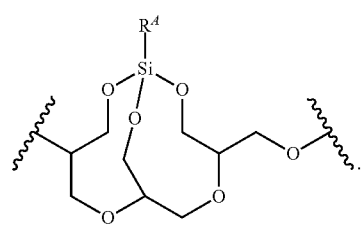
In one embodiment of Formula XXIX, Z is
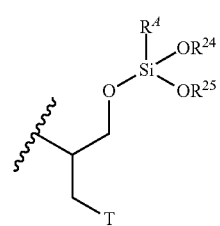
and L is
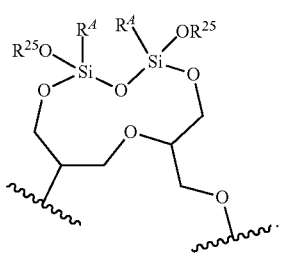
In one embodiment of Formula XXIX, Z is
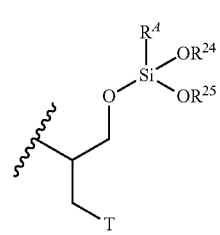
and L is
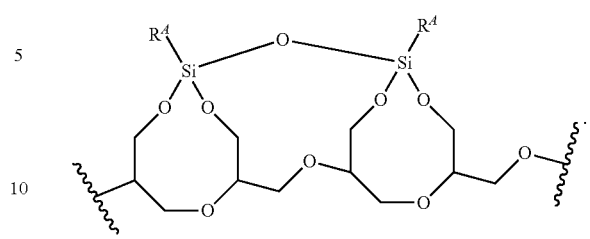
In one embodiment of Formula XXIX, Z is
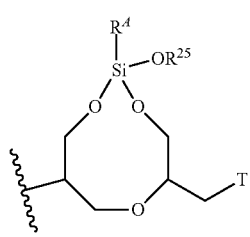
and L is
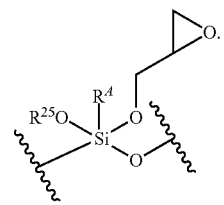
In one embodiment of Formula XXIX, Z is
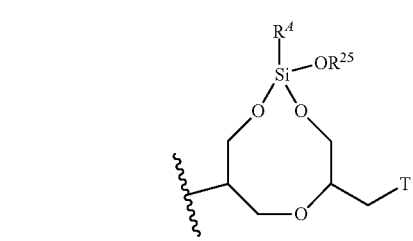
and L is
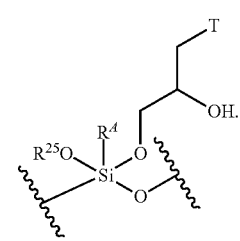

In one embodiment of Formula XXIX, Z is
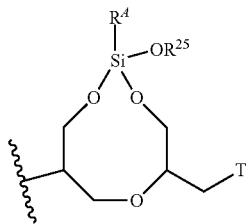
and L is
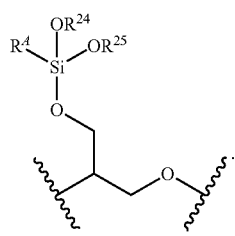
In one embodiment of Formula XXIX, Z is
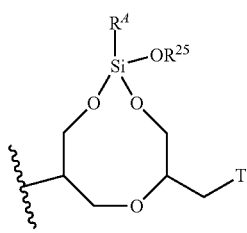
and L is
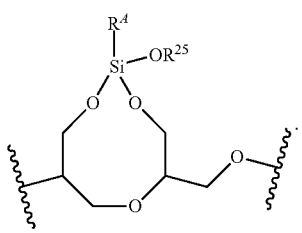
In one embodiment of Formula XXIX, Z is
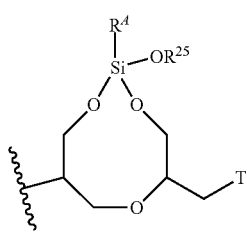
and L is
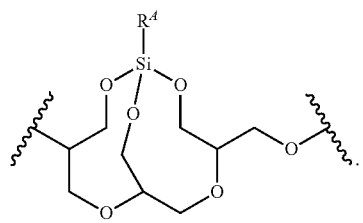
In one embodiment of Formula XXIX, Z is
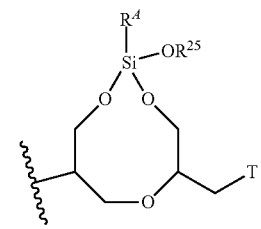
and L is
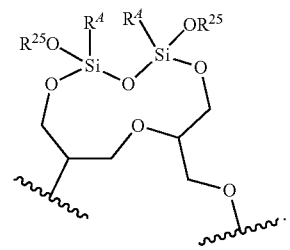
In one embodiment of Formula XXIX, Z is
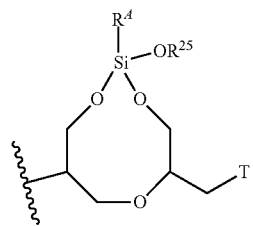
and L is
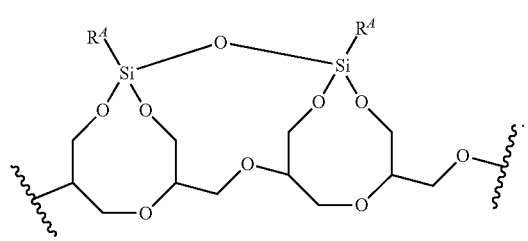

In one embodiment of Formula XXIX, Z is
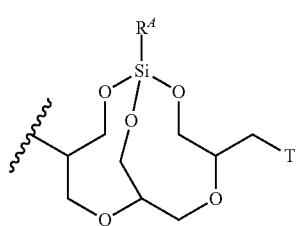
and L is
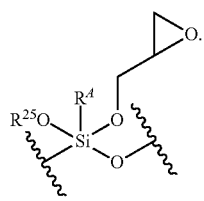
In one embodiment of Formula XXIX, Z is
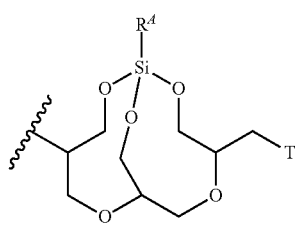
and L is
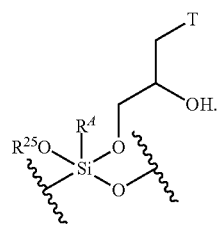
In one embodiment of Formula XXIX, Z is
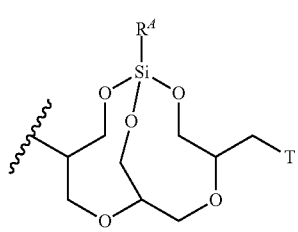
and L is
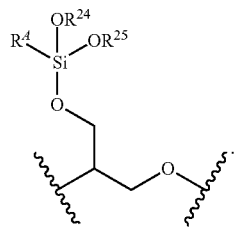
In one embodiment of Formula XXIX, Z is
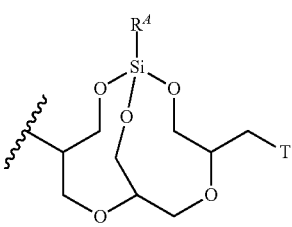
and L is
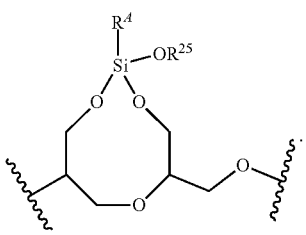
In one embodiment of Formula XXIX, Z is
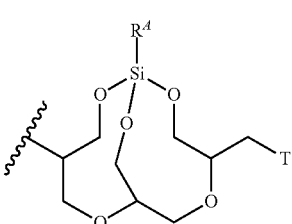
and L is
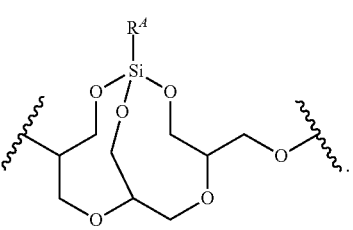

In one embodiment of Formula XXIX, Z is
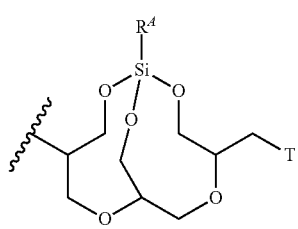
and L is
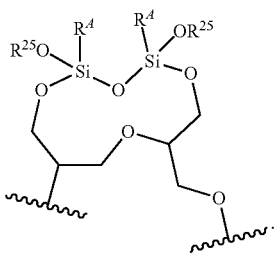
In one embodiment of Formula XXIX, Z is
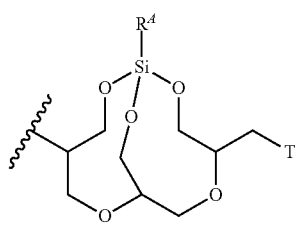
and L is
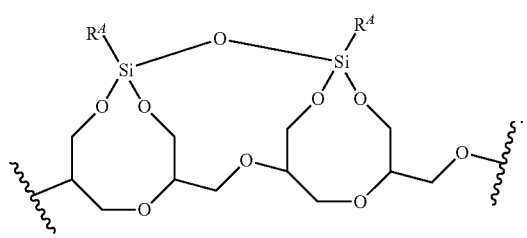
In one embodiment of Formula XXIX, Z is
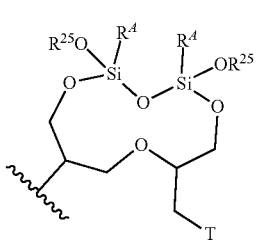
and L is
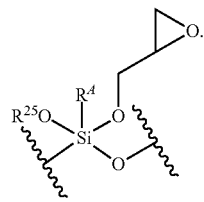
In one embodiment of Formula XXIX, Z is
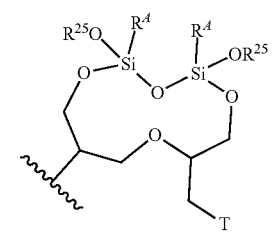
and L is
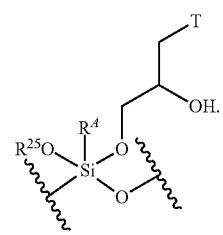
In one embodiment of Formula XXIX, Z is
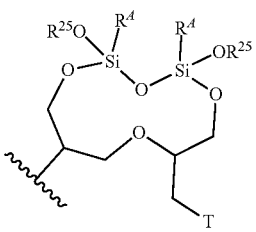
and L is
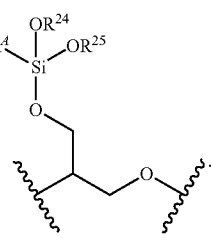

In one embodiment of Formula XXIX, Z is
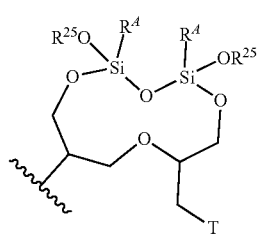
and L is
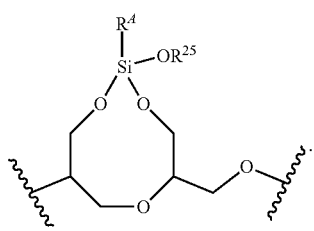
In one embodiment of Formula XXIX, Z is
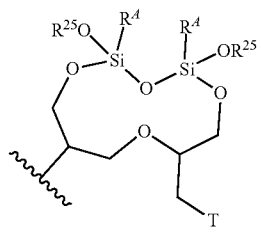
and L is
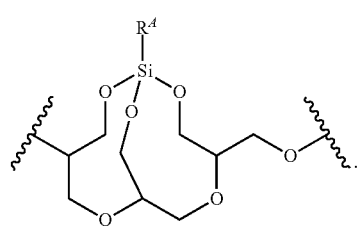
In one embodiment of Formula XXIX, Z is
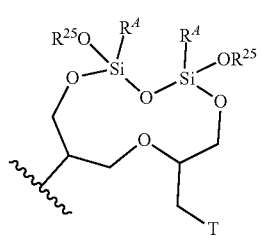
and L is
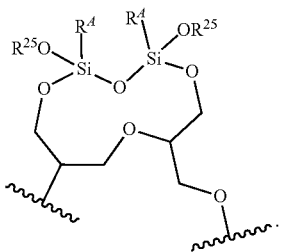
In one embodiment of Formula XXIX, Z is
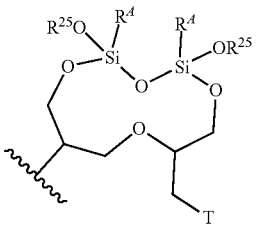
and L is
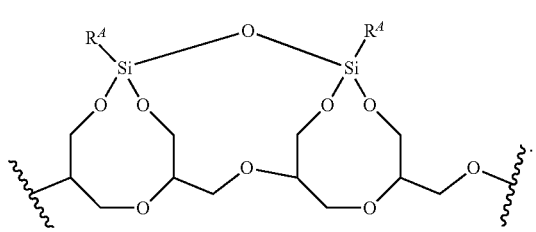
In one embodiment of Formula XXIX, Z is
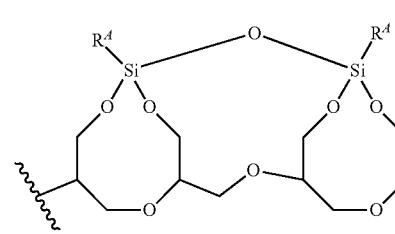
and L is
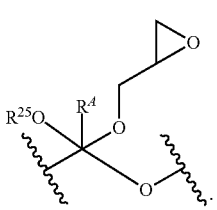

In one embodiment of Formula XXIX, Z is
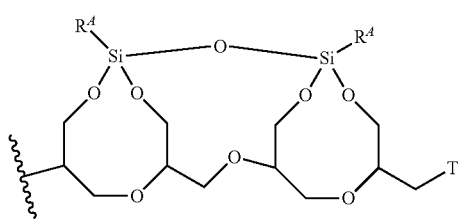
and L is
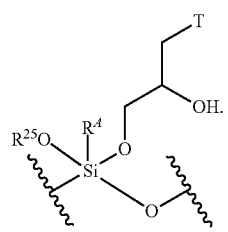
In one embodiment of Formula XXIX, Z is
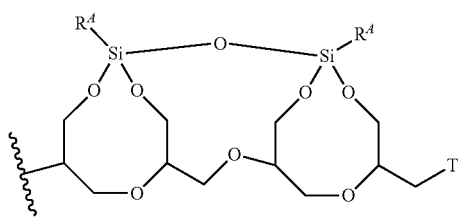
and L is
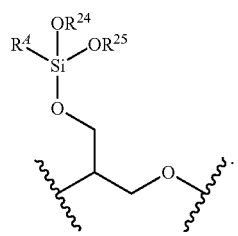
In one embodiment of Formula XXIX, Z is
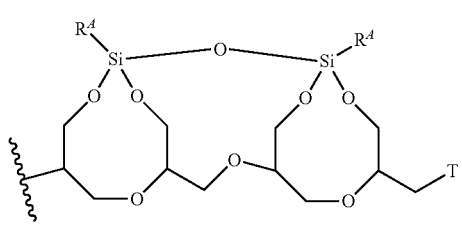
and L is
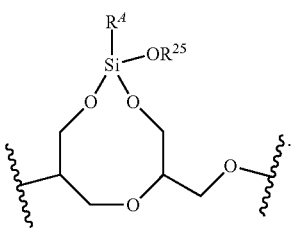
In one embodiment of Formula XXIX, Z is
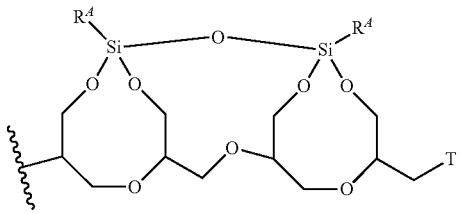
and L is
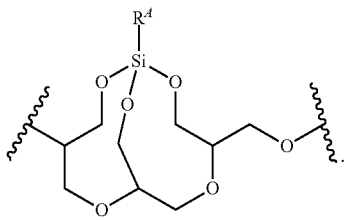
In one embodiment of Formula XXIX, Z is
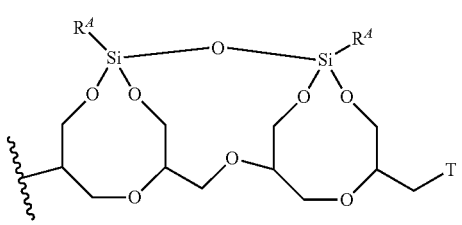

and L is
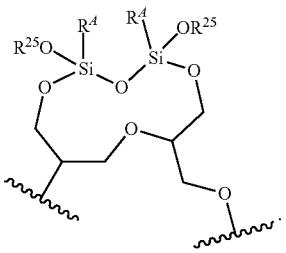
In one embodiment of Formula XXIX, Z is
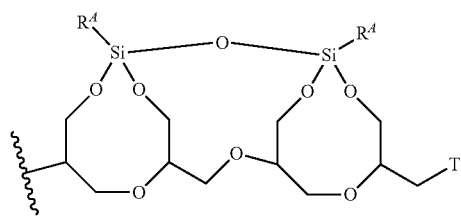
and L is
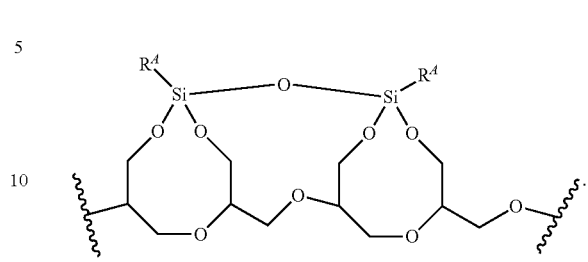
In some embodiments of Formula XXIX,
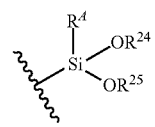
is selected from:
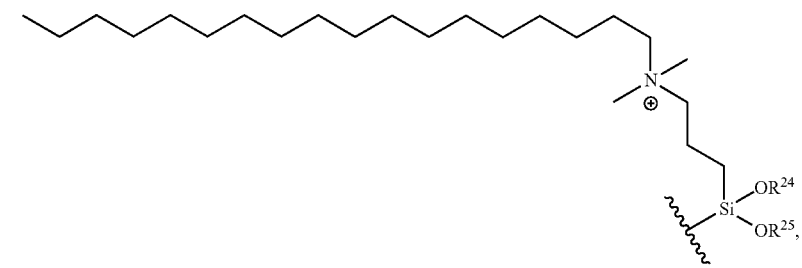
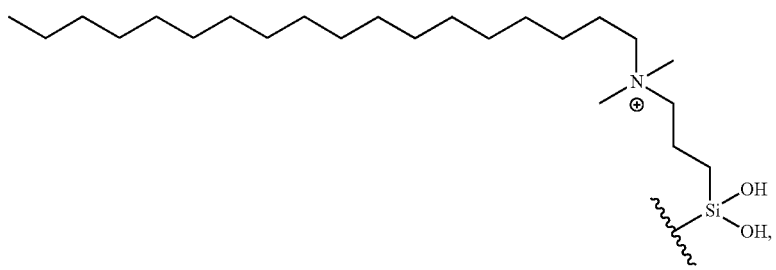
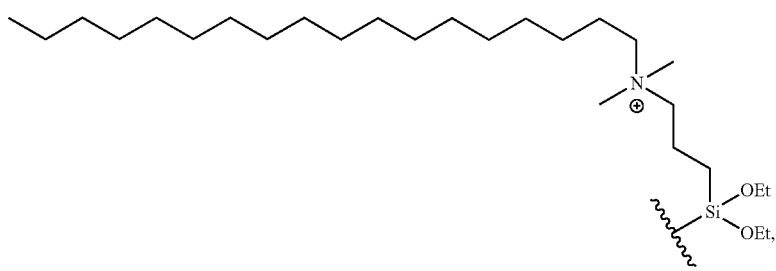

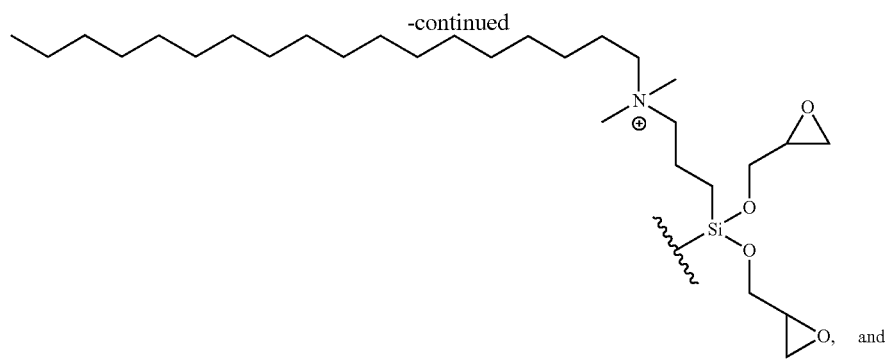
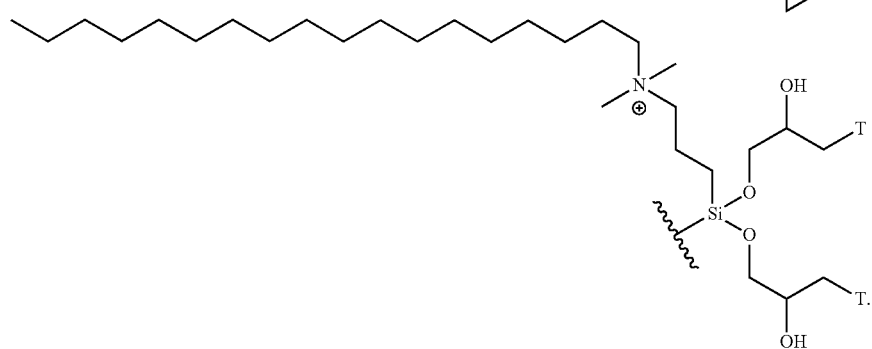
In some embodiments of Formula XXIX,
is selected from:
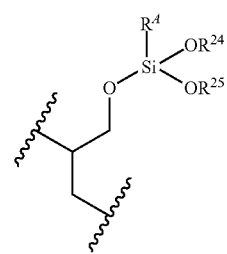
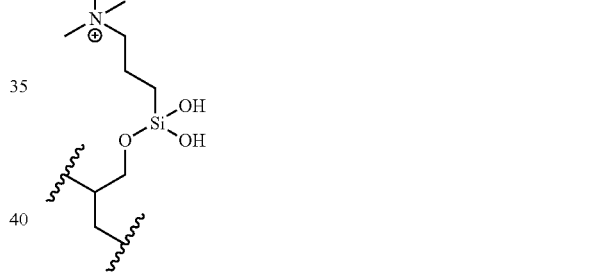
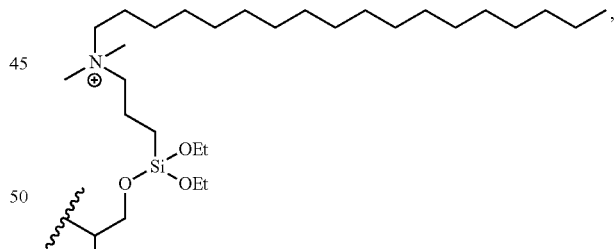
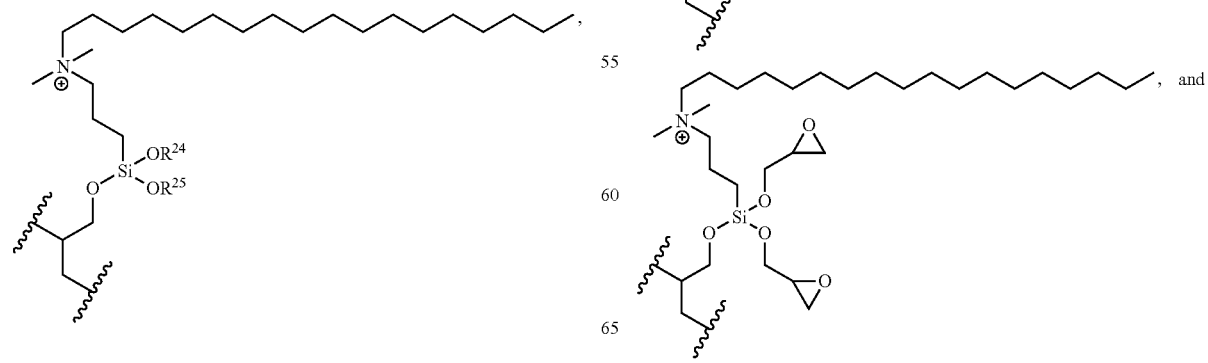

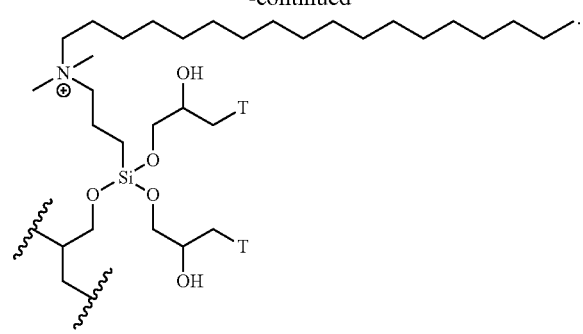
In some embodiments of Formula XXIX,
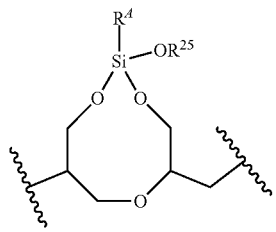
is selected from:
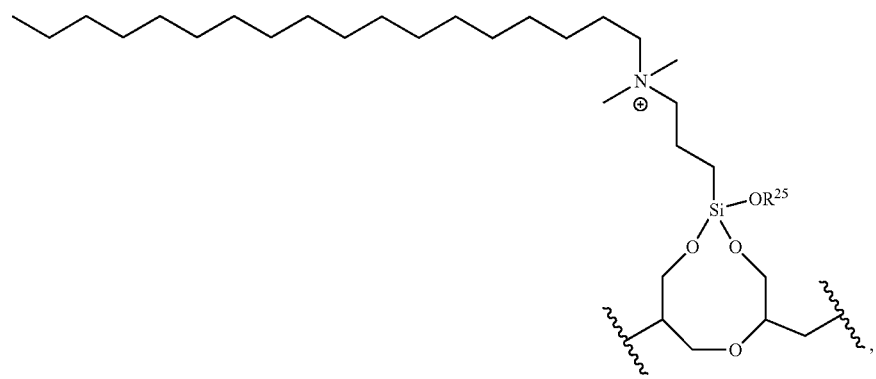
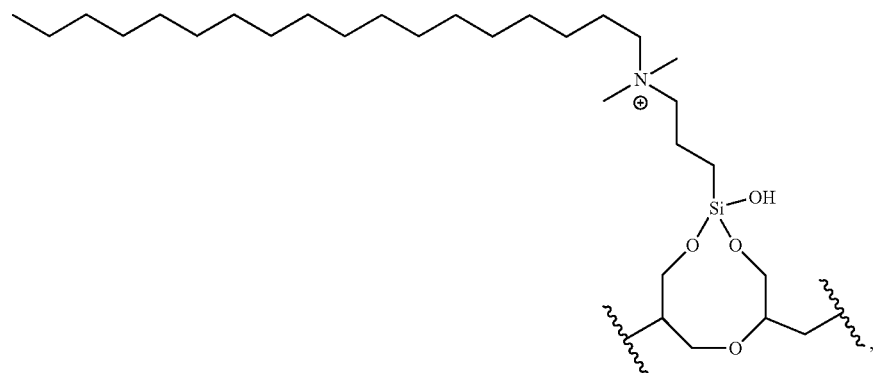
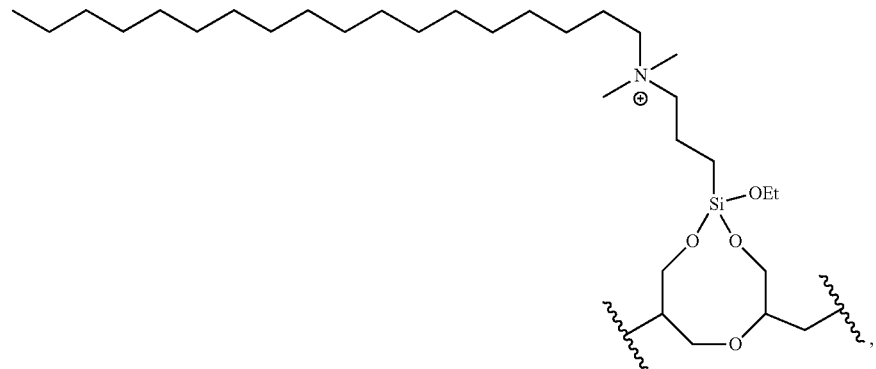

-continued
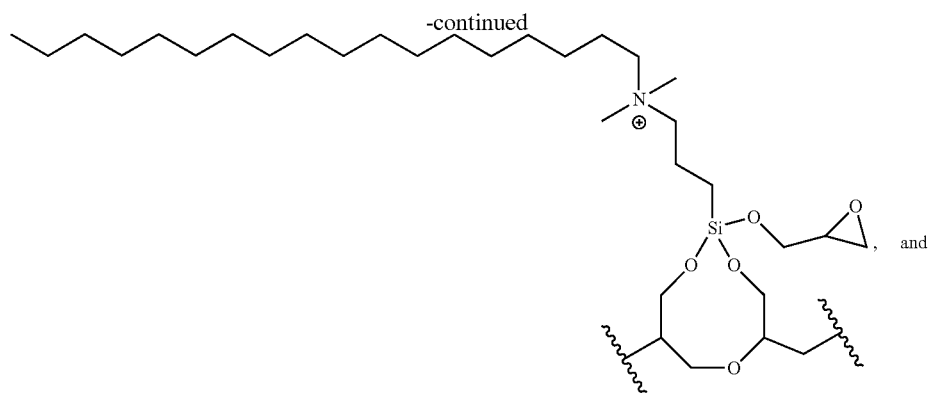, and
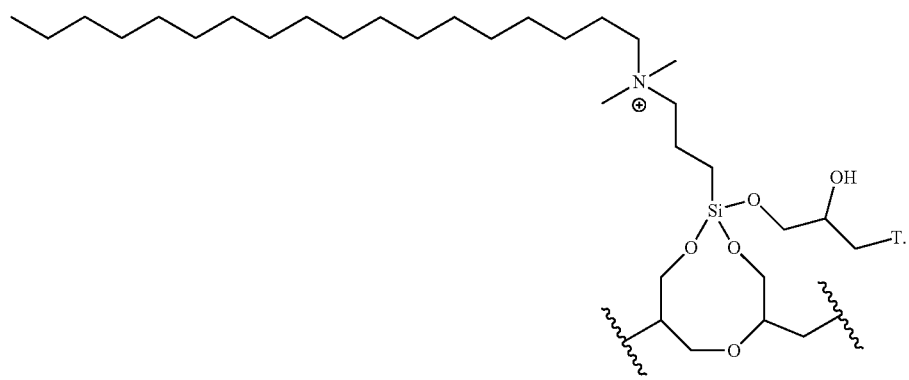
In some embodiments of Formula XXIX,
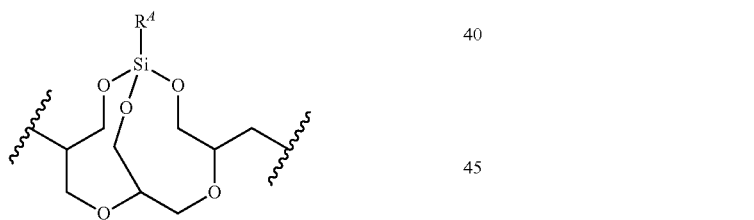
is
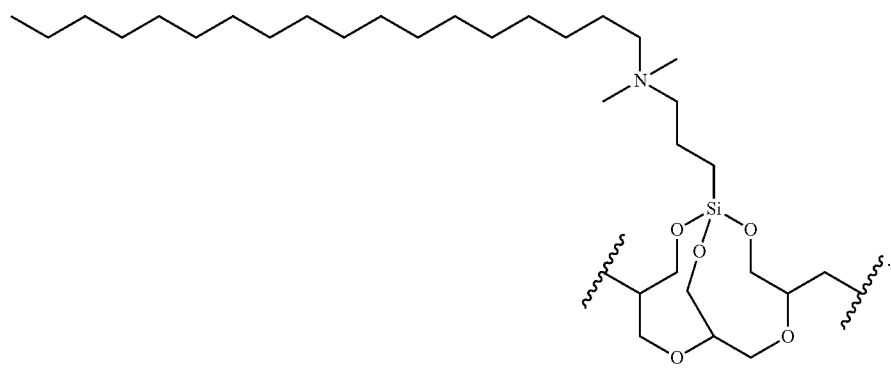.

In some embodiments of Formula XXIX,
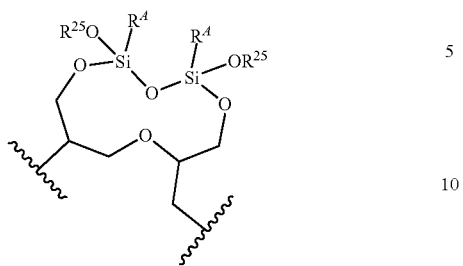
is selected from:
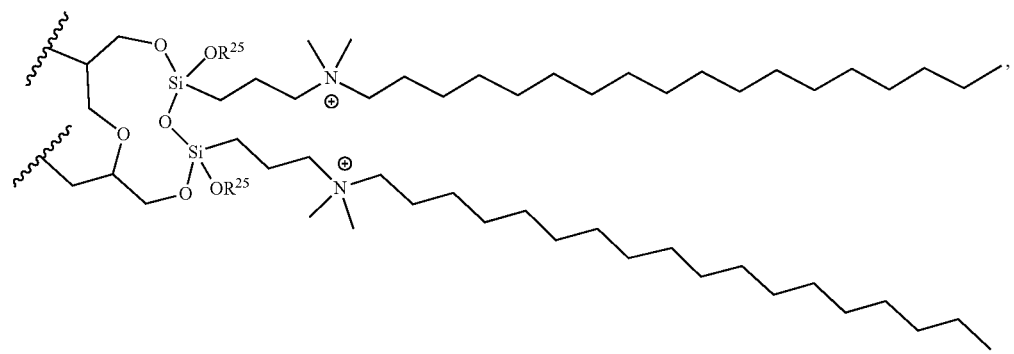
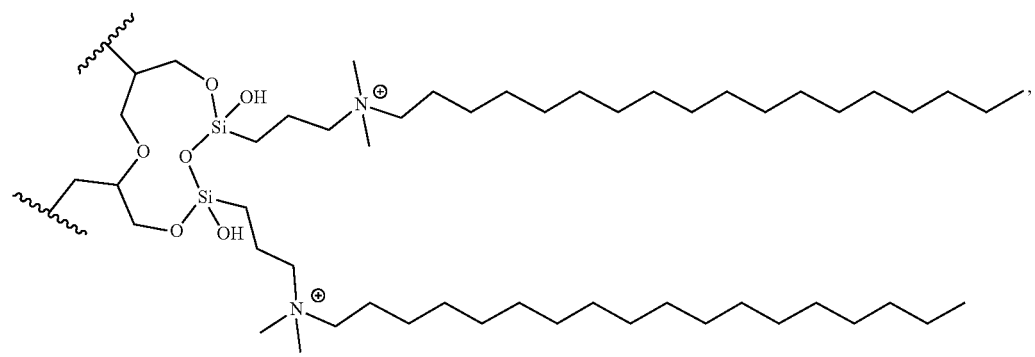
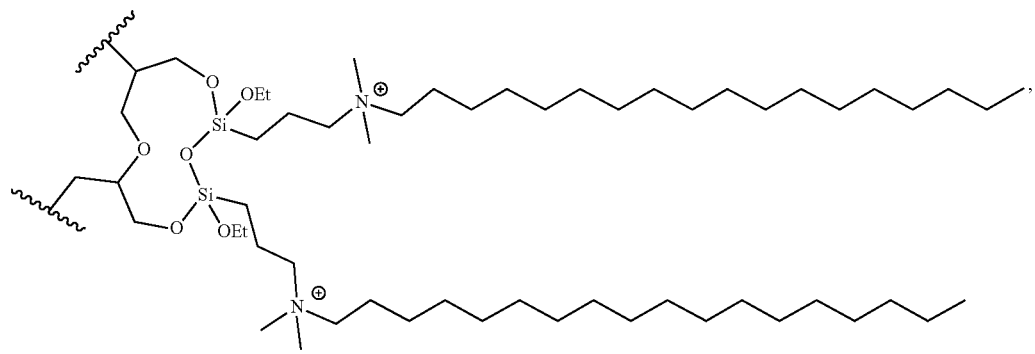

-continued
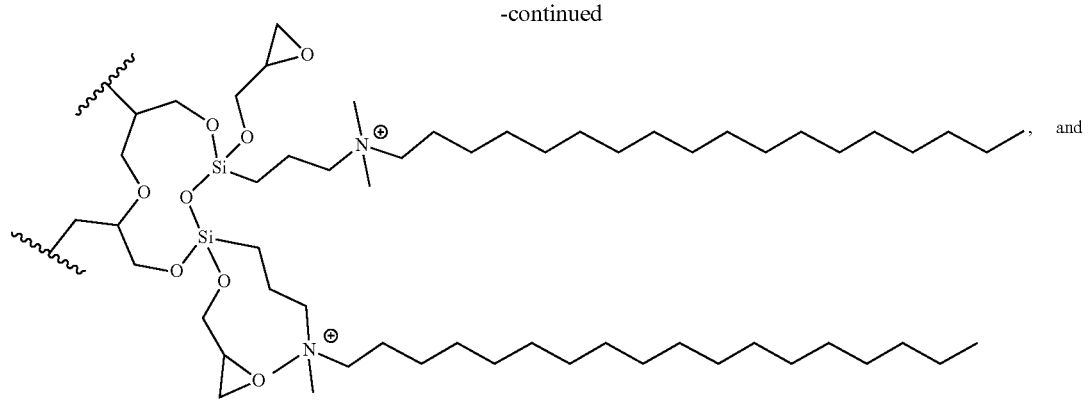
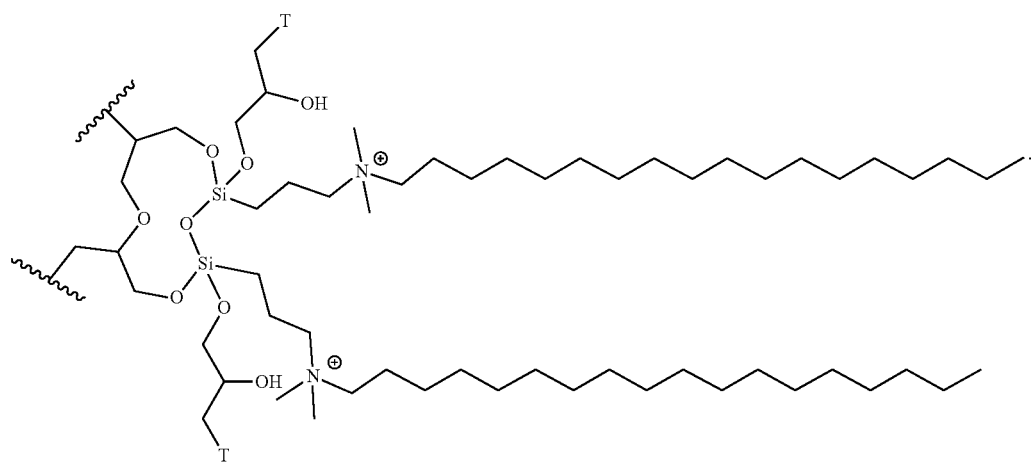
In some embodiments of Formula XXIX,
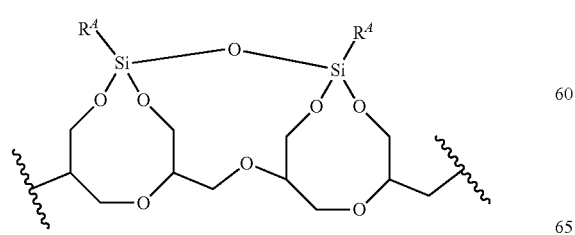

is

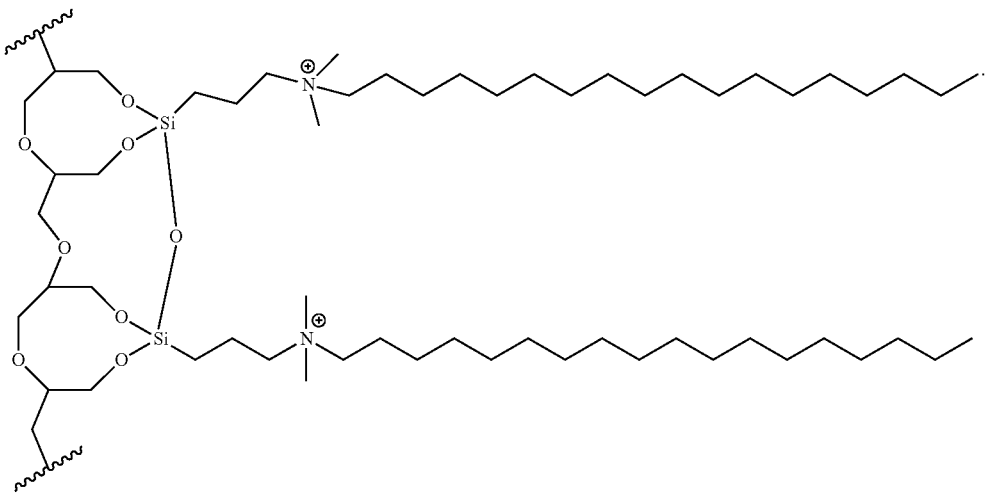 [SMILES: *CC1CO[Si]2(CCC[N+](C)(C)CCCCCCCCCCCCCCCCCC)OCC(CO1)OCC1CO[Si](CCC[N+](C)(C)CCCCCCCCCCCCCCCCCC)(OCC(*)CO1)O2]

Methods for the Treatment of an Infection

The present invention includes a method for treating infections in a host with an effective amount of one or more quaternary ammonium compounds or compositions as described herein. In one embodiment the infection is treated directly with a solution containing one or more quaternary ammonium compounds of the present invention (which may be reconstituted from a sterilized lyophilized powder).

Nonlimiting examples of infections that can be treated with the compounds described herein are as follows.

Biofilms

Biofilms can develop in many environments, including on surfaces in healthcare settings, equipment and medical devices, and most importantly, on skin, ears, wounds, and other in vivo topical areas in humans and animals. These sessile microbial communities are profoundly different than that of their planktonic counterparts. While estimates vary, as many as 40% of the genes of a bacterium may undergo up or down regulation in the transition from the planktonic to the biofilm state in order to assume specialized functions (see Davies D. G., Parsek M. R., Pearson J. P., Iglewski B. H., Costerton J. W., Greenberg E. P. "The involvement of cell-to-cell signals in the development of a bacterial biofilm" Science. 1998, 280:295-298; and Hall-Stoodley L., Costerton J. W., Stoodley P. "Bacterial biofilms: From the natural environment to infectious diseases" Nat. Rev. 2004, 2:95-108). "What was once defined as the formation of a community of microorganisms attached to a surface has come to be recognized as a complex developmental process that is multifaceted and dynamic in nature." (see Kostakioti M., Hadjifrangiskou M., Hultgren, S. "Bacterial Biofilms: Development, Dispersal, and Therapeutic Strategies in the Dawn of the Postantibiotic Era" Cold Spring Harb Perspect Med 2013, 3:a010306).

Up to 80% of human bacterial infections are associated with biofilms. Biofilm communities can cause "persistent infections [that are] resistant to conventional antimicrobial treatment and is today a major cause of treatment failure" (see Romling, U. Balsalobre, C. "Biofilm infections, their resilience to therapy and innovative treatment strategies." Journal of Internal Medicine, 2004, 272: 541-561). When microbial organisms form a biofilm in vivo, they can become resistant not only to antimicrobial drugs but also to the host's own immune defenses. Antibiotics designed to combat infections have been traditionally developed to kill planktonic bacteria under the assumption that these drugs would kill the same bacteria in different forms. However, the same bacterium is different in the biofilm state than in the planktonic state due to the dramatic shift in expression of genes. These changes in gene expression have emergent properties that are not predictable based on studies of planktonic cells alone. Bacteria protected within biofilms are up to one thousand times more resistant to antibiotics than they are in the planktonic form (see Rasmussen T B, Givskov M. Int J Med Microbiol. 2006, 296(2-3):149-161).

Clinically, biofilms are responsible for many common persistent and chronic infections in humans and animals due to their acquired and inherent resistance to antimicrobial agents and the selection for phenotypic variants. Such resistance tends to be multi-factorial, and biofilms typically include mixed fungal/bacterial species that may enhance rejection of antimicrobial agents. (see Flemming H.-C., Wingender J., Szewzyk U. Steinberg, P., Rice S. A., Kjelleberg, S. "Biofilms: An emergent form of bacterial life" Nature Reviews Microbiology 2016, 14:563-575; and Al-Fattani M. A and Douglas L. J. "Biofilm matrix of *Candida albicans* and *Candida tripicalis*: chemical composition and role in drug resistance" Journal of Medical Microbiology 2006; 55:999-1008).

Biofilms are often composed of several layers of cells. The layered nature of a biofilm causes uneven exposure to oxygen and nutrients by individual organisms, particularly for organisms present within deeper layers, leading to an environment that may produce altered metabolic activity. Often, the organisms in these deeper layers, known as "persister cells" are present in a quiescent state. These quiescent cells are often buttressed from chemical agents by the layers of cells above them and thus are exposed to lower quantities of treatment than those on the surface of the biofilm. For example, antibiotic efficacy often decreases for deeper layers of a biofilm due to cells in the upper layers consuming most of the antibiotic before it dissipates to lower layers, resulting in ineffective concentrations reaching the deeper layers (Romling and Balsalobre, 551). This phenomenon results in the incomplete elimination of a biofilm during many antimicrobial treatment regimens, resulting in the survival of resistant cells capable of recolonizing, and thus creating a situation of chronic or persistent infection (Musk, Jr. D. and Hergenrother, P. "Chemical Countermeasures for the Control of Bacterial Biofilms: Effective Compounds and Promising Targets" Current Medicinal Chemistry 2006, 13:2163-2177).

By genetically encoding information identifying the antibiotics encountered, the persister cells enable the new colony to recognize and resist such treatment regimens in the future. This genetic information may be transferred and shared with other bacterium in several ways, such as by electrical signaling, conjugation, mutation and heterologous expression, thus exponentially expanding "antibiotic resistance" against a wide spectrum of available drugs and leading to the development of "superresistant" strains of pathogenic organisms (Davies, J and Davies, D. "Origins and Evolution of Antibiotic Resistance" Microbiology and Molecular Biology Reviews 2010, 417-433; and Humphries, J., Xiong, L., Liu, J., Prindle, A., Yuan, F., Arjes, H. A., Tsimring, L. and Gurol, S. "Species-Independent Attraction to Biofilms through Electrical Signaling" Cell 2017, 168: 200-209).

The formation and maintenance of mature biofilms are intimately linked to the production of an extracellular matrix. The multiple layers of cells and EPS may constitute a complex and compact structure within which biocides find it difficult to penetrate and reach internal layers, thus hampering their efficacy (see Bridier, et. al. "Resistance of bacterial biofilms to disinfectants: a review" Biofouling 2011, Vol. 27). Because biocides are often highly chemically reactive molecules, the presence of organic matter such as proteins, nucleic acids or carbohydrates can profoundly impair their efficacy, and potential interactions between antimicrobials and biofilm components may also contribute to their limited penetration into the biofilm.

Eye infections of the greatest frequency include red eyes, bacterial or viral conjunctivitis (pink eye), corneal ulcers, corneal keratitis, bacterial, fungal, herpal infectious keratitis, endophthalmitic, and blepharitis (lid infections). Conjunctivitis is the most common eye infection with viral conjunctivitis being the most common form. The most common causes of bacterial conjunctivitis are *Haemophilus influenza*, *Streptococcus pneumoniae* and *Staphylococcus aureus*. (Antibiotics versus placebo for acute bacterial conjunctivitis. Sheikh A, Hurwitz B., Cochrane Database Syst Rev. 2006 Apr. 19; (2):CD001211) Both viral and bacterial conjunctivitis present with a red eye and are highly contagious. Blepharitis is inflammation of the eyelids. It's a common cause of sore, red eyelids and crusty eyelashes. Lid margins can be infected due to bacterial or fungal infections, with accumulation forming a biofilm. Parasitic eyelash mites called *Demodex* feed on the biofilm, which in turn leads to an overgrowth of these mites that causes a worsening of the eyelid inflammation.

Bacterial infection is the most common cause of infectious keratitis. Common bacteria include *S. aureus*, coagulase-negative staphylococci, *S. pneumoniae* and *Pseudomonas aeruginosa*. (Sharma A, Taniguchi J. Review: Emerging strategies for antimicrobial drug delivery to the ocular surface: Implications for infectious keratitis. Ocul Surf 2017; 15:670-9.; Green M, Apel A, Stapleton F. Risk factors and causative organisms in microbial keratitis. Cornea 2008; 27:22-7.) *P. aeruginosa* is the most common microorganism implicated in bacterial keratitis among contact lens wearers. *Acanthamoeba* is suspected if a patient has been swimming or in a spa while wearing contact lenses. (Stapleton F, Dart J K, Seal D V, Matheson M. Epidemiology of *Pseudomonas aeruginosa* keratitis in contact lens wearers. Epidemiol Infect 1995; 114:395-402.)

Dry eye syndrome or dry eye disease (DED), is one of the most common eye conditions worldwide. Often, dry eye is accompanied by an inflammation of the lid margins, and that may go relatively unnoticed as a cause rather than a result of dry eye. The blepharitis is often treated with ointment (erythromycin often) and that seems to help. There are suggestive 4 stages of dry eye syndrome. Stage 1 involves the lash follicles, where a biofilm can establish itself. Stage 2 involves both the lash follicles and the meibomian glands and may explain obvious vs. non-obvious meibominan gland dysfunction (MGD). Because the biofilm blocks the large meibomian gland orifices (a combination of biofilm and poor or altered meibum). Stage 2 takes longer to achieve. Stage 3 involves the follicles, meibomian glands and the accessory lacrimal glands of Krause and Wolfring. The distance, narrow ducts and constant tear flushing serve to protect these glands for decades, making them the last glands affected by biofilm formation. Stage 4 occurs when the structural integrity of the eyelid finally breaks down due to the chronic inflammation, which can for example manifest clinically as lid laxity, floppy eyelid syndrome, ectropion and entropion. (Rynerson J M, Perry H D. DEBS—a unification theory for dry eye and blepharitis. Clin Ophthalmol. 2016; 10: 2455-67; Baudouin C. Ocular surface and external filtration surgery: mutual relationships. Dev Ophthalmol. 2012; 50:64-78; Baudouin C, Messmer E M, Aragona P, et al.

Revisiting the vicious circle of dry eye disease: a focus on the pathophysiology of meibomian gland dysfunction. Br J Ophthalmol. 2016; 100(3):300-6) Ear infections can occur in the outer ear canal (otitis externa), inner ear (otitis interna) or middle ear canal (otitis media). Most ear infections occur in the middle ear, when bacteria or virus grows, causing the accumulation of fluid, swelling, and inflammation. The infections can be chronic and generally due to biofilm accumulation. Recent clinical studies provide evidence that almost all chronic OM cases are accompanied by a bacterial biofilm behind the tympanic membrane (eardrum) and within the middle ear. Biofilms are typically very thin, and cannot be recognized using a regular otoscope. Otitis media (OM) is the most common illness in children in the United States with 3/4 of children under the age of 3 having OM at least once. Even though most cases are chronic infections, long-term or permanent damage to the ear can still occur. Acute otitis media may clear in one to two weeks without treatment, or may need to be treated with antibiotics. About 50% of antibiotic prescriptions for children less than 3 years old are given for ear infections. However, in the case of chronic OM, antibiotics may no longer be helpful, surgery is usually required, to place a tympanostomy tube in the tympanic membrane of the middle ear.

Periodontal or gum disease is a pathological inflammatory condition of the gum and bone support (periodontal tissues) surrounding the teeth. The two most common periodontal diseases are gingivitis which is the inflammation of the gum at the necks of the teeth, and periodontitis which is inflammation affecting the bone and tissues of the teeth.

In another embodiment an infection is treated by applying a dressing comprising one or more compounds of the present invention as an antimicrobial composition to the site of infection, wherein the dressing releases one or more compounds of the present invention into the site of infection. The infection may involve the presence of bacteria, fungi, viruses, amoebas, or a combination of infectious species thereof. Gingivitis occurs in both chronic and acute forms. Acute gingivitis is usually associated with specific infections, micro-organisms, or trauma. Chronic inflammation of the gum tissue surrounding the teeth is associated with the bacterial biofilm (plaque) that covers the teeth and gums.

Topical application also includes treatment of mouth/lip care, mouth ulcers and cold sores. Cold sores are contagious and strict hygiene measures should be adopted when a person is infected. Primary oral infection with the virus responsible for cold sores herpes simplex virus (HSV). After the primary oral infection, HSV may remain inactive only to be activated later as the more common herpes labialis, or "cold sores". Triggers for reactivation are well known and include sunlight, trauma, tiredness, stress, and menstruation. The most common form of mouth ulcer is called minor aphthous ulceration. Usually one to five small ulcers appear (less than 1 mm in diameter) on the inside of lips or cheeks, floor of the mouth or tongue. The ulcers tend to be concentrated towards the front of the mouth. Other more serious causes of mouth ulcers include herpes infection.

In another embodiment an infection is treated by applying a dressing comprising one or more compounds of the present invention as an antimicrobial composition to the site of infection, wherein the dressing releases one or more compounds of the present invention into the site of infection. The infection may involve the presence of bacteria, fungi, viruses, amoebas, or a combination of infectious species thereof.

In one embodiment, treatment of an infection comprises placing a dressing comprising an antimicrobial composition as described herein in or on the site of infection.

In another embodiment, treatment of an infection comprises placing an antimicrobial composition containing one or more compounds of the present invention at the site of infection. The length of time that the compound or composition is applied is such that antimicrobial treatment is still effective or the infection has resolved. The treatment may be applied continuously, with concurrent successive applications after an appropriate time frame, or in alternation with another treatment for the infection after an appropriate time frame. The quaternary ammonium compounds described herein may be applied at the site of infection in a host at the appropriate interval as determined by a healthcare provider. In some embodiments, the quaternary ammonium compounds described herein are placed at the site of infection for a day or less. In other embodiments, the quaternary ammonium compounds described herein are placed at a site of infection for a week or more.

An effective amount of the antimicrobial composition as described herein, or the antimicrobial composition described herein in combination or alternation with, or preceded by, concomitant with or followed by another active pharmaceutical agent, can be used in an amount sufficient to inhibit the progression of disorder, for example an infection, caused by the presence of an infectious organism in or on a host; cause a regression of a disorder caused by the presence of an infectious organism in or on a host; cause a cure of a disorder caused by the presence of an infectious organism in or on a host; or inhibit or prevent the development of a disorder caused by the presence of an infectious organism near, in or on a host. The method of treatment can be administered once a day (q.d.), twice a day (b.i.d.), three times a day (t.i.d.), four times a day (q.i.d.), once every other day (Q2d), once every third day (Q3d), as needed, or using any dosing schedule that provides treatment of an infection as described herein.

In some embodiments, the method of treating and/or preventing an infection comprises placing a dressing saturated with the antimicrobial composition in the site of a wound and/or infection. The dressing may be saturated with the antimicrobial composition directly before placement into the site of a wound and/or infection or may be manufactured and packaged presaturated. In other embodiments, the method of treating and/or preventing an infection comprises placing a dressing in the site of a wound and/or infection followed by subsequent saturation of the dressing with the antimicrobial composition. The antimicrobial composition may be added after placement of the dressing by dropper, syringe, or other suitable means.

In one embodiment, one or more of the quaternary ammonium compounds, or pharmaceutical composition as described herein, are used to treat or to prevent a medical disorder which is mediated by the presence of a bacterium, for example a bacterial infection. In one embodiment, the quaternary ammonium compounds of the present invention may be used to treat a disorder, typically an infection, caused by a pathogenic bacterium. In one embodiment, a method is provided comprising administering an effective amount of a quaternary ammonium compound, or composition thereof described herein to a subject to treat an infection caused by a bacterium.

In one embodiment, one or more of the quaternary ammonium compounds of the present invention may be used to treat a disorder, typically an infection, caused by a gram-positive bacterium. In one embodiment, a method is provided comprising administering an effective amount of a quaternary ammonium compound, or composition thereof as described herein to treat an infection caused by a gram-positive bacterium.

Non-limiting example of gram-positive bacteria which may be treated using the quaternary ammonium compounds of the present invention either alone or in combination with another therapeutic include: *Actinomyces* species including *Actinomyces israelii, Actinomyces naeslundii, Actinomyces viscosus, Actinomyces odontolyticus*, and *Actinomyces pyogenes; Bacillus* species including *Bacillus anthracis, Bacillus cereus*, and *Bacillus subtilis; Clostridium* species including *Clostridium botulinum, Clostridium difficile, Clostridium perfringens, Clostridium sordellii*, and *Clostridium tetani; Corynebacterium* species including *Corynebacterium diphtheriae, Corynebacterium jeikeium, Corynebacterium minutissimum, Corynebacterium mucifaciens, Corynebacterium pseudotuberculosis, Corynebacterium striatum, Corynebacterium tenuis*, and *Corynebacterium ulcerans; Enterococcus* species including *Enterococcus casseliflavus, Enterococcus faecalis, Enterococcus faecium, Enterococcus raffinosus*, and *Enterococcus hirae; Leuconostoc* species including *Leuconostoc pseudomesenteroides; Micrococcus* species such as *Micrococcus luteus; Nocardia* species including *Nocardia asteroides; Propionibacterium* species including *Propionibacterium acnes; Staphylococcus* species including *Staphylococcus aureus, Staphylococcus capitis, Staphylococcus epidermidis, Staphylococcus haemolyticus, Staphylococcus hominis, Staphylococcus lugdunensis, Staphylococcus pasteuri*, and *Staphylococcus saprophyticus*; and *Streptococcus* species including *Streptococcus agalactiae, Streptococcus anginosus, Streptococcus bovis, Streptococcus dysgalactiae, Streptococcus mitis, Streptococcus mutans, Streptococcus pneumoniae, Streptococcus pyogenes, Streptococcus sanguinis, Streptococcus suis*, and *Streptococcus viridans*.

In one embodiment, the quaternary ammonium compounds of the present invention may be used to treat a disorder, typically an infection, caused by a gram-negative bacterium. In one embodiment, a method is provided comprising administering an effective amount of a quaternary ammonium compound, or composition thereof described herein to treat an infection caused by a gram-negative bacterium.

Non-limiting examples of gram-negative bacteria which may be treated using the quaternary ammonium compounds of the present invention either alone or in combination with another therapeutic include: Acinetobacter species including Acinetobacter baumannii and Acinetobacter iwoffii; Aeromonas species including Aeromonas veronii biovar sobria (previously Aeromonas sobria), Aeromonas caviae, and Aeromonas hydrophila; Alcaligenes/Achromobacter species including Alcaligenes faecalis and Alcaligenes xylosoxidans; Bacteroides species including Bacteroides fragilis; Bartonella species including Bartonella bacillformis, Bartonella clarridgeiae, Bartonella elizabethae, Bartonella henselae, Bartonella koehlerae, Bartonalla naantalienis, Bartonella quintana, Bartonella rochalimae, Bartonella vinsonii, and Bartonella washoensis; Bordetella species including Bordetella bronchispetica, Bordetella pertussis, and Bordetella parapertussis; Borrelia species including Borrelia afzelii, Borrelia burgdorferi, Borrelia crocidurae, Borrelia duttoni, Borrelia garinii, Borrelia hermsii, Borrelia hispanica, Borellia miyamotoi, Borrelia parkeri, Borrelia persica, Borrelia recurrentis, Borrelia turicatae, and Borrelia venezuelensis; Brevundimonas species including Brevundimonas diminuta and Brevundimonas vesicularis; Brucella species including Brucella abortus, Brucella canis, Brucella melitensis, and Brucella suis; Burkholderia species including Burkholderia cepacia, Burkholderia mallei, and Burkholderia pseudomallei; Campylobacter species including Campylobacter jejuni, Campylobacter coli, Campylobacter upsaliensis, Campylobacter lari, and Campylobacter coli; Chlamydia/Chlamidophila species including Chlamydophila pneumoniae, Chlamydophila psittaci, Chlamidophila pecorum, and Chlamydia trachomatis; Citrobacter species including Citrobacter amalonaticus, Citrobacter freundii, Citrobacter koseri, and Citrobacter diversus; Coxiella burnetti; Ehrlichia species including Ehrlichia canis and Ehrlichia chaffeensis; Enterobacter species including Enterobacter aerogenes and Enterobacter cloacae; Escherichia species including Escherichia coli; Francisella species including Francisella novicida, Francisella philomiragia, and Francisella tularensis; Haemophilus species including Haemophilus influenzae and Haemophilus ducreyi; Helicobacter species including Helicobacter pylori; Klebsiella species including Klebsiella granulomatis, Klebsiella oxytoca, and Klebsiella pneumoniae; Leclercia adecarboxylata; Legionella species including Legionella pneumophila; Leptospira species including Leptospira interrogans, Leptospira noguchii, Leptospira santarosai, and Leptospira weilii; Listeria species including Listeria monocytogenes; Moraxella species including Moraxella catarrhalis, Moraxella lacunata, and Moraxella bovis; Morganella species including Morganella morganii; Mycoplasma species including Mycoplasma amphoriforme, Mycoplasma buccale, Mycoplasma faucium, Mycoplasma fermentans, Mycoplasma genitalium, Mycoplasma hominis, Mycoplasma lipophilum, Mycoplasma orale, Mycoplasma penetrans, Mycoplasma pirum, Mycoplasma pneumoniae, Mycoplasma primatum, Mycoplasma salivarium, and Mycoplasma spermatophilum; Neisseria species including Neisseria meningitidis and Neisseria gonorrhoeae; Orientia species including Orientia tsutsugamushi and Orientia chuto; Pantoea species including Pantoea agglomerans; Paracoccus species including Paracoccus yeei; Prevotella species including Prevotella intermedia and Prevotella melaninogenica; Proteus species including Proteus mirabilis, Proteus penneri, and Proteus vulgaris; Providencia species including Providencia rettgeri and Providencia stuartii; Pseudomonas species including Pseudomonas aeruginosa, Pseudomonas oryzihabitans, Pseudomonas plecoglossidica, and Pseudomonas stutzeri; Ralstonia species including Ralstonia pickettii and Ralstonia insidiosa; Rickettsia species including Rickettsia africae, Rickettsia akari, Rickettsia australis, Rickettsia conorii, Rickettsia felis, Rickettsia japonica, Rickettsia prowazekii, Rickettsia rickettsia, Rickettsia sibirica, and Rickettsia typhi; Roseomonas species including Roseomonas gilardii; Salmonella species including Salmonella bongori, Salmonella enterica, Salmonella paratyphi, Salmonella typhi, and Salmonella typhimurium; Serratia species including Serratia marcescens, Serratia liquefaciens, Serratia rubidaea, and Serratia odoriferae; Shigella species including Shigella dysenteriae and Shigella sonnei; Sphingomonas species including Sphingomonas mucosissima and Sphingomonas paucimobilus; Stenotrophomas species including Stenotrophomas maltophilia; Treponema species including Treponema carateum, Treponema paraluiscuniculi, and Treponema pallidum; Ureaplasma species including Ureaplasma urealyticum; Vibrio species including Vibrio cholera, Vibrio parahaemolyticus, and Vibrio vulnificus; and Yersinia species including Yersinia enterocolitica, Yersinia pestis, and Yersinia pseudotuberculosis.

In one embodiment, the quaternary ammonium compounds of the present invention may be used to treat a disorder, typically an infection, caused by a mycobacterium. In one embodiment, a method is provided comprising administering an effective amount of a quaternary ammonium compound, or composition thereof described herein to treat an infection caused by a mycobacterium.

Non-limiting examples of mycobacteria which may be treated using the quaternary ammonium compounds of the present invention either alone or in combination with another therapeutic include Mycobacterium abcessus, Mycobacterium africanum, Mycobacterium agri, Mycobacterium aichiense, Mycobacterium alvei, Mycobacterium arabiense, Mycobacterium aromaticivorans, Mycobacterium arosiense, Mycobacterium arupense, Mycobacterium aquaticum, Mycobacterium asiaticum, Mycobacterium aubagnese, Mycobacterium aurum, Mycobacterium austroafricanum, Mycobacterium avium, Mycobacterium avium paratuberculosis, Mycobacterium avium silvaticum, Mycobacterium avium hominussuis, Mycobacterium bacteremicum, Mycobacterium barrassiae, Mycobacterium boenickei, Mycobacterium bohemicum, Mycobacterium bolletii, Mycobacterium botniense, Mycobacterium bovis, Mycobacterium branderi, Mycobacterium brisbanense, Mycobacterium brumae, Mycobacterium canariasense, Mycobacterium canettii, Mycobacterium caprae, Mycobacterium chimaera, Mycobacterium chelonae, Mycobacterium chitae, Mycobacterium chubuense, Mycobacterium colombiense, Mycobacterium conceptionense, Mycobacterium confluentis, Mycobacterium conspicuum, Mycobacterium cookii, Mycobacterium cosmeticum, Mycobacterium diernhoferi, Mycobacterium doricum, Mycobacterium duvali, Mycobacterium elephantis, Mycobacterium fallax, Mycobacterium farcinogenes, Mycobacterium flavescens, Mycobacterium florentinum, Mycobacterium fortuitum, Mycobacterium frederikbergense, Mycobacterium gadium, Mycobacterium

*gastri, Mycobacterium genavense, Mycobacterium gilvum, Mycobacterium gordonae, Mycobacterium haemophilum, Mycobacterium hassiacum, Mycobacterium heidelbergense, Mycobacterium heckshornense; Mycobacterium hiberniae, Mycobacterium hodleri, Mycobacterium holsaticum, Mycobacterium houstonense, Mycobacterium icosiumassilensis, Mycobacterium immunogenum, Mycobacterium indicus pranii, Mycobacterium intacellulare, Mycobacterium intracellulare, Mycobacterium interjectum, Mycobacterium intermedium, Mycobacterium iranicum, Mycobacterium kansasii, Mycobacterium komossense, Mycobacterium kubicae, Mycobacterium lentiflavum, Mycobacterium leprae, Mycobacterium lepraemurium, Mycobacterium lepromatosis, Mycobacterium hflandii, Mycobacterium llatzerense, Mycobacterium madagascariense, Mycobacterium mageritense, Mycobacterium malmoense, Mycobacterium marinum, Mycobacterium massiliense, Mycobacterium massilipolynesiensis, Mycobacterium microti, Mycobacterium monacense, Mycobacterium montfiorense, Mycobacterium morokaense, Mycobacterium mucogenicum, Mycobacterium mungi, Mycobacterium murale, Mycobacterium nebraskense, Mycobacterium neoaurum, Mycobacterium neworleansense, Mycobacterium nonchromogenicum, Mycobacterium obuense, Mycobacterium orygis, Mycobacterium palustre, Mycobacterium parascofulaceum, Mycobacterium parafortuitum, Mycobacterium perigrinum, Mycobacterium phlei, Mycobacterium phocaicum, Mycobacterium pinnipedii, Mycobacterium porcinum, Mycobacterium pseudoshottsii, Mycobacterium psychotolerans, Mycobacterium pulveris, Mycobacterium pyrenivorans, Mycobacterium saskatchewanense, Mycobacterium sediminis, Mycobacterium senegalense, Mycobacterium septicum, Mycobacterium shimoidei, Mycobacterium shottsii, Mycobacterium simiae, Mycobacterium smegmatis, Mycobacterium sphagni, Mycobacterium stephanolepidis, Mycobacterium suricattae, Mycobacterium szulgai, Mycobacterium talmoniae, Mycobacterium terrae, Mycobacterium thermoresistibile, Mycobacterium triplex, Mycobacterium triviale, Mycobacterium tuberculosis, Mycobacterium tusciae, Mycobacterium ulcerans, Mycobacterium vaccae, Mycobacterium vanbaalenii, Mycobacterium xenopi,* and *Mycobacterium yongonense.*

Non-limiting examples of disorders mediated by a bacterium that may be treated by the quaternary ammonium compounds of the present invention, either alone or in combination with another therapeutic, include actinomycosis, anaplasmosis, anthrax, bacillary angiomatosis, actinomycetoma, bacterial pneumonia, bacterial vaginosis, bacterial endocarditis, bartonellosis, botulism, boutenneuse fever, brucellosis, bejel, brucellosis spondylitis, bubonic plague, Buruli ulcer, Bairnsdale ulcer, bacillary dysentery, campylobacteriosis, Carrion's disease, cat-scratch disease, cellulitis, chancroid, chlamydia, chlamydia conjunctivitis, clostridial myonecrosis, cholera, *Clostridium difficile* colitis, diphtheria, Daintree ulcer, donavanosis, dysentery, erhlichiosis, epidemic typhus, fried rice syndrome, five-day fever, floppy baby syndrome, Far East scarlet-like fever, gas gangrene, glanders, gonorrhea, granuloma inguinale, human necrobacillosis, necrotizing fasciitis, hemolytic-uremic syndrome, human ewingii ehrlichiosis, human monocytic ehrlichiosis, human granulocytic anaplasmosis, infant botulism, Izumi fever, Kawasaki disease, Kumusi ulder, lymphogranuloma venereum, Lemierre's syndrome, Legionellosis, leprosy, leptospirosis, listeriosis, Lyme disease, lymphogranuloma venereum, Malta fever, Mediterranean fever, myonecrosis, mycoburuli ulcer, mucocutaneous lymph node syndrome, meliodosis, meningococcal disease, murine typhus, *Mycoplasma* pneumonia, mycetoma, neonatal conjunctivitis, nocardiosis, Oroya fever, ophthalmia neonatorum, ornithosis, Pontiac fever, peliosis hepatis, pneumonic plague, postanginal shock including sepsis, pasteurellosis, pelvic inflammatory disease, pertussis, plague, pneumococcal infection, pneumonia, psittacosis, parrot fever, pseudotuberculosis, Q fever, quintan fever, rabbit fever, relapsing fever, rickettsialpox, Rocky Mountain spotted fever, rat-bite fever, Reiter syndrome, rheumatic fever, salmonellosis, scarlet fever, sepsis, septicemic plague, Searls ulcer, shigellosis, soft chancre, syphilis, streptobacillary fever, scrub typhus, Taiwan acute respiratory agent, Trench fever, trachoma, tuberculosis, tularemia, typhoid fever, typhus, tetanus, toxic shock syndrome, undulant fever, ulcus molle, *Vibrio parahaemolyticus* enteritis, Whitmore's disease, walking pneumonia, Waterhouse-Friderichsen syndrome, yaws, and yersiniosis.

In one embodiment, one or more of the quaternary ammonium compounds, or pharmaceutical composition as described herein, are used to treat or to prevent a medical disorder which is mediated by the presence of a fungus, for example a fungal infection. In one embodiment, the quaternary ammonium compounds of the present invention may be used to treat a disorder, typically an infection, caused by a pathogenic fungus. In one embodiment, a method is provided comprising administering an effective amount of a quaternary ammonium compound, or composition thereof described herein to a subject to treat an infection caused by a fungus.

Non-limiting examples of fungi which may be treated using the quaternary ammonium compounds of the present invention either alone or in combination with another therapeutic include: *Absidia* species including *Absidia corymbifera; Alterania* species including *Alterania alternate; Aspergillus* species including *Aspergillus clavatus, Aspergullus flavus, Aspergillus fumigatus, Aspergillus niger, Aspergillus sydowii, Aspergillus terreus, Aspergillus versicolor,* and *Aspergillus* verrucaria; *Aureobasidium* species including *Aureobasidium pullans; Batrachochytrium* species including *Batrachochytrium dendrobatidis* and *Batrachochytrium salamandrivorans; Blastomyces* species including *Blastomyces dermatitidis; Candida* species including *Candida albicans, Candida dubliniensis, Candida glabrata, Candida parapsilosis, Candida rugosa,* and *Candida tropicalis; Chaetomium* species including *Chaetomium globsum; Cladosporium* species including *Cladosporium cladosporoides; Coccidioides* species including *Coccidioides immitis* and *Coccidioides posadasii; Cryptococcus* species including *Cryptococcus albidus, Cryptococcus gattii, Cryptococcus laurentii, Cryptococcus neoformans,* and *Cryptococcus uniguttulatus;* Cunninghamella species; *Curvularia* species including *Curvularia brachyspora, Curvularia clavata, Curvularia geniculata, Curvularia lunata, Curvularia pallescens, Curvularia senegalensis,* and *Curvularia verruculosa; Dreschslera* species including *Dreschlera australiensis; Epidermophyton* species including *Epidermophyton floccosum; Fonsecaea* species including *Fonsecaea compacta* and *Fonsecaea pedrosoi; Fusarium* species including *Fusarium solani, Fusarium oxysporum,* and *Fusarium chlamydosporum, Geotrichum* species including *Geotrichum capitatum, Geotrichum candidum,* and *Geotricum clavatum; Gliomastix* species including *Gliomastix cerealis; Gloeophyllum* species including *Gloeophyllum trabeum; Histoplasma* species including *Histoplasma capsulatum* and *Histoplasma capsulatum* var. *faciminosum; Malassezia* species including *Malassezia furfur* and *Malassezia globosa; Microsporum* species; *Monilia* species including *Monilia grisea*; *Mucor* species including *Mucor indicus*; *Paracoccidioides* species including *Paracoccidioides brasiliensis*; *Penicillium* species; *Piedraia* species including *Piedraia hortae* and *Piedraia quintanilhae*; *Phialophora* species including *Phialophora verrucosa*; *Phoma* species including *Phoma fimeti*; *Pithomyces* species including *Pithomyces chartarum*; *Pneumocystis* species including *Pneumocystis carinii* and *Pneumocystis jirovecii*; *Poria* species including *Poria placenta*; *Rhizopus* species including *Rhizopus* microspores, *Rhizopus oryzae*, and *Rhizopus stolonfer*; *Scolecobasidium* species including *Scolecobasidium humicola*; *Sporothrix* species including *Sporothrix brasiliensis*, *Sporothrix globosa*, and *Sporothrix schenckii*; and *Trichoderma* species including *Trichoderma viride*; and *Trichophyton* species including *Trichosporon beigehii*, *Trichophyton concentricum*, *Trichophyton interdigitale*, *Trichophyton mentagrophytes*, *Trichophyton rubrum*, and *Trichophyton tonsurans*.

Non-limiting examples of disorders mediated by a fungus that may be treated by the quaternary ammonium compounds of the present invention, either alone or in combination with another therapeutic, include Aspergillosis, black piedra, blastomycosis, candidiasis, chromoblastomycosis, chytridiomycosis, coccidioimycosis, cryptococcosis, dermatophytosis, geotrichosis, histoplasmosis, mucormycosis, paracoccidioidomycosis, pneumocystis pneumonia, sporotrichosis, *Tinea barbae*, *Tinea capitis*, *Tinea corporis*, *Tinea cruris*, *Tinea manum*, *Tinea nigra*, *Tinea unguium*, *Tinea versicolor*, white piedra, and zygomycosis.

In one embodiment, one or more of the quaternary ammonium compounds, or pharmaceutical composition as described herein, are used to treat or to prevent a medical disorder which is mediated by the presence of amoeba, for example an amoebal infection. In one embodiment, the quaternary ammonium compounds of the present invention may be used to treat a disorder, typically an infection, caused by a pathogenic amoeba. In one embodiment, a method is provided comprising administering an effective amount of a quaternary ammonium compound, or composition thereof described herein to a subject to treat an infection caused by an amoeba.

Non-limiting examples of amoeba which may be treated using the quaternary ammonium compounds of the present invention either alone or in combination with another therapeutic include: *Acanthamoeba* species; *Balamuthia* species including *Balamuthia mandrillaris*; *Dientamoeba* species including *Dientamoeba fragilis*; *Endolimax* species including *Endolimax nana*; *Entamoeba* species including *Entamoeba* Bangladeshi, *Entamoeba coli*, *Entamoeba dispar*, *Entamoeba gingivalis*, *Entamoeba hartmanni*, *Entamoeba histolytica*, *Entamoeba moshkovskii*, and *Entamoeba polecki*; *Iodamoeba* species including *Iodamoeba butschlii*; *Naegleria* species including *Naegleria fowleri*; and *Sappinia* species including *Sappinia diploidea* and *Sappinia pedata*.

Non-limiting examples of disorders mediated by an amoeba that may be treated by the quaternary ammonium compounds of the present invention, either alone or in combination with another therapeutic, include amoebiasis, amoebic dysentery, amoebic liver abscess, cutaneous amoebiasis, amoebic brain abscess, amebiasis cutis, *Acanthamoeba keratitis*, cutaneous acanthamoebiasis, granulomatous amoebic encephalitis, *Balamuthia* amoebic encephalitis, and Sappinia amoeba encephalitis.

In one embodiment, the quaternary ammonium compounds of the present invention may be used to treat an inflammatory disorder caused by the presence of an infectious organism, for example a bacterium, a fungus, a virus, or an amoeba as described herein.

Non-limiting examples of such inflammatory disorders include adenoiditis, appendicitis, arteritis, ascending cholangitis, balanitis, blepharitis, bronchitis, bursitis, cellulitis, cerebral vasculitis, cervicitis, chemosis, cholecystitis, chondritis, choroioamnionitis, colitis, conjunctivitis, constrictive pericarditis, cryptitis, dacryoadenitis, dermatitis, diabetic ulcer, duodenal lymphocytosis, encephalitis, endocarditis, endometritis, endotheliitis, enteritis, enterocolitis, eosinophilis fasciitis, epididymitis, esophagitis, folliculitis, gastritis, gingivitis, glomerulonephritis, glossitis, hepatitis, infectious arthritis, ileitis, intertrigo, keratitis, keratoconjunctivitis, labyrithitis, lymphadenitis, mastitis, mastoiditis, myocarditis, myopericarditis, myositis, necrotizing fasciitis, nephritis, omaphalitis, oophoritis, ophthalmitis, orchitis, osteitis, osteomyelitis, pancreatitis, paraproctitis, parotitis, pericarditis, perichondritis, perifolliculitis, periodontitis, peritonitis, pharyngitis, phlebitis, pleurisy, pneumonitis, pulmonitis, proctitis, prostatitis, pulpitis, pyelonephritis, pyomyositis, retinal vasculitis, rheumatic fever, rhinitis, scleritis, salpingitis, sialadenitis, sinusitis, stomatitis, synovitis, septicemia, tenosynovitis, thyroiditis, tonsillitis, tularemia, urethritis, uveitis, vaginitis, vasculitis, and vulvitus.

In some embodiments, the quaternary ammonium compounds of the present invention used to treat a skin infection in a host, for example a human. The infection may be caused by a bacterium, a fungus, an amoeba, or a virus as described herein. In one embodiment, a method is provided comprising administering an effective amount of a quaternary ammonium compound, or composition thereof described herein to a host, for example a human, to treat a skin infection. In another embodiment, the method is used to treat a skin infection in another mammal, for example a cat, a dog, a cow, a pig, or a horse.

Examples of bacterial cutaneous infections that may be treated by the quaternary ammonium compounds of the present invention include, but are not limited to: African tick bite fever; American tick bite fever (*Rickettsia parkeri* infection); Bacillary angiomatosis; Bejel (endemic syphilis); Blastomycosis-like pyoderma (pyoderma vegetans); Blistering distal dactylitis; Botryomycosis; Brill-Zinsser disease; Brucellosis (Bang's disease, Malta fever, undulant fever); Bubonic plague; Bullous impetigo; Cat scratch disease (cat scratch fever, English-Wear infection, inoculation lymphoreticulosis, subacute regional lymphadenitis); Cellulitis; Chancre; Chancroid (soft chancre, ulcus molle); Chronic lymphangitis; Chronic recurrent erysipelas; Chronic undermining burrowing ulcers (Meleney gangrene); Condylomata lata; Cutaneous actinomycosis; Dermatitis gangrenosa (gangrene of the skin); Ecthyma; Ecthyma gangrenosum; Elephantiasis nostras; Endemic typhus (murine typhus); Epidemic typhus (epidemic louse-borne typhus); Erysipelas (ignis sacer, Saint Anthony's fire); Erysipeloid of Rosenbach; Erythema marginatum; Erythrasma; Felon; Flea-borne spotted fever; Flinders Island spotted fever; Flying squirrel typhus; Folliculitis; Fournier gangrene (Fournier gangrene of the penis or scrotum); Furunculosis (boil); Gas gangrene (clostridial myonecrosis, myonecrosis); Glanders (equinia, farcy, malleus); Gonococcemia (arthritis-dermatosis syndrome, disseminated gonococcal infection); Gonorrhea (clap); Gram-negative folliculitis; Gram-negative toe web infection; Granuloma inguinale (Donovanosis, granuloma genitoinguinale, granuloma inguinale tropicum, granuloma venereum, granuloma venereum genitoinguinale, lupoid form of groin ulceration, serpiginous ulceration of the groin, ulcerating granuloma of the pudendum, ulcerating sclerosing granuloma); Green nail syndrome; Hospital furunculosis; Hot tub folliculitis (*Pseudomonas aeruginosa* folliculitis); Human granulocytotropic anaplasmosis; Human monocytotropic ehrlichiosis; Impetigo contagiosa; Japanese spotted fever; Leptospirosis (Fort Bragg fever, pretibial fever, Weil's disease); Listeriosis; Ludwig's angina; Lupoid sycosis; Lyme disease (Afzelius' disease, Lyme borreliosis); Lymphogranuloma venereum (climatic bubo, Durand-Nicolas-Favre disease, lymphogranuloma inguinale, poradenitis inguinale, strumous bubo); Malakoplakia (malacoplakia); Mediterranean spotted fever (Boutonneuse fever); Melioidosis (Whitmore's disease); Meningococcemia; Missouri Lyme disease; Necrotizing fasciitis (flesh-eating bacteria syndrome); Neonatal toxic shock-like exanthematous disease; Noma neonatorum; North Asian tick typhus; Ophthalmia neonatorum; Oroya fever (Carrion's disease); Perianal cellulitis (perineal dermatitis, streptococcal perianal disease); Periapical abscess; Pinta; Pitted keratolysis (keratolysis plantare sulcatum, keratoma plantare sulcatum, ringed keratolysis); Plague; Primary gonococcal dermatitis; Pseudomonal Pyoderma; *Pseudomonas* hot-foot syndrome; Pyogenic paronychia; Pyomyositis; Q fever; Queensland tick typhus; Rat-bite fever; Recurrent toxin-mediated perineal erythema; Rhinoscleroma; Rocky Mountain spotted fever; Scarlet fever; Scrub typhus (Tsutsugamushi fever); Shigellosis; Staphylococcal scalded skin syndrome (pemphigus neonatorum, Ritter's disease); Streptococcal intertrigo; Superficial pustular folliculitis (impetigo of Bockhart, superficial folliculitis); Sycosis vulgaris (barber's itch, sycosis barbae); Syphilid; Syphilis (lues); Tick-borne lymphadenopathy; Toxic shock syndrome (streptococcal toxic shock syndrome, streptococcal toxic shock-like syndrome, toxic streptococcal syndrome); Trench fever (five-day fever, quintan fever, urban trench fever); Tropical ulcer (Aden ulcer, jungle rot, Malabar ulcer, tropical phagedena); Tularemia (deer fly fever, Ohara's disease, Pahvant Valley plague, rabbit fever); Verruga peruana; and Yaws (bouba, frambosie, parangi, pian).

Examples of mycobacterial cutaneous infections that may be treated by the quaternary ammonium compounds of the present invention include, but are not limited to: Aquarium granuloma (fish-tank granuloma, swimming-pool granuloma); Borderline lepromatous leprosy; Borderline leprosy; Borderline tuberculoid leprosy; Buruli ulcer (Bairnsdale ulcer, Searl ulcer, Searle's ulcer); Erythema induratum (Bazin disease); Histoid leprosy; Lepromatous leprosy; Leprosy (Hansen's disease); Lichen scrofulosorum (tuberculosis cutis lichenoides); Lupus vulgaris (tuberculosis luposa); Miliary tuberculosis (disseminated tuberculosis, tuberculosis cutis acuta generalisata, tuberculosis cutis disseminata); Papulonecrotic tuberculid; Primary inoculation tuberculosis (cutaneous primary complex, primary tuberculous complex, tuberculous chancre); Scrofuloderma (tuberculosis cutis colliquativa); Tuberculosis cutis orificialis (acute tuberculous ulcer, orificial tuberculosis); Tuberculosis verrucosa cutis (lupus verrucosus, prosector's wart, warty tuberculosis); Tuberculous cellulitis; Tuberculous gumma (metastatic tuberculous abscess, metastatic tuberculous ulcer); and Tuberculoid leprosy.

Examples of fungal cutaneous infections that may be treated by the quaternary ammonium compounds of the present invention include, but are not limited to: African histoplasmosis; Alternariosis; Antibiotic candidiasis (iatrogenic candidiasis); Black piedra; Candidal intertrigo; Candidal onychomycosis; Candidal paronychia; Candidal vulvovaginitis; Candidid; Chromoblastomycosis (chromomycosis, cladosporiosis, Fonseca's disease, Pedroso's disease, phaeosporotrichosis, verrucous dermatitis); Chronic mucocutaneous candidiasis; Coccidioidomycosis (California disease, desert rheumatism, San Joaquin Valley fever, valley fever); Congenital cutaneous candidiasis; Cryptococcosis; Dermatophytid; Diaper candidiasis; Disseminated coccidioidomycosis (coccidioidal granuloma); Distal subungual onychomycosis; Entomophthoromycosis; Erosio interdigitalis blastomycetica; Favus; Fungal folliculitis (majocchi granuloma); Fusariosis; Geotrichosis; Granuloma gluteale infantum; Histoplasmosis (cave disease, Darling's disease, Ohio Valley disease, reticuloendotheliosis); Hyalohyphomycosis; Kerion; Lobomycosis (keloidal blastomycosis, lacaziosis, Lobo's disease); Mucormycosis; Mycetoma (Madura foot, maduromycosis); North American blastomycosis (blastomycetic dermatitis, blastomycosis, Gilchrist's disease); Onychomycosis (dermatophytic onychomycosis, ringworm of the nail, *tinea unguium*); Oral candidiasis (thrush); Otomycosis; Perianal candidiasis; Perleche (angular cheilitis); Phaeohyphomycosis; *Piedra* (trichosporosis); Pityrosporum folliculitis; Primary cutaneous aspergillosis; Primary cutaneous coccidioidomycosis; Primary cutaneous histoplasmosis; Primary pulmonary coccidioidomycosis; Primary pulmonary histoplasmosis; Progressive disseminated histoplasmosis; Proximal subungual onychomycosis; Rhinosporidiosis; South American blastomycosis (Brazilian blastomycosis, paracoccidioidal granuloma, paracoccidioidomycosis); Sporotrichosis (rose-gardener's disease); Systemic candidiasis; *Tinea barbae* (barber's itch, ringworm of the beard, tinea sycosis); *Tinea capitis* (herpes tonsurans, ringworm of the hair, ringworm of the scalp, scalp ringworm, tinea tonsurans); *Tinea corporis* (ringworm, tinea circinata, tinea glabrosa); *Tinea corporis gladiatorum*; *Tinea cruris* (crotch itch, eczema marginatum, gym itch, jock itch, ringworm of the groin); *Tinea faciei; Tinea imbricate* (tokelau); *Tinea incognito; Tinea manuum; Tinea nigra* (superficial phaeohyphomycosis, *tinea nigra* palmaris et plantaris); *Tinea pedis* (athlete's foot, ringworm of the foot); *Tinea versicolor* (dermatomycosis furfuracea, *pityriasis versicolor, Tinea flava*); White *piedra*; White superficial onychomycosis; and Zygomycosis (phycomycosis).

In some embodiments, the quaternary ammonium compounds of the present invention may be used to treat an ocular infection in a host, for example a human. Ocular infections that may be treated by the quaternary ammonium compounds of the present invention include, but are not limited to, conjunctivitis, uveitis, styes, blepharitis, chalazion, corneal ulcers and infections, dacryoadenitis, scleritis, keratitis, and iritis. In one embodiment, a method is provided comprising administering an effective amount of a quaternary ammonium compound, or composition thereof, described herein to a subject, for example a human, to treat an ocular infection. In another embodiment, the method is used to treat an ocular infection in another mammal, for example a rabbit, cat, a dog, a cow, a pig, or a horse.

In some embodiments, the quaternary ammonium compounds of the present invention may be used to treat corneal keratitis in a host, for example a human. Corneal keratitis may be caused by a number of infectious organisms, including: bacteria such as *Staphylococcus aureus* and *Pseudomonas aeruginosa*; fungi such as *Fusarium, Candida, Aspergillus,* and *Curvularia* species; viruses such as Herpes simplex and Herpes zoster; and amoeba such as *Acanthamoeba* species, or combinations thereof.

In one embodiment, the quaternary ammonium compounds of the present invention are used to treat bacterial keratitis in a host, for example a human. In another embodiment, the quaternary ammonium compounds of the present invention are used to treat fungal keratitis in a host, for example a human.

In another embodiment, the quaternary ammonium compounds of the present invention are used to treat viral keratitis in a host, for example a human. In another embodiment, the quaternary ammonium compounds of the present invention are used to treat *Acanthamoebic keratitis* in a host, for example a human. In another embodiment, the method is used to treat corneal keratitis in another mammal, for example a rabbit, cat, a dog, a cow, a pig, or a horse.

In some embodiments, the quaternary ammonium compounds of the present invention may be used to treat conjunctivitis in a host, for example a human. Conjunctivitis may be caused by a number of infectious organisms, including bacteria such as *Staphylococcus aureus, Haemophilus influenzae, Streptococcus pneumoniae* and *Pseudomonas aeruginosa*; and viruses such as adenovirus and enterovirus.

In one embodiment, the quaternary ammonium compounds of the present invention are used to treat bacterial conjunctivitis in a host, for example a human. In one embodiment, the quaternary ammonium compounds of the present invention are used to treat viral conjunctivitis in a host, for example a human. In another embodiment, the method is used to treat conjunctivitis in another mammal, for example a rabbit, cat, a dog, a cow, a pig, or a horse.

In some embodiments, the quaternary ammonium compounds of the present invention may be used to treat an ear infection in a host, for example a human. The ear infection may be present within the outer ear and/or ear canal (otitis externa), the middle ear (otitis media), or the inner ear (otitis interna). In one embodiment, a method is provided comprising administering an effective amount of a quaternary ammonium compound, or composition thereof described herein to a subject to treat an ear infection. In another embodiment, the method is used to treat an ear infection in another animal, for example a cat, a dog, a cow, a pig, or a horse.

In some embodiments, the method of treatment involves application of a dressing comprising an effective amount of a quaternary ammonium compound of the present invention, either alone or as a pharmaceutical composition, to the site of infection in a host in need thereof. The dressing is preferably shaped to fit within the space provided by the external auditory canal. The dressing may be malleable, allowing it to be compressed and shaped to fit within the external auditory canal, or it may be rigid, ensuring it will sit against the walls of the external auditory canal to ensure proper contact and transfer of the antimicrobial composition. In some embodiments, the dressing is only placed in the external auditory canal for a day or less. In other embodiments, the dressing is placed in the external auditory canal for a week or more.

In some embodiments, the method of treatment of an infection in the ear canal of a host in need thereof involves application of the dressing into the ear canal of the host and subsequent saturation of the dressing with the antimicrobial composition. This method would allow for sequential or continuous application of the antimicrobial composition while the dressing is in place. In one embodiment, the dressing is composed of a dissolvable material, requiring placement into the ear canal before saturation with the antimicrobial composition. In another embodiment, the dressing is composed of polymeric foam that will expand upon subsequent wetting with the antimicrobial composition.

In some embodiments, a method of treating or preventing an infection in a chronic wound is provided comprising administering an effective amount of a quaternary ammonium compound of the present invention, either alone or in an antimicrobial composition, to the chronic wound in a host in need thereof, for example a human. Three types of chronic wounds are venous ulcers, diabetic ulcers, and decubitus ulcers. In some embodiment, a method of treating or preventing an infection in a chronic wound is provided comprising applying a dressing containing one or more quaternary ammonium compounds of the present invention, either alone or in a composition, to the site of infection in a host in need thereof.

In some embodiments, the quaternary ammonium compounds of the present invention may be used to treat a fungal nail infection, i.e. onychomycosis, in a host, for example a human. Preparations for use in the treatment of nail infections must be able to penetrate deep in the nail bed. In such embodiments, the antimicrobial composition is formulated using a solvent, for example dimethyl sulfoxide, that is able to penetrate the nail bed of a host. In one embodiment, a method is provided comprising administering an effective amount of a quaternary ammonium compound, or composition thereof described herein to a subject to treat a fungal nail infection.

Antimicrobial Compositions

Active quaternary ammonium compounds described herein can be administered to a host in need thereof as the neat chemical, but are more typically administered as antimicrobial composition that includes an effective amount for a host, typically a human, in need of such treatment of an active quaternary ammonium compound as described herein. Thus, in one embodiment, the disclosure provides antimicrobial compositions comprising an effective amount of a quaternary ammonium compound together with at least one pharmaceutically acceptable carrier for any of the uses described herein. The pharmaceutical composition may contain a compound as the only active agent, or, in an alternative embodiment, the compound and at least one additional active agent. In a typical formulation, the selected compound of the present invention is provided in a sterilized, lyophilized form that is reconstituted on use.

An effective amount of an active quaternary ammonium compound as described herein, or the active quaternary ammonium compound described herein in combination or alternation with, or preceded by, concomitant with or followed by another active agent, can be used in an amount sufficient to (a) inhibit the progression of an infection described herein; (b) cause a regression of an infection described herein; (c) cause a cure of an infection described herein; or (d) inhibit or prevent the development of an infection described herein. Accordingly, an effective amount of an active quaternary ammonium compound, or composition described herein will provide a sufficient amount of the active agent when administered to a patient to provide a clinical benefit.

The exact amount of the active quaternary ammonium compound or antimicrobial composition described herein to be delivered to the host, typically a human, in need thereof, will be determined by the health care provider to achieve the desired clinical benefit.

In certain embodiments the antimicrobial composition is in a dosage form that contains from about 0.1 mg to about 2000 mg, from about 10 mg to about 1000 mg, from about 100 mg to about 800 mg, or from about 200 mg to about 600 mg of the active compound and optionally from about 0.1 mg to about 2000 mg, from about 10 mg to about 1000 mg, from about 100 mg to about 800 mg, or from about 200 mg to about 600 mg of an additional active agent in a unit dosage form. Examples are dosage forms with at least about 0.5, 1, 1.5, 2, 2.5, 3, 3.5, 4, 4.5, 5, 10, 15, 20, 25, 50, 75, 100, 150, 200, 250, 300, 350, 400, 450, 500, 550, 600, 650, 700, 750, 800, 900, 1000, 1100, 1200, 1250, 1300, 1400, 1500, or 1600 mg of active compound. In one embodiment, the dosage form has at least about 1 mg, 5 mg, 10 mg, 25 mg, 50 mg, 75 mg, 100 mg, 200 mg, 400 mg, 500 mg, 600 mg, 1000 mg, 1200 mg, or 1600 mg of active compound. The dosage form can be administered, for example, once a day (q.d.), twice a day (b.i.d.), three times a day (t.i.d.), four times a day (q.i.d.), once every other day (Q2d), once every third day (Q3d), as needed, or any dosage schedule that provides treatment of a disorder described herein.

The antimicrobial composition may for example include a molar ratio of the active compound and an additional active agent that achieves the desired result. For example, the pharmaceutical composition may contain a molar ratio of at least about 0.5:1, at least about 1:1, at least about 2:1, at least about 3:1, or from about 1.5:1 to about 4:1 of an additional active agent in combination with the active compound (additional active agent: active compound) described herein.

Quaternary ammonium compounds disclosed herein or used as described herein may be administered topically, by spray, cream, gel, foam, via implant, including ocular implant, transdermally, as an ophthalmic solution, in dosage unit formulations containing conventional pharmaceutically acceptable carriers. For ocular delivery, the quaternary ammonium compound can be administered, as desired, for example, as a solution, suspension, or other formulation via an immediate or controlled release fashion or via an ocular device, or topically administered formulation, for example a solution or suspension provided as an eye drop.

The antimicrobial composition may be formulated as any pharmaceutically useful form, e.g., as an aerosol, a cream, a gel, foam, a microparticle, a nanoparticle, an injection or infusion solution, a transdermal patch, a subcutaneous patch, a dry powder, in a medical device, parenteral formulation, or an ophthalmic solution or suspension. Some dosage forms are subdivided into suitably sized unit doses containing appropriate quantities of the active components, e.g., an effective amount to achieve the desired purpose.

Compositions, and methods of manufacturing such compositions, suitable for administration as contemplated herein are known in the art. Examples of known techniques include, for example, U.S. Pat. Nos. 4,983,593, 5,013,557, 5,456,923, 5,576,025, 5,723,269, 5,858,411, 6,254,889, 6,303,148, 6,395,302, 6,497,903, 7,060,296, 7,078,057, 7,404,828, 8,202,912, 8,257,741, 8,263,128, 8,337,899, 8,431,159, 9,028,870, 9,060,938, 9,211,261, 9,265,731, 9,358,478, and 9,387,252, incorporated by reference herein.

The antimicrobial compositions contemplated here can optionally include a carrier. Carriers must be of sufficiently high purity and sufficiently low toxicity to render them suitable for administration to the patient being treated. The carrier can be inert or it can possess pharmaceutical benefits of its own. The amount of carrier employed in conjunction with the quaternary ammonium compound is sufficient to provide a practical quantity of material for administration per unit dose of the quaternary ammonium compound. Classes of carriers include, but are not limited to, binders, buffering agents, coloring agents, diluents, disintegrants, emulsifiers, fillers, flavorants, glidents, lubricants, pH modifiers, preservatives, stabilizers, surfactants, solubilizers, tableting agents, and wetting agents.

Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils.

Examples of other matrix materials, fillers, or diluents include lactose, mannitol, xylitol, microcrystalline cellulose, calcium diphosphate, and starch. Examples of surface active agents include sodium lauryl sulfate and polysorbate 80.

Examples of drug complexing agents or solubilizers include the polyethylene glycols, caffeine, xanthene, gentisic acid and cylodextrins. Examples of disintegrants include sodium starch gycolate, sodium alginate, carboxymethyl cellulose sodium, methyl cellulose, colloidal silicon dioxide, and croscarmellose sodium.

Examples of binders include methyl cellulose, microcrystalline cellulose, starch, and gums such as guar gum, and tragacanth. Examples of lubricants include magnesium stearate and calcium stearate.

Examples of pH modifiers include acids such as citric acid, acetic acid, ascorbic acid, lactic acid, aspartic acid, succinic acid, phosphoric acid, and the like; bases such as sodium acetate, potassium acetate, calcium oxide, magnesium oxide, trisodium phosphate, sodium hydroxide, calcium hydroxide, aluminum hydroxide, and the like, and buffers generally comprising mixtures of acids and the salts of said acids.

Optional other active agents may be included in a pharmaceutical composition, which do not substantially interfere with the activity of the quaternary ammonium compound of the present invention.

Non-limiting examples of aqueous solutions as can be used in the carrier include distilled water, saline, plasma, bone marrow aspirate, buffers, such as Hank's Buffered Salt Solution (HBSS), HEPES (4-(2-hydroxyethyl)-1-piperazineethanesulfonic acid), Ringers buffer, ProVisc®, diluted ProVisc®, ProVisc® diluted with PBS, Krebs buffer, Dulbecco's PBS, normal PBS, sodium hyaluronate solution, simulated body fluids, plasma platelet concentrate, tissue culture medium, an aqueous solution comprising an organic solvent, and mixtures thereof. The solution in all instances can be sterilized in a suitable manner known to those in the art.

In some examples, the antimicrobial composition contains a hydrogel. The hydrogel should be biocompatible such that it can be administered to a patient without an undesired effect. Hydrogels are well known in the art and are the subject of extensive literature and patents. The hydrogel is present in an amount effective to provide the desired viscosity and moistening properties as needed for the desired application, for example in the treatment of infected wounds. The specific amount of hydrogel used depends on a number of factors including, for example and without limitation, the specific chemical composition of hydrogel used, the molecular weight of the specific hydrogel used, the viscosity of the desired antimicrobial composition, and the level of water retainment and release desired for the particular hydrogel.

In one embodiment, the hydrogel controls the rate of release of one or more quaternary ammonium compounds of the present invention. In one embodiment, the hydrogel is biodegradable. Examples of useful hydrogel carriers include, but are not limited to, poly(vinyl alcohol), sodium polyacrylate, poly(acrylamide), poly(N-vinyl-2-pyrrolidone), poly(N-isopropylacrylamide), cross-linked carboxymethylcellulose, cross-linked polyethylene glycol, poly (lactic acid), hyaluronic acid, sodium alginate, agarose, starch, chitosan, and methylcellulose, copolymers thereof, derivatives thereof, and mixtures thereof.

In some examples, the antimicrobial composition contains a hydrocolloid. In some embodiments, the hydrocolloid may interact with the site of infection by forming a gel. A hydrocolloid may be present to provide combined moisture and absorptivity in sites where it is deemed necessary. The hydrocolloid may include, but is not limited to, natural gums such as Arabic gum, ghatti gum, karaya gum, tragacanth gum, guar gum, locust bean gum, acacia gum; seaweed extracts such as agar, algin, alginate salts and carrageenan, cereal gums, starches, microbial gums such as dextran gum and xanthan gum, pectins, gelatins, casein, collagens, polyvinylpyrrolidone, low methoxyl pectin, propyleneglycol alginates, carboxymethyl locust bean gum, carboxymethyl guar gum, and modified forms that have been oxidized, acetylated, carboxylated, esterified, methylated, aminated, etherated, sulfated, borated, or phosphated.

In certain embodiments, the antimicrobial composition for administration further includes a quaternary ammonium compound as described herein and optionally comprises one or more of a phosphoglyceride; phosphatidylcholine; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohol such as polyethylene glycol (PEG); polyoxyethylene-9-lauryl ether; a surface active fatty acid, such as palmitic acid or oleic acid; fatty acid; fatty acid monoglyceride; fatty acid diglyceride; fatty acid amide; sorbitan trioleate (Span®85) glycocholate; sorbitan monolaurate (Span®20); polysorbate 20 (Tween®20); polysorbate 60 (Tween®60); polysorbate 65 (Tween®65); polysorbate 80 (Tween®80); polysorbate 85 (Tween®85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebroside; dicetylphosphate; dipalmitoylphosphatidylglycerol; stearylamine; dodecylamine; hexadecyl-amine; acetyl palmitate; glycerol ricinoleate; hexadecyl sterate; isopropyl myristate; tyloxapol; poly(ethylene glycol)5000-phosphatidylethanolamine; poly(ethylene glycol)400-monostearate; phospholipid; synthetic and/or natural detergent having high surfactant properties; deoxycholate; cyclodextrin; chaotropic salt; ion pairing agent; glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid; pullulan, cellulose, microcrystalline cellulose, hydroxypropyl methylcellulose (HPMC), hydroxycellulose (HC), methylcellulose (MC), dextran, cyclodextran, glycogen, hydroxyethylstarch, carageenan, glycon, amylose, chitosan, N,O-carboxylmethylchitosan, algin and alginic acid, starch, chitin, inulin, konjac, glucommannan, pustulan, heparin, hyaluronic acid, curdlan, and xanthan, mannitol, sorbitol, xylitol, erythritol, maltitol, and lactitol, a pluronic polymer, polyethylene, polycarbonate (e.g. poly(1,3-dioxan-2one)), polyanhydride (e.g. poly(sebacic anhydride)), polypropylfumarate, polyamide (e.g. polycaprolactam), polyacetal, polyether, polyester (e.g., polylactide, polyglycolide, polylactide-co-glycolide, polycaprolactone, polyhydroxyacid (e.g. poly((β-hydroxyalkanoate))), poly(orthoester), polycyanoacrylate, polyvinyl alcohol, polyurethane, polyphosphazene, polyacrylate, polymethacrylate, polyurea, polystyrene, and polyamine, polylysine, polylysine-PEG copolymer, and poly(ethyleneimine), poly(ethylene imine)-PEG copolymer, glycerol monocaprylocaprate, propylene glycol, Vitamin E TPGS (also known as d-α-Tocopheryl polyethylene glycol 1000 succinate), gelatin, titanium dioxide, polyvinylpyrrolidone (PVP), hydroxypropyl methyl cellulose (HPMC), hydroxypropyl cellulose (HPC), methyl cellulose (MC), block copolymers of ethylene oxide and propylene oxide (PEO/PPO), polyethyleneglycol (PEG), sodium carboxymethylcellulose (NaCMC), hydroxypropylmethyl cellulose acetate succinate (HPMCAS).

In some embodiments, the antimicrobial composition may include polymers for controlled delivery of the described compounds, including, but not limited to pluronic polymers, polyesters (e.g., polylactic acid, poly(lactic-co-glycolic acid), polycaprolactone, polyvalerolactone, poly(1,3-dioxan-2one)); polyanhydrides (e.g., poly(sebacic anhydride)); polyethers (e.g., polyethylene glycol); polyurethanes; polymethacrylates; polyacrylates; and polycyanoacrylates. In some embodiments, polymers may be modified with polyethylene glycol (PEG), with a carbohydrate, and/or with acyclic polyacetals derived from polysaccharides. See, e.g., Papisov, 2001, ACS Symposium Series, 786:301, incorporated by reference herein.

In some embodiments, the antimicrobial composition contains a biodegradable polymer. The biodegradable polymer should be biocompatible such that it can be administered to a patient without an undesired effect. Biodegradable polymers are well known in the art and are the subject of extensive literature and patents. The biodegradable polymers or combination of polymers can be selected to provide the desired characteristics for the chosen application including, but not limited to, the appropriate mix of hydrophobic and hydrophilic qualities, half-life and degradation kinetics, compatibility with one or more quaternary ammonium compounds of the present invention to be delivered, and the appropriate behavior at the site of application.

In one embodiment, the biodegradable polymer gelates in the presence of an aqueous solution such as is present in the site of a wound or infection. In one embodiment, the biodegradable polymer carrier provides release of one or more quaternary ammonium compounds of the present invention into the site of infection at a desired rate. Examples of useful biodegradable polymers include, but are not limited to, poly(lactic acid), polyglycolic acid, poly(D, L-lactide-co-glycolide), poly(D,L-lactic acid), polyesters, poly(caprolactone), poly(3-hydroxybutyrate), poly(s-caproic acid), poly(p-dioxanone), poly(propylene fumarate), poly(orther esters), polyol/diketene acetals, poly(sebacic anhydride), poly(maleic anhydride), poly(carboxybis-carboxyphenoxyphosphazene), poly[bis(p-carboxyphenoxy) methane], poly(amino acids), or copolymers thereof.

Optional active ingredients may be included in the antimicrobial composition which do not substantially interfere with the activity of one or more quaternary ammonium compounds of the present invention used in the present invention. In certain embodiments, two or more of the carrier components may be combined as deemed necessary for the particular application.

In some embodiments, the antimicrobial composition further comprises one or more additional additives. These quaternary ammonium compounds may be included to increase the efficacy of the desired antimicrobial composition in penetrating the site of infection being treated, to aid in tissue healing or symptom abatement at the site of infection if it is deemed necessary, or to increase the effective shelf life of the antimicrobial composition either alone or in combination with other active agents.

In some embodiments, the antimicrobial composition further comprises a surfactant. The surfactant can be added to help facilitate penetration of one or more quaternary ammonium compounds of the present invention into subsurface layers of a biofilm present at the site of infection by disrupting the complex hydrophobic/hydrophilic interactions between biofilm layers if one or more compounds of the present invention alone prove insufficient for this purpose. The surfactant additive selected can be chosen to provide desired characteristics to the antimicrobial composition, such as stability of the surfactant and one or more compounds of the present invention in the appropriate carrier, level of desired penetration into the biofilm, and level of reactivity with other components in the composition. An appropriate surfactant would be able to be chosen by one skilled in the art. In some embodiments, the surfactant can facilitate leaching of one or more compounds of the present invention from the selected carrier.

In some embodiments, the surfactant can facilitate leaching of one or more compounds of the present invention from either a formulated microparticle or polymeric nanoparticle. Examples of appropriate surfactants include, but are not limited to, octenidine dihydrochloride, cetrimonium bromide (CTAB), cetylpyridinium chloride (CPC), benzalkonium chloride (BAC), benzethonium chloride (BZT), dimethyldioctadecylammonium chloride, dioctadecyldimethylammonium bromide (DODAB), cocamidopropyl hydroxysultaine (CAHS), cocamidopropyl betaine (CAPB), cocamide MEA, sodium oxychlorosene, or combinations thereof.

In some embodiments, the antimicrobial composition further comprises a buffer. Some of the other potential additives to the antimicrobial composition may require very narrow pH ranges to optimally function. A buffer can be provided at appropriate concentrations to maintain an optimized pH range. The optimized buffer for the particularly desired application would be known to known to those skilled in the art. Examples of appropriate buffers include, but are not limited to, salts of citrates, sulfonates, carbonates, acetate, borates, gluconates, phosphates, or combinations thereof.

In some embodiments, the antimicrobial composition further comprises appropriate enzymes. The enzymes can be added to assist in disrupting the established biofilm by either decomposition of the extracellular polymeric substances (EPS) or by suppressing cell to cell communications, sent via ion channels in the form of electrical signals, to coordinate their behavior. In some embodiments, the enzymes may be proteolytic enzymes. Proteolytic enzymes may be able to act upon some of the polymeric materials present in the EPS, allowing increased penetration of the antimicrobial composition. Examples of proteolytic enzymes include, but are not limited to, collagenase, cellulase, keratinase, papain, bromelain, trypsin, thermolysin, or combinations thereof.

In some embodiments, the antimicrobial composition further comprises an appropriate tissue growth promoter. In some applications, the biofilm-induced infection that is being treated is present within a wound. Inclusion of an appropriate tissue growth promoter may help facilitate regrowth of tissue within the present wound during the time of infection treatment with the dressing. Examples of appropriate tissue growth promoters include, but are not limited to, endothelial cell growth factors (ECGF), epidermal growth factors (EGF), fibroblast growth factors (FGF), hepatocyte growth factors (HGF), nerve growth factors (NGF), platelet-derived growth factors (PDGF), transforming growth factors (TGF), or combinations thereof.

In some embodiments, the antimicrobial composition further comprises a preservative. While one or more quaternary ammonium compounds of the present invention antimicrobial in nature, an additional preservative may be optionally included dependent on the desired shelf life of the antimicrobial composition. Examples of appropriate preservatives include, but are not limited to, methylparaben, propylparaben, benzyl alcohol, benzalkonium chloride, sorbic acid, phenol, phenylethyl alcohol, BHA, BHT, or combinations thereof.

In some embodiments, the antimicrobial composition further comprises an antioxidant. An antioxidant may be necessary to stabilize any other additive present within the antimicrobial composition from air oxidation over a suitable shelf life. Examples of appropriate antioxidants include, but are not limited to ascorbic acid, BHA, BHT, sodium bisulfite, vitamin E, sodium metabisulfite, propyl gallate, or combinations thereof.

In some embodiments, the antimicrobial composition further comprises an astringent. Addition of an astringent to the antimicrobial composition may be desirable by causing surface tissues that contain an infection to shrink, allowing ready penetration of the antimicrobial composition into the infected space. Examples of appropriate astringents include, but are not limited to, zinc oxide, ferric oxide, zinc sulfate, silver nitrate, potassium permanganate, aluminum chloride, aluminum acetate, formaldehyde, Burow's solution, tincture of benzoin, or combinations thereof.

Antimicrobial compositions suitable for topical application to the skin preferably take the form of an ointment, cream, lotion, foam, paste, gel, spray, aerosol, or oil. Carriers which may be used include petroleum jelly, lanoline, polyethylene glycols, alcohols, transdermal enhancers, and combinations of two or more thereof.

Antimicrobial compositions suitable for transdermal administration may be presented as discrete patches adapted to remain in intimate contact with the epidermis of the recipient for a prolonged period of time. Antimicrobial compositions suitable for transdermal administration may also be delivered by iontophoresis (see, for example, *Pharmaceutical Research* 3 (6):318 (1986)) and typically take the form of an optionally buffered aqueous solution of the active compound. In one embodiment, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Many methods and devices for drug delivery to the eye are known in the art. Non-limiting examples are described in the following patents and patent applications (fully incorporated herein by reference). Examples are U.S. Pat. No. 8,192,408 titled "Ocular trocar assembly" (Psivida Us, Inc.); U.S. Pat. No. 7,585,517 titled "Transcleral delivery" (Macusight, Inc.); U.S. Pat. Nos. 5,710,182 and 5,795,913 titled "Ophthalmic composition" (Santen OY); U.S. Pat. No. 8,663,639 titled "Formulations for treating ocular diseases and conditions", U.S. Pat. No. 8,486,960 titled "Formulations and methods for vascular permeability-related diseases or conditions", U.S. Pat. Nos. 8,367,097 and 8,927,005 titled "Liquid formulations for treatment of diseases or conditions", U.S. Pat. No. 7,455,855 titled "Delivering substance and drug delivery system using the same" (Santen Pharmaceutical Co., Ltd.); WO/2011/050365 titled "Conformable Therapeutic Shield For Vision and Pain" and WO/2009/

145842 titled "Therapeutic Device for Pain Management and Vision" (Forsight Labs, LLC); U.S. Pat. Nos. 9,066,779 and 8,623,395 titled "Implantable therapeutic device", WO/2014/160884 titled "Ophthalmic Implant for Delivering Therapeutic Substances", U.S. Pat. Nos. 8,399,006, 8,277, 830, 8,795,712, 8,808,727, 8,298,578, and WO/2010/088548 titled "Posterior segment drug delivery", WO/2014/152959 and US20140276482 titled "Systems for Sustained Intraocular Delivery of Low Solubility Compounds from a Port Delivery System Implant", U.S. Pat. Nos. 8,905,963 and 9,033,911 titled "Injector apparatus and method for drug delivery", WO/2015/057554 titled "Formulations and Methods for Increasing or Reducing Mucus", U.S. Pat. Nos. 8,715,712 and 8,939,948 titled "Ocular insert apparatus and methods", WO/2013/116061 titled "Insertion and Removal Methods and Apparatus for Therapeutic Devices", WO/2014/066775 titled "Ophthalmic System for Sustained Release of Drug to the Eye", WO/2015/085234 and WO/2012/019176 titled "Implantable Therapeutic Device", WO/2012/065006 titled "Methods and Apparatus to determine Porous Structures for Drug Delivery", WO/2010/141729 titled "Anterior Segment Drug Delivery", WO/2011/050327 titled "Corneal Denervation for Treatment of Ocular Pain", WO/2013/022801 titled "Small Molecule Delivery with Implantable Therapeutic Device", WO/2012/019047 titled "Subconjunctival Implant for Posterior Segment Drug Delivery", WO/2012/068549 titled "Therapeutic Agent Formulations for Implanted Devices", WO/2012/019139 titled "Combined Delivery Methods and Apparatus", WO/2013/040426 titled "Ocular Insert Apparatus and Methods", WO/2012/019136 titled "Injector Apparatus and Method for Drug Delivery", WO/2013/040247 titled "Fluid Exchange Apparatus and Methods" (ForSight Vision4, Inc.).

Additional non-limiting examples of how to deliver the active compounds are provided in WO/2015/085251 titled "Intracameral Implant for Treatment of an Ocular Condition" (Envisia Therapeutics, Inc.); WO/2011/008737 titled "Engineered Aerosol Particles, and Associated Methods", WO/2013/082111 titled "Geometrically Engineered Particles and Methods for Modulating Macrophage or Immune Responses", WO/2009/132265 titled "Degradable compounds and methods of use thereof, particularly with particle replication in non-wetting templates", WO/2010/099321 titled "Interventional drug delivery system and associated methods", WO/2008/100304 titled "Polymer particle composite having high fidelity order, size, and shape particles", WO/2007/024323 titled "Nanoparticle fabrication methods, systems, and materials" (Liquidia Technologies, Inc. and the University of North Carolina at Chapel Hill); WO/2010/009087 titled "Iontophoretic Delivery of a Controlled-Release Formulation in the Eye", (Liquidia Technologies, Inc. and Eyegate Pharmaceuticals, Inc.) and WO/2009/132206 titled "Compositions and Methods for Intracellular Delivery and Release of Cargo", WO/2007/133808 titled "Nanoparticles for cosmetic applications", WO/2007/056561 titled "Medical device, materials, and methods", WO/2010/065748 titled "Method for producing patterned materials", WO/2007/081876 titled "Nanostructured surfaces for biomedical/biomaterial applications and processes thereof" (Liquidia Technologies, Inc.).

Additional non-limiting examples of methods and devices for drug delivery to the eye include, for example, WO2011/106702 and U.S. Pat. No. 8,889,193 titled "Sustained delivery of therapeutic agents to an eye compartment", WO2013/138343 and U.S. Pat. No. 8,962,577 titled "Controlled release formulations for the delivery of HIF-1 inhibitors", WO/2013/138346 and US2013/0272994 titled "Non-Linear Multiblock Copolymer-Drug Conjugates for the Delivery of Active Agents", WO2005/072710 and U.S. Pat. No. 8,957,034 titled "Drug and Gene Carrier Particles that Rapidly Move Through Mucus Barriers", WO2008/030557, US2010/0215580, US2013/0164343 titled "Compositions and Methods for Enhancing Transport Through Mucous", WO2012/061703, US2012/0121718, and US2013/0236556 titled "Compositions and Methods Relating to Reduced Mucoadhesion", WO2012/039979 and US2013/0183244 titled "Rapid Diffusion of Large Polymeric Nanoparticles in the Mammalian Brain", WO2012/109363 and US2013/0323313 titled "Mucus Penetrating Gene Carriers", WO 2013/090804 and US2014/0329913 titled "Nanoparticles with enhanced mucosal penetration or decreased inflammation", WO2013/110028 titled "Nanoparticle formulations with enhanced mucosal penetration", WO2013/166498 and US2015/0086484 titled "Lipid-based drug carriers for rapid penetration through mucus linings" (The Johns Hopkins University); WO2013/166385 titled "Pharmaceutical Nanoparticles Showing Improved Mucosal Transport", US2013/0323179 titled "Nanocrystals, Compositions, And Methods that Aid Particle Transport in Mucus" (The Johns Hopkins University and Kala Pharmaceuticals, Inc.); WO/2015/066444 titled "Compositions and methods for ophthalmic and/or other applications", WO/2014/020210 and WO/2013/166408 titled "Pharmaceutical nanoparticles showing improved mucosal transport" (Kala Pharmaceuticals, Inc.); U.S. Pat. No. 9,022,970 titled "Ophthalmic injection device including dosage control device", WO/2011/153349 titled "Ophthalmic compositions comprising pbo-peo-pbo block copolymers", WO/2011/140203 titled "Stabilized ophthalmic galactomannan formulations", WO/2011/068955 titled "Ophthalmic emulsion", WO/2011/037908 titled "Injectable aqueous ophthalmic composition and method of use therefor", US2007/0149593 titled "Pharmaceutical Formulation for Delivery of Receptor Tyrosine Kinase Inhibiting (RTKi) Compounds to the Eye", U.S. Pat. No. 8,632,809 titled "Water insoluble polymer matrix for drug delivery" (Alcon, Inc.).

In another aspect, an ocular formulation is provided comprising one or more compounds described herein, in a carrier that is suitable to the eye. The appropriate carrier must avoid compounds that are toxic or irritating to the eye to prevent unwanted side effects or damage to the eye. Examples of components that are not suitable for use in an ocular formulation include corrosives such as strongly alkaline or acidic substances such as urea or ammonia, strong surfactants, and substances with known ocular toxicity such as methanol and hydrogen peroxide.

In another aspect, a formulation for the treatment of onychomycosis is also provided comprising one or more compounds described herein, in a carrier that is capable or penetrating the nail bed to deliver the active compounds therein. One representative example of a carrier able to penetrate the nail bed is dimethyl sulfoxide.

Additional non-limiting examples of drug delivery devices and methods include, for example, US20050009910 titled "Delivery of an active drug to the posterior part of the eye via subconjunctival or periocular delivery of a prodrug", US 20130071349 titled "Biodegradable polymers for lowering intraocular pressure", U.S. Pat. No. 8,481,069 titled "Tyrosine kinase microspheres", U.S. Pat. No. 8,465,778 titled "Method of making tyrosine kinase microspheres", U.S. Pat. No. 8,409,607 titled "Sustained release intraocular implants containing tyrosine kinase inhibitors and related methods", U.S. Pat. No. 8,512,738 and US 2014/0031408 titled "Biodegradable intravitreal tyrosine kinase implants", US 2014/0294986 titled "Microsphere Drug Delivery System for Sustained Intraocular Release", U.S. Pat. No. 8,911,768 titled "Methods For Treating Retinopathy With Extended Therapeutic Effect" (Allergan, Inc.); U.S. Pat. No. 6,495,164 titled "Preparation of injectable suspensions having improved injectability" (Alkermes Controlled Therapeutics, Inc.); WO 2014/047439 titled "Biodegradable Microcapsules Containing Filling Material" (Akina, Inc.); WO 2010/132664 titled "Compositions And Methods For Drug Delivery" (Baxter International Inc. Baxter Healthcare SA); US20120052041 titled "Polymeric nanoparticles with enhanced drugloading and methods of use thereof" (The Brigham and Women's Hospital, Inc.); US20140178475, US20140248358, and US20140249158 titled "Therapeutic Nanoparticles Comprising a Therapeutic Agent and Methods of Making and Using Same" (BIND Therapeutics, Inc.); U.S. Pat. No. 5,869,103 titled "Polymer microparticles for drug delivery" (Danbiosyst UK Ltd.); U.S. Pat. No. 8,628,801 titled "Pegylated Nanoparticles" (Universidad de Navarra); US2014/0107025 titled "Ocular drug delivery system" (Jade Therapeutics, LLC); U.S. Pat. No. 6,287,588 titled "Agent delivering system comprised of microparticle and biodegradable gel with an improved releasing profile and methods of use thereof", U.S. Pat. No. 6,589,549 titled "Bioactive agent delivering system comprised of microparticles within a biodegradable to improve release profiles" (Macromed, Inc.); U.S. Pat. Nos. 6,007,845 and 5,578,325 titled "Nanoparticles and microparticles of non-linear hydrophilic/hydrophobic multiblock copolymers" (Massachusetts Institute of Technology); US20040234611, US20080305172, US20120269894, and US20130122064 titled "Ophthalmic depot formulations for periocular or subconjunctival administration (Novartis Ag); U.S. Pat. No. 6,413,539 titled "Block polymer" (Poly-Med, Inc.); US 20070071756 titled "Delivery of an agent to ameliorate inflammation" (Peyman); U.S. Pat. No. 6,706,289 titled "Methods and compositions for enhanced delivery of bioactive molecules" (PR Pharmaceuticals, Inc.); and U.S. Pat. No. 8,663,674 titled "Microparticle containing matrices for drug delivery" (Surmodics).

Dressings

In one embodiment, the antimicrobial composition containing one or more compounds of the present invention is dispersed in a suitable dressing. The dressing that is chosen should allow release of the desired antimicrobial composition over a period of time dependent upon the desired application. The dressing can be wetted before placement at the site of infection by saturation with the antimicrobial composition, even though it may be additionally moistened due to exudate at the site of infection. Alternatively, the dressing can be placed at the site of a wound and/or infection and subsequently saturated with the antimicrobial composition, for example by application of the antimicrobial composition by dropper or syringe, or other suitable means such as liquid, cream, gel, spray, foam, paste, powder, or wipe.

In an additional embodiment, a dry powder formulation containing the compound of the present invention is impregnated within the dressing and subsequently wetted upon interaction with exudate or other bodily fluids at the site of infection. The dressing may be placed in or on the location of an infection involving a biofilm. The dressing may adhere to the location of a wound and/or infection to provide suitable localization, or may not adhere to the location of the infection in order to prevent undesired tissue damage upon removal. The dressing may be rigid, to allow for it to be held in place during treatment, or may be malleable to allow for placement and adherence in the desired location. Additionally, the dressing may comprise additional additives that ensure the maintenance of a moist environment at the site of infection. The dressing must be composed of a material that is hypoallergenic and non-toxic in order to be acceptably applied to a living host. In a preferred embodiment, the dressing would absorb the antimicrobial composition and would then subsequently release the antimicrobial composition once placed in the site of infection involving a biofilm.

In certain embodiments, the dressing has a bulk density that is low enough to allow the antimicrobial composition to be incorporated within, but high enough to provide sufficient structural integrity. The dressing should be porous to provide sufficient intercalation of the antimicrobial composition among the material, allowing space for sufficient wetting with the antimicrobial composition along with efflux into the site of treatment. The level of porosity of the dressing should be high enough to allow sufficient wetting with the antimicrobial composition, but should still allow for the dressing to have sufficient material strength.

In certain embodiments, the dressing is fashioned from a flexible polymeric material that provides sufficient porosity but still provides structural integrity in the desired application. In certain embodiments, two or more of the dressing components may be combined, as deemed necessary for the particular application, into a composite material. In some cases, the two or more components may be present in layers. In other cases, the two or more components may be impregnated or intercalated into each other. The combination of dressing components may be necessary for structural integrity to ensure placement, positioning, and functioning at the site of infection.

In some embodiments, the dressing comprises a polymer foam. The polymer foam may allow release of the desired antimicrobial composition by either diffusion, ionic interactions, or by degradation of the material composition of the dressing. In some embodiments, the polymer foam can absorb exudate that may occur due to infection involving the presence of a biofilm. In some embodiments, the polymer foam is biodegradable or non-degradable, depending upon the intended use within the patient.

Examples of materials suitable for the formation of a polymer foam include, but are not limited to, cellulose and cellulose derivatives, microcrystalline cellulose, calcium alginate, polyacrylic acid, polyethylene glycol, polypropylene glycol, divinyl glycol, polyethylene oxide, polypropylene oxide, carboxymethyl cellulose, hydroxyethyl cellulose, polylactide, polyglycolide, polymethacrylic acid, poly-γ-benzyl-L-glutamate, polypropylene fumarate, poly-F-caprolactone, poly-butylene terephthalate, polyvinyl alcohol, polyvinyl ether, poly-1-vinyl-2-pyrrolidinone, 2,5 dimethyl-1,5-hexadiene, divinyl benzene, polystyrene-divinyl benzene, polyanhydrides such as polybis(p-carboxy-phenoxy) propane-co-sebacic acid, polyhydroxyalkanoates such as poly-β hydroxybutyrate or poly-β-butyrolactone, or alkyl-substituted silica gel formed from reagents such as tetraethylorthosilicate and dimethyldiethoxysilane. In preferred embodiments, the polymer foam is composed of polyurethane. In another preferred embodiment, the polymer foam is composed of cellulose. In yet another embodiment, the polymer foam is composed of calcium alginate.

In some embodiments, the dressing comprises a fabric composition. The fabric composition may be composed of fibers including natural fibers, synthetic fibers, cellulose, or mixtures thereof. Examples of acceptable fibers include, but are not limited to, cotton, polyester, wool, silk, or rayon. The fabric composition may have varying levels of absorbency depending on the desired application. The fabric composition may additionally be coated with an appropriate polymer composition that effects absorbance and dispersion of the active compound or additional additives.

In some embodiments, the dressing additionally comprises a polymeric film. A polymeric film may be desirable to ensure proper sealing of the dressing to maintain moisture at the treatment site. In preferred embodiments, the polymeric film comprises an adhesive side that adheres to the edges of the site of the infection to provide a seal and a non-adhesive side. In one embodiment, the polymeric film is composed of polyurethane.

In some embodiments, the dressing additionally comprises a collagen matrix. A collagen matrix may be included in applications where it would be deemed desirable, such as providing a template in wound healing. The collagen matrix may be present as a gel, pad, paste, or sheet. The collagen matrix may be derived from a bovine, porcine, equine, or avian source. The collagen matrix may be composed of type I, II, III, IV, or V collagen. In some embodiments, the collage matrix may interact with the site of infection caused by a biofilm by forming a gel. Additional macromolecular structures, such as hyaluronic acid, fibronectin, laminin, proteoglycans or mixtures thereof, may be incorporated into the collagen matrix. In some embodiments, the collagen matrix is chemically cross-linked.

In some embodiments, the dressing is composed of a dissolvable material. A dressing composed of a dissolvable material can allow for the dressing to be placed in the site of a wound and/or infection without the need for retrieval upon completion of the treatment. Non-limiting examples of suitable dissolvable materials for the dressing include, but are not limited to, poly(lactic acid), polyglycolic acid, poly (caprolactone), poly(3-hydroxybutyrate), poly(s-caproic acid), poly(propylene fumarate), poly(sebaic anhydride), poly(maleic anhydride), poly(ethenol), poly(dioxanone), polyglactin 910, starch, collagen, chitosan, or mixtures thereof. In one embodiment, the dressing is composed of starch foam that slowly dissolves upon contact with the antimicrobial composition.

In some embodiments, the dressing further comprises one or more additives. The addition of an additive may be necessary to aid in binding of the antimicrobial composition to the dressing or to aid in release of the antimicrobial composition from the dressing into the site of a wound and/or infection. The addition of an additive may also be necessary to favorably change the material properties of the dressing or to enhance binding of the dressing to the site of a wound and/or infection to ensure sufficient delivery of the antimicrobial composition.

In some embodiments, a permeation enhancer is added to the dressing. Permeation enhancers are compounds that increase the level of permeation of the antimicrobial composition provided from the dressing into the layers of the biofilm and any under- or overlaying tissues. Examples of appropriate permeation enhancers include, but are not limited to, ethanol, polyethylene glycol, isopropyl myristate, glycerol trioleate, linolenic acid, glycerol monooleate, glycerol monolaurate, n-decyl alcohol, capric acid, and fatty acid esters, fatty acid alcohols, fatty acid monoglycerides, fatty acid acetates, fatty acid diethanolamides, fatty acid N,N-dimethylamides, or combinations thereof.

In some embodiments, a tissue adhesion agent is added to the dressing. In some applications, adhesion of the dressing would be desirable to ensure sufficient delivery of one or more compounds of the present invention contained in the antimicrobial composition to the biofilm. In many cases, the components of the dressing when impregnated with the antimicrobial composition will have enough adhesion properties to provide sufficient adherence to the tissue containing the infectious biofilm. Such adhesion may not be enough to provide proper support of the dressing on the infected tissue, necessitating the addition of additional tissue adhesion agents. Examples of appropriate adhesion agents include, but are not limited to, hydroxypropylmethylcellulose, carboxymethylcellulose, polylactide-co-glycolide, chitosan, chitosan ester or trimethylenechloride chitosan, sodium alginate, poloxamer, Carbopol, pectin, polyacrylic acid, hyaluronic acid, polyvinyl alcohol, polyvinylpyrrolidone, polycarbophil, or mixtures thereof.

In some embodiments, a plasticizer is added to the dressing. Addition of a plasticizer may be appropriate in order to soften and increase the flexibility of the components of the dressing in certain applications. The improved softness and flexibility increases the number of locations the dressing can be placed within the living host. Some examples of appropriate plasticizers include, but are not limited to, glycerin, water, polyethylene glycol, propylene glycol, sorbitol, and triacetin. Plasticizers are typically added in an amount from about 5% to about 25% by weight.

In some embodiments, the dressing is designed for placement in a body cavity, for example the external auditory canal so that it might treat infections therein. In one embodiment, the dressing is of such a size and shape as to fit within the external auditory canal. In another embodiment, the dressing is malleable such that it can be compressed before placement in the ear, followed by subsequent re-expansion once properly placed. In another embodiment, the dressing for placement in the external auditory canal is composed of a polymer foam of sufficient porosity to allow intercalation and efflux of the antimicrobial composition described herein.

Lyophilized Powder Formulations for Use in the Present Invention

In some embodiments, one or more active quaternary ammonium compounds of the present invention can be provided as a lyophilized powder formulation. Lyophilized powder formulations can be prepared, for example, by a low temperature dehydration process that removes residual solvents by sublimation rather than boiling. Lyophilization is the preferred method for the formulation of sensitive solid materials as it typically maintains the integrity of the product due to the low temperature used in processing. Additionally, lyophilized solids can be reconstituted more quickly and easily due to the presence of microscopic pores formed by the process. The high vacuum used during lyophilization ensures thorough removal of any undesired volatile components such as methanol, ethanol, or other volatile organic substances. In one embodiment, the lyophilized powder formulation of the quaternary ammonium compounds and products described herein contains less than about 5%, about 4%, about 3%, about 2%, about 1%, about 0.5%, or about 0.01% of methanol by weight. Methods for the lyophilization of solids, particularly of sensitive materials used in pharmaceutical applications, are known in the art. Lyophilization may be performed using any number of commercially available apparatuses, for example a shelf-cabinet, contact, radiant, or microwave assisted lyophilizer.

Typical lyophilization procedures are composed of four steps. In the first step (Pre-Treatment), the active quaternary ammonium compound is dissolved in an appropriate solvent and additional excipients are optionally added as required to increase stability, preserve appearance, or improve later processing. Additionally, solutions of the active quaternary ammonium compound may be concentrated as appropriate to aid in the freezing and later sublimation processes. Additionally, components may undergo initial individual quick freezing to ensure formation of a free-flowing solid upon completion of the lyophilization.

In the second step (freezing), the solution of the active compound is frozen in a vessel below its triple point to ensure that sublimation rather than melting will occur. Optionally, the material can be cycled up and down in temperature in a process called annealing. If the compound to be lyophilized is an amorphous solid, it may not have a triple point and instead has a critical point. Amorphous solids must be maintained below the critical point temperature during the entirety of the lyophilization process to prevent melt-back or collapse of the solid during the subsequent drying steps. For sensitive materials, the freezing step is often performed quickly by lowering the temperature of the material to between about −50 and −80° C. This prevents the formation of large solvent crystals that may diminish the structure integrity of the material being lyophilized and lead to poor texture.

In the third step (primary drying), the pressure of the vessel is lowered (typically to the range of a few millibars) and a minimum of heat is applied to the material for the solvent to sublime. Pressure is typically controlled by the application of a partial vacuum. A small amount of heat may be applied to facilitate sublimation of the solvent molecules. Typically, this heat is applied via conduction or radiation due to the low air density within the vessel.

In the final step (secondary drying), the temperature is raised higher than in the primary drying phase to remove any residual unfrozen solvent molecules. The rise in temperature is required to break any physico-chemical interactions that may have formed between the solvent molecules and the frozen material. Additionally, the pressure is typically lowered compared to the primary drying step to encourage desorption.

Upon completion of the lyophilization process, the vacuum is typically broken with an inert gas, for example nitrogen, and sealed in an appropriate container. Typical containers include sealed ampoules comprising sealed glass that is broken open at the time of desired application. The active material may be subsequently reconstituted at the time of application by using an appropriate carrier such as those that are described herein, for example sterile water or glycerin.

Microparticles and Nanoparticles for Use in the Present Invention

In some embodiments, a compound or product described herein is provided in the form of a microparticle or nanoparticle which may be polymeric or non-polymeric. The desired microparticles or nanoparticles can be formed using a method to provide pharmaceutically suitable microparticles.

In some embodiments, the microparticles or nanoparticles are dispersed in water or other pharmaceutically appropriate carrier.

In one embodiment, the microparticles or nanoparticles allow controlled release of the desired antimicrobial agent by slow dissolution of one or more compounds of the present invention in the chosen carrier or in the moisture present at the site of infection.

In one embodiment, the microparticles or anaoparticles are combined with an appropriate polymer matrix for use during processing. The appropriate polymer matrix is chosen such that the rate of dissolution of one or more compounds of the present invention into the carrier is controlled at the site of infection.

In another embodiment, the microparticles or nanoparticles are embedded within a dressing as described herein.

Microparticles and nanoparticles can be formed using any suitable method for the formation of microparticles known in the art. Microparticles assembled with two-dimensional nanostructures, such as CNT's, can be equipped with improved mechanical and electrical properties without sacrificing permeability at the molecular level to assist in the desired placement of the compound (Kim, M., Choi, M. G., Ra, H. W., Park, S. B., Kim, Y.-J., & Lee, K. (2018). Encapsulation of Multiple Microalgal Cells via a Combination of Biomimetic Mineralization and LbL Coating. *Materials,* 11(2), 296).

The method employed for particle formation will depend on a variety of factors, including the characteristics of one or more compounds of the present invention, as well as the desired particle size and size distribution. The type of compound being incorporated into the microparticles may also be a factor as some compositions are unstable in the presence of certain solvents, in certain temperature ranges, or in certain pH ranges.

Particles having an average particle size of between about 1 micron and 100 microns are useful as microparticles in the compositions described herein. In typical embodiments, the particles have an average particle size of between about 1 micron and 40 microns, more typically between about 10 microns and about 40 microns, more typically between about 20 microns and about 40 microns. The particles can have any shape but are generally spherical in shape.

Particles having an average particle size of between about 1 and 100 nanometers (nm) are useful as nanoparticles in the compositions described herein. In typical embodiments, the particles have an average particle size of between about 1 nm and 75 nm, more typically between about 10 microns and about 40 microns, more typically between about 20 microns and about 40 microns. The particles can have any shape but are also generally spherical in shape.

Nanoparticles are useful for delivery through mucosal barriers where very small particles have an advantage of easier travel through the mucus than larger particles. This is useful for ocular delivery, as the eye is covered with a mucosal barrier.

In circumstances where a monodispersed population of particles is desired, the particles may be formed using a method which produces a monodisperse population of microparticles. Alternatively, methods producing polydispersed microparticle distributions can be used, and the particles can be separated using methods known in the art, such as sieving, following particle formation to provide a population of particles having the desired average particle size and particle distribution.

Common techniques for preparing microparticles and nanoparticles include, but are not limited to, solvent evaporation, hot melt particle formation, solvent removal, spray drying, phase inversion, coacervation, and low temperature casting. Suitable methods of particle formation are briefly described below. Pharmaceutically acceptable excipients, including pH modifying agents, disintegrants, preservatives, and antioxidants, can optionally be incorporated into the particles during particle formation.

In some embodiments, the desired microparticles and nanoparticles are obtained through a solvent evaporation method. In one aspect, a method is provided whereby one or more quaternary ammonium compounds of the present invention or polymer matrix and one or more compounds of the present invention, is dissolved or dispersed in a volatile organic solvent, such as methylene chloride, acetone, acetonitrile, 2-butanol, 2-butanone, t-butyl alcohol, benzene, chloroform, cyclohexane, 1,2-dichloroethane, diethyl ether, ethanol, ethyl acetate, heptane, hexane, methyl tert-butyl ether, pentane, petroleum ether, isopropyl alcohol, n-propanol, tetrahydrofuran, or mixtures thereof. The organic solution containing one or more quaternary ammonium compounds of the present invention is then suspended in an aqueous solution that contains a surfactant, such as poly (vinyl alcohol). The resulting emulsion is stirred until most of the organic solvent is evaporated, leaving solid microparticles. The resulting microparticles are rinsed with water and dried in a lyophilizer overnight. Microparticles with different sizes and morphologies can be obtained with this method.

Solvent removal can be used to prepare particles from compounds of the present invention that are deemed hydrolytically unstable. In one aspect, a method is provided whereby, one or more quaternary ammonium compounds of the present invention are dissolved or dispersed in a volatile organic solvent such as methylene chloride, acetone, acetonitrile, 2-butanol, 2-butanone, t-butyl alcohol, benzene, chloroform, cyclohexane, 1,2-dichloroethane, diethyl ether, ethanol, ethyl acetate, heptane, hexane, methyl tert-butyl ether, pentane, petroleum ether, isopropyl alcohol, n-propanol, tetrahydrofuran, or mixtures thereof. This mixture is then suspended by stirring in an organic oil (such as silicon oil, castor oil, paraffin oil, or mineral oil) to form an emulsion. Solid particles form from the emulsion, which can subsequently be isolated from the supernatant. The external morphology of spheres produced with this technique is highly dependent upon the identity of one or more quaternary ammonium compounds of the present invention.

In some embodiments, the microparticles are formed by using an oil-in-water emulsion. In one aspect, a method is provided whereby one or more quaternary ammonium compounds of the present invention are dissolved or dispersed in a volatile organic solvent such as methylene chloride, acetone, acetonitrile, 2-butanol, 2-butanone, t-butyl alcohol, benzene, chloroform, cyclohexane, 1,2-dichloroethane, diethyl ether, ethanol, ethyl acetate, heptane, hexane, methyl tert-butyl ether, pentane, petroleum ether, isopropyl alcohol, n-propanol, tetrahydrofuran, or mixtures thereof. This mixture is then suspended by stirring in an aqueous solution of a surfactant to form an emulsion. Solid particles form from the emulsion, which can subsequently be isolated from the supernatant. The external morphology of the spheres produced with this technique is highly dependent upon the identity of one or more compounds of the present invention.

In some embodiments, the microparticles are derived by spray drying. In one aspect, a method is provided whereby one or more compounds of the present invention are dissolved in an organic solvent such as methylene chloride, acetone, acetonitrile, 2-butanol, 2-butanone, t-butyl alcohol, benzene, chloroform, cyclohexane, 1,2-dichloroethane, diethyl ether, ethanol, ethyl acetate, heptane, hexane, methyl tert-butyl ether, pentane, petroleum ether, isopropyl alcohol, n-propanol, tetrahydrofuran, or mixtures thereof. The mixture is pumped through a micronizing nozzle driven by a flow of compressed gas, and the resulting aerosol is suspended in a heated cyclone of air, allowing the solvent to evaporate from the microdroplets, forming particles. Particles ranging between 0.1-10 microns can be obtained using this method.

Particles can be formed from one or more compounds of the present invention using a phase inversion method. In one aspect a method is provided whereby, one or more compounds of the present invention are dissolved in a solvent, and the solution is poured into a strong non-solvent for the substrate to spontaneously produce, under favorable conditions, microparticles. The method can be used to produce particles in a wide range of sizes, including, for example, from about 100 nanometers to about 10 microns, typically possessing a narrow particle size distribution.

In some embodiments, the particles can be formed from one or more compounds of the present invention using coacervation. Techniques for particle formation using coacervation are known in the art, for example, in GB-B-929 406; GB-B-929 50 1; and U.S. Pat. Nos. 3,266,987, 4,794,000, and 4,460,563.

In some embodiments, the particles can be formed from one or more compounds of the present invention by low temperature casting. Methods for very low temperature casting of microspheres are described in U.S. Pat. No. 5,019,400 to Gombotz et al. In one aspect, a method is provided whereby one or more compounds of the present invention is dissolved in an appropriate solvent. The mixture is then atomized into a vessel containing a liquid non-solvent at a temperature below the freezing point of the organosilicon QAC solution which freezes the droplets. As the droplets and the non-solvent for the organosilicon QAC are warmed, the solvent in the droplets thaws and is extracted into the non-solvent, hardening the microspheres.

In certain embodiments, one or more compounds of the present invention can be incorporated into a polymeric nanoparticle, e.g. for convenience of delivery, targeted delivery or extended release delivery. The use of materials in nanoscale provides one the ability to modify fundamental physical properties such as solubility, diffusivity, blood circulation half-life, release characteristics of one or more compounds of the present invention, or immunogenicity. A number of nanoparticle-based therapeutic and diagnostic agents have been developed for the treatment of cancer, diabetes, pain, asthma, allergy, and infections. These nanoscale agents may provide more effective or more convenient routes of administration, lower therapeutic toxicity, extend the product life cycle, and ultimately reduce healthcare costs. As therapeutic delivery systems, nanoparticles can provide targeted delivery and controlled release.

In addition, nanoparticle-based delivery can be used to release one or more compounds of the present invention at a sustained rate and thus lower the frequency of administration, deliver one or more compounds of the present invention in a targeted manner to minimize side effects, or to deliver one or more compounds of the present invention and an additional pharmaceutical active simultaneously for combination therapy to generate a synergistic effect and suppress drug resistance. Among these products, liposomal drugs and polymer-based conjugates account for a large proportion of the products. See, Zhang, L., et al., Nanoparticles in Medicine: Therapeutic Applications and Developments, Clin. Pharm. and Ther., 83(5):761-769, 2008.

Methods for producing nanoparticles are known in the art. For example, see Muller, R. H., et al., Solid lipid nanoparticles (SLN) for controlled drug delivery—a review of the state of the art, Eur. H. Pharm. Biopharm., 50:161-177, 2000; U.S. Pat. No. 8,691,750 to Consien et al.; WO 2012/145801 to Kanwar. U.S. Pat. No. 8,580,311 to Armes, S. et al.; Petros, R. A. and DeSimone, J. M., Strategies in the design of nanoparticles for therapeutic applications, Nature Reviews/Drug Discovery, vol. 9:615-627, 2010; U.S. Pat. Nos. 8,465,775; 8,444,899; 8,420,124; 8,263,129; 8,158,728; 8,268,446; Pellegrino et al., 2005, Small, 1:48; Murray et al., 2000, Ann. Rev. Mat. Sci., 30:545; and Trindade et al., 2001, Chem. Mat., 13:3843; all incorporated herein by reference. Additional methods have been described in the literature (see, e.g., Doubrow, Ed., "Microcapsules and Nanoparticles in Medicine and Pharmacy," CRC Press, Boca Raton, 1992; Mathiowitz et al., 1987, J. Control. Release, 5:13; Mathiowitz et al., 1987, Reactive Polymers, 6:275; and Mathiowitz et al., 1988, J. Appl. Polymer Sci., 35:755; U.S. Pat. Nos. 5,578,325 and 6,007,845; P. Paolicelli et al., "Surface-modified PLGA-based Nanoparticles that can Efficiently Associate and Deliver Virus-like Particles" Nanomedicine. 5(6):843-853 (2010)), U.S. Pat. No. 5,543,158 to Gref et al., or WO publication WO2009/051837 by Von Andrian et al. Zauner et al., 1998, Adv. Drug Del. Rev., 30:97; and Kabanov et al., 1995, Bioconjugate Chem., 6:7; (PEI; Boussif et al., 1995, Proc. Natl. Acad. Sci., USA, 1995, 92:7297), and poly(amidoamine) dendrimers (Kukowska-Latallo et al., 1996, Proc. Natl. Acad. Sci., USA, 93:4897; Tang et al., 1996, Bioconjugate Chem., 7:703; and Haensler et al., 1993, Bioconjugate Chem., 4:372; Putnam et al., 1999, Macromolecules, 32:3658; Barrera et al., 1993, J. Am. Chem. Soc., 115:11010; Kwon et al., 1989, Macromolecules, 22:3250; Lim et al., 1999, J. Am. Chem. Soc., 121:5633; and Zhou et al., 1990, Macromolecules, 23:3399). Examples of these polyesters include poly(L-lactide-co-L-lysine) (Barrera et al., 1993, J. Am. Chem. Soc., 115:11010), poly(serine ester) (Zhou et al., 1990, Macromolecules, 23:3399), poly(4-hydroxy-L-proline ester) (Putnam et al., 1999, Macromolecules, 32:3658; and Lim et al., 1999, J. Am. Chem. Soc., 121:5633), and poly(4-hydroxy-L-proline ester) (Putnam et al., 1999, Macromolecules, 32:3658; and Lim et al., 1999, J. Am. Chem. Soc., 121:5633; U.S. Pat. Nos. 6,123,727; 5,804,178; 5,770,417; 5,736,372; 5,716,404; 6,095,148; 5,837,752; 5,902,599; 5,696,175; 5,514,378; 5,512,600; 5,399,665; 5,019,379; 5,010,167; 4,806,621; 4,638,045; and 4,946,929; Wang et al., 2001, J. Am. Chem. Soc., 123:9480; Lim et 84 al., 2001, J. Am. Chem. Soc., 123:2460; Langer, 2000, Acc. Chem. Res., 33:94; Langer, 1999, J. Control. Release, 62:7; and Uhrich et al., 1999, Chem. Rev., 99:3181; Concise Encyclopedia of Polymer Science and Polymeric Amines and Ammonium Salts, Ed. by Goethals, Pergamon Press, 1980; Principles of Polymerization by Odian, John Wiley & Sons, Fourth Edition, 2004; Contemporary Polymer Chemistry by Allcock et al., Prentice-Hall, 1981; Deming et al., 1997, Nature, 390: 386; and in U.S. Pat. Nos. 6,506,577, 6,632,922, 6,686,446, and 6,818,732; C. Astete et al., "Synthesis and characterization of PLGA nanoparticles" J. Biomater. Sci. Polymer Edn, Vol. 17, No. 3, pp. 247-289 (2006); K. Avgoustakis "Pegylated Poly(Lactide) and Poly(Lactide-Co-Glycolide) Nanoparticles: Preparation, Properties and Possible Applications in Drug Delivery" Current Drug Delivery 1:321-333 (2004); C. Reis et al., "Nanoencapsulation I. Methods for preparation of drug-loaded polymeric nanoparticles" Nanomedicine 2:8-21 (2006); P. Paolicelli et al., "Surface-modified PLGA-based Nanoparticles that can Efficiently Associate and Deliver Virus-like Particles" Nanomedicine. 5(6): 843-853 (2010); U.S. Pat. No. 6,632,671 to Unger Oct. 14, 2003, all incorporated herein by reference.

Combination Therapy

In one embodiment, an active compound, or composition as described herein may be provided in combination or alternation with or preceded by, concomitant with or followed by, an effective amount of at least one additional therapeutic agent, for example, for treatment of a disorder listed herein. Non-limiting examples of additional active agents for such combination therapy are provided below. In the described below and herein generally, whenever any of the terms referring to an active compound, or composition as described herein are used, it should be understood that pharmaceutically acceptable salts, or compositions are considered included, unless otherwise stated or inconsistent with the text.

In one embodiment, an active compound, or composition as described herein may be used in combination or alternation with an antibiotic.

In one embodiment, the antibiotic is an aminoglycoside. In one embodiment, the antibiotic is selected from amikacin, gentamicin, kanamycin, neomycin, netilmicin, tobramycin, paromomycin, streptomycin, and spectinomycin.

In one embodiment, the antibiotic is an ansamycin. In one embodiment, the antibiotic is selected from geldanamycin, herbimycin, and rifaximin.

In one embodiment, the antibiotic is a carbapenem. In one embodiment, the antibiotic is selected from ertapenem, doripenem, imipenem, panipenem, biapenem, tebipenem, and meropenem.

In one embodiment, the antibiotic is a cephalosporin. In one embodiment, the antibiotic is selected from cefacetrile, cefadroxil, cephalexin, cefaloglycin, cefalonium, cefaloridine, cefalotin, cefapirin, cefatrizine, cefazaflur, cefazedone, cefazolin, cefradrine, cefroxadine, and ceftezole. In one embodiment, the antibiotic is selected from cefaclor, cefonicid, cefprozil, cefuroxime, cefuzonam, cefmetazole, cefotetan, cefoxitin, loracarbef, cefbuperazone, cefminox, cefoxitin, and cefotiam. In one embodiment, the antibiotic is selected from cefcapene, cefdaloxime, cefdinir, cefditoren, cefetamet, cefixime, cefmenoxime, cefodizime, cefotaxime, cefovecin, cefpimizole, cefpodoxime, cefteram, ceftamere, ceftibuten, ceftiofur, ceftiolene, ceftizoxime, ceftriaxone, cefoperazone, ceftazidime, and latamoxef. In one embodiment, the antibiotic is selected from cefclidine, cefepime, cefluprenam, cefoselis, cefozopran, cefpirome, cefquinome, and flomoxef. In one embodiment, the antibiotic is selected from ceftobiprole, ceftaroline, and ceftolozane.

In one embodiment, the antibiotic is a glycopeptide. In one embodiment, the antibiotic is selected from teicoplanin, vancomycin, telavancin, dalbavancin, ramoplanin, decaplanin, and oritavancin.

In one embodiment, the antibiotic is a lincosamide. In one embodiment, the antibiotic is selected from lincomycin, clindamycin, and pirlimycin. In one embodiment, the antibiotic is daptomycin.

In one embodiment, the antibiotic is a macrolide. In one embodiment, the antibiotic is selected from azithromycin, clarithromycin, erythromycin, fidaxomicin, telithromycin, carbomycin A, josamycin, kitasamycin, midecamycin, oleandomycin, solithromycin, spiramycin, troleandomycin, tylosin, and roxithromycin.

In one embodiment, the antibiotic is a ketolide. In one embodiment, the antibiotic is selected from telithromycin, cethromycin, and solithromycin.

In one embodiment, the antibiotic is a monobactam. In one embodiment, the antibiotic is selected from aztreonam. In one embodiment, the antibiotic is a nitrofuran. In one embodiment, the antibiotic is selected from diruazone, furazolidone, nifurfoline, nifuroxazide, nifurquinazol, nifurtoinol, nifurzide, nitrofural, and nitrofurantoin.

In one embodiment, the antibiotic is an oxazolidinone. In one embodiment, the antibiotic is selected from linezolid, posizolid, tedizolid, radezolid, torezolid, and cycloserine.

In one embodiment, the antibiotic is a penicillin. In one embodiment, the antibiotic is selected from penicillin G, penicillin K, penicillin N, penicillin O, and penicillin V. In one embodiment, the antibiotic is selected from meticillin, nafcillin, oxacillin, cloxacillin, dicloxacillin, and flucoxacillin. In one embodiment, the antibiotic is selected from ampicillin, amoxicillin, pivampicillin, hetacillin, bacampicillin, metampicillin, talampicillin, and epicillin. In one embodiment, the antibiotic is selected from carbenicilin, ticarcillin, and temocillin. In one embodiment, the antibiotic is selected from mezlocillin and piperacillin. In one embodiment, the antibiotic is selected from clavulanic acid, sulbactam, and tazobactam.

In one embodiment, the antibiotic is a polypeptide antibiotic. In one embodiment, the antibiotic is selected from bacitracin, colistin, and polymyxin B.

In one embodiment, the antibiotic is a quinolone or fluoroquinolone antibiotic. In one embodiment, the antibiotic is selected from flumequine, oxolinic acid, rosoxacin, cinoxacin, nalidixic acid, and piromidic acid. In one embodiment, the antibiotic is selected from ciprofloxacin, fleroxacin, lomefloxacin, nadifloxacin, norfloxacin, ofloxacin, pefloxacin, rufloxacin, and enoxacin. In one embodiment, the antibiotic is selected from balofloxacin, grepafloxacin, levofloxacin, pazufloxacin, sparfloxacin, temafloxacin, and tosufloxacin. In one embodiment, the antibiotic is selected from clinafloxacin, gatifloxacin, moxifloxacin, sitafloxacin, prulifloxacin, besifloxacin, gemifloxacin, trovafloxacin, delafloxacin, and ozenoxacin. In one embodiment, the antibiotic is a sulfonamide. In one embodiment, the antibiotic is selected from sulfacetamide, sulfadiazine, sulfadimidine, sulfafurazole, sulfisomidine, sulfadoxine, sulfamethoxazole, sulfamoxole, sulfanitran, sulfadimethoxine, sulfamethoxypyridazine, sulfametoxydiazine, sulfadoxine, sulfametopyrazine, terephtyl, mafenide, sulfanilamide, sulfasalazine, sulfisoxazole, and sulfonamicochrysoidine.

In one embodiment, the antibiotic is a tetracycline. In one embodiment, the antibiotic is selected from tetracycline, chlortetracycline, oxytetracycline, demeclocycline, lymecycline, meclocycline, metacycline, minocycline, and rolitetracycline. In one embodiment, the antibiotic is selected from clofazimine, dapsone, capreomycin, cycloserine, ethambutol, ethionamide, isoniazid, pyrazinamide, rifampicin, rifabutin, rifapentine, and streptomycin. In another embodiment, the antibiotic is selected from arsphenamide, chloramphenicol, fosfomycin, fusidic acid, metronidazole, mupirocin, platensimycin, quinupristin, dalfopristin, thiamphenicol, tigecycline, and trimethoprim.

In one embodiment, an active compound, or composition as described herein may be used in combination or alternation with an antifungal drug. In one embodiment, the antifungal drug is an azole antifungal. In one embodiment, the antifungal drug is selected from bifonazole, butoconazole, clotrimazole, econazole, fenticonazole, isoconazole, ketoconazole, luliconazole, miconazole, omoconazole, oxiconazole, sertaconazole, sulconazole, and tioconazole. In one embodiment, the antifungal drug is selected from albaconazole, efinaconazole, epoxiconazole, fluconazole, isavuconazole, itraconazole, posaconazole, propiconazole, ravuconazole, terconazole, and voriconazole.

In one embodiment, the antifungal drug is abafungin. In one embodiment, the antifungal drug is an echinocandin.

In one embodiment, the antifungal drug is selected from anidulafungin, caspofungin, and micafungin.

In one embodiment, the antifungal drug is a polyene antifungal. In one embodiment, the antifungal drug is selected from amphotericin B, candicidin, filipin, hamycin, natamycin, nystatin, and rimocidin. In one embodiment, the antifungal drug is selected from griseofulvin, terbinafine, and flucytosine.

Representative Examples of the Present Invention

Preparation of Compounds of Formula I, II, III, IV, V, VI, VII, VIII, and IX.

In one embodiment, Formula X is an intermediate for the synthesis of a compound of Formula I through Formula IX; wherein Formula X is selected from:

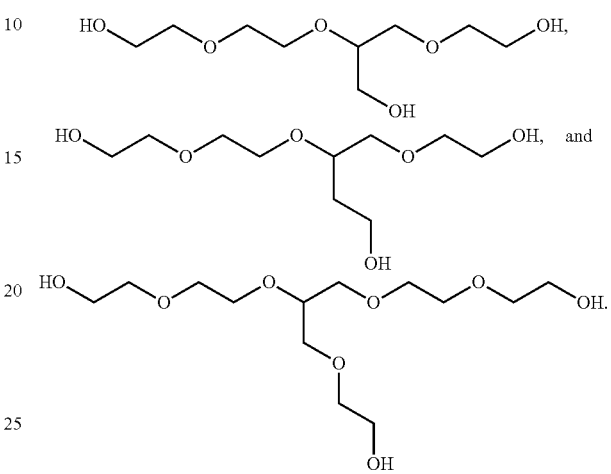

In an alternate embodiment, Formula X is an intermediate for the synthesis of a compound of Formula I through Formula IX; wherein Formula X is selected from:

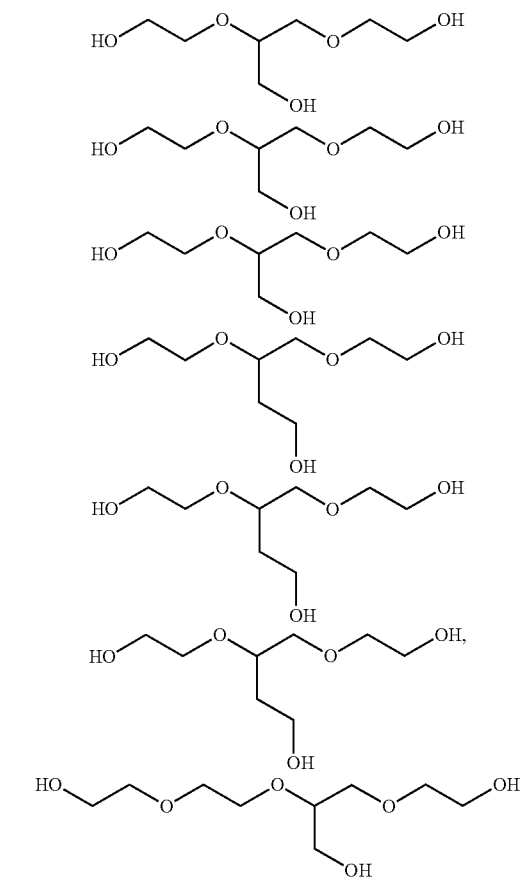

-continued

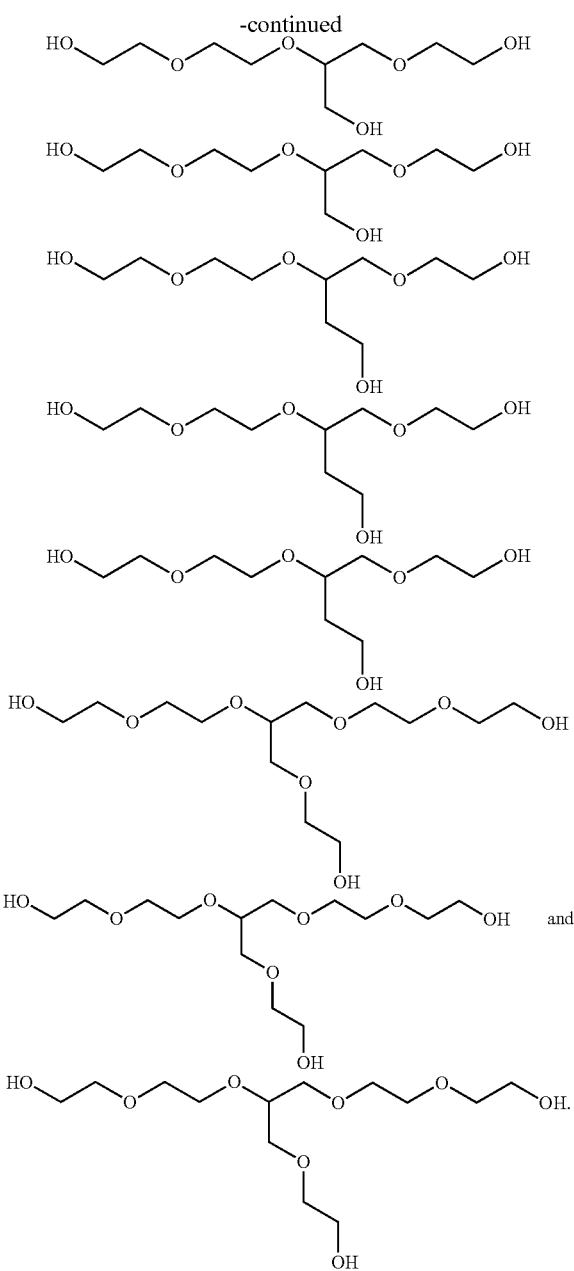

In one embodiment a compound having a Formula I through Formula IX, is prepared by:

Step 1) synthesizing a compound of Formula Z

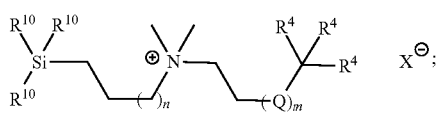

wherein:
each $R^{10}$ is independently hydroxyl, ethoxy, or halogen;
X— is an appropriate counter ion for example chloride or hydroxide; and
wherein $R^4$, n, m, and Q are defined herein; and Step 2) reacting Formula Z with a compound of Formula X.

In one embodiment the compound of Formula Z is a triol.

Step 1: Synthesizing a Compound of Formula Z

As a non-limiting example, a method for the synthesis of an organosilicon QAC as used in this disclosure (3-(Trihydroxysilyl)propyl-N-octadecyl-N,N-dimethylammonium chloride) without the concomitant production of methanol is provided in the following scheme:

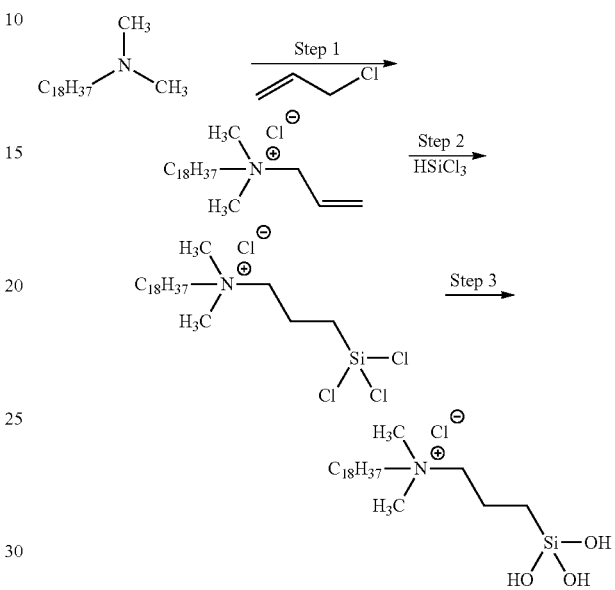

In step 1, N,N-dimethyloctadecan-1-amine can be reacted with 3-chloro-1-propene at elevated temperature in organic solvent to provide N-allyl-N,N-dimethyloctadecan-1-ammonium chloride. In some embodiments, the reaction may be performed at a temperature from about 25° C. to about 100° C. In some embodiments, the reaction may be performed in an organic solvent in which the starting components are soluble, such as tetrahydrofuran and toluene, among others.

In step 2, N-allyl-N,N-dimethyloctadecan-1-ammonium chloride can be reacted with trichlorosilane in the presence of an organometallic catalyst in organic solvent at elevated temperature to provide 3-(trichlorosilyl)-N-propyl-N,N-dimethyloctadecyl ammonium chloride. In some embodiments, the organometallic catalyst is a platinum compound (see U.S. Pat. No. 3,923,705 incorporated by reference for its teaching of platinum catalysis). In one embodiment, the organometallic catalyst is hexachloroplatinic acid. In another embodiment, the organometallic catalyst is bis(divinyltetramethyldisiloxane)platinum(0), known as Karstedt's catalyst, which is described in Karstedt's U.S. Pat. Nos. 3,715,334 and 3,814,730. In one embodiment, the organic solvent is toluene. In another embodiment, the organic solvent in tetrahydrofuran. In some embodiments, the temperature is greater than about 60° C.

In Step 3, 3-(trichlorosilyl)-N-propyl-N,N-dimethyloctadecyl ammonium chloride is reacted with water in the presence of base in organic solvent to provide 3-(trihydroxysilyl)propyl-N-octadecyl-N,N-dimethylammonium chloride. In one embodiment, three equivalents of water are used. In one embodiment, the base is sodium hydroxide. In one embodiment, the organic solvent is tetrahydrofuran.

Organosilicon QACs of the formula $((HO)_3Si)(C_1-C_3alkyl)N(CH_3)_2(C_1-C_{20}alkyl)^+X^-$ are typically free monomeric species in solution when solubilized at low concentrations. In particular, 3-(trihydroxysilyl)propyl-N-octadecyl-N,N-dimethylammonium chloride is available commercially as an aqueous solution. However, most commercially available solutions are produced by hydrolysis of the trimethoxysilane QAC precursor 3-(trimethoxysilyl)propyl-N-octadecyl-N,N-dimethylammonium chloride, which hydrolyses upon addition to water and concomitantly releases three equivalents of methanol.

In one embodiment, the organosilicon QACs and their solutions used herein can be prepared via a process that does not use methanol as a solvent, reactant/reagent, or does not produce methanol as a reaction byproduct. The organosilicon QACs used herein may be present in concentrations from about 0.1% to about 5%. In preferred embodiments, the organosilicon QAC is used at a concentration from about 1% to about 2%. In one embodiment, the organosilicon QAC is used at a concentration of at least about 2%. In one embodiment the organosilicon QAC is prepared in a solution with a compound of Formula X to afford a stabilized solution.

In some embodiments, the organosilicon QAC is isolated as a solid monomeric species. Methods for the synthesis and isolation of solid monomeric silanetriols are known in the art, see, e.g. Shimojima et al. J. Am. Chem. Soc. 2005, 127, 14108-14116. In one embodiment, the solid silanetriol QAC is isolated using the following method. Upon completion of hydrolysis of the trichlorosilane QAC precursor, the volume of solvent is reduced by half under vacuum, and the desired silanetriol QAC is triturated from the remaining solution using a non-polar solvent such as hexanes. The precipitated silanetriol QAC is filtered, washed with an additional quantity of non-polar solvent, and dried under vacuum to provide the desired silanetriol QAC. Examples of non-polar solvents that can be used in this protocol include, but are not limited to, hexanes, pentane, petroleum ether, toluene, xylenes, or combinations thereof. The isolated silanetriol QAC can then be stored at cold temperatures, e.g. no greater than about −10° C., or used directly in the preparation of aqueous solutions at desired concentrations as used in the desired antimicrobial composition. In one embodiment, the organosilicon QAC is impregnated within the dressing as a solid that subsequently dissolves upon contact with moisture present at the site of the wound and/or infection upon placement.

To ensure applications that can be used in living hosts, the organosilicon QACs as used herein preferably does not contain methanol. In one embodiment, organosilicon QACs may be prepared by a method that does not use methanol as a solvent, reactant/reagent, or does not produce methanol as a reaction byproduct. In one particular embodiment, the organosilicon QAC can be produced by a method that does not produce methanol upon hydrolysis in aqueous solution.

Traditional methods for the synthesis of organosilicon QACs of the above formula typically are via hydrolysis of a trimethoxysilane, leading to the concomitant production of methanol as a byproduct. To avoid production of this toxic byproduct and potential contamination in any relevant applications, organosilane QACs as used in this invention may be prepared from a trichlorosilane QAC precursor via hydrolysis in the presence of base.

In particular, the organosilicon QACs as used in this disclosure can be prepared by hydrolysis of a trichlorosilane QAC of the formula $(Cl_3Si)(C_1\text{-}C_3\text{alkyl})N(CH_3)_2(C_1\text{-}C_{20}\text{alkyl})^+X^-$ in the presence of base. Hydrolysis of the relevant trichlorosilane QAC precursors leads to concomitant formation of biologically benign chloride instead of toxic methanol. Trichlorosilane QAC precursors can be synthesized using methods known to those skilled in the art. In some embodiments, the trichlorosilane QAC precursor is synthesized by hydrosilylation of an appropriate alkenyl-substituted precursor with trichlorosilane in the presence of a catalyst. Alternatively, preparation of the organosilicon QACs may be performed using methods standard in the art, followed by removal of methanol. Residual methanol may be removed by heating, vacuum, or a combination thereof. Alternatively, residual methanol may be removed by reaction with another compound, such as an acyl chloride or fatty acid.

Step 2: Reacting Formula Z with a Compound of Formula X.

As shown in the schematic below, a compound of Formula I, II, III, IV, V, VI, VII, VIII, or IX, is prepared by reaction a compound of Formula Z with a compound of Formula X, in solution:

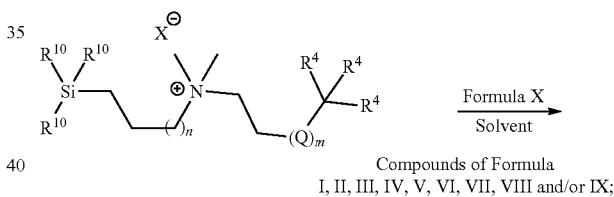

Compounds of Formula
I, II, III, IV, V, VI, VII, VIII and/or IX;

wherein $R^4$, $R^{10}$, n, m, Q, and X— are as defined herein.

The resulting solution may contain substantially only a compound of Formula I, II, III, IV, V, VI, VII, VIII, or IX or a mixture of compounds of these formulas.

Preparation of Compounds of Formula XI, XII, and XIII.

In one embodiment a compound of Formula XI, XII, or XIII is prepared by reacting a compound of Formula Z with a tris(2-hydroxyethyl)methylammonium halide salt in solution.

For example, the schematic below shows the reaction of a compound of Formula Z with a tris(2-hydroxyethyl)methylammonium halide salt to produce a compound of Formula XI, Formula XII and/or Formula XIII:

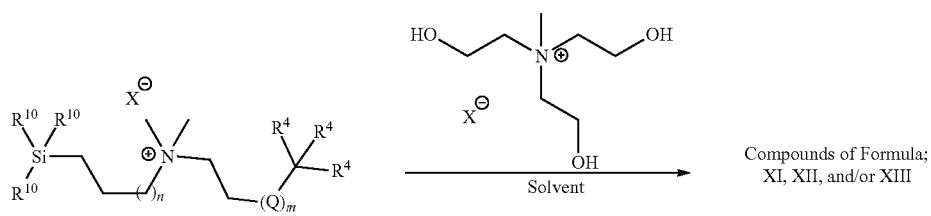

Compounds of Formula;
XI, XII, and/or XIII wherein $R^4$, $R^{10}$, n, m, Q, and X— are as defined herein.

The resulting solution may contain substantially only a compound of Formula XI, XII, or XIII or a mixture of compounds of these formulas.

Example 1. General Synthesis of Compounds of Formula X

Route 1

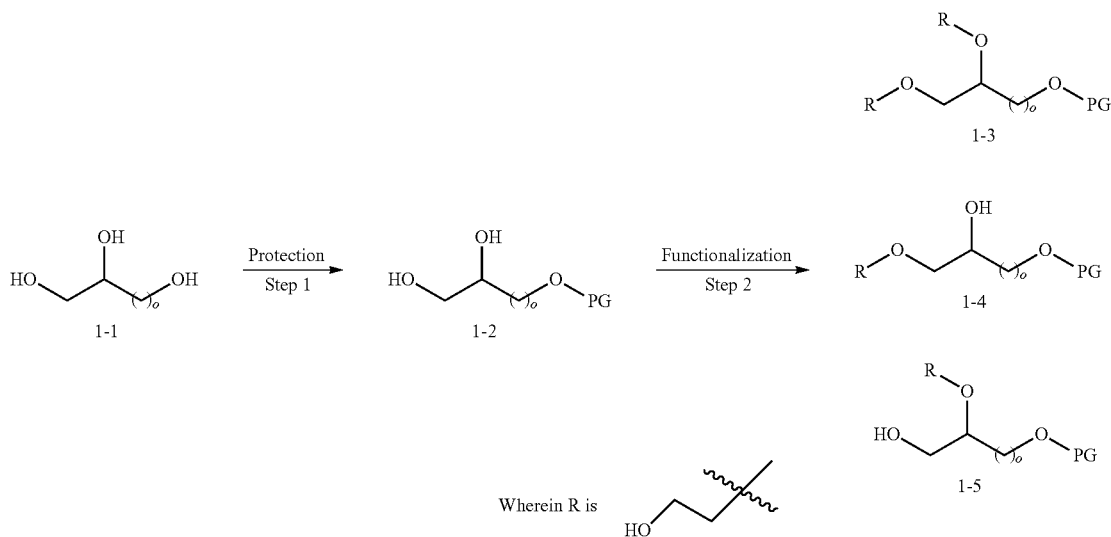

In Step 1 the appropriate starting reagent Compound 1-1 is selectively protected with a desired protecting group. In Step 2 the remaining alcohol functional groups are functionalized with "R." While in principle a mixture of Compound 1-3, Compound 1-4, and Compound 1-5 may theoretically result adjustment of conditions can be used to increase the formation of the desired compound. For example, using more than two equivalents of electrophilic reagent will favor and may even exclusively afford compound 1-3. Alternatively using a limiting amount of electrophilic reagent will favor compound 4. Even compound 1-5 can be obtained with enhanced selectively through methods known in the art. For example a transient protecting group (such as TMS) may be used to temporarily block the primary alcohol functionality and allow for functionality of the secondary alcohol.

Then upon removal of the protecting group desired compounds of Formula X may be isolated. A representative, non-limiting, example is provided below.

Example 2. Representative Synthesis of Compounds of Formula X

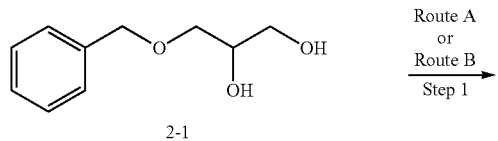

Step 1 Route A

Utilizing the phase-transfer-catalyzed reaction described in the Journal of Organic Chemistry, Volume 54, Issue 4, 857-60, Compound 2-2 can be isolated in 75% yield. This synthesis has been applied to this actual structure, and is applicable to other intermediates to synthesize compounds of Formula X.

Step 1 Route B

Utilizing the alkylation reduction strategy described in Tetrahedron Letters, Volume 24, Issue 5, 457-60, Compound 2—can be produced. This synthesis has been applied to this actual structure, and is applicable to other intermediates to synthesize compounds of Formula X.

Step 2

Palladium on carbon is added to a solution of Compound 2-2 in tert-butyl alcohol. This solution is then stirred or shaken under a hydrogen gas atmosphere to afford Compound 2-3. Compound 2-3 is then purified by techniques known to the skilled artisan such as extraction, column chromatography, and/or distillation.

Example 3. Synthesis of 2,2'-((4-Hydroxybutane-1,2-diyl)bis(oxy))bis(ethan-1-ol)

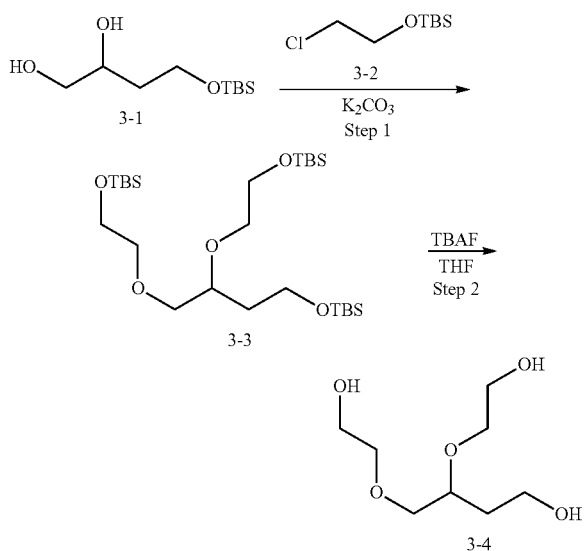

Step 1

The synthesis of 4-((tert-butyldimethylsilyl)oxy)butane-1,2-diol 3-1 has been previously described in *Eur. J. Org. Chem.* 2014, 25:5549-56. Reaction of 3-1 with tert-butyl(2-chloroethoxy)dimethylsilane 3-2 (previously synthesized as described in Tetrahedron 2014, 70-7229-40) in the presence of potassium carbonate can provide 8-(2-((tert-butyldimethylsilyl)oxy)ethyl)-2,2,3,3,14,14,15,15-octamethyl-4,7,10,13-tetraoxa-3,14-disilahexadecane 3-3.

Step 2

Reaction of 3-3 with tetrabutylammonium fluoride in THF can provide 2,2'-((4-hydroxybutane-1,2-diyl)bis(oxy))bis(ethan-1-ol) 3-4. Compound 3-4 can then be purified by techniques known to the skilled artisan such as extraction, column chromatography, and/or distillation.

Example 4. Synthesis of 3-(2-Hydroxyethoxy)-2-(2-(2-hydroxyethoxy)ethoxy)propan-1-ol

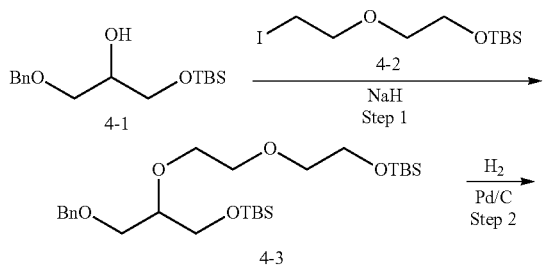

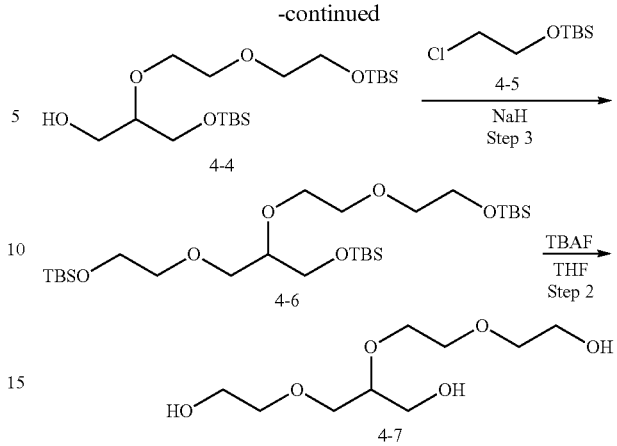

Step 1

The synthesis of 1-(benzyloxy)-3-((tert-butyldimethylsilyl)oxy)propan-2-ol 4-1 has been previously described in *Org. Lett.* 2009, 11:5466-9. Deprotonation of 4-1 by sodium hydride followed by subsequent reaction with tert-butyl(2-(2-iodoethoxy)ethoxy)dimethylsilane 4-2 (previously synthesized as described in *ChemBioChem* 2015, 16:64-9) can provide 6-((benzyloxy)methyl)-2,2,3,3,14,14,15,15-octamethyl-4,7,10,13-tetraoxa-3,14-disilahexadecane 4-3.

Step 2

Reaction of 4-3 with hydrogen in the presence of catalytic palladium on carbon can provide 11-(((tert-butyldimethylsilyl)oxy)methyl)-2,2,3,3-tetramethyl-4,7,10-trioxa-3-siladodecan-12-ol 4-4.

Step 3

Deprotonation of 4-4 by sodium hydride followed by subsequent reaction with tert-butyl(2-chloroethoxy)dimethylsilane 4-5 can provide 9-(((tert-butyldimethylsilyl)oxy)methyl)-2,2,3,3,17,17,18,18-octamethyl-4,7,10,13,16-pentaoxa-3,17-disilanonadecane 4-6.

Step 4

Reaction of 4-6 with tetrabutylammonium fluoride in THF can provide 3-(2-hydroxyethoxy)-2-(2-(2-hydroxyethoxy)ethoxy)propan-1-ol 4-7. Compound 4-7 can then be purified by techniques known to the skilled artisan such as extraction, column chromatography, and/or distillation.

Example 5. Synthesis of 4-(2-Hydroxyethoxy)-3-(2-(2-hydroxyethoxy)ethoxy)butan-1-ol

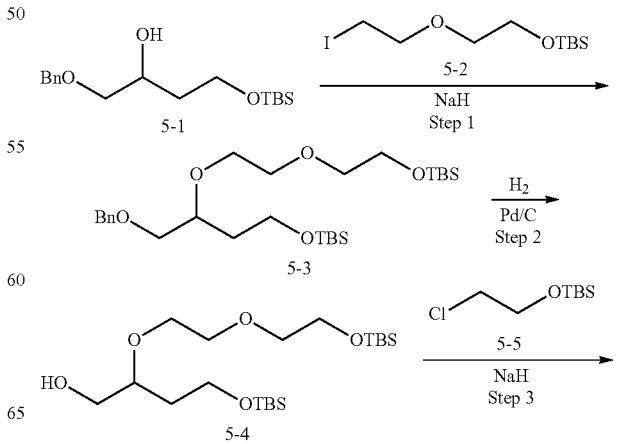

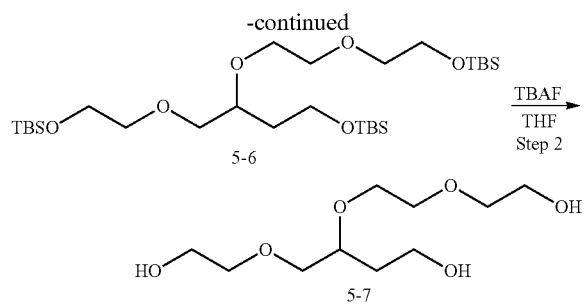

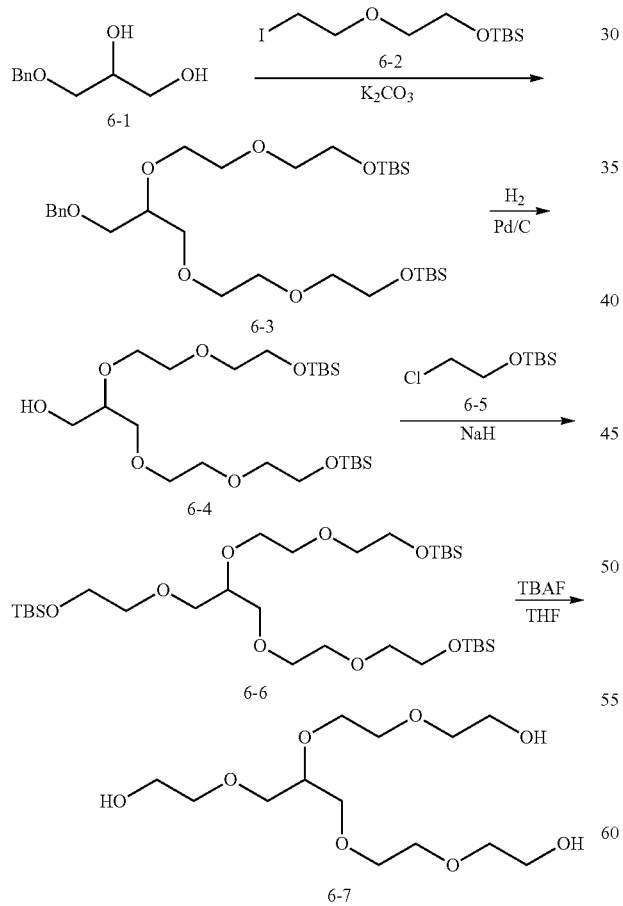

The synthesis of 4-(2-hydroxyethoxy)-3-(2-(2-hydroxyethoxy)ethoxy)butan-1-ol 5-7 can occur by the same process as in Example 4 but begins with 1-(benzyloxy)-4-((tert-butyldimethylsilyl)oxy)butan-2-ol 5-1 as starting material. The synthesis of compound 5-1 has been previously described in Tetrahedron: Asymmetry 2009, 20-2635-8. Compound 5-7 can be purified by techniques known to the skilled artisan such as extraction, column chromatography, and/or distillation.

Example 6. Synthesis of 7-((2-Hydroxyethoxy)methyl)-3,6,9,12-tetraoxatetradecane-1,14-diol The synthesis of 7-((2-hydroxyethoxy)methyl)-3,6,9,12-tetraoxatetradecane-1,14-diol 6-7 can occur by the same process as in Example 4 but begins with 3-(benzyloxy)propane-1,2-diol 6-1 as starting material. Compound 6-7 can be purified by techniques known to the skilled artisan such as extraction, column chromatography, and/or distillation.

Example 7. Synthesis of 3-(Tris(2-hydroxyethyl)ammonio)propane-1-sulfonate

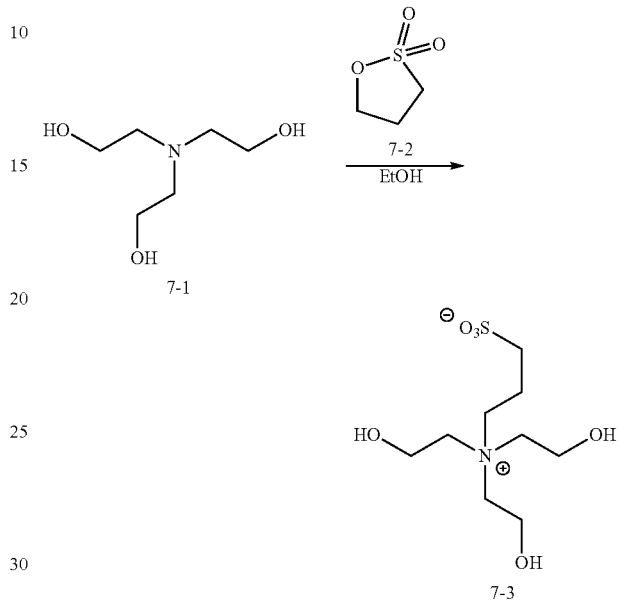

Reaction of 2,2',2''-nitrilotris(ethan-1-ol) 7-1 with 1,2-oxathiolane 2,2-dioxide 7-2 in refluxing ethanol can provide 3-(tris(2-hydroxyethyl)ammonio)propane-1-sulfonate 7-3, which can then be purified by techniques known to the skilled artisan such as extraction, column chromatography, and/or distillation.

Example 8. Synthesis of 2-Hydroxy-3-(tris(2-hydroxyethyl)ammonio)propane-1-sulfonate

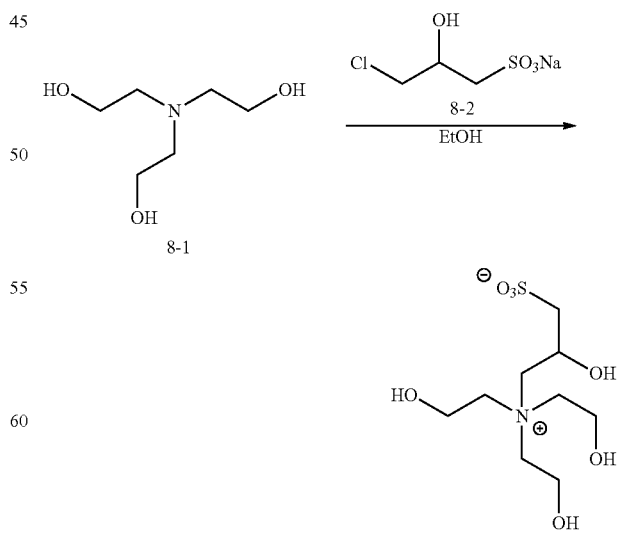

Reaction of 2,2',2''-nitrilotris(ethan-1-ol) 8-1 with sodium 3-chloro-2-hydroxypropane-1-sulfonate 8-2 in refluxing ethanol can provide 2-hydroxy-3-(tris(2-hydroxyethyl)ammonio)propane-1-sulfonate 8-3, which can then be purified by techniques known to the skilled artisan such as extraction, column chromatography, and/or distillation.

Example 9. Preparation of a Stable Solution of N-(3-(2,5,8,11,12-Pentaoxa-1-silabicyclo[5.4.2]tridecan-1-yl)propyl)-N,N-dimethyloctadecan-1-aminium Chloride

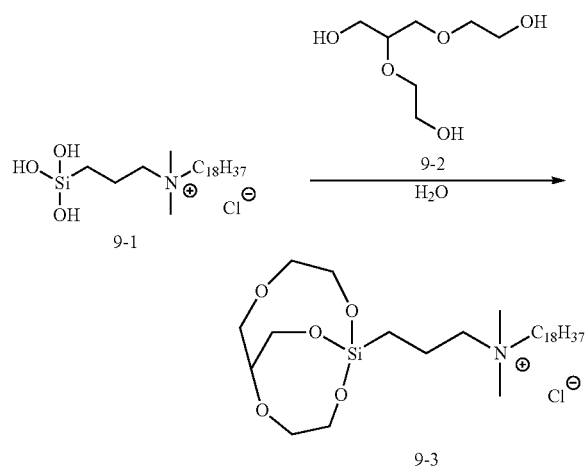

To a 5% solution of 3-(trihydroxysilyl)-N-propyl-N,N-dimethyloctadecyl ammonium chloride (9-1, 1 equivalent) in water is added 2,2'-((3-hydroxypropane-1,2-diyl)bis(oxy))bis(ethan-1-ol) (9-2, 1 equivalent), and the reaction mixture is stirred for 24 hours to prepare a solution of N-(3-(2,5,8,11,12-pentaoxa-1-silabicyclo[5.4.2]tridecan-1-yl)propyl)-N,N-dimethyloctadecan-1-aminium chloride (9-3) that is equilibrating with its equivalent isomers of Formulas I, II, and III.

Alternate Example 9

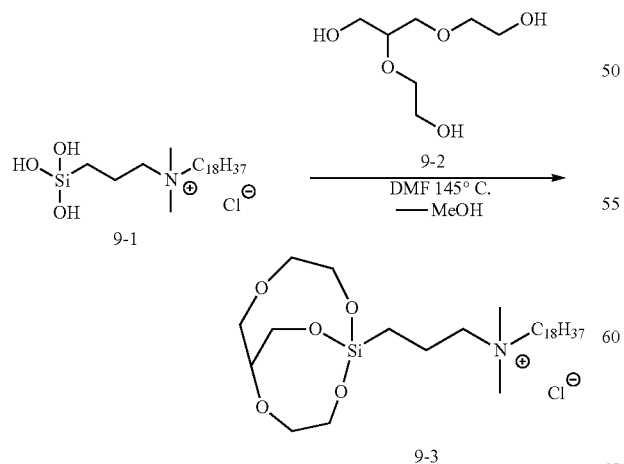

A 500 mL round bottom reaction vessel was outfitted with a heating mantle, magnetic stir bar, downward condenser, receiving flask, oil bubbler, an immersion thermoprobe for the pot, and a thermoprobe for the head. The reactor is charged with 30 mL of a 67% solution of dimethyloctadecyl [3-(trimethoxysilyl)propyl]ammonium chloride (9-1), 7.26 g of 2,2'-((3-hydroxypropane-1,2-diyl)bis(oxy))bis(ethan-1-ol)2,2'-((3-hydroxypropane-1,2-diyl)bis(oxy))bis(ethan-1-ol) (9-2 1 eq) and ~150 mL of DMF. The mixture is heated to 145° C. (pot temp) and the methanol is collected until the head temp drops and no more MeOH is evolved. The reaction is then cooled and DMF evaporated. Toluene (150 mL) is added, stirred at room temp for 1 hour, and then evaporated. Acetonitrile (150 mL) is added, stirred at room temp for 1 hour, and then evaporated. The resultant product was placed under high vac overnight to yield an off-white viscous liquid (9-3) that is equilibrating with its equivalent isomers of Formulas I, II, and III.

Example 10. Preparation of a Lyophilized Solid Preparation of N-(3-(2,5,8,11,12-Pentaoxa-1-silabicyclo[5.4.2]tridecan-1-yl)propyl)-N,N-dimethyloctadecan-1-aminium Chloride A solution of the parent compound is prepared in water according to Example 9. A sample of the solution is lyophilized using a LyoStar freeze dryer using the following 74 hour cycle:

1.) the sample is attached at atmospheric pressure and initially held at 5° C. for 60 minutes;
2.) the sample is slowly cooled to −55° C. over 120 minutes and then maintained at that temperature for another 120 minutes;
3.) the sample is warmed up to −15° C. over 60 minutes and then maintained at that temperature for 300 minutes;
4.) the sample is again slowly cooled to −55° C. over 120 minutes and maintained at that temperature for 120 minutes;
5.) pressure is lowered to 100 μm Hg and the sample is maintained at a temperature of −55° C. for 150 minutes;
6.) the sample is warmed up to −25° C. over 20 minutes and then maintained at that temperature for 40 hours;
7.) the sample is warmed up to 40° C. over 6 hours and then maintained at that temperature for 7 hours; and
8.) the sample is cooled to warm temperature over 20 minutes and then repressurized with nitrogen to provide a lyophilized power of N-(3-(2,5,8,11,12-pentaoxa-1-silabicyclo[5.4.2]tridecan-1-yl)propyl)-N,N-dimethyl-octadecan-1-aminium chloride.

The lyophilized solid formulation may be stored sealed under nitrogen indefinitely and may subsequently be reconstituted for application by diluting it with sterile medical grade saline or glycerin. A similar procedure may be used for preparing lyophilized solid preparations from any of the aqueous solutions provided in the below examples.

Example 11. Preparation of a Stable Solution of 1-(3-(Dimethyl(octadecyl)ammonio)propyl)-5-methyl-2,8,9-trioxa-5-aza-1-silabicyclo[3.3.3]undecan-5-ium Dichloride

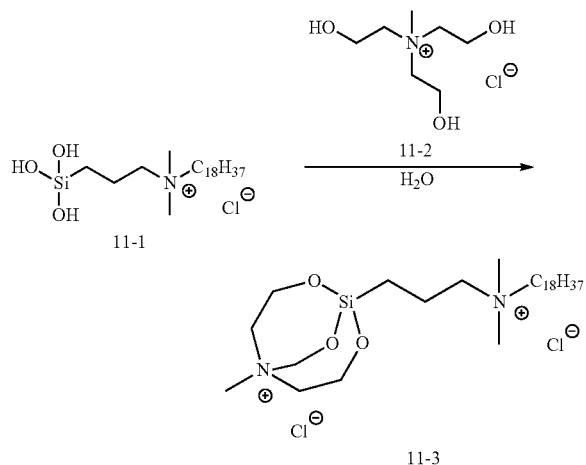

To a 5% solution of 3-(trihydroxysilyl)-N-propyl-N,N-dimethyloctadecyl ammonium chloride 11-1 (1 equivalent) in water is added 2-hydroxy-N,N-bis(2-hydroxyethyl)-N-methylethan-1-aminium chloride 11-2 (1 equivalent), and the reaction mixture is stirred for 24 hours to prepare a solution of 1-(3-(dimethyl(octadecyl)ammonio)propyl)-5-methyl-2,8,9-trioxa-5-aza-1-silabicyclo[3.3.3]undecan-5-ium dichloride 11-3 that is equilibrating with its equivalent isomers of Formulas XI, XII, and XIII.

Alternate Example 11

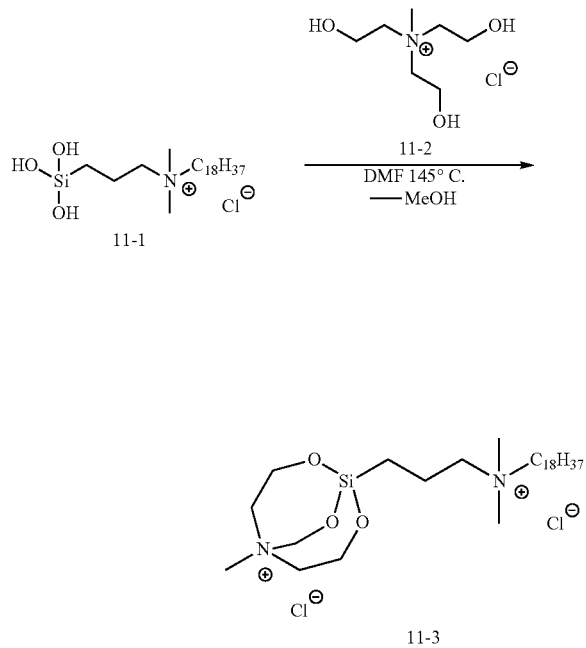

A 500 mL round bottom reaction vessel was outfitted with a heating mantle, magnetic stir bar, downward condenser, receiving flask, oil bubbler, an immersion thermoprobe for the pot, and a thermoprobe for the head. The reactor is charged with 30 mL of a 67% solution of dimethyloctadecyl [3-(trimethoxysilyl)propyl]ammonium chloride (9-1), 8.04 g of 2-hydroxy-N,N-bis(2-hydroxyethyl)-N-methylethan-1-aminium chloride (11-2 1 eq) and ~150 mL of DMF. The mixture is heated to 145° C. (pot temp) and the methanol is collected until the head temp drops and no more MeOH is evolved. The reaction is then cooled and DMF evaporated. Toluene (150 mL) is added, stirred at room temp for 1 hour, and then evaporated. Acetonitrile (150 mL) is added, stirred at room temp for 1 hour, and then evaporated. The resultant product was placed under high vac overnight to yield an off-white viscous liquid (9-3) that is equilibrating with its equivalent isomers of Formulas XI, XII, and XIII.

Example 12. Preparation of a Stable Solution of 3-(1-(3-(Dimethyl(octadecyl)ammonio)propyl)-2,8,9-trioxa-5-aza-1-silabicyclo[3.3.3]undecan-5-ium-5-yl)-2-hydroxypropane-1-sulfonate Chloride

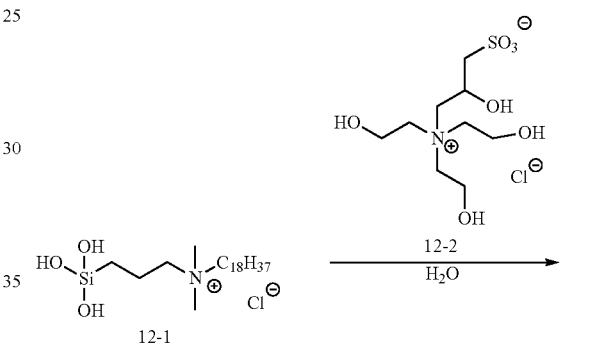

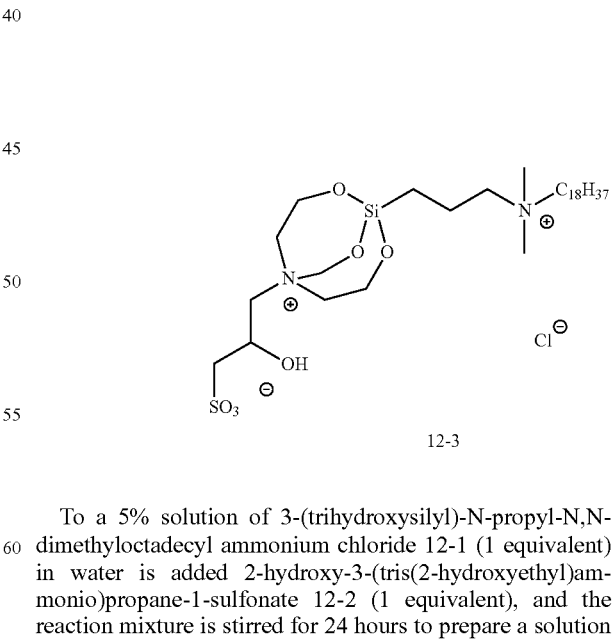

To a 5% solution of 3-(trihydroxysilyl)-N-propyl-N,N-dimethyloctadecyl ammonium chloride 12-1 (1 equivalent) in water is added 2-hydroxy-3-(tris(2-hydroxyethyl)ammonio)propane-1-sulfonate 12-2 (1 equivalent), and the reaction mixture is stirred for 24 hours to prepare a solution of 3-(1-(3-(dimethyl(octadecyl)ammonio)propyl)-2,8,9-trioxa-5-aza-1-silabicyclo[3.3.3]undecan-5-ium-5-yl)-2-hydroxypropane-1-sulfonate chloride 12-3 that is equilibrating with its equivalent isomers of Formulas XIV, XV, and XVI.

Alternate Example 12

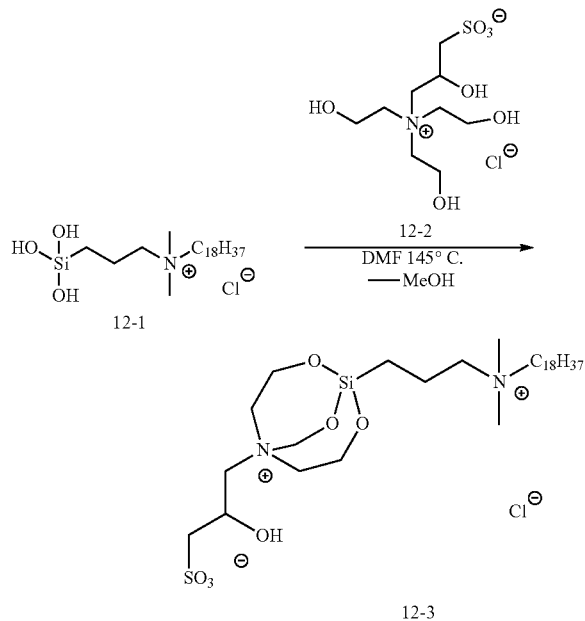

12-3

A 500 mL round bottom reaction vessel was outfitted with a heating mantle, magnetic stir bar, downward condenser, receiving flask, oil bubbler, an immersion thermoprobe for the pot, and a thermoprobe for the head. The reactor is charged with 30 mL of a 67% solution of dimethyloctadecyl [3-(trimethoxysilyl)propyl]ammonium chloride (12-1), 11.5 g of 2-hydroxy-3-(tris(2-hydroxyethyl)ammonio)propane-1-sulfonate (12-2 1 eq) and ~150 mL of DMF. The mixture is heated to 145° C. (pot temp) and the methanol is collected until the head temp drops and no more MeOH is evolved. The reaction is then cooled and DMF evaporated. Toluene (150 mL) is added, stirred at room temp for 1 hour, and then evaporated. Acetonitrile (150 mL) is added, stirred at room temp for 1 hour, and then evaporated. The resultant product was placed under high vac overnight to yield an off-white solid (12-3) that is equilibrating with its equivalent isomers of Formulas XIV, XV, and XVI.

Example 13. Preparation of a Stable Solution of 1-(3-(Dimethyl(octadecyl)-14-azaneyl)propyl)-N,N,N-trimethyl-2,8,9-trioxa-1-silabicyclo[3.3.3]undecan-5-aminium Dichloride

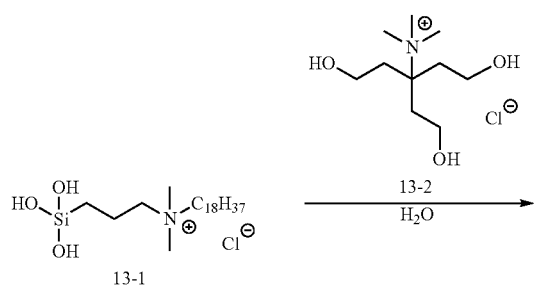

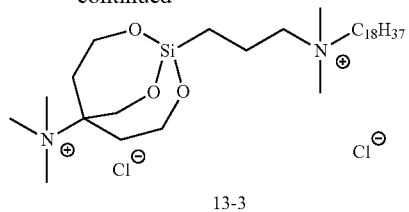

13-3

To a 5% solution of 3-(trihydroxysilyl)-N-propyl-N,N-dimethyloctadecyl ammonium chloride 13-1 (1 equivalent) in water is added 1,5-dihydroxy-3-(2-hydroxyethyl)-N,N,N-trimethylpentan-3-aminium chloride 13-2 (1 equivalent), and the reaction mixture is stirred for 24 hours to prepare a solution of 1-(3-(dimethyl(octadecyl)-14-azaneyl)propyl)-N,N,N-trimethyl-2,8,9-trioxa-1-silabicyclo[3.3.3]undecan-5-aminium dichloride 13-3 that is equilibrating with its equivalent isomers of Formulas XVII, XVIII, and XIX.

Alternate Example 13

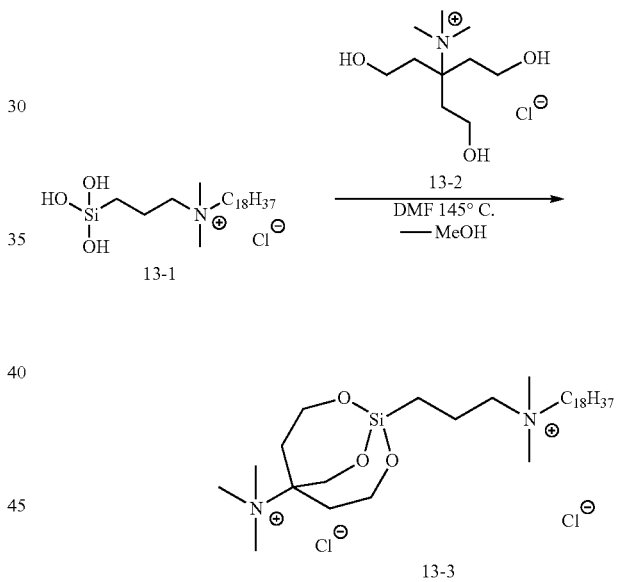

A 500 mL round bottom reaction vessel was outfitted with a heating mantle, magnetic stir bar, downward condenser, receiving flask, oil bubbler, an immersion thermoprobe for the pot, and a thermoprobe for the head. The reactor is charged with 30 mL of a 67% solution of dimethyloctadecyl [3-(trimethoxysilyl)propyl]ammonium chloride (13-1), 9.7 g of 1,5-dihydroxy-3-(2-hydroxyethyl)-N,N,N-trimethylpentan-3-aminium chloride (13-2 1 eq) and ~150 mL of DMF. The mixture is heated to 145° C. (pot temp) and the methanol is collected until the head temp drops and no more MeOH is evolved. The reaction is then cooled and DMF evaporated. Toluene (150 mL) is added, stirred at room temp for 1 hour, and then evaporated. Acetonitrile (150 mL) is added, stirred at room temp for 1 hour, and then evaporated. The resultant product was placed under high vac overnight to yield an off-white solid (13-3) that is equilibrating with its equivalent isomers of Formulas XVII, XVIII, and XIX.

Example 14. Synthesis of Sodium; 3-[[1-[3-[dim-ethyl(octadecyl)ammonio]propyl]-2,6,7-trioxa-1-silabicyclo[2.2.2]octan-4-yl]amino]-2-hydroxy-propane-1-sulfonate; chloride

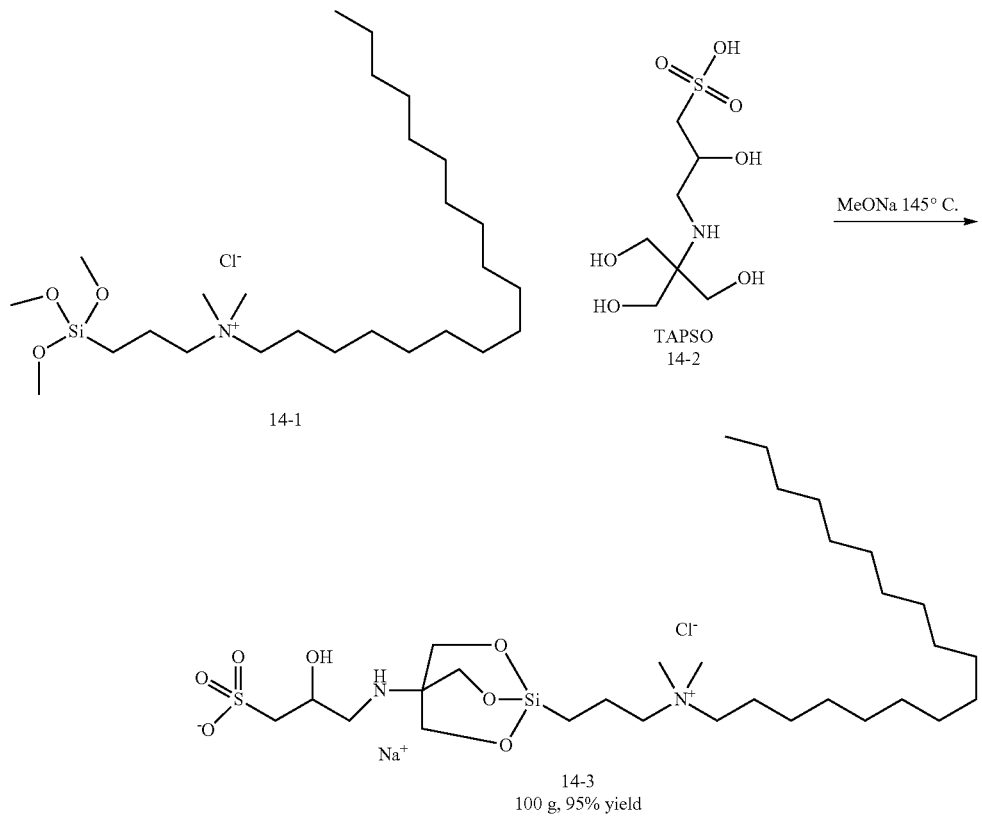

A 72% solution of dimethyloctadecyl[3-(trimethoxysilyl)propyl]ammonium chloride 14-1 in methanol was evaporated and dried to constant weight. 46 g of dimethyloctadecyl[3-(trimethoxysilyl)propyl]ammonium chloride 14-1 was dissolved in 250 mL MeOH with stirring and 24 g of TAPSO 14-2 added. To the resulting suspension was added 18 mL (2 eq) of a 25% sodium methoxide in methanol. The resulting clear solution was stirred overnight and then evaporated at reduced pressure. 200 mL of DMF was added, stirred 2 h, and evaporated at 60 C under high vac. This process was repeated a second time and then repeated with toluene. The resulting solid 14-3 was dried under high vacuum overnight at 50 C. NMR is consistent with the proposed structure. The product is an off-white solid.

Example 15. Antimicrobial Screening Assays

The antimicrobial activity of the compounds described herein can be determined using any number of standard in vitro or in vivo assays known in the art. For example, the minimum inhibitory concentration (MIC) activity of the compounds described herein can be determined using the disk diffusion susceptible test (also known as the Kirby-Bauer test) or the broth dilution test, or any other suitable in vitro assay known in the art to determine the susceptibility of a microorganism to an antimicrobial. In addition, in vivo assays, for example in vivo methods for evaluating topical antimicrobial agents such as occlusion assays or rabbit eye efficacy testing may be used to characterize the antimicrobial activity of the compounds described herein.

Disk Diffusion Susceptibility Test

One particularly suitable test is the disk diffusion susceptibility test (see Jan Hudzicki, Kirby-bauer disk diffusion susceptibility test protocol, December 2009, American Society for Microbiology, incorporated herein by reference). In the disk diffusion susceptibility test, a known concentration of a compound described herein is absorbed on a disk of filter paper (generally 6-mm) and placed on a Mueller-Hinton (MH) agar plate or other suitable agar plate used for testing the particular antimicrobial. Water is immediately absorbed into the disk from the agar and the compound begins to diffuse into the surrounding agar. The rate of diffusion through the agar is not as rapid as the rate of extraction of the compound out of the disk, therefore the concentration of the compound is highest closest to the disk and a logarithmic reduction in concentration occurs as the distance from the disk increases (see, e.g., Jorgensen, J. H., and J. D. Turnidge. 2007. Susceptibility test methods: dilution and disk diffusion methods, p. 1152-1172. In P. R. Murray, E. J. Baron, J. H. Jorgensen, M. L. Landry, and M. A. Pfaller (ed.), Manual of clinical microbiology, 9th ed. ASM Press, Washington, D.C., incorporated herein by reference). The rate of diffusion of the compound through the agar is dependent on the diffusion and solubility properties of the drug in MH agar and the molecular weight of the compound (see, e.g., Bauer, A. W., W. M. M. Kirby, J. C. Sherris, and M. Turck. 1966. Antibiotic susceptibility testing by a standardized single disk method. Am. J. Clin. Pathol. 36:493-496, incorporated herein in its entirety). Larger molecules will diffuse at a slower rate than lower molecular weight compounds. These factors, in combination, result in the compound having a unique breakpoint zone size indicating susceptibility to that compound. The disk diffusion method can also be used to test antifungals (see, for example, CLSI M44; Clinical and Laboratory Standards Institute Method for Antifungal Disk Diffusion Susceptibility Testing of Yeasts; Approved Guideline 2nd Wayne: Clinical and Laboratory Standards Institute; 2009, incorporated herein). To test antifungal activity, the use of Mueller-Hinton agar supplemented with 2% glucose is recommended, providing a suitable growth for most yeasts, and 0.5 mg/L methylene blue dye medium (enhances the zone edge definition) minimizing the trailing effect. The pH of the medium should be between 7.2 and 7.4 after gelling and the agar should be 4 cm high. The inoculum is standardized to 0.5 McFarland using a densitometer and plates should be incubated at 35° C. for between 24 hours and 48 hours.

If the agar plate has been inoculated with a suspension of the pathogen to be tested prior to the placing of disks on the agar surface, simultaneous growth of the bacteria and diffusion of the compound occurs. Growth occurs in the presence of the compound when the bacteria reach a critical mass and can overpower the inhibitory effects of the compound. The estimated time of a bacterial suspension to reach critical mass is 4 to 10 hours for most commonly recovered pathogens, but is characteristic of each species, and influenced by the media and incubation temperature. The size of the zone of inhibition of growth is influenced by the depth of the agar, since the antimicrobial diffuses in three dimensions, thus a shallow layer of agar will produce a larger zone of inhibition than a deeper layer. The point at which critical mass of the antimicrobial is reached is demonstrated by a sharply marginated circle of microbial growth around the disk. The concentration of compound at this margin is called the critical concentration and is approximately equal to the minimum inhibitory concentration obtained in broth dilution susceptibility tests. Although not all fastidious or slow growing bacteria can be accurately tested by this method, the disk test has been standardized for testing streptococci, *Haemophilus influenzae*, and *N. meningitidis* through use of specialized media, incubation conditions, and specific zone size interpretive criteria (see, e.g., Clinical and Laboratory Standards Institute, Performance standards for antimicrobial disk susceptibility tests. Approved standard M2-A10, 2009, Wayne, PA Clinical and Laboratory Standards Institute, incorporated herein by reference).

Antimicrobial Gradient Diffusion Method

Additional assays may also be used. For example, the antimicrobial gradient diffusion method uses the principle of establishment of an antimicrobial concentration gradient in an agar medium as a means of determining susceptibility (see, e.g., Reller et al., Antimicrobial Susceptibility Testing: A Review of General Principles and Contemporary Practices, Clinical Infectious Diseases, Volume 49, Issue 11, 1 Dec. 2009, Pages 1749-1755). The Etest (bioMerieux AB BIODISK) is a commercial version available in the United States. It employs thin plastic test strips that are impregnated on the underside with a dried antibiotic concentration gradient and are marked on the upper surface with a concentration scale. As many as 5 or 6 strips may be placed in a radial fashion on the surface of an appropriate 150-mm agar plate that has been inoculated with a standardized organism suspension like that used for a disk diffusion test. After overnight incubation, the tests are read by viewing the strips from the top of the plate. The MIC is determined by the intersection of the lower part of the ellipse shaped growth inhibition area with the test strip.

Broth Dilution Susceptibility Test

In addition to or in alternative, the antimicrobial activity of a compound described herein can be determined through the use of a broth dilution susceptibility test (see, e.g., Reller et al., Antimicrobial Susceptibility Testing: A Review of General Principles and Contemporary Practices, Clinical Infectious Diseases, Volume 49, Issue 11, 1 Dec. 2009, Pages 1749-1755). This procedure uses serial dilutions (usually 2×) of a compound of interest (eg, 0.25, 0.5, 1, 2, 4, 8, and 16 µg/mL) in a liquid growth medium dispensed in, e.g., test tubes or standard trays containing 96 wells. The compound-containing tubes are inoculated with a standardized suspension of the microbe, for e.g., 1-5×10$^5$ CFU/mL for bacterial cultures). Following overnight incubation at, e.g., 35° C., the tubes are examined for visible microbial growth as evidenced by turbidity. The lowest concentration of antibiotic that prevents growth generally represents the minimal inhibitory concentration (MIC). The advantage of this technique is the generation of a quantitative result (i.e., the MIC).

Currently, phenotypic assays to perform in vitro antifungal broth dilution susceptibility tests for either yeasts or filamentous fungi (also termed molds) include two universally recognized standard methods, Clinical and Laboratory Standards Institute (CLSI) (Clinical and Laboratory Standards Institute. M27-A3: Reference Method for Broth Dilution Antifungal Susceptibility Testing of Yeasts; Approved Standard-3rd ed.; CLSI: Wayne, PA, USA, 2008.; Clinical and Laboratory Standards Institute. M38-A2: Reference Method for Broth Dilution Antifungal Susceptibility Testing of Filamentous Fungi; Approved Standard-2nd ed.; CLSI: Wayne, PA, USA, 2008, incorporated herein by reference) and the European Committee on Antimicrobial Susceptibility Testing (EUCAST) (Arendrup et al., EUCAST-AFST. EUCAST technical note on the EUCAST definitive document EDef 7.2: Method for the determination of broth dilution minimum inhibitory concentrations of antifungal agents for yeasts EDef 7.2 (EUCAST-AFST). Clin. Microbiol. Infect. 2012, 18, E246-E247; Arendrup et al., Subcommittee on Antifungal Susceptibility Testing (AFST) of the ESCMID European Committee for Antimicrobial Susceptibility Testing (EUCAST). In EUCAST Method for the Determination of Broth Dilution Minimum Inhibitory Concentrations of Antifungal Agents for Conidia Forming Moulds Version 9.3; EUCAST: Vaxjo, Sweden, 2015, incorporated herein by reference), which apply the broth microdilution method (BMD). Both measure antifungal activity, expressed as the minimum inhibitory concentration (MIC) of an antifungal drug, which indicates the minimal drug concentration that inhibits fungal growth. Despite some methodological differences (e.g., glucose concentration, inoculum size, reading endpoint, etc.) between the two, CLSI and EUCAST have been proven to yield, upon completion of testing, comparable MIC data for all classes of antifungal agents (see, e.g., Posteraro et al., The future of fungal susceptibility testing. Future Microbiol. 2014, 9, 947-967; Pfaller et al., Comparison of the broth microdilution (BMD) method of the European Committee on Antimicrobial Susceptibility Testing with the 24-hour CLSI BMD method for testing susceptibility of *Candida* species to fluconazole, posaconazole, and voriconazole by use of epidemiological cutoff values. J. Clin. Microbiol. 2011, 49, 845-850; Pfaller et al., Progress in antifungal susceptibility testing of *Candida* spp. by use of Clinical and Laboratory Standards Institute broth microdilution methods, 2010 to 2012. J. Clin. Microbiol. 2012, 50, 2846-2856, incorporated herein by reference).

Minimum Bactericidal Concentration (MBC) Assay

Additional assays may be performed to further characterize the antimicrobial activity of the compounds described herein. For example, the minimum bactericidal concentration (MBC) or minimum lethal concentration (MLC) may be determined following the M26-A guidelines of the Clinical and Laboratory Standards Institute (Barry et el., A-26: Methods for determining Bactericidal Activity of Antimicrobial Agents; Approved Guidelines, September 1999, Vol. 19(18), incorporated herein by reference. The minimum bactericidal concentration (MBC) is the lowest concentration of an antibacterial agent required to kill a particular bacterium. It can be determined from broth dilution minimum inhibitory concentration (MIC) tests by sub-culturing to agar plates that do not contain the test agent. The MBC is identified by determining the lowest concentration of antibacterial agent that reduces the viability of the initial bacterial inoculum by >99.9%. The MBC is complementary to the MIC; whereas the MIC test demonstrates the lowest level of antimicrobial agent that inhibits growth, the MBC demonstrates the lowest level of antimicrobial agent that results in microbial death.

Additional Useful In Vitro Assays

Additional assays well-known in the art that may be used to test the antimicrobial activity, including antibacterial and antifungal activity, include the agar well diffusion methods, the agar plug diffusion method, the cross streak method, the poisoned food method, thin-layer chromatography bioautography, agar dilution methods, the time-kill test (time-kill curve), ATP bioluminescence test, and the flow cytofluorometric method (see Balouiri et al., Methods for in vitro evaluating antimicrobial activity: A review. Journal of Pharmaceutical Analysis, Vol. 6, No. 2, April 2016; pg. 71-79, incorporated herein by reference). Assays well-known in the art that may be used to test the anti-viral activity of the compounds described herein include cytopathic effect (CPE) inhibitory assays (see, e.g., Schmidtke et al., A rapid assay for evaluation of antiviral activity against coxsackie virus B3, influenza virus A, and herpes simplex virus type 1. J Virol Methods. 2001 June; 95(1-2):133-43; Cotarelo et al., Cytopathic effect inhibition assay for determining the in-vitro susceptibility of herpes simplex virus to antiviral agents, Journal of Antimicrobial Chemotherapy, Volume 44, Issue 5, November 1999, Pages 705-708, incorporated herein by reference).

In Vivo Topical Assays

In addition to the in vitro assays described above, the antimicrobial efficacy activity of the compounds described herein can be characterized using suitable in vivo assays. For example, an occlusion test measures the ability of an agent to prevent the expansion of the resident microflora which occurs when an impermeable dressing is applied to the forearm (see, e.g., Leyden et al. Updated in vivo Methods for Evaluating Topical Antimicrobial Agents on Human Skin, Journal of Investigative Dermatology, 72: 165-170 (1979), incorporated herein by reference). The principle of this test is that the micro flora of the forearm skin is sparse (101 to 102 organisms per square cm). An impermeable dressing will increase surface moisture by preventing diffusional water loss and thus enhance bacterial growth. The density of resident organisms increases significantly, with counts frequently reaching millions per sq cm by 48 hr. The organisms involved in this expansion are primarily gram-positive cocci and diphtheroids. The procedure is as follows: on each arm 0.1 ml of a compound is delivered to each of two 5-cm squares (25 sq cm), by a plastic tuberculin syringe (0.1 ml). Each site is immediately covered with a 5-em square of impermeable plastic, e.g., Saran Wrap. The site is occlusively sealed by encircling the limb with plastic tape (Dermiclear). A strip of wide white-backed adhesive tape (Zonas, Johnson & Johnson) is placed between each test site to prevent the possibility of translocation of test agents and organisms from one site to another. A third site on each arm is treated with 0.1 ml of the vehicle. The control site is always prepared first to prevent its potential contamination by the test substances. After 24 hr of occlusion, the 3 sites on one arm are quantitatively sampled. The opposite arm is sampled after 48 hr.

Additional or alternative tests include the expanded flora test, persistence test, ecological shift test, and serum inactivation test, which are known in the art (see, e.g., Leyden et al. Updated in vivo Methods for Evaluating Topical Antimicrobial Agents on Human Skin, Journal of Investigative Dermatology, 72: 165-170 (1979), incorporated herein by reference).

In vivo testing to determine the efficacy of a compound described herein for use in the eye to treat an infection are also well known. For example, the compound described herein can be tested against targeted microbial infections by induced infections in rabbit eyes, and treating the rabbit (see, generally, Deren et al., Comparison of antifungal efficacies of moxifloxacin, liposomal amphotericin B, and combination treatment in experimental *Candida albicans* endophthalmitis in rabbits. Can J Microbiol. 2010 January; 56(1): 1-7. doi: 10.1139/w09-112, incorporated herein by reference).

Exemplary Disk Diffusion Susceptibility Test

An exemplary disk diffusion susceptibility test for testing the antibacterial activity of a compound described herein is provided below.

Mueller-Hinton Agar

Mueller-Hinton agar (MH agar) is the standard medium for use in routine susceptibility testing of, for example, nonfastidious bacteria, including, for example, aerobic or facultative bacteria. MH agar may be purchased as prepared agar plates from Remel (Lenexa, KS), BD BBL (Franklin Lakes, NJ), or any other supplier of prepared agar plates. Follow the manufacturer's recommendation for storage of prepared plates. MH agar can also be prepared from dehydrated media available from companies such as Remel, BD BBL, or any other supplier of dehydrated media. Prepare the media according to the manufacturer's directions.

Formula for Mueller-Hinton agar per liter of purified water:

| | |
|---|---|
| Beef, Infusion from | 300.0 g |
| Casamino acid, technical | 17.5 g |
| Starch | 1.5 g |
| Agar | 17.0 g |

Suspend the components listed above in 1 liter of purified water. Mix thoroughly. Heat with frequent agitation and boil for 1 minute to completely dissolve the components. Autoclave at 121° C. for 15 minutes. Dispense as desired. Allow to solidify at room temperature, then store at 4 to 8° C. Mueller-Hinton agar is stable for approximately 70 days (per Remel Technical Services, 1 Sep. 2009) from the date of preparation. If MH agar plates are prepared from dehydrated media, the plates should be poured to a depth of 4 mm (approximately 25 ml of liquid agar for 100-mm plates and 60 ml of liquid agar for 150-mm plates, but in any case to a measured depth of 4 mm. pH of the MH agar should fall between 7.2 and 7.4 at room temperature after solidification and should be tested when the media is first prepared.

Antimicrobial Susceptibility Disks

Impregnate a disk of standard filter paper (approximately 6-mm) with a known concentration (e.g., 1 µg/ml) of a compound, for example a compound of Formula I, described herein in a suitable growth medium and allow to dry at 4° C.

McFarland Standard

McFarland standards are suspensions of either barium sulfate or latex particles that allow visual comparison of bacterial density. Commercially prepared standards are available for purchase from companies such as Remel or BD BBL. These often include a Wickerham card, which is a small card containing parallel black lines. A 0.5 McFarland standard is equivalent to a bacterial suspension containing between $1 \times 10^8$ and $2 \times 10^8$ CFU/ml of *E. coli*. McFarland standard may be prepared as describe below:

1. Add a 0.5-ml aliquot of a 0.048 mol/liter $BaCl_2$ (1.175% wt/vol $BaCl_2$ $2H_2O$) to 99.5 ml of 0.18 mol/liter $H_2SO_4$ (1% vol/vol) with constant stirring to maintain a suspension.
2. Verify the correct density of the turbidity standard by measuring absorbance using a spectrophotometer with a 1-cm light path and matched cuvette. The absorbance at 625 nm should be 0.08 to 0.13 for the 0.5 McFarland standard.
3. Transfer the barium sulfate suspension in 4- to 6-ml aliquots into screw-cap tubes of the same size as those used in standardizing the bacterial inoculums.
4. Tightly seal the tubes and store in the dark at room temperature.
5. Prior to use, vigorously agitate the barium sulfate standard on a mechanical vortex mixer and inspect for a uniformly turbid appearance. Replace the standard if large particles appear. If using a standard composed of latex particles, mix by inverting gently, not on a vortex mixer.
6. As the bacterial colonies are added to the saline in the "preparation of the inoculum" step of the procedure, compare the resulting suspension to the McFarland standard. This is done by holding both the standard and the inoculum tube side by side and no more than 1 inch from the face of the Wickerham card (with adequate light present) and comparing the appearance of the lines through both suspensions. Do not hold the tubes flush against the card. If the bacterial suspension appears lighter than the 0.5 McFarland standard, more organisms should be added to the tube from the culture plate. If the suspension appears more dense than the 0.5 McFarland standard, additional saline should be added to the inoculum tube in order to dilute the suspension to the appropriate density.

Preparation of Mueller-Hinton Plate

1. Allow a MH agar plate (one for each organism to be tested) to come to room temperature. It is preferable to allow the plates to remain in the plastic sleeve while they warm to minimize condensation.
2. If the surface of the agar has visible liquid present, set the plate inverted, ajar on its lid to allow the excess liquid to drain from the agar surface and evaporate. Plates may be placed in a 35° C. incubator or in a laminar flow hood at room temperature until dry (usually 10 to 30 minutes).
3. Appropriately label each MH agar plate for each organism to be tested.

Preparation of Inoculum

1. Using a sterile inoculating loop or needle, touch four or five isolated colonies of the organism to be tested, for example, an organism selected from *Pseudomonas* (Gram-negative), *Proteus* (genus of Gram-negative Proteobacteria), *Staphylococcus* (Gram-positive), MRSA (methicillin resistant *S. aureus*), *Escherichia coli* (Gram-negative), *Klebsiella* (Gram-negative), *Enterococcus* (Gram-positive), or *Haemophilus influenzae*,
2. Suspend the organism in 2 ml of sterile saline.
3. Vortex the saline tube to create a smooth suspension.
4. Adjust the turbidity of this suspension to a 0.5 McFarland standard by adding more organism if the suspension is too light or diluting with sterile saline if the suspension is too heavy.
5. Use this suspension within 15 minutes of preparation.

Inoculation of the MH Plate

1. Dip a sterile swab into the inoculum tube.
2. Rotate the swab against the side of the tube (above the fluid level) using firm pressure, to remove excess fluid. The swab should not be dripping wet.
3. Inoculate the dried surface of a MH agar plate by streaking the swab three times over the entire agar surface; rotate the plate approximately 60 degrees each time to ensure an even distribution of the inoculum.
4. Rim the plate with the swab to pick up any excess liquid.
5. Discard the swab into an appropriate container.
6. Leaving the lid slightly ajar, allow the plate to sit at room temperature at least 3 to 5 minutes, but no more than 15 minutes, for the surface of the agar plate to dry before proceeding to the next step arrow indicates the path of the swab.

Placement of the Antimicrobial Disks

Place the appropriate antimicrobial-impregnated disks on the surface of the agar. Disks should not be placed closer than 24 mm (center to center) on the MH agar plate. Ordinarily, no more than 12 disks should be placed on a 150-mm plate or more than 5 disks on a 100-mm plate. Avoid placing disks close to the edge of the plate as the zones will not be fully round and can be difficult to measure. Each disk must be pressed down with forceps to ensure complete contact with the agar surface or irregular zone shapes may occur. If the surface of the agar is disrupted in any way (a disk penetrating the surface, visible lines present due to excessive pressure of the swab against the plate during inoculation, etc.) the shape of the zone may be affected.

Incubation of the Plates

Incubate the inoculated plates at a temperature range of 35° C.±2° C. Results are read after about 18 hours of incubation.

This specification has been described with reference to embodiments of the invention. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included with the scope of invention.

We claim:
1. A quaternary ammonium compound of Formula:

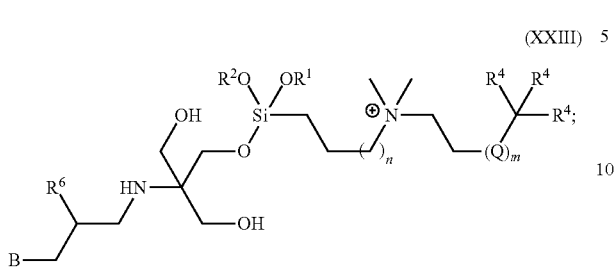
(XXIII)

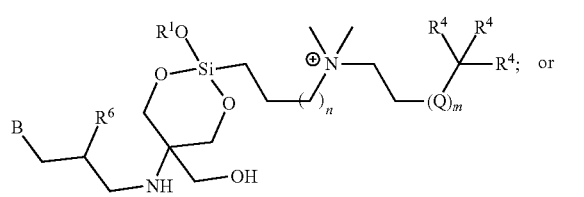
(XXIV)

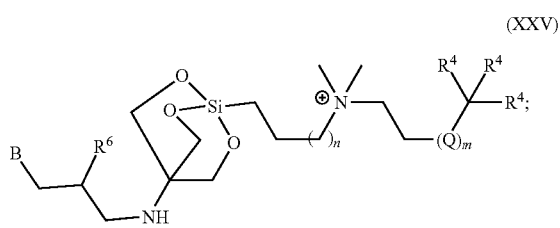
(XXV)

wherein the quaternary amine has a balancing pharmaceutically acceptable anion;
wherein
m is 5, 6, 7, 8, 9, 10, 11, 12, 13, 14, 15, 16, or 17;
n is 0, 1, or 2;
Q is —$CR^4R^4$—;
$R^1$ and $R^2$ are independently at each occurrence selected from the group consisting of hydrogen and ethyl;
$R^4$ is independently at each occurrence selected from the group consisting of hydrogen, $C_{1-3}$alkyl, $C_{2-4}$alkenyl, $C_{2-4}$alkynyl, halogen, and halo$C_{1-3}$alkyl;
$R^6$ is independently at each occurrence selected from the group consisting of hydrogen, hydroxy, and $C_1$-$C_6$alkoxy;
B is independently at each occurrence selected from the group consisting of

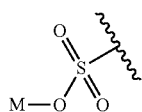

and

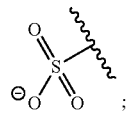
;

and

M is hydrogen, sodium, potassium, cesium, or lithium.

2. The quaternary ammonium compound of claim 1, wherein at least two $R^4$ substituents are hydrogen.

3. The quaternary ammonium compound of claim 1, wherein the balancing anion is selected from the group consisting of chloride, fluoride, iodide, bromide, hydroxide, chlorite, chlorate, formate, acetate, lactate, benzoate, and salicylate anion.

4. The quaternary ammonium compound of claim 1, wherein B is

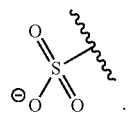
.

5. The quaternary ammonium compound of claim 1, wherein B is

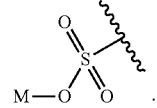
.

6. The quaternary ammonium compound of claim 5, wherein M is selected from the group consisting of sodium and potassium.

7. The quaternary ammonium compound of claim 1 of formula:

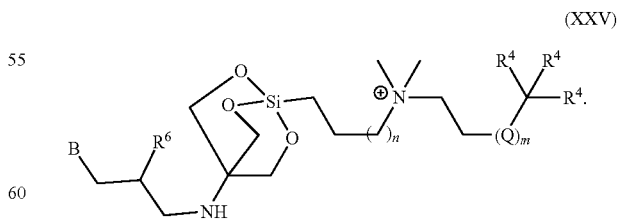
(XXV)

8. The quaternary ammonium compound of claim 1 that is a zwitterion.

9. The quaternary ammonium compound of claim 1 of formula:

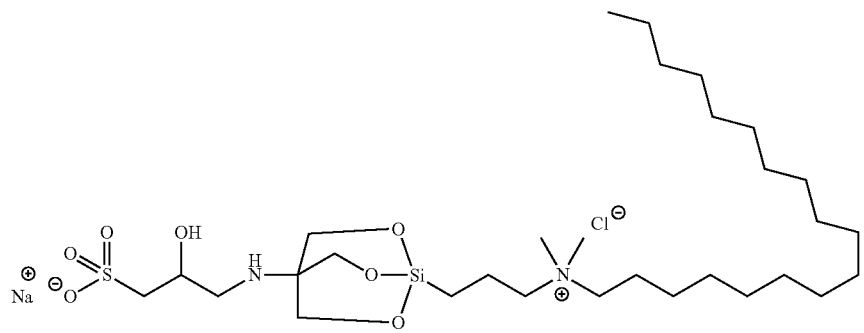

10. The quaternary ammonium compound of claim 1 of formula:

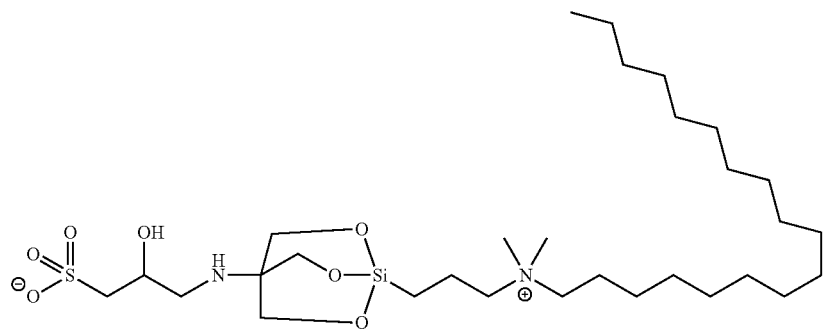

11. The quaternary ammonium compound of claim 1, wherein the compound is a lyophilized powder.

12. A pharmaceutical composition comprising a compound of claim 1 and a pharmaceutically acceptable excipient.

13. The pharmaceutical composition of claim 12, wherein the composition is suitable for topical delivery.

14. The pharmaceutical composition of claim 13, wherein the composition is in the form of a liquid, cream, gel, spray, foam, wipe, powder, paste, or solid.

15. A method of treating a topical infection, wherein the treatment comprises administering an effective amount of a compound of claim 1 to a host in need thereof.

16. The method of claim 15, wherein the host is human.

17. The method of claim 15, wherein the host is a dog, cat, horse, or bovine.

18. The method of claim 15, wherein the infection is bacterial, fungal, amoeba, or viral.

19. The method of claim 18, wherein the infection is caused by *Staphylococcus aureus, Pseudomonas aeruginosa, Fusarium, Aspergillus, Candida albicans, Curvularia* spp., *Haemophilus influenzae*, or *Acanthamoebic keratitis*.

20. The method of claim 15, wherein the infection is an ear infection; wherein the infection is an outer ear (otitis externa) infection, a middle ear (otitis media) infection, or an inner ear (otitis interna) infection; a nail infection, an infection in a chronic wound, or an infection that causes periodontal disease.

* * * * *